United States Patent
Niewöhner, et al.

(10) Patent No.: US 6,878,708 B2
(45) Date of Patent: Apr. 12, 2005

(54) IMIDAZOTRIAZINONES AND THE USE THEREOF

(75) Inventors: Ulrich Niewöhner, deceased, late of Wermelskirchen (DE); by Maria Niewöhner, legal representative, Wermelskirchen (DE); Mazen Es-Sayed, Langenfeld (DE); Thomas Lampe, Wuppertal (DE); Helmut Haning, Milford, CT (US); Gunter Schmidt, Wuppertal (DE); Karl-Heinz Schlemmer, Wuppertal (DE); Erwin Bischoff, Wuppertal (DE); Klaus Dembowsky, Boston, MA (US); Elisabeth Perzborn, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/220,560

(22) PCT Filed: Feb. 20, 2001

(86) PCT No.: PCT/EP01/01871

§ 371 (c)(1),
(2), (4) Date: Feb. 6, 2003

(87) PCT Pub. No.: WO01/64677

PCT Pub. Date: Sep. 7, 2001

(65) Prior Publication Data

US 2004/0097498 A1 May 20, 2004

(30) Foreign Application Priority Data

Mar. 2, 2000 (DE) .......................................... 100 10 067

(51) Int. Cl.$^7$ ................... C07D 487/04; A61K 31/4188; A61P 15/10
(52) U.S. Cl. ....................... 514/243; 544/184; 544/112; 514/234.5
(58) Field of Search ................................. 544/184, 112; 514/243, 234.5

(56) References Cited

U.S. PATENT DOCUMENTS 6,362,178 B1    3/2002   Niewöhner et al. ......... 544/184

FOREIGN PATENT DOCUMENTS

| EP | 0526004 | 2/1993 |
| WO | 9428902 | 12/1994 |
| WO | 9924433 | 5/1999 |

OTHER PUBLICATIONS

Lucas et al. Pharmacological Reviews 52 (3), 375–413, 2000.*

Dumaitre, B., and Dodiac, N., "Synthesis and Cyclic GMP Phosphodiesterase Inhibitory Activity of a Series of 6–Phenylpyrazolo[3,4–d]pyrimidinones", J. Med. Chem., 39: 1635–1644 (1996).

* cited by examiner

Primary Examiner—Venkataraman Balasubramanian
(74) Attorney, Agent, or Firm—Susan M. Pellegrino

(57) ABSTRACT

Novel imidazotriazinones of general formula (I), a method for the production and the pharmaceutical use thereof are disclosed.

12 Claims, No Drawings

IMIDAZOTRIAZINONES AND THE USE THEREOF

The present invention relates to novel imidazotriazinones, to processes for their preparation and to their use as medicaments, in particular as inhibitors of cGMP-metabolizing phosphodiesterases.

The published specificiation DE-OS 2811780 describes imidazotriazines as bronchodilators having spasmolytic activity and inhibitory activity against phosphodiesterases which metabolize cyclic adenosine monophosphate (cAMP-PDEs, nomenclature according to Beavo: PDE III and PDE IV). An inhibitory action against phosphodiesterases which metabolize cyclic guanosine monophosphate [cGMP-PDEs, nomeclature according to Beavo and Reifsnyder (Trends in Pharmacol. Sci. 11, 150–155, 1990) PDE I, PDE II and PDE V] has not been described. Furthermore, FR-22 13 058, CH-59 46 71, DE-22 55 172, DE-23 64 076 and EP-000 9384 describe imidazotriazinones which do not have a substituted aryl radical in the 2 position and are likewise said to be bronchodilatators having cAMP-PDE-inhibitory action.

WO-A-99/24433 likewise describes imidazotriazinones as inhibitors of cGMP-metabolizing phosphodiesterase; however, these compounds, by definition, all have a sulfonamide group in the phenyl ring in the position para to the alkoxy group.

An increase in the cGMP concentration can lead to beneficial antiaggregatory, antithrombotic, antiprolific, antivasospastic, vasodilative, natriuretic and diuretic effects. It can influence the short- or long-term modulation of vascular and cardiac inotropy, of the pulse and of cardiac conduction (J. C. Stoclet, T. Keravis, N. Komas and C. Kugnier, Exp. Opin. Invest. Drugs (1995), 4 (11), 1081–1100). Inhibition of cGMP-PDEs can also enhance erections. Accordingly, such compounds are suitable for treatings erectile dysfunction.

The present invention accordingly relates to novel imidazotriazinones of the general formula (I)

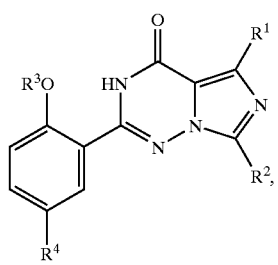

(I)

in which
$R^1$ represents $(C_1-C_6)$-alkyl,
$R^2$ represents $(C_3-C_8)$-cycloalkyl or $(C_1-C_{12})$-alkyl,
$R^3$ represents $(C_1-C_6)$-alkyl,
$R^4$ represents a radical of the formulae

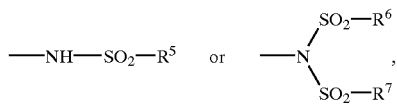

in which
$R^5$, $R^6$ and $R^7$ are identical or different and represent vinyl or $(C_1-C_6)$-alkyl which is optionally substituted up to 3 times by identical or different substituents from the group consisting of trifluoromethyl, halogen, $(C_1-C_6)$-alkoxy or by radicals of the formulae

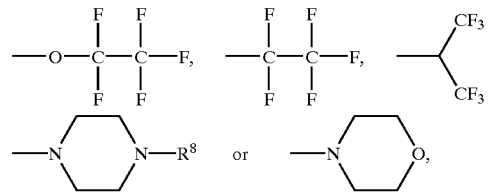

in which
$R^8$ represents hydrogen or $(C_1-C_4)$-alkyl, or
$R^5$, $R^6$ and/or $R^7$ represents $(C_6-C_{12})$-aryl which is optionally substituted up to 3 times by identical or different substituents from the group consisting of halogen, trifluoromethyl, nitro, cyano, carboxyl, $(C_1-C_6)$-alkyl and $(C_1-C_6)$-alkoxy or
$R^5$ represents quinolyl or a 5- to 6-membered aromatic or saturated heterocycle having up to 3 heteroatoms from the group consisting of S, N and O, which heterocycle may optionally be substituted up to 3 times, in the case of an N function also via this N function, by identical or different substituents from the group consisting of halogen and $(C_1-C_6)$-alkyl or
$R^5$ represents a radical of the formulae

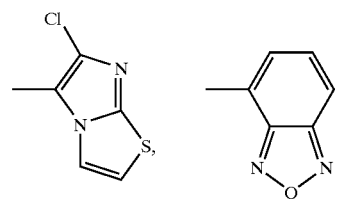

or $-NR^9R^{10}$
in which
$R^9$ and $R^{10}$ are identical or different and represent hydrogen. $(C_1-C_6)$-alkyl or phenyl, or
$R^4$ represents carboxyl or represents a radical of the formulae

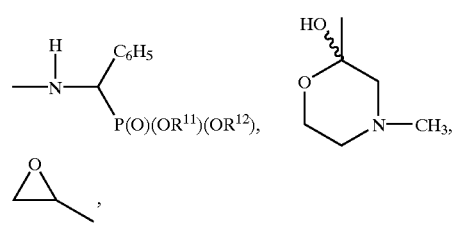

$-CO-R^{13}$ or $-O-R^{14}$ in which
$R^{11}$ and $R^{12}$ are identical or different and represent hydrogen or $(C_1-C_4)$-alkyl,
$R^{13}$ represents $(C_1-C_6)$-alkyl,
$R^{14}$ represents $(C_1-C_6)$-alkyl which is optionally substituted up to 3 times by identical or different substituents from the group consisting of hydroxyl, phenyl or by a radical of the formula $-NR^{15}R^{16}$,
in which
$R^{15}$ and $R^{16}$ are identical or different and represent hydrogen, phenyl or $(C_1-C_4)$-alkyl which for its part may be substituted by phenyl, or R⁴ represents a radical of the formula —NH—CO—NR¹⁷R¹⁸,
in which
R¹⁷ and R¹⁸ are identical or different and represent hydrogen or (C₁–C₆)-alkyl which is optionally substituted by hydroxyl or by a radical of the formulae

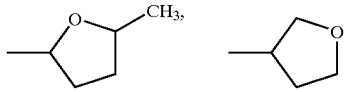

or —NR¹⁹R²⁰,
in which
R¹⁹ and R²⁰ are identical or different and represent hydrogen, phenyl or (C₁–C₆)-alkyl or
R¹⁷ and R¹⁸ together with the nitrogen atom to which they are attached form a heterocyclic ring of the formulae

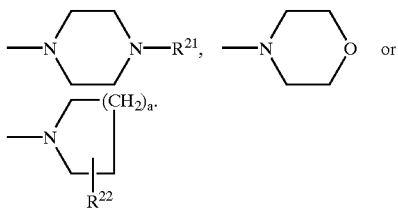

in which
R²¹ represents hydrogen or (C₁–C₆)-alkyl,
a represents either 1 or 2,
R²² represents hydroxyl or (C₁–C₆)-alkyl which is optionally substituted by hydroxyl, or
R¹⁷ and/or R¹⁸ represent (C₆–C₁₂)-aryl which is optionally substituted by halogen, trifluoroethyl or by —SCF₃ or
R¹⁷ represents hydrogen and
R¹⁸ represents a radical of the formula —SO₂—R²³,
in which
R²³ represents (C₁–C₆)-alkyl or (C₆–C₁₂)-aryl which is optionally substituted by halogen,
or represents a radical of the formulae

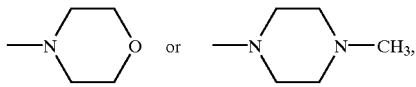

or
R⁴ represents a radical of the formula

—NH—CO-R²⁴, in which
R²⁴ represents a radical of the formula

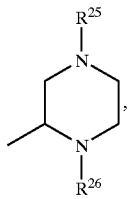

in which

R²⁵ and R²⁶ are identical or different and represent hydrogen, (C₁–C₆)-alkyl or (C₁–C₆)-alkoxycarbonyl,
or
R²⁴ represents (C₁–C₆)-alkyl which is optionally substituted by (C₆–C₁₂)-aryl which for its part may be substituted by hydroxyl or (C₁–C₆)-alkoxy or
(C₁–C₆)-alkyl optionally substituted by a radical of the formula —(SO₂)ᵦ—R²⁷,
in which
b represents either 0 or 1 and
R²⁷ represents a radical of the formulae

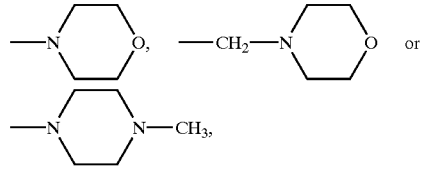

or
R⁴ represents (C₁–C₁₂)-alkyl which is optionally substituted up to 3 times by identical or different radicals from the group consisting of hydroxyl, azide, phenyl or by radicals of the formulae —NR²⁸R²⁹, —O—CO—R³⁰ or —P(O){O—[(C₁–C₆)-alkyl]}₂,
in which
R²⁸ and R²⁹ are identical or different and represent hydrogen, phenyl or (C₁–C₆)-alkyl which is optionally substituted by hydroxyl, (C₁–C₆)-alkoxy or phenyl, or
R²⁸ and R²⁹ together with the nitrogen atom to which they are attached form a heterocyclic ring of the formulae

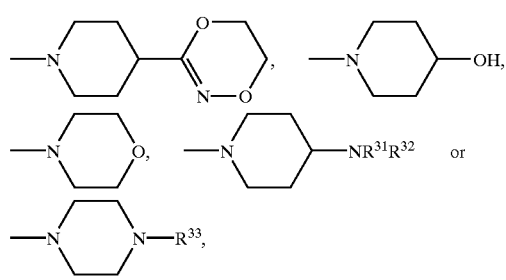

in which
R³¹ and R³² are identical or different and represent hydrogen or (C₁–C₆)-alkyl
R³³ represents (C₁–C₆)-alkyl, benzyl, (C₁–C₆)-alkoxycarbonyl, (C₁–C₆)-alkylcarbonyl, carboxyl, pyridyl, pyrimidyl or phenyl which is optionally substituted by (C₁–C₆)-alkoxy, and
R³⁰ represents (C₁–C₆)-alkyl, or
(C₁–C₁₂)-alkyl optionally substituted by triazolyl which for its part may be substituted up to 2 times by identical or different substituents from the group consisting of halogen, phenyl, tetrahydrofuran), tetrahydropyranyl, (C₁–C₆)-alkoxycarbonyl, aminocarbonyl or by (C₁–C₆)-alkyl, where the latter may optionally be substituted by hydroxyl, (C₁–C₆)-alkoxy or by a radical of the formulae NR³⁴R³⁵ or —O—CO—R³⁶,
in which
R³⁴ and R³⁵ are identical or different and represent hydrogen or (C₁–C₆)-alkyl,
R³⁶ represents (C₁–C₆)-alkyl, or $R^4$ represents a radical of the formula —CO—$R^{37}$,
in which
$R^{37}$ represents a radical of the formulae

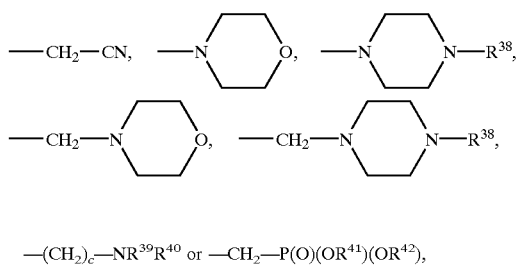

in which
$R^{38}$ represents hydrogen or $(C_1-C_6)$-alkyl,
c represents either 0 or 1,
$R^{39}$ and $R^{40}$ are identical or different and represent hydrogen or $(C_1-C_6)$-alkyl which is optionally substituted by hydroxyl,
$R^{41}$ and $R^{42}$ are identical or different and represent $(C_1-C_6)$-alkyl, or
$R^4$ represents a 5-membered heterocycle having up to 3 heteroatoms from the group consisting of S, N and O, which heterocycle is optionally substituted altogether up to 3 times, in the case of an N function also via this N function, by identical or different substituents from the group consisting of halogen, trifluoromethyl or by phenyl which for its part may be mono- or polysubstituted by halogen or trifluoromethyl,
and/or is optionally substituted by $(C_3-C_6)$-cycloalkyl, pyrryl or by $(C_1-C_{12})$-alkyl which for its part may be substituted by cyano, trifluoromethyl, $(C_1-C_6)$-alkoxycarbonyl, $(C_1-C_6)$-alkoxy, amino or by phenyl or nitro-substituted phenyl,
and/or may optionally be substituted by —$NR^{43}R^{44}$, —NH—CO—CO—$R^{45}$, —NH—CO—$R^{46}$,

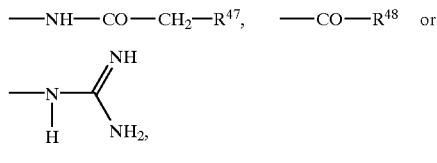

in which
$R^{43}$ and $R^{44}$ are identical or different and represent hydrogen, benzyl, $(C_1-C_6)$-alkyl or phenyl which is optionally substituted by halogen or trifluoromethyl,
$R^{45}$ represents $(C_1-C_6)$-alkoxy,
$R^{46}$ represents $(C_1-C_6)$-alkyl or phenyl,
$R^{47}$ represents hydroxyl, $(C_1-C_6)$-alkoxy or a radical of the formula —O—CO—$R^{49}$,
in which
$R^{49}$ represents $(C_1-C_4)$-alkyl
$R^{48}$ represents a radical of the formula —$CH_2$—CN or phenyl which is optionally substituted by halogen, trifluoromethyl or $(C_1-C_6)$-alkoxy,
and their tautomers and their pharmaceutically acceptable salts, hydrates and prodrugs.

Depending on the substitution pattern, the compounds of the general formula (I) according to the invention may exist in stereoisomeric forms which are either like image and mirror image (enantiomers), or which are not like image and mirror image (diastereomers). The invention relates both to the enantiomers or diastereomers and to their respective mixtures. The racemic forms can, just like the diastereomers, be separated in a known manner into the stereoisomerically uniform constituents.

Certain compounds of the general formula (I) may furthermore be present in tautomeric forms. This is known to the person skilled in the art, and such compounds are also within the scope of the invention.

Physiologically acceptable, i.e. pharmaceutically acceptable, salts can be salts of the compounds according to the invention with inorganic or organic acids. Preference is given to salts with inorganic acids such as, for example, hydrochloric acid, hydrobromic acid, phosphoric acid or sulfuric acid, or salts with organic carboxylic or sulfonic acids such as, for example, acetic acid, propionic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid or naphthalenedisulfonic acid.

Pharmaceutically acceptable salts that may be mentioned are also salts with customary bases, such as, for example, alkali metal salts (for example sodium salts or potassium salts), alkaline earth metal salts (for example calcium salts or magnesium salts) or ammonium salts derived from ammonia or organic amines such as, for example, diethyl amine, triethylamine, ethyldiisopropylamine, procaine, dibenzylamine, N-methylmorpholine, dihydroabietylamine or methylpiperidine.

"Hydrates" according to the invention are those forms of the compounds of the above general formula (I) which, in solid or liquid state, form a molecular compound (solvate) with water by hydrataion. In the hydrates, the water molecules form an adduct by intramolecular forces, in particular hydrogen bonds. Solid hydrates contain water as water of crystallization in stoichiometric ratios, it not being necessary for the water molecules to be equivalent with respect to their binding state. Examples of hydrates are sesquihydrates, monohydrates dihydrates or trihydrates. Also suitable are the hydrates of salts of the compounds according to the invention.

"Prodrugs" according to the invention are forms of the compounds of the above general formula (I) which, for their part, may be biologically active or inactive, but which can be converted into the corresponding biologically active form (for example metabolically, solvolytically or by other means).

$(C_1-C_{12})$-Alkyl denotes a straight-chain or branched alkyl radical having 1 to 12 carbon atoms. Examples which may be mentioned are: methyl, ethyl, n-propyl, isopropyl, n-butyl, isobutyl, tert-butyl, n-pentyl and n-hexyl. Derived from this definition are, in an analogous manner, the corresponding alkyl groups having fewer carbon atoms, such as, for example, $(C_1-C_6)$-alkyl and $(C_1-C_4)$-alkyl. Generally, preference is given to $(C_1-C_4)$-alkyl.

$(C_3-C_8)$-Cycloalkyl denotes a cyclic alkyl radical having 3 to 8 carbon atoms. Examples which may be mentioned are: cyclopropyl, cyclobutyl, cyclopentyl, cyclohexyl, cycloheptyl or cyclooctyl. Derived from this definition are, in an analogous manner, the corresponding cycloalkyl groups having fewer carbon atoms, such as, for example, $(C_3-C_5)$-cycloalkyl. Preference is given to cyclopropyl, cyclopentyl and cyclohexyl.

$(C_1-C_6)$-Alkoxy denotes a straight-chain or branched alkoxy radical having 1 to 6 carbon atoms. Examples which may be mentioned are: methoxy, ethoxy, n-propoxy, isopropoxy, n-butoxy, isobutoxy, tert-butoxy, n-pentoxy and n-hexoxy. Derived from this definition are, in an analogous manner, the corresponding alkoxy groups having fewer carbon atoms, such as, for example, $(C_1-C_6)$-alkoxy and $(C_1-C_4)$-alkoxy. In general, preference is given to $(C_1-C_4)$-alkoxy.

Also derived from this definition is the meaning of the corresponding component of other, more complex substituents, such as, for example, alkoxycarbonyl.

$(C_6-C_{12})$-Aryl denotes an aromatic radical having 6 to 12 carbon atoms. Examples which may be mentioned are: phenyl and naphthyl.

5- to 6-membered aromatic or saturated heterocycle having up to 3 heteroatoms from the group consisting of S, N and O denotes either a heteroaromatic radical which is attached via a ring carbon atom of the heteroaromatic compound or, if appropriate, also via a ring nitrogen atom of the heteroaromatic compound; examples which may be mentioned are: pyridyl, pyrimidyl, pyridazinyl, pyrazinyl, thienyl, furyl, pyrrolyl, pyrazolyl, imidazolyl, thiazolyl, oxazolyl or isoxazolyl, preference being given to pyridyl, pyrimidyl, pyridazinyl, furyl and thienyl, or denotes a saturated heterocycle which is attached via a ring carbon atom or a ring nitrogen atom, or denotes a $(C_5-C_6)$-cycloalkyl radical as mentioned above: examples which may be mentioned are: tetrahydrofuryl, pyrrolidinyl, piperidinyl, piperazinyl, morpholinyl, thiomorpholinyl, cyclopentyl and cyclohexyl, piperidinyl, morpholinyl and pyrrolidinyl being preferred.

Preference is given to compounds of the general formula (I) according to the invention
in which
$R^1$ represents $(C_1-C_4)$-alkyl,
$R^2$ represents cyclopentyl, cycloheptyl or $(C_1-C_{10})$-alkyl,
$R^3$ represents $(C_1-C_4)$-alkyl,
$R^4$ represents a radical of the formulae

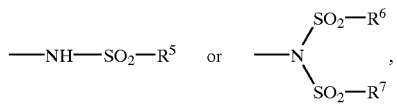

in which
$R^5$, $R^6$ and $R^7$ are identical or different and represent vinyl or $(C_1-C_4)$-alkyl which is optionally substituted up 3 times by identical or different substituents from the group consisting of trifluoromethyl, chlorine, $(C_1-C_4)$-alkoxy or by radicals of the formulae

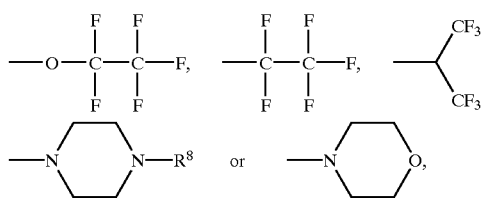

in which
$R^8$ represents hydrogen, methyl or ethyl, or
$R^5$, $R^6$ and/or $R^7$ represent phenyl which is optionally substituted up to 3 times by identical or different substituents from the group consisting of halogen, trifluoromethyl, nitro, cyano, carboxyl, $(C_1-C_4)$-alkyl and $(C_1-C_4)$-alkoxy or $R^5$ represents quinolyl or a radical of the formulae

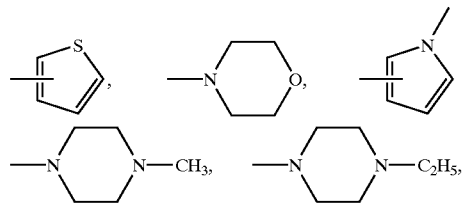

which may optionally be substituted up to 2 times by identical or different substituents from the group consisting of chlorine and $(C_1-C_4)$-alkyl or
$R^5$ represents a radical of the formulae

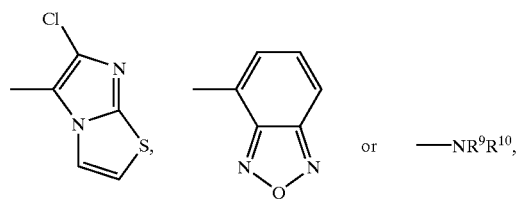

in which
$R^9$ and $R^{10}$ are identical or different and represent hydrogen $(C_1-C_6)$-alkyl or phenyl, or
$R^4$ represents carboxyl or represents a radical of the formulae

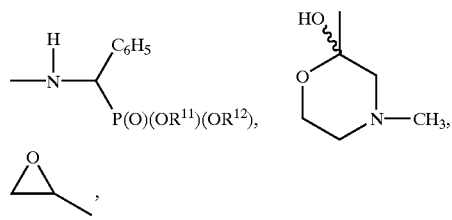

—CO—$R^{13}$ or —O—$R^{14}$, in which $R^{11}$ and $R^{12}$ are identical or different and represent hydrogen or $(C_1-C_4)$-alkyl,
$R^{13}$ represents $(C_1-C_4)$-alkyl,
$R^{14}$ represents $(C_1-C_4)$-alkyl which is optionally substituted up 3 times by identical or different substituents from the group consisting of hydroxyl, phenyl or by a radical of the formula —NR$^{15}$R$^{16}$,
in which
$R^{15}$ and $R^{16}$ are identical or different and represent hydrogen, phenyl or $(C_1-C_4)$-alkyl which for its part may be substituted by phenyl, or
$R^4$ represents a radical of the formula —NH—CO—NR$^{17}$R$^{18}$,
in which
$R^{17}$ and $R^{18}$ are identical or different and represent hydrogen or $(C_1-C_4)$-alkyl which is optionally substituted by hydroxyl or by a radical of the formulae

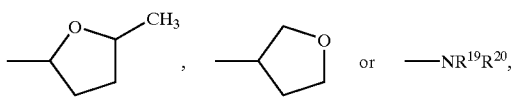 or —NR$^{19}$R$^{20}$, in which
R$^{19}$ and R$^{20}$ are identical or different and represent hydrogen, phenyl or (C$_1$–C$_4$)-alkyl or
R$^{17}$ and R$^{18}$ together with the nitrogen atom to which they are attached form a heterocyclic ring of the formulae

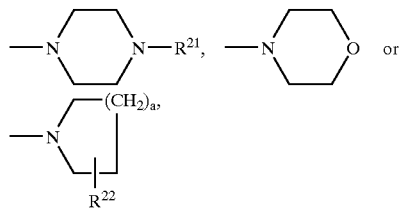

in which
R$^{21}$ represents hydrogen or (C$_1$–C$_4$)-alkyl,
a represents either 1 or 2,
R$^{22}$ represents hydroxyl or (C$_1$–C$_4$)-alkyl which is optionally substituted by hydroxyl, or
R$^{17}$ and/or R$^{18}$ represent phenyl which is optionally substituted by chlorine, trifluoroethyl or by —SCF$_3$ or
R$^{17}$ represents hydrogen and
R$^{18}$ represents a radical of the formula —SO$_2$—R$^{23}$,
in which
R$^{23}$ represents (C$_1$–C$_4$)-alkyl or phenyl which is optionally substituted by halogen,
or represents a radical of the formulae

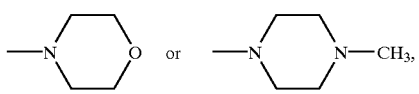

or
R$^4$ represents a radical of the formula

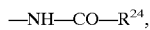

in which
R$^{24}$ represents a radical of the formula

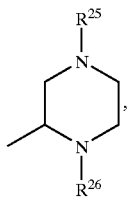

in which
R$^{25}$ and R$^{26}$ are identical or different and represent hydrogen, (C$_1$–C$_4$)-alkyl or (C$_1$–C$_4$)-alkoxycarbonyl, or
R$^{24}$ represents (C$_1$–C$_4$)-alkyl which is optionally substituted by phenyl which for its part may be substituted by hydroxyl or (C$_1$–C$_4$)-alkoxy or
(C$_1$–C$_4$)-alkyl optionally substituted by a radical of the formula —(SO$_2$)$_b$—R$^{27}$, in which
b represents either 0 or 1 and
R$^{27}$ represents a radical of the formulae

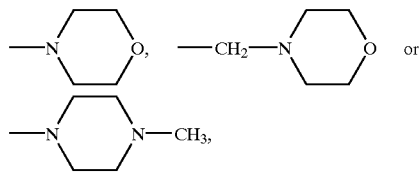

or

R$^4$ represents (C$_1$–C$_{11}$)-alkyl which is optionally substituted up to 3 times by identical or different substituents from the group consisting of hydroxyl, azide, phenyl or by radicals of the formulae —NR$^{28}$R$^{29}$, —O—CO—R$^{30}$ or —P(O){O—[(C$_1$–C$_6$)-alkyl]}$_2$,
in which
R$^{28}$ and R$^{29}$ are identical or different and represent hydrogen, phenyl or (C$_1$–C$_4$)-alkyl which is optionally substituted by hydroxyl (C$_1$–C$_4$)-alkoxy or phenyl, or
R$^{28}$ and R$^{29}$ together with the nitrogen atom to which they are attached form a heterocyclic ring of the formulae

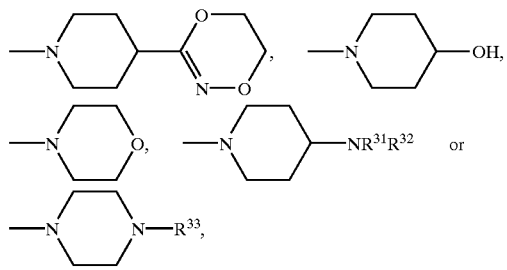

in which
R$^{31}$ and R$^{32}$ are identical or different and represent hydrogen or (C$_1$–C$_4$)-alkyl
R$^{33}$ represents (C$_1$–C$_4$)-alkyl, benzyl, (C$_1$–C$_4$)-alkoxycarbonyl, (C$_1$–C$_4$)-alkylcarbonyl, carboxyl, pyirdyl, pyrimidyl or phenyl which is optionally substituted by (C$_1$–C$_4$)-alkoxy, and
R$^{30}$ represents (C$_1$–C$_6$)-alkyl, or
(C$_1$–C$_{11}$)-alkyl is optionally substituted by triazolyl which for its part may be substituted up to 2 times by identical or different substituents from the group consisting of halogen, phenyl, tetrahydrofuranyl, tetrahydropyranyl, (C$_1$–C$_4$)-alkoxycarbonyl, aminocarbonyl or by (C$_1$–C$_4$)-alkyl, where the latter may optionally be substituted by hydroxyl, (C$_1$–C$_4$)-alkoxy or by a radical of the formulae NR$^{34}$R$^{35}$ or —O—CO—R$^{36}$,
in which
R$^{34}$ and R$^{35}$ are identical or different and represent hydrogen or (C$_1$–C$_4$)-alkyl,
R$^{36}$ represents (C$_1$–C$_4$)-alkyl, or
R$^4$ represents a radical of the formula —O—R$^{37}$,
in which $R^{37}$ represents a radical of the formulae

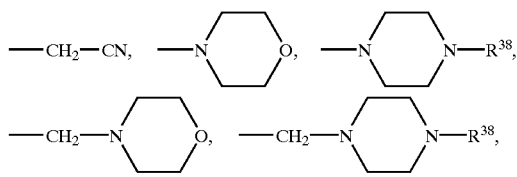

—$(CH_2)_c$—$NR^{39}R^{40}$ or —$CH_2$—$P(O)(OR^{41})(OR^{42})$, in which
$R^{38}$ represents hydrogen or $(C_1-C_4)$-alkyl,
c represents either 0 or 1,
$R^{39}$ and $R^{40}$ are identical or different and represent hydrogen or $(C_1-C_4)$-alkyl which is optionally substituted by hydroxyl,
$R^{41}$ and $R^{42}$ are identical or different and represent $(C_1-C_4)$-alkyl, or
$R^4$ represents a radical of the formula

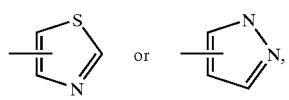

which is optionally substituted altogether up to 3 times, in the case of the pyrazole also via the N function, by identical or different substitutents from the group consisting of chlorine, trifluoromethyl or by phenyl which for its part may be mono- or polysubstituted by chlorine or trifluoromethyl,
and/or is optionally substituted by cyclopentyl, cyclohexyl, pyrryl or by $(C_1-C_{12})$-alkyl which for its part may be substituted by cyano, trifluoromethyl, $(C_1-C_4)$-alkoxycarbonyl, $(C_1-C_4)$-alkoxy, amino or by phenyl or nitro-substituted phenyl,
and/or may optionally be substituted by —$NR^{43}R^{44}$, —NH—CO—CO—$R^{45}$, —NH—CO—$R^{46}$,

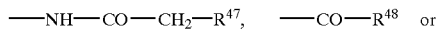

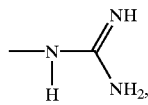

in which
$R^{43}$ and $R^{44}$ are identical or different and represent hydrogen, benzyl, $(C_1-C_4)$-alkyl or phenyl which is optionally substituted by halogen or trifluoromethyl,
$R^{45}$ represents $(C_1-C_5)$-alkoxy,
$R^{46}$ represents $(C_1-C_5)$-alkyl or phenyl,
$R^{47}$ represents hydroxyl, $(C_1-C_4)$-alkoxy or a radical of the formula —O—CO—$R^{49}$,
in which
$R^{49}$ represents $(C_1-C_3)$-alkyl
$R^{48}$ represents a radical of the formula —$CH_2$—CN or phenyl which is optionally substituted by chlorine, trifluoromethyl or $(C_1-C_4)$-alkoxy,
and their tautomers and their pharmaceutically acceptable salts, hydrates and prodrugs.

Particular preference is given to compounds of the general formula (I) according to the invention,
in which $R^1$ represents $(C_1-C_4)$-alkyl,
$R^2$ represents cyclopentyl, cyclohexyl, cycloheptyl or $(C_1-C_{10})$-alkyl,
$R^3$ represents $(C_1-C_4)$-alkyl,
$R^4$ represents a radical of the formulae

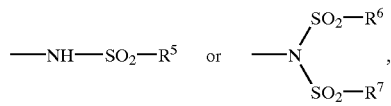

in which
$R^5$, $R^6$ and $R^7$ are identical or different and represent vinyl or $(C_1-C_4)$-alkyl which is optionally substituted up to 3 times by identical or different substituents from the group consisting of trifluoromethyl, chlorine, $(C_1-C_4)$-alkoxy or by radicals of the formulae

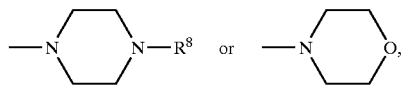

in which
$R^8$ represents hydrogen, methyl or ethyl, or
$R^5$, $R^6$ and/or $R^7$ represent phenyl which is optionally substituted up to 3 times by identical or different substituents from the group consisting of halogen, cyano, $(C_1-C_4)$-alkyl and $(C_1-C_4)$-alkoxy or
$R^5$ represents a radical of the formulae

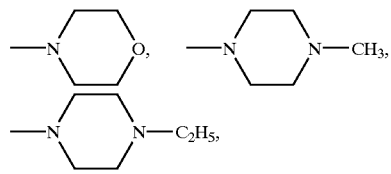

which may optionally be substituted up to 2 times by identical or different substituents from the group consisting of chlorine and $(C_1-C_4)$-alkyl or
$R^5$ represents a radical of the formula —$NR^9R^{10}$,
in which
$R^9$ and $R^{10}$ are identical or different and represent hydrogen, $(C_1-C_4)$-alkyl or phenyl, or
$R^4$ represents carboxyl or represents a radical of the formulae

or

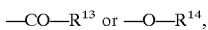

in which
$R^{13}$ represents $(C_1-C_4)$-alkyl,
$R^{14}$ represents $(C_1-C_4)$-alkyl which is optionally substituted up to 3 times by identical or different substituents from the group consisting of hydroxyl or by a radical of the formula —$NR^{15}R^{16}$, in which
$R^{15}$ and $R^{16}$ are identical or different and represent hydrogen or $(C_1-C_4)$-alkyl which for its part may be substituted by phenyl, or $R^4$ represents a radical of the formula —NH—CO—$NR^{17}R^{18}$, in which $R^{17}$ and $R^{18}$ are identical or different and represent hydrogen or $(C_1-C_4)$-alkyl which is optionally substituted by hydroxyl, or $R^{17}$ and $R^{18}$ together with the nitrogen atom to which they are attached form a heterocyclic ring of the formulae

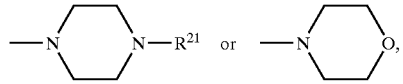

in which $R^{21}$ represents hydrogen or $(C_1-C_4)$-alkyl, or $R^{17}$ and/or $R^{18}$ represent phenyl which is optionally substituted by chlorine, trifluoroethyl or by —$SCF_3$ or $R^{17}$ represents hydrogen and $R^{18}$ represents a radical of the formula —$SO_2$—$R^{23}$, in which $R^{23}$ represents $(C_1-C_4)$-alkyl or phenyl which is optionally substituted by halogen, or represents a radical of the formulae

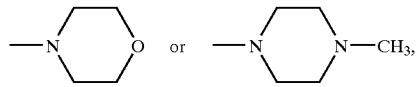

or $R^4$ represents a radical of the formula

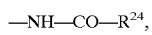
—NH—CO—$R^{24}$, in which $R^{24}$ represents $(C_1-C_4)$-alkyl which is optionally substituted by phenyl which for its part may be substituted by hydroxyl or $(C_1-C_4)$-alkoxy or $(C_1-C_4)$-alkyl is optionally substituted by a radical of the formula

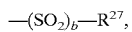
—$(SO_2)_b$—$R^{27}$, in which b represents either 0 or 1 and $R^{27}$ represents a radical of the formulae

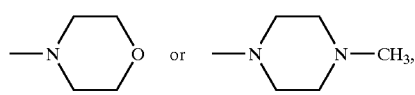

or $R^4$ represents $(C_1-C_6)$-alkyl which is optionally substituted up to 3 times by identical or different substituents from the group consisting of hydroxyl, phenyl or by radicals of the formulae —$NR^{28}R^{29}$ or —O—CO—$R^{30}$, in which $R^{28}$ and $R^{29}$ are identical or different and represent hydrogen, phenyl or $(C_1-C_4)$-alkyl which is optionally substituted by hydroxyl, $(C_1-C_4)$-alkoxy or phenyl, or $R^{28}$ and $R^{29}$ together with the nitrogen atom to which they are attached form a heterocyclic ring of the formulae

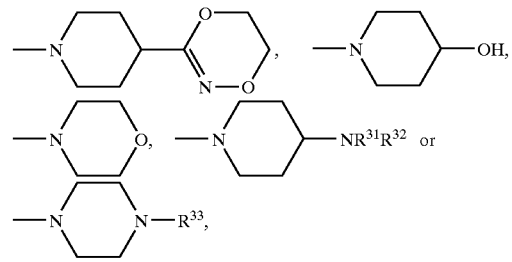

in which $R^{31}$ and $R^{32}$ are identical or different and represent hydrogen or $(C_1-C_4)$-alkyl $R^{33}$ represents $(C_1-C_4)$-alkyl, benzyl, $(C_1-C_4)$-alkoxycarbonyl, $(C_1-C_4)$-alkylcarbonyl carboxyl, pyridyl, pyrimidyl or phenyl which is optionally substituted by $(C_1-C_4)$-alkoxy, and $R^{30}$ represents $(C_1-C_6)$-alkyl, or $(C_1-C_6)$-alkyl is optionally substituted by triazolyl which for its part may optionally be substituted up to 2 times by identical or different substituents from the group consisting of $(C_1-C_4)$-alkyl, where the latter may optionally be substituted by hydroxyl or $(C_1-C_4)$-alkoxy, in which or $R^4$ represents a radical of the formula —CO—$R^{37}$, in which $R^{37}$ represents a radical of the formulae

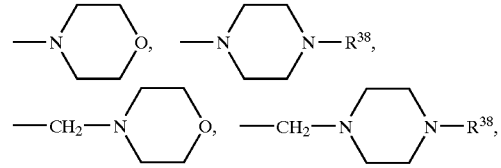

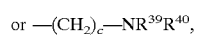
or —$(CH_2)_c$—$NR^{39}R^{40}$, in which $R^{38}$ represents hydrogen or $(C_1-C_4)$-alkyl, c represents either 0 or 1, $R^{39}$ and $R^{40}$ are identical or different and represent hydrogen or $(C_1-C_4)$-alkyl which is optionally substituted by hydroxyl, or $R^4$ represents a radical of the formula

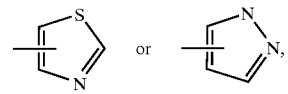

which is optionally substituted altogether up to 3 times, in the case of the pyrazole also via the N function, by identical or different substituents from the group consisting of trifluoromethyl or by phenyl which for its part may be mono- or polysubstituted by chlorine or trifluoromethyl, and/or is optionally substituted by cyclopentyl, cyclohexyl or by $(C_1-C_6)$-alkyl which for its part may be substituted by $(C_1-C_4)$-alkoxy, amino or by phenyl, and/or may optionally be substituted by —$NR^{43}R^{44}$, —NH—CO—$R^{46}$, —NH—CO—$CH_2$—$R^{47}$ or —CO—$R^{48}$, in which $R^{43}$ and $R^{44}$ are identical or different and represent hydrogen, benzyl, $(C_1-C_4)$-alkyl or phenyl which is optionally substituted by halogen or trifluoromethyl, $R^{46}$ represents $(C_1-C_4)$-alkyl or phenyl, $R^{47}$ represents hydroxyl or $(C_1-C_4)$-alkoxy, $R^{48}$ represents phenyl which is optionally substituted by chlorine, trifluoromethyl or $(C_1-C_4)$-alkoxy, and their tautomers and their pharmaceutically acceptable salts, hydrates and prodrugs.

Very particular preference is given to the compounds according to the invention having the structures below:

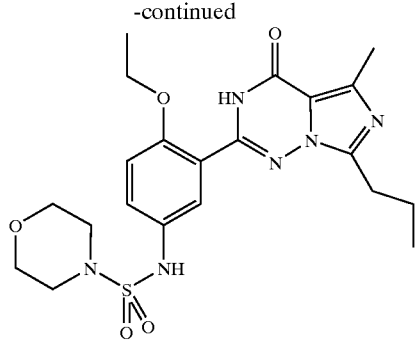

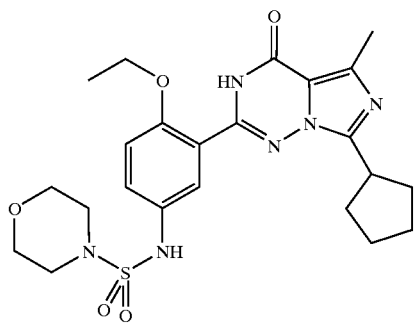

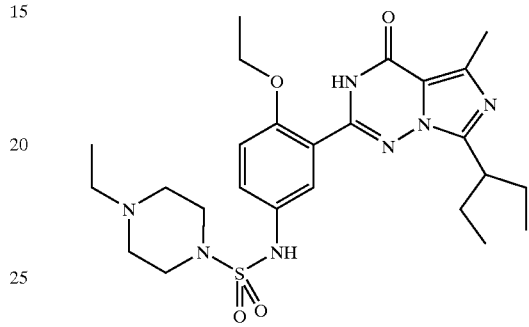

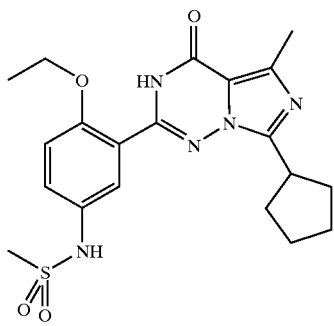

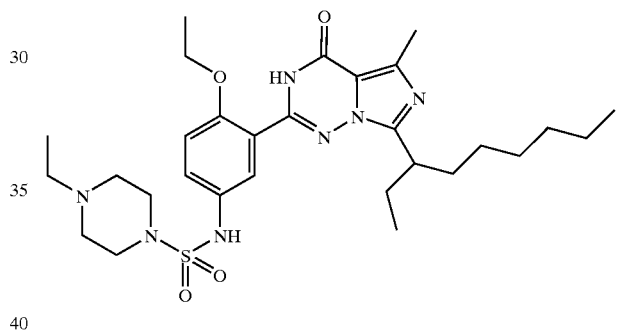

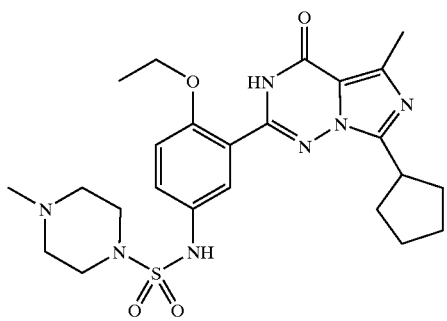

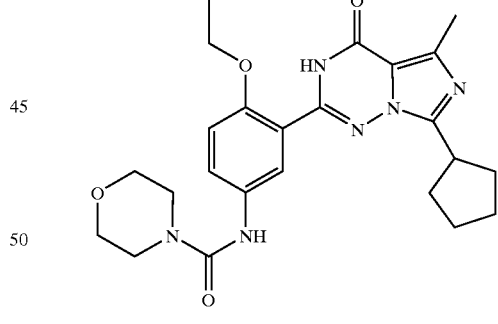

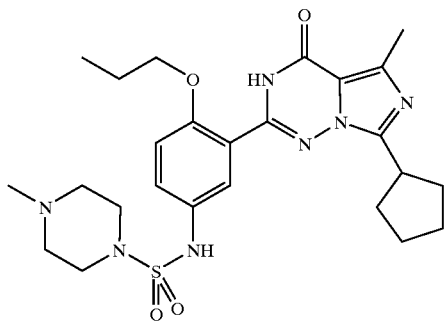

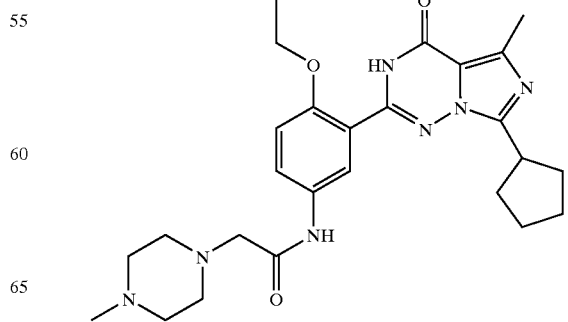

-continued
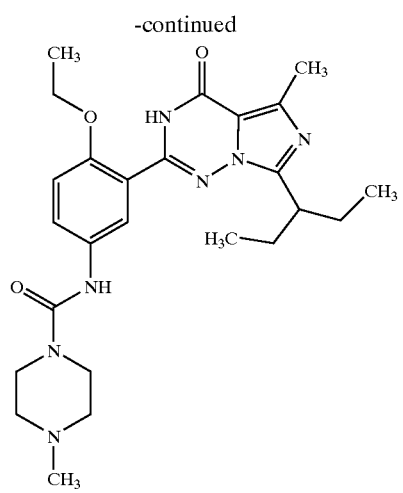
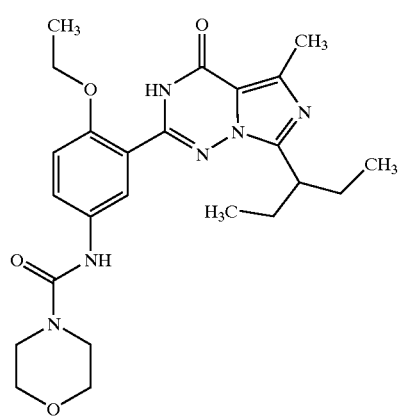
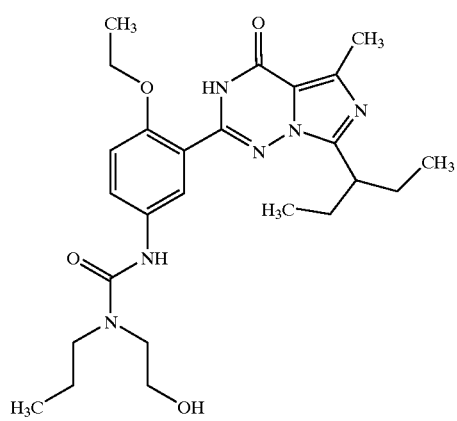
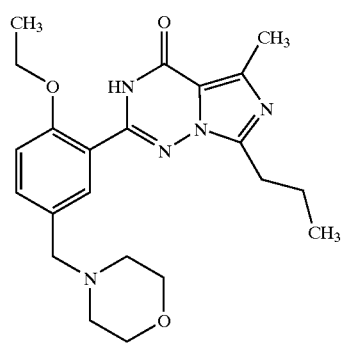
-continued
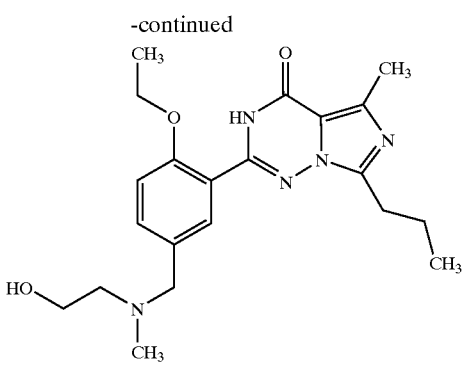
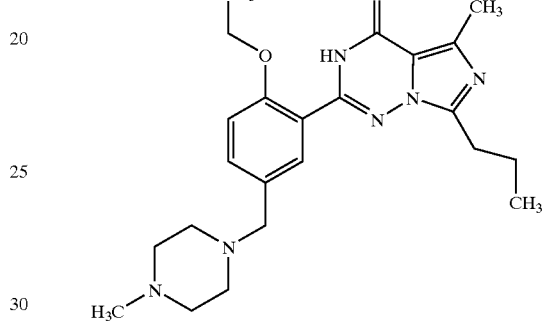
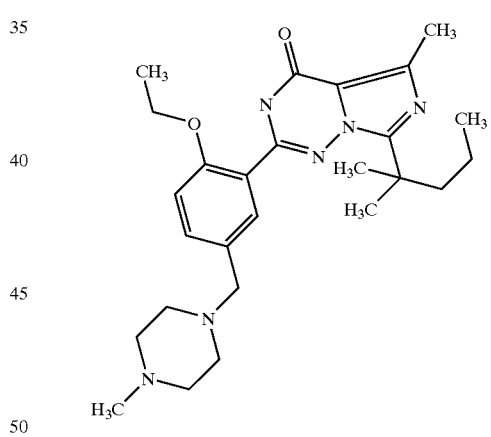
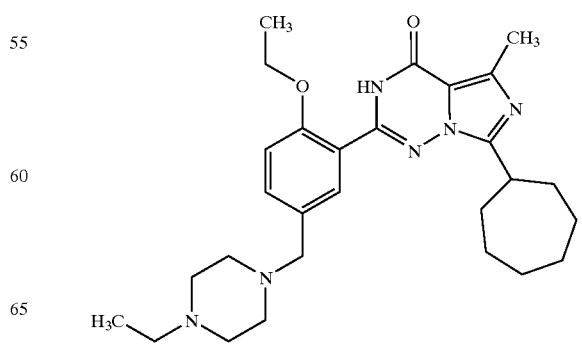

-continued

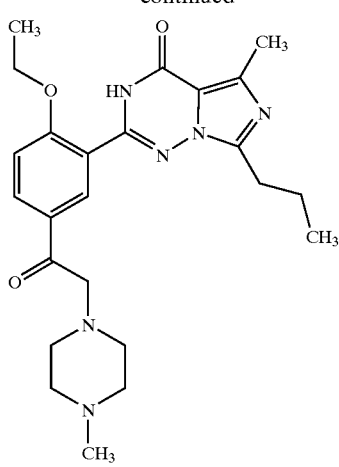

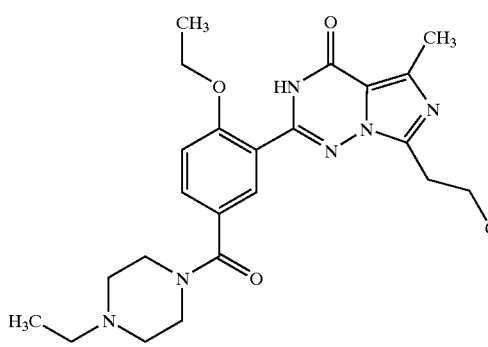

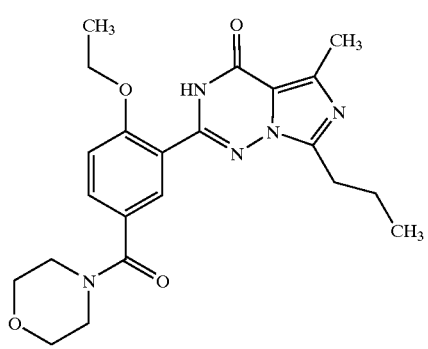

-continued

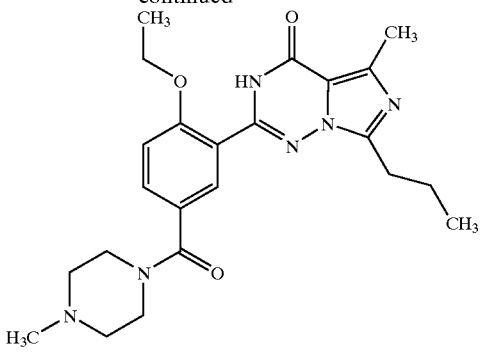

and their tautomers and their pharmaceutically acceptable salts, hydrates and prodrugs.

The compounds of the general formula (I) according to the invention are obtained when

[A] in the case that $R^4$ is a radical as defined above which is attached via a nitrogen atom, compounds of the general formula (II)

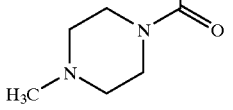

(II)

in which
$R^1$, $R^2$ and $R^3$ are as defined above
are initially converted, by reaction with $HNO_3/CF_3CO_2H$, into the compounds of the general formula (III)

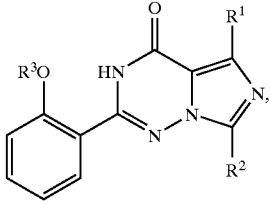

(III)

in which
$R^1$, $R^2$ and $R^3$ are as defined above,
in a next step reduced with $H_2/Pd$—C to give amines of the general formula (IV)

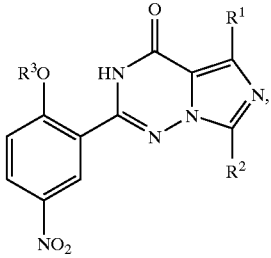

(IV)

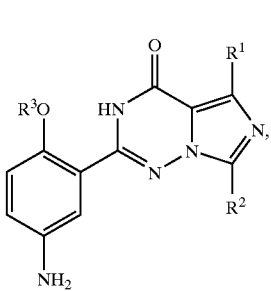

in which

R$^1$, R$^2$ and R$^3$ are as defined above, and finally reacted with compounds of the general formula (V)

$$A\text{—}D \quad (V),$$

in which if

A represents the radicals R$^5$, R$^6$ or R$^7$ listed above under R$^4$,

D represents the radical —SO$_2$Cl, and if

A represents the radical R$^{24}$ listed above under R$^4$,

D represents the radical —CO—Cl and if

A represents the radicals R$^{17}$ or R$^{18}$ listed above under R$^4$,

D represents the radicals —NH—CO—Cl, —N=C=O or —SO$_2$—N=C=O, in inert solvents, if appropriate in the presence of a base and/or an auxiliary, or

[B] if R$^4$ represents a radical as defined above which is attached via —NH—CO, alternatively compounds of the general formula (IV) are initially reacted with a bifunctional spacer B and then with compounds of the general formula (VI)

$$HNR^{49}R^{50} \quad (VI),$$

in which if

B denotes a radical of the formula Cl—CH$_2$—CO—Cl,

R$^{49}$ and R$^{50}$ together with the nitrogen atom to which they are attached are within the scope of the meaning of R$^{27}$ given above, and if B denotes a radical of the formula Cl—CO—OCCl$_3$, R$^{49}$ and R$^{50}$ are within the scope of the meanings of R$^{17}$ and R$^{18}$ given above, and if B denotes a radical of the formula ClSO$_2$—N=C=O, R$^{49}$ and R$^{50}$ together with the nitrogen atom to which they are attached are within the scope of the meaning of R$^{23}$ given above, if appropriate in an inert solvents, or

[C] if R$^4$ represents a radical as defined above which is attached via a carbon atom, compounds of the general formula (II) are initially converted by reaction with formaldehyde/HCl into the compounds of the general formula (VII)

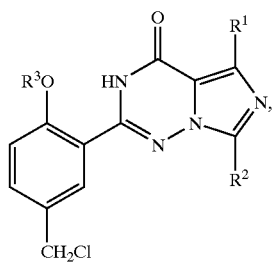

(VII)

in which

R$^1$, R$^2$ and R$^3$ are as defined above, and then, by methods familiar to the person skilled in the art, reacted with amines to give the corresponding benzylamines, with phosphites to give the corresponding phosphonates, with azide and subsequently alkynes to give the corresponding triazoles, or

[D] if R$^4$ represents a radical as defined above which is attached via —CO— or represents one of the heterocycles listed above, initially compounds of the general formula (II) are, by reaction with Br—CH$_2$—CO—Br in the presence of AlCl$_3$, converted into compounds of the general formula (VIII)

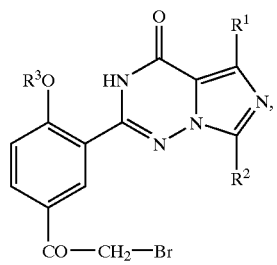

(VIII)

in which

R$^1$, R$^2$ and R$^3$ are as defined above, and then, by methods familiar to the person skilled in the art, reacted with SmJ$_2$ to give the corresponding acetophenones.

with Br$_2$/NaOH to give carboxylic acids and then with amines to give the corresponding amides, with NaBH$_4$/NaOH to give epoxides and then with amines to give the corresponding α-hydroxyamines.

with KCN and then hydrazines to give the corresponding aminopyrazoles, with thioureas to give the corresponding 2-aminothiazoles, with thioamides to give the corresponding thiazoles with phosphates to give the corresponding β-ketophosphonates, with amines to give the corresponding α-aminoketones or

[E] in the case that R$^4$ is a radical as defined above which is attached via an oxygen atom, compounds of the general formula (IX)

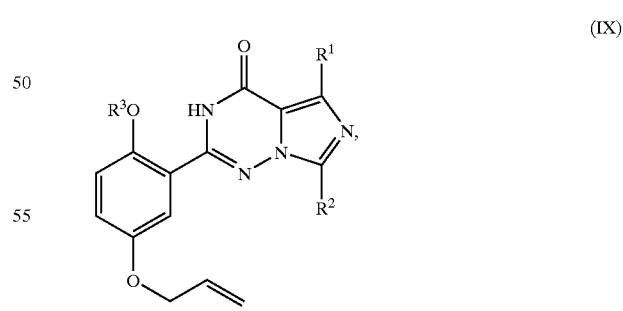

(IX)

in which

R$^1$, R$^2$ and R$^3$ are as defined above are initially converted, by reaction with meta-chloroperbenzoic acid (m-CPBA) into compounds of the general formula (X)

(X)
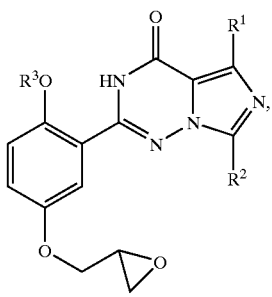
in which
R¹, R² and R³ are as defined above,
and then reacted with the corresponding amines of the general formula (XI)
$$HNR^{15}R^{16} \qquad (XI),$$
in which
R¹⁵ and R¹⁶ are as defined above.
The processes according to the invention can be illustrated in an exemplary manner by the formula schemes below:
[A]
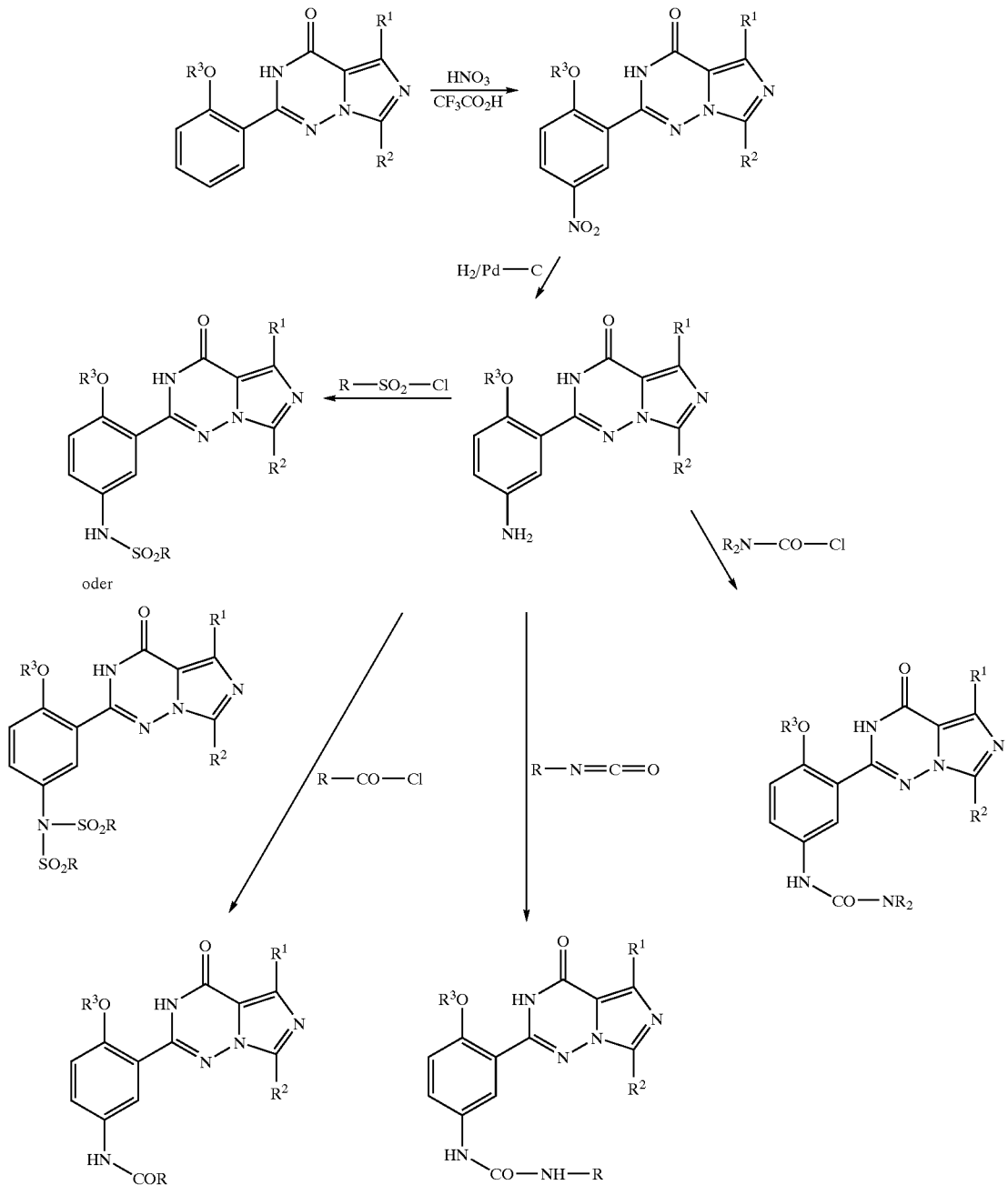

-continued
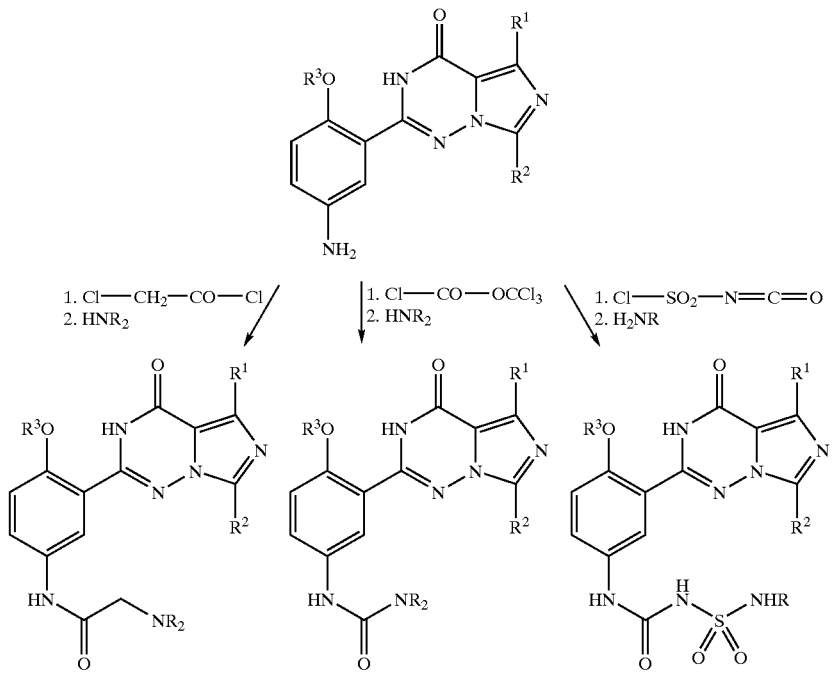
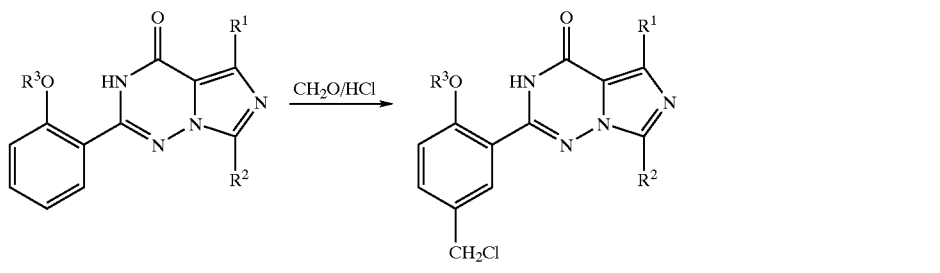
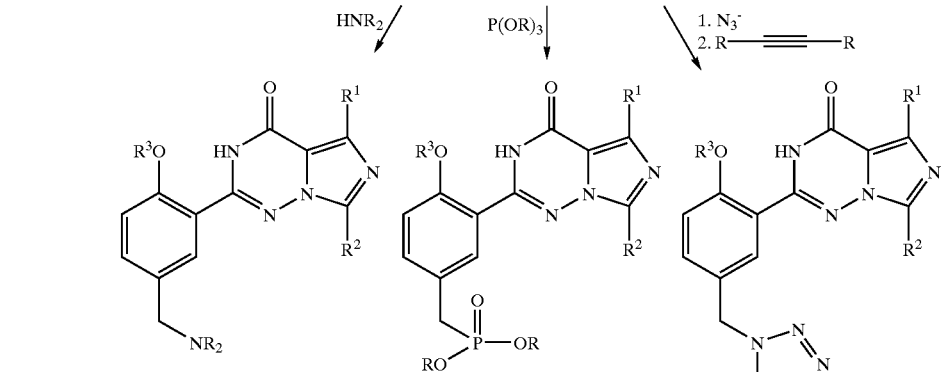
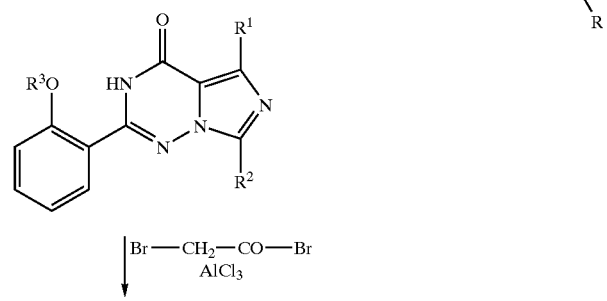

-continued

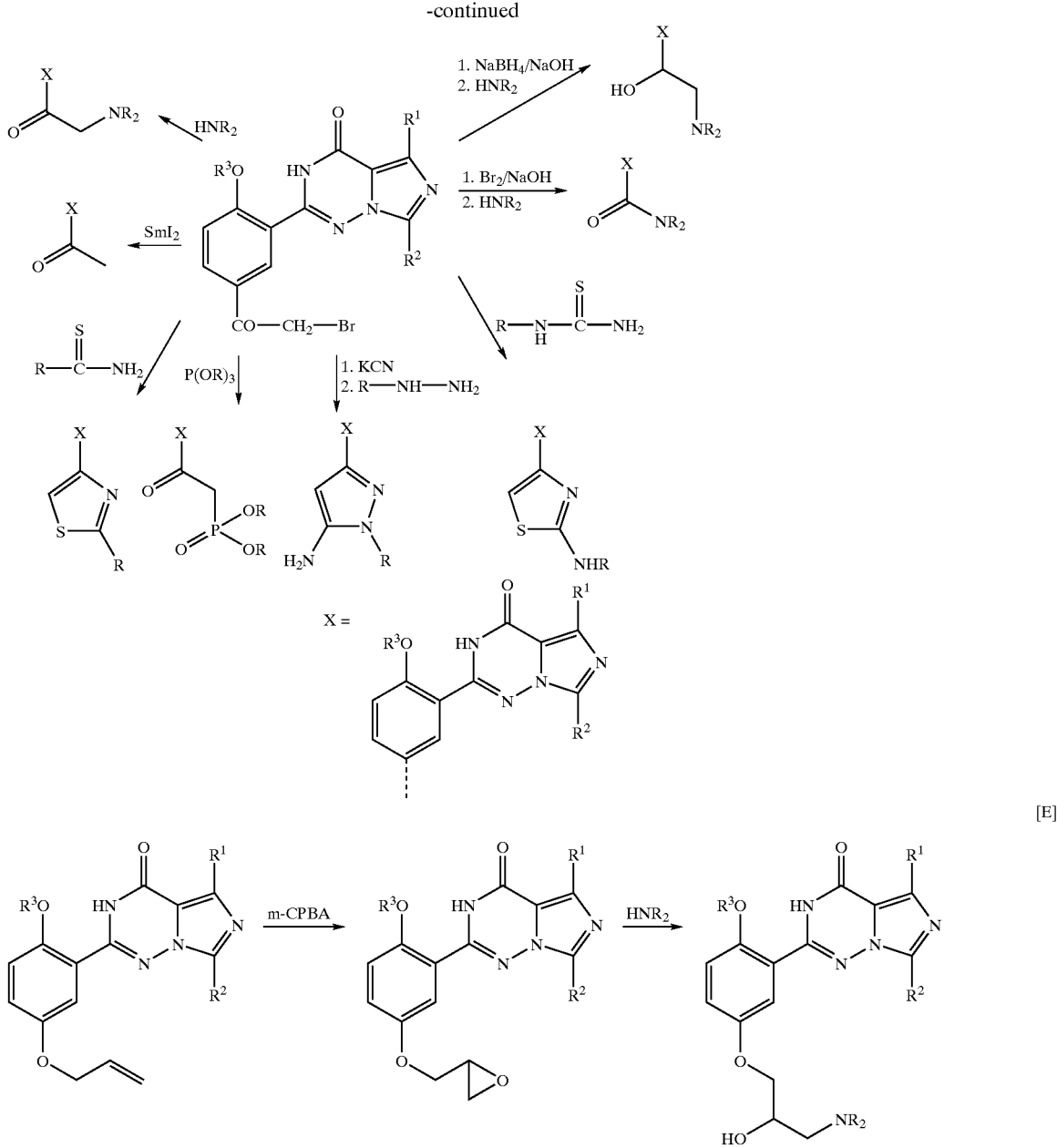

Solvents which are suitable for the individual steps are the customary organic solvents which do not change under the reaction conditions. These preferably include ethers, such as diethyl ether, dioxane, tetrahydrofuran, dimethlyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethane, trichloroethylene or chlorobenzene, or ethyl acetate, dimethylformamide, hexamethylphosphoric triamide, acetonitrile, acetone, dimethoxyethane or pyridine. It is also possible to use mixtures of the solvents mentioned.

The reaction temperatures can generally be varied within a relatively wide range. In general, the reactions are carried out in a range of from −20° C. to 200° C., preferably from 0° C. to 70° C.

The process steps according to the invention are generally carried out at atmospheric pressure. However, it is also possible to operate under elevated pressure or reduced pressure (for example in a range of from 0.5 to 5 bar).

The reactions can be carried out, for example, in a temperature range of from 0° C. to room temperature and at atmospheric pressure.

The compounds of the general formula (II) can be prepared by converting compounds of the general formula (XII)

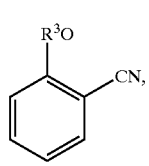

(XII)

in which
$R^3$ is as defined above by reaction of the nitrile group into the corresponding amidines, reacting these initially with hydrazine and then with compounds of the general formula (XIII)

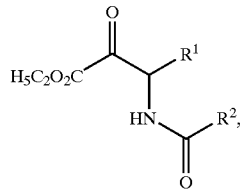
(XIII)

in which
R¹ and R² are as defined above,
to the compounds of the general formula (XIV)

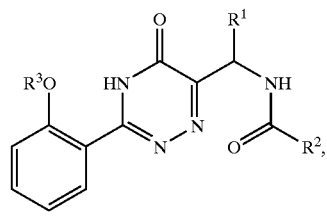
(XIV)

in which
R¹, R² and R³ are as defined above
and then cyclizing these by action of POCl₃ to give compounds of the general formula (II). For details of this process, reference can be made to WO-A-99/24433, the content of which is hereby included in its entirety by reference.

Most of the compounds of the general formulae (III), (IV), (VII), (VIII), and (X) are novel and can be prepared as described above.

The compounds of the general formulae (V), (VI), (XI), (XII), (XIII) and (XIV) are known per se or can be prepared by customary methods.

Some of the compounds of the general formula (IX) are novel, and they can be prepared by converting compounds of the general formula (XV)

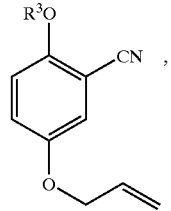
(XV)

in which
R³ is as defined above
by reaction of the nitrile group into the corresponding amidines, which are then reacted with hydrazine and subsequently with compounds of the general formula (XII) and finally cyclized with POCl₃ to give the corresponding compounds of the general formula (IX).

The compounds of the general formula (XV) are known per se or can be prepared by customary methods.

The compounds of the general formula (I) according to the invention have an unforeseeable, useful spectrum of pharmacological action.

They inhibit either one or more of the cGMP-metabolizing phosphodiesterases(PDE I, PDE II and PDE V). This results in an increase of cGMP. The differentiated expression of the phosphodiesterases in different cells, tissues and organs and the differentiated subcululoar localization of these enzymes allows, in combination with the selective inhibitors according to the invention, the different cGMP-regulated processes to be addressed selectively.

The compounds according to the invention moreover intensify the action of substances, such as, for example, EDRF (endothelium-derived relaxing factor), ANP (atrial natriuretic peptide), of nitrovasodilators and other substances which increase the cGMP concentration by a mode different to that of phosphadiesterase inhibitors.

Accordingly, the compounds of the general formula (I) according to the invention are suitable for the prophylaxis and/or treatment of disorders in which an increase of the cGMP concentration is beneficial, i.e. cGMP-related diseases. These include cardiovascular disorders, disorders of the urogenital system and cerebrovascular disorders.

In the context of the present invention, the term "cardiovascular disorders" includes disorders such as, for example, hypertension, neuronal hypertonia, stable and unstable angina, peripheral and cardial vasculopathies, arrhythmiae, thromboembolic disorders and ischemias such as myocardial infarction, stroke, transitory and ischemic attacks, angina pectoris, obstruction of peripheral circulation, prevention of restenoses after thrombolysis therapy, percutaneous transluminal angioplasty (PTA), percutaneous transluminal coronary angioplasties (PTCA) and bypass.

Furthermore, the compounds of the general formula (I) according to the invention may also be of importance for cerebrovascular disorders, cerebral ischemia, stroke, reperfusion damage, cerebral trauma, edema or cerebral thrombosis.

In addition, the present compounds are also suitable for improving perception, concentration power, learning power or memory power after cognitive disorders, such as occur, for example, in situations/illnesses/syndromes such as mild cognitive impairment, age-associated learning and memory disorders, age-associated memory loss, vascular dementia, craniocerebral trauma, stroke, dementia which occurs after strokes (post-stroke dementia), post-traumatic craniocerebral trauma, general concentration disorders, concentration disorders in children with learning and memory problems, Alzheimier's disease, vascular dementia, dementia with Lewy bodies, dementia with degeneration of the frontal lobes including Pick's disease, Parkinson's disease, progressive nuclear palsy, dementia with corticobasal degeneration, amyolateral sclerosis (ALS). Huntington's disease, multiple sclerosis, thalamic degeneration, Creutzfeld-Jacob dementia, HIV dementia, schizophrenia with dementia or Korsakoff psychosis.

Owing to their relaxing action on smooth muscles, they are suitable for treating disorders of the urogenital system such as hypertrophy of the prostate, incontinence and in particular for the treatment of erectile dysfunction and female sexual dysfunction.

Activity of the Phosphordiesterases (PDEs)

The cGMP-stimulable PDE II, the cGMP-inhibitable PDE II and the cAMP-specific PDE IV were isolated either from porcine or bovine heart myocardium. The $Ca^{2+}$-calmodulin-stimulable PDE I was isolated from porcine aorta, porcine brain or preferably from bovine aorta. The cGMP-specific PDE V was obtained from porcine small intestine, porcine aorta, human blood platelets and preferably from bovine aorta. Purification was carried out by anionic exchange chromatography on MonoQ$^R$ Pharmacia essentially according to the method of M. Hoey and Miles D. Houslay, Biochemical Pharmacology, Vol. 40, 193–202 (1990) and C. Lugman et al. Biochemical Pharmacology, Vol. 35 1743–1751 (1986).

The enzyme activity was determined in a test batch of 100 µl in 20 mM tris/HCl buffer pH 7.5 which contains 5 mM $MgCl_2$, 0.1 mg/ml bovine serum albumin and either 800 Bq of $^3$HcAMP or $^3$HcGMP. The final concentration of the corresponding nucleotides is $10^{-6}$ mol/l. The reaction is started by addition of the enzyme and the amount of enzyme is proportioned such that about 50% of the substrate is converted during the incubation time. To test cGMP-stimulate PDE II, $^3$HcAMP is used as substrate and $10^{-6}$ mol/l unlabeled cGMP are added to the mixture. To test $Ca^{2+}$-calmodulin-dependent PDE I, 1 µM of $CaCl_2$ and 0.1 µM of calmodulin are additionally added to the reaction mixture. The reaction is stopped by addition of 100 µl of acetonitrile which contains 1 mM of cAMP and 1 mM of AMP. 100 µl of the reaction mixture are separated by HPLC, and the products of the separation are determined on-line in a quantitative manner using a flow scintillation counter. What is measured is the substance concentration at which the reaction rate is reduced by 50%. Additionally, the "phosphodiesterase [$^3$H] cAMP-SPA enzyme assay" and the "phosphodiesterase [$^3$H] cGMP-SPA enzyme assay" from Amersham Life Science were used for testing. The test was carried out according to the test protocol of the manufacturer. To determine the activity of PDE II, the [$^3$H] cAMP SPA assay was used, and $10^{-6}$ M cGMP were added to the reaction mixture to activate the enzyme. To measure PDE I, $10^{-7}$ M calmodulin and 1 µM $CaCl_2$ were added to the reaction mixture. PDE V was measured using the [$^3$H] cGMP SPA assay.

In principle, inhibition of one or more phosphodiesterases of this type results in an increase of the cGMP concentration. Thus, the compounds are of interest for all therapies in which an increase in the cGMP concentration is considered to be beneficial.

The cardiovascular effects were investigated using normotensive and SH rats and dogs. The substances were administered intravenously or orally.

The study for erection-triggering action was carried out using awake rabbits[H. Naganuma, T. Egashira, J. Fuji. Clinical and Experimental Pharmacology and Physiology 20, 177–183 (1993)]. The substances were administered orally or parenterally.

The novel active compounds and their physiologically acceptable salts (for example hydrochlorides, maleates or lactates) can be converted in a known manner into the customary formulations, such as tablets, coated tablets, pills, granules, aerosols, syrups, emulsions, suspensions and solutions, using inert non-toxic, pharmaceutically suitable excipients or solvents. In this case, the therapeutically active compound should in each case be present in a concentration of from approximately 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, it optionally being possible, for example, to use organic solvents as auxiliary solvents if the diluent used is water.

Administration is carried out in a customary manner, preferably orally, transdermally or parenterally, for example perlingually, buccally, intravenously, nasally, rectally or inhalatively.

For human use, in the case of oral administration, doses of from 0.001 to 50 mg/kg, preferably 0.01 mg/kg–20 mg/kg, are generally administered. In the case of parenteral administration, for example nasally, buccally or inhalatively via mucosa, it is good practice to use doses of 0.001 mg/kg–0.5 mg/kg.

In spite of this, if appropriate it may be necessary to depart from the amounts mentioned, namely depending on the body weight or the administration route, on the individual response toward the medicament, the manner of its formulation and the time or interval at which administration takes place. Thus, in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

The compounds according to the invention are also suitable for use in veterinary medicine. For use in veterinary medicine, the compounds or their non-toxic salts can be administered in a suitable formulation in accordance with general veterinary practice. Depending on the kind of animal to be treated, the veterinary surgeon can determine the administration route and the dosage.

The present invention is illustrated by the examples below, however, the invention is by no means limited by these examples.

In the structural formulae given below which contain the radical

this always denotes

Preparation of the Precursors

EXAMPLE 1A

2-Butyrylaminopropionic Acid

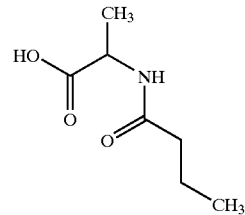

22.27 g (250 mmol) of D,L-alanine and 55.66 g (550 mmol) of triethylamine are dissolved in 250 ml of dichloromethane, and the solution is cooled to 0° C. 59.75 g (550 mmol) of trimethylsilyl chloride are added dropwise, and the solution is stirred at room temperature for 1 hour and at 40° C. for one hour. After cooling to −10° C., 26.64 g (250 mmol) of butyryl chloride are added dropwise, and the resulting mixture is stirred at −10° C. for 2 hours and at room temperature for one hour. With ice-cooling, 125 ml of water are added dropwise, and the reaction mixture is stirred at room temperature for 15 minutes. The aqueous phase is evaporated to dryness, the residue is triturated with acetone and the mother liquor is filtered off with suction. Following removal of the solvent, the residue is chromatographed. The resulting product is dissolved in 3N aqueous sodium hydroxide solution, and the resulting solution is evaporated to dryness. The residue is taken up in conc. HCl and again evaporated to dryness. The residue is triturated with acetone, the precipitated solid is filtered off with suction and the solvent is removed under reduced pressure. This gives 28.2 g (71%) of a viscous oil which crystallizes after some time.

200 MHz $^1$H-NMR (DMSO-d6): 0.84 (t, 3H); 1.22 (d, 3H); 1.50 (hex, 2H); 2.07 (t, 2H); 4.20 (quin., 1H); 8.09 (d, 1H).

EXAMPLE 2A

2-Butyrylaminobutyric Acid

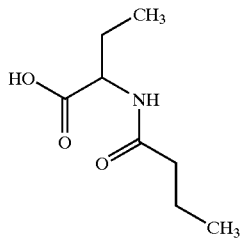

25.78 g of 2-aminobutyric acid (250 mmol) and 55.66 g (550 mmol) of triethylamine are dissolved in 250 ml of dichloromethane, and the solution is cooled to 0° C. 59.75 g (550 mmol) of trimethylsilyl chloride are added dropwise, and the solution is stirred at room temperature for 1 hour and at 40° C. for one hour. After cooling to −10° C., 26.64 g (250 mmol) of butyryl chloride are added dropwise, and the resulting mixture is stirred at −10° C. for 2 hours and at room temperature for one hour. With ice-cooling, 125 ml of water are added dropwise, and the reaction mixture is stirred at room temperature for 15 minutes. Aqueous sodium hydroxide solution is added to the organic phase, and the organic solvent is removed under reduced pressure. The residue is acidified and the precipitated solid is triturated once with water and twice with petroleum ether and dried under reduced pressure at 45° C. 29.1 g (67%) of a colorless solid.

200 MHz $^1$H-NMR (DMSO-d6):0.88 (2t, 6H); 1.5 (quart., 2H); 1.65 (m, 2H); 2.09 (t, 2H); 4.10 (m, 1H) 8.01 (d, 1H); 12.25 (s,m 1H).

EXAMPLE 3A 2-(2-Ethyl)butanoylaminopropionic Acid

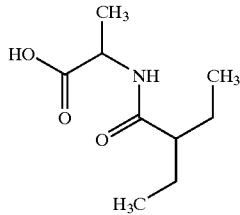

24.5 g (0.275 mol) of D,L-alanine are initially charged in 250 ml of dichloromethane, and 61.2 g (0.605 mol) of triethylamine are added. The mixture is cooled to 0° C., and 65.7 g (0.605 mol) of trimethylsilyl chloride are added. The mixture is stirred at room temperature for one hour and at 40° C. for one hour. The mixture is cooled to −10° C., and 37 g (0.275 mol) of 2-ethylbutyryl chloride are slowly added dropwise. The mixture is stirred at −10° C. for two hours and at room temperature overnight. The mixture is cooled in an ice bath, and 150 ml of water are added. 50 g (1.25 mol) of NaOH, dissolved in 100 ml of water, are added and the aqueous phase is separated off and concentrated. The residue is again taken up in water and acidified with concentrated hydrochloric acid, the aqueous solution is extracted repeatedly with dichloromethane and the organic phase is dried over Na$_2$SO$_4$ and concentrated.

Yield: 43.55 g (84.6% of theory) 200 MHz $^1$H-NMR (CDCl$_3$): 0.91 (t, 6H); 1.5 (d, 3H); 1.52–1.73 (m, 4H); 1.99 (m, 1H); 4.61 (quin, 1H); 6.25 (d, 1H); 6.76 (bs, 1H).

EXAMPLE 4A 2-(2,2-Dimethyl)pentanoylaminopropionic Acid

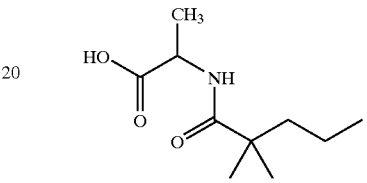

48.04 g (344.2 mmol) of D,L-alanine methyl ester hydrochloride and 76.67 g (757.2 mmol) of triethylamine are dissolved in 600 ml of dichloromethane, and 56 g (344.2 mmol) of 2,2-dimethylpentanoyl chloride in 50 ml of dichloromethane are added dropwise at 0° C. The mixture is stirred at RT for 2 h, filtered off and washed with 10% strength HCl solution, saturated sodium bicarbonate solution and saturated sodium chloride solution. The mixture is dried over sodium sulfate and then concentrated. The residue is taken up in methanol, and a solution of 55 g (1377 mmol) of sodium hydroxide in 300 l of water is added. The mixture is stirred at RT for 2 hours and then filtered off, and the methanol is evaporated under reduced pressure. The aqueous phase is acidified using concentrated hydrochloric acid solution and extracted with ethyl acetate (2×). The combined ethyl acetate phases are dried over sodium sulfate and concentrated. The residue is crystallized from ether.

Yield: 30 g (40.5%) M.p.: 168° C.

EXAMPLE 5A

2-Heptanoylaminopropionic Acid

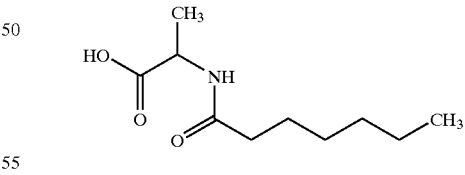

30 g (291 mmol) of D,L-alanine methyl ester hydrochloride and 64.77 g (640 mmol) of triethylamine are initially charged in 300 ml of dry methylene chloride at 0° C. 43.24 g (291 mmol) of heptanoyl chloride in 50 ml of methylene chloride are added dropwise. The mixture is allowed to warm to RT and stirred at this temperature for 2 h. The precipitate is filtered off and the methylene chloride phase is extracted with saturated sodium bicarbonate solution and with saturated sodium chloride solution and dried over sodium sulfate. The solvent is removed under reduced pressure and the residue is dissolved in 300 ml of methanol.

300 ml of water, in which 46.55 g (1164 mmol) sodium hydroxide are dissolved, are added to this solution, and the mixture is stirred at RT for 2 h. The mixture is filtered, the methanol is evaporated using a rotary evaporator and the aqueous phase that remains is acidified to pH 1–2 using conc. Hcl. The precipitated product is filtered off and dried. Extraction of the aqueous phase with ethyl acetate gives a second product fraction.

Yield: 50 g (85.4%) $^1$H-NMR (CD$_3$OD): 0.9 (t, 3H); 1.2–1.4 (m, 9H); 1.6 (quin., 2H); 2.2 (t, 2H); 4.38 (quar., 1H).

EXAMPLE 6A

2-Octanoylaminopropionic Acid

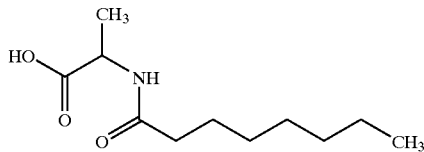

The preparation is carried out analogously to the procedure of example 1A using 16.5 g (0.185 mol) of D,L-alanine, 41.23 g (0.407 mol) of triethylamine, 44.27 g (0.407 mol) of trimethylsilyl)l chloride and 30.12 g (0.185 mol) of octanoyl chloride. The product crystallizes from toluene/n-hexane.

Yield: 34.3 g (86%) $^1$H-NMR (CD$_3$OD): 0.9 (t, 3H); 1.2–1.4 (m, 11H); 1.6 (quin. 2H); 2.2 (t, 2H); 4.35 (quar 1H).

EXAMPLE 7A

2-Decanoylaminopropionic Acid

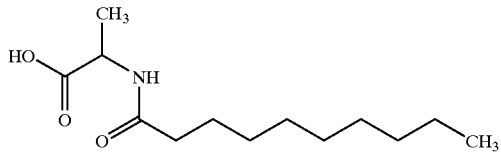

The preparation is carried out analogously to the procedure of example 4A using 19.0 g (184 mmol) of D,L-alanine methyl ester hydrochloride and 35.14 g (184 mmol) of decanoyl chloride.

Yield: 37.3 g (83.2%) $^1$H-NMR (CD$_3$OD): 0.9 (t, 3H); 1.2–1.4 (m, 15H); 1.6 (m, 2H); 2.2 (t, 2H); 4.35 (quar., 1H).

EXAMPLE 8A 2-(2-Ethyl)octanoylaminopropionic Acid

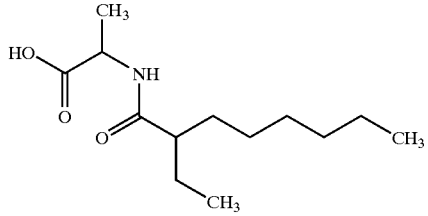

18.6 g (0.211 mol) of D,L-alanine and 46.6 g (0.41 mol) of triethylamine are initially charged in 300 ml of dichloromethane. At 0° C., 50.09 g (0.461 mol) of trimethylsilyl chloride are added dropwise, and the mixture is stirred at room temperature for 1 h and then at 40° C. for 1 h. The solution is cooled to −10° C., and 40 g (0.21 mol) of 2-ethyloctanoyl chloride in 50 ml of dichloromethane are added dropwise. The mixture is stirred at room temperature overnight, 100 ml of water are then added dropwise with ice-cooling and the mixture is stirred for 10 minutes. The phases are separated, the aqueous phase is reextracted twice with in each case 100 ml of dichloromethane and the combined organic phases are dried over sodium sulfate and concentrated under reduced pressure. The residue is crystallized from toluene by adding n-hexane and is dried at 60° C.

Yield: 3.9 g (78.2%) $^1$H-NMR (CDCl$_3$): 0.9 (m, 6h); 1.25 (pseudo s, 8H); 1.45 (d, 3H); 1.4–1.7 (m, 4H); 2.0 (m, 1H); 4.6 (quin. 1H); 6.1 (d, 1H).

EXAMPLE 9A

2-Cyclopentanoylaminopropionic Acid

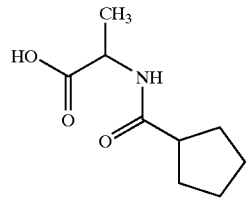

16.8 g (0.189 mol) of D,L-alanine and 41.98 g (0.415 mol) of triethylamine are initially charged in 200 ml of dichloromethane. At 0° C., 45.07 g (0.415 mol) of trimethylsilyl chloride are added dropwise, and the mixture is stirred at room temperature for 1 h and then at 40° C. for 1 h. The solution is cooled to −100° C., and 25 g (0.189 mol) of cyclopentanecarbonyl chloride are added dropwise. The mixture is stirred at −10° C. for 2 h and at room temperature for 1 h. With ice-cooling, 100 ml of water are added dropwise, the mixture is stirred for 10 min. and the resulting precipitate is filtered off with suction. The precipitate is washed with 300 ml of water and then with 300 ml of diethyl ether and subsequently dried at 60° C.

Yield: 25.8 g (73.9% of theory) $^1$H-NMR (CD$_3$OD): 1.35 (d, 3H); 1.5–1.9 (m, 8H); 2.7 (quin, 1H); 4.5 (quar., 1H):

EXAMPLE 10A

2-Cyclopentanoylaminobutyric Acid

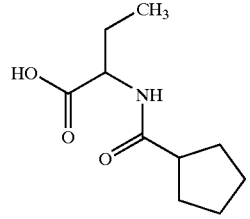

10.31 g of 2-aminobutyric acid (100 mmol) and 22.26 g (220 mmol) of triethylamine are dissolved in 100 ml of dichloromethane, and the solution is cooled to 0° C. 23.90 g (220 mmol) of trimethylsilyl chloride are added dropwise, and the solution is stirred at room temperature for 1 hour and at 40° C. for one hour. After cooling to −10° C., 13.26 g (100 mmol) of cyclopentanecarbonyl chloride are added dropwise, and the resulting mixture is stirred at −10° C. for 2 hours and at room temperature for one h.

With ice-cooling, 50 ml of water are added dropwise, and the reaction mixture is stirred at room temperature for 15 minutes. The mixture is diluted with water and dichloromethane and the resulting precipitate is filtered off with suction: 11.1 g (55%) of a colorless solid. The dichloromethane phase is dried over sodium sulfate and the solvent is removed under reduced pressure. The residue is triturated with toluene and the precipitate is filtered off with suction: 5.75 g (28%) of a colorless solid.

200 MHz $^1$H-NMR (DMSO-$d_6$): 0.88 (t, 3H); 1.61 (m, 10H); 2.66 (m, 1H); 4.09 (hex., 1H); 7.97 (d, 1H); 12.44 (s, 1H).

EXAMPLE 11A

2-Cycloheptanoylaminopropionic Acid

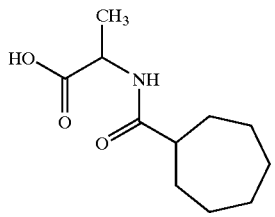

The preparation is carried out analogously to the procedure of example 4A using 20 g (143 mmol) of D,L-alanine methyl ester hydrochloride and 23.02 g (143 mmol) of cycloheptanoyl chloride.

Yield: 16 g (52.4%) $^1$H-NMR (CD$_3$OD): 1.35 (d, 3H); 1.45–1.65 (m, 8H); 1.7–1.95 (m, 4H); 2.35 (m, 1H); 4.25 (quar., 1H).

EXAMPLE 12A

2-Ethoxybenzonitrile

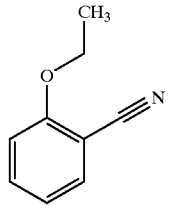

25 g (210 mmol) of 2-hydroxybenzonitrile, 87 g of potassium carbonate and 34.3 g (314.8 mmol) of ethyl bromide are refluxed in 500 ml of acetone overnight. The solid is filtered off, the solvent is removed under reduced pressure and the residue is distilled under reduced pressure. This gives 30.0 g (97%) of a colorless liquid.

200 MHz $^1$H-NMR (DMSO-$d_6$): 1.48 (t, 3H); 4.15 (quart., 2H); 6.99 (dt, 2H); 7.51 (dt, 2H).

EXAMPLE 13A

2-Ethoxybenzamidine Hydrochloride

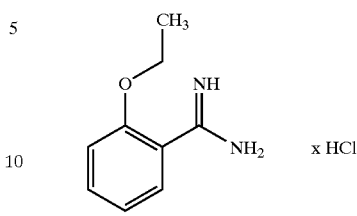

21.4 g (400 mmol) of ammonium chloride are suspended in 375 ml of toluene, and the suspension is cooled to 0° C. 200 ml of a 2 M solution of trimethylaluminum in hexane are added dropwise, and the mixture is stirred at room temperature until the evolution of gas has ceased. Following addition of 29.44 g (200 mmol) of 2-ethoxybenzonitrile, the reaction mixture is stirred at 80° C. (bath) overnight. The cooled reaction mixture is, with ice-cooling, added to a suspension of 100 g of silica gel and 950 ml of chloroform, and the mixture is stirred at room temperature for 30 minutes. The mixture is filtered off with suction and the filter cake is washed with the same amount of methanol. The mother liquor is concentrated, the resulting residue is triturated with a mixture of dichloromethane and methanol (9:1), the solid is filtered off with suction and the mother liquor is concentrated. This gives 30.4 g (76%) of a colorless solid.

200 MHz $^1$H-NMR (DMSO-$d_6$): 1.36 (t, 3H); 4.12 (quart., 2H); 7.10 (t, 1H); 7.21 (d, 1H); 7.52 (m, 2H); 9.30 (s, broad, 4H).

EXAMPLE 14A

2-Propoxybenzonitrile

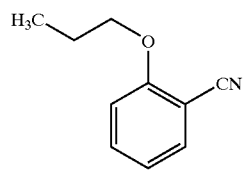

75 g (630 mmol) of 2-hydroxybenzonitrile, 174 g (1.26 mol) of potassium carbonate and 232.3 g (1.89 mol) of n-propyl bromide in 1 l of acetone are refluxed overnight. The solid is filtered off, the solvent is removed under reduced pressure and the residue is distilled under reduced pressure.

B.p.: 89° C. (0.7 mbar) Yield: 95.1 g (93.7% of theory)

EXAMPLE 15A

2-Propoxybenzamidine Hydrochloride

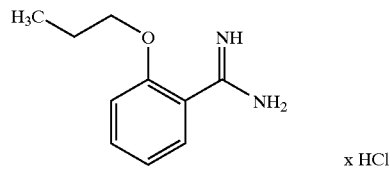

21.41 g (400 ml) of ammonium chloride are suspended in 400 ml of toluene and cooled to 0–5° C. 200 ml of a 2 M solution of trimethylaluminum in hexane are added dropwise, and the mixture is stirred at room temperature until the evolution of gas has ceased. Following addition of 32.2 g (200 mmol) of 2-propoxybenzonitrile, the reaction mixture is stirred at 80° C. (bath) overnight. The cooled reaction mixture is, with ice-cooling, added to a suspension of 300 g of silica gel and 2.85 ml of ice-cooled chloroform and stirred for 30 minutes. The mixture is filtered off with suction and the filter cake is washed with the same amount of methanol. The solvent is distilled off under reduced pressure, the residue is triturated in 500 ml of a mixture of dichloromethane and methanol (9:1), the solid is filtered off and the mother liquor is concentrated. The residue is triturated with petroleum ether and filtered off with suction. This gives 22.3 g (52%) of product.

200 MHz $^1$H-NMR (CD$_3$OD): 1.05 (t, 3H); 1.85 (sex. 2H); 4.1 (t, 2H); 7.0–7.2 (m, 2H); 7.5–7.65 (m, 2H).

EXAMPLE 16A 2-(2-Ethoxyphenyl)-5-methyl-7-propyl-3H-imidazo[5,1-f][1,2,4]-triazin-4-one

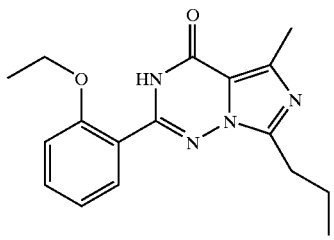

7.16 g (45 mmol) of 2-butanoylaminopropionic acid (example 1A) and 10.7 g of pyridine are dissolved in 45 ml of tetrahydrofuran and, after addition of a spatula tip of 4-dimethylaminopyridine, heated at reflux. 12.29 g (90 mmol) of monoethyl oxalyl chloride are slowly added dropwise, and the reaction mixture is refluxed for 3 hours. The mixture is poured into ice-water and extracted 3 times with ethyl acetate, and the extracts are dried over sodium sulfate and concentrated. The residue is taken up in 15 ml of ethanol and refluxed with 2.15 g of sodium bicarbonate for 2.5 hours. The cooled solution is filtered.

With ice-cooling, 2.25 g (45 mmol) of hydrazine monohydrate are added dropwise to a solution of 9.03 g (45 mol) of 2-ethoxybenzamidine hydrochloride (example 13A) in 45 ml of ethanol, and the mixture is stirred at room temperature for 10 minutes. The ethanolic solution described above is added dropwise to this suspension, and the mixture is stirred at 70° C. for 4 hours. The mixture is filtered, the solution is concentrated, the residue is partitioned between dichloromethane and water and the organic phase is, after drying over sodium sulfate, concentrated.

The residue is taken up in 60 ml of 1,2-dichloroethane, and 7.5 ml of phosphorus trichloride are added dropwise. After 2 hours of stirring under reflux, the mixture is cooled, diluted with dichloromethane and extracted twice with saturated sodium bicarbonate solution. The organic phase is dried and the solvent is removed under reduced pressure. Chromatography with ethyl acetate and crystallization give 4.00 g (28.0% of theory) of a white solid.

$^1$H-NMR (200 MHz, CDCl$_3$): 1.02 (t, 3H), 1.56 (t, 3H), 1.89 (hex, 2H), 2.67 (s, 3H), 3.00 (t, 2H), 4.26 (quar, 2H), 7.05 (m, 2H), 7.50 (dt, 1H), 8.17 (dd, 1H), 10.00 (s, 1H); TLC: R$_f$=0.42 (dichloromethane:methanol=95:5).

EXAMPLE 17A 2-(2-Ethoxyphenyl)-5-ethyl-7-propyl-3H-imidazo[5,1-f][1,2,4]triazin-4-one

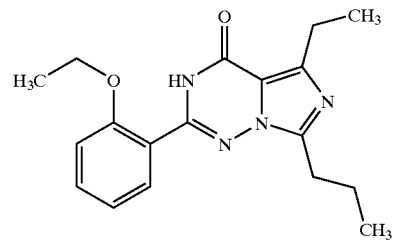

The preparation is carried out analogously to the procedure of example 16A using 29.06 g (167.8 mmol) of 2-butanoylaminobutyric acid (Example 2A) and 33.6 (167.8 mmol) of 2-ethoxybenzamidine hydrochloride (Example 13A). Purification is carried out by silica gel chromatography (mobile phase: CH$_2$Cl$_2$/CH$_3$OH 50:1).

Yield: 7.4 g (12.4%) R$_f$=0.46 (CH$_2$Cl$_2$/CH$_3$OH=20:1) $^1$H-NMR (200 MHz, CDCl$_3$): 1.32 (t, 3H); 1.57 (t, 32H); 1.94 (m, 8H); 3.03 (quart, 2H); 3.64 (quin, 1H); 4.27 (quart, 2H); 7.06 (d, 1H); 7.12 (t, 1H); 7.50 (dt, 1H); 8.16 (dd, 1H); 9.91 (s, 1H).

EXAMPLE 18A 2-(2-Ethoxyphenyl)-5-methyl-7-(1-ethylpropyl)-3H-imidazo[5,1-f][1,2,4]-triazin-4-one

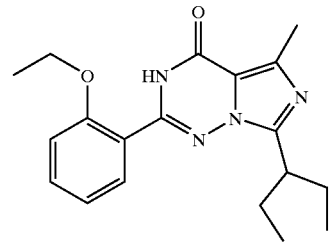

The preparation is carried out analogously to the procedure of example 16A using 21.45 g (0.1 mol) of 2-(2-ethyl)butyrylaminopropionic acid (example 3A) and 20.6 g (0.1 mol) of 2-ethoxybenzamidine hydrochloride (example 13A). Purification is carried out by silica gel chromatography using the mobile phase dichloromethane/methanol 60:1.

Yield: 7.22 g (21.3% of theory). $^1$H-NMR (200 MHz, CDCl$_3$): 0.87 (t, 6H), 1.57 (t, 3H), 1.88 (m, 4H), 2.67 (s, 3H), 3.28 (m, 1H), 4.28 (quar, 2H), 7.05 (d, 1H), 7.13 (dt, 1H), 8.15 (dd, 1H).

EXAMPLE 19A 2-(2-Ethoxyphenyl)-5-methyl-7-(1,1-dimethylbutyl)-3H-imidazo[5,1-f][1,2,4]triazine-4-one

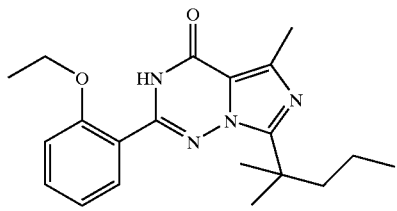

The preparation is carried out analogously to the procedure of example 16A using 22.85 g (0.1 mol) of 2-(2,2-dimethyl)pentanoylaminopropionic acid (example 4A) and 20.6 g (0.1 mol) of 2-ethoxybenzamidine hydrochloride (example 13A). Purification is carried out by silica gel chromatography (mobile phase: $CH_1Cl_2/CH_3OH=50:1$).

Yield: 6.56 g (18.5%) $^1$H-NMR (200 MHz, $CD_3OD$): 0.82 (t, 3H); 1.1 (m, 2H); 1.45 (t, 3H); 1.5 (s, 6H); 1.95 (m, 2H); 2.57 (s, 3h); 4.2 (quar., 2H); 7.1 (t, 1H); 7.18 (d, 1H); 7.52 (dt, 1H); 7.72 (dd, 1H).

EXAMPLE 20A 2-(2-Ethoxyphenyl)-5-methyl-7-hexyl-3H-imidazo]5,1-f][1,2,4]triazin-4-one

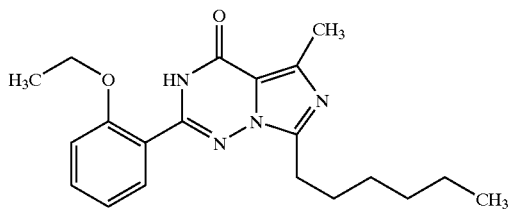

The preparation is carried out analogously to the procedure of example 16A using 14.1 g (70 mmol) of 2-heptanoylaminopropionic acid (example 5A) and 14.05 g (70 mmol) of 2-ethoxybenzamidine hydrochloride (example 13A). The purification of the product is carried out by silica gel chromatography using the mobile phase petroleum ether/ethyl acetate 1:1.

Yield: 3.5 g (14.1%) $^1$-NMR ($CD_3OD$): 0.9 (t, 3H); 1.3–1.45 (m, 6H); 1.4 (t, 3H); 1.7–1.9 (m, 2H); 2.15 (s, 3H); 3.1 (t, 2H); 4.2 (quar., 2H); 7.1 (t, 1H); 7.15 (d, 1H); 7.05 (td, 1H); 7.7 (dd, 1H).

EXAMPLE 21A 2-(2-Ethoxyphenyl)-5-methyl-7-heptyl-3H-imdazo-[5,1-f[]1,2,4]triazin-4-one

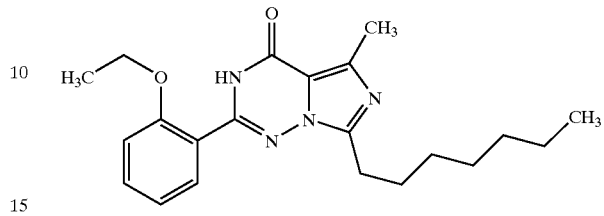

The preparation is carried out analogously to the procedure of example 16A using 14.7 g (68.1 mmol) of 2-octanoylaminopropionic acid (example 6A) and 13.66 g (68.1 mmol) of 2-ethoxybenzamidine hydrochloride (example 13A). The purification of the product is carried out by silica gel chromatography using the mobile phase dichloromethane/methanol 50:1.

Yield: 4.65 g (18.5%), oil $^1$H-NMR ($CD_3OD$): 0.85 (t, 3H); 1.2–1.4 (m, 8H); 1.45 (t, 3H); 2.8 (quin, 2H); 2.6 (s, 3H); 3.0 (t, 2H), 4.2 (quar, 2H); 7.1 (t, 1H); 7.2 (d, 1H); 7.55 (td, 1H), 7.7 (dd, 1H).

EXAMPLE 22A 2-(2-Ethoxyphenyl)-5-methyl-7-nonyl-3H-imidazo[5,1-f]-[1,2,4-]-triazin-4-one

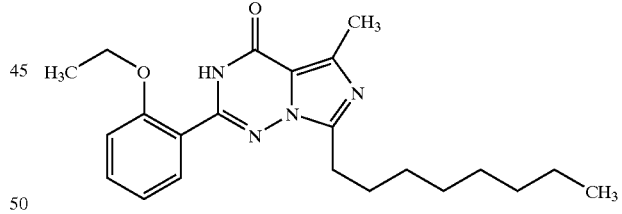

The preparation is carried out analogously to the procedure of example 16A using 7.0 g (70 mmol) of 2-decanoylaminopropionic acid (example 7A) and 14.05 g (70 mmol) of 2-ethoxybenzamidine hydrochloride (example 13A). The purification of the product is carried out by silica gel chromatography using the mobile phase petroleum ether/ethyl acetate 1:1.

Yield: 3.5 g (14.1%) $^1$H-NMR ($CD_3OD$): 0.9 (t, 3H); 1.3–1.45 (m, 6H); 1.4 (t, 3H); 1.7–1.9 (m, 2H); 2.15 (s, 3H); 3.1 (t, 2H); 4.2 (quar., 2H); 7.1 (t, 1H); 7.15 (d, 1H); 7.05 (td, 1H), 7.7 (dd, 1H).

EXAMPLE 23A 2-(2-Ethoxyphenyl)-5-methyl-7-(2-ethylheptyl)-3H-imidazo[5,1-f][1,2,4]-triazin-4-one

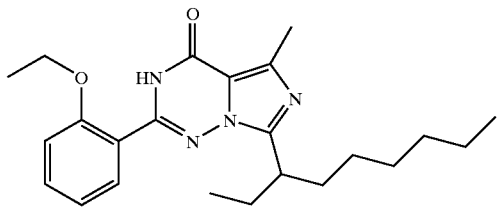

The preparation is carried out analogously to the procedure of example 16A using 10.95 g (45 mmol) of 2-(2-ethyl) octanoylaminopropionic acid (example 8A) and 9.03 g (45 mmol) of 2-ethoxybenzamidine hydrochloride (example 13A). Purification is carried out by silica gel chromatography using cyclohexane/ethyl acetate.

Yield: 7.22 g (21.3% of theory) $^1$H-NMR (200 MHz, CDCl$_3$): 0.75–0.90 (m, 6H), 1.10–1.40 (m, 8H), 1.50 (t, 3H), 1.80–2.05 (m, 4H), 2.70 (s, 3H), 3.40 (quin., 1H), 4.30 (t, 2H), 7.05–7.20 (pseudo quar, 2H), 7.50 (td, 1H), 8.20 (dd, 1H), 10.40 (s, 1H).

EXAMPLE 24A 2-(2-Propoxyphenyl)-5-methyl-7-(2-ethylheptyl)-3H-imidazo[5,1-f][1,2,4]triazin-4-one

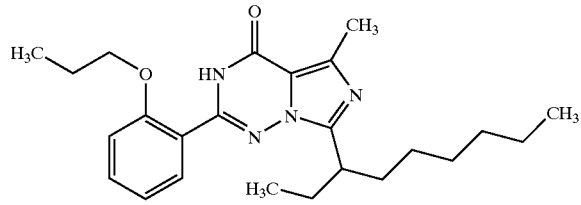

The preparation is carried out analogously to the procedure of example 16A using 10.95 g (45 mmol of 2-(2-ethyl) octanoylaminopropionic acid (example 8A) and 9.66 g (45 mmol) of 2-propoxybenzamidine hydrochloride (example 13A). Purification of the product is carried out by silica gel chromatography using the mobile phase dichloromethane/methanol 60:1.

Yield: 3.7 g (20%), yellow oil $^1$H-NMR (CDCl$_3$): 0.75–0.9 (m, 6H); 1.15 (t, 3h); 1.1–1.35 (m, 8H); 1.75–2.1 (m, 6h); 2.7 (s, 3H); 3.4 (quin, 1H); 4.2 (t, 2H); 7.05–7.2 (pseudo quar, 2H); 7.5 (td, 1H); 8.2 (dd, 1H); 10.2 (broad, 1H).

EXAMPLE 25A 2-(2-Ethoxyphenyl)-5-methyl-7-cyclopentyl-3H-imidazo[5,1-f][1,2,4]-triazin-4-one

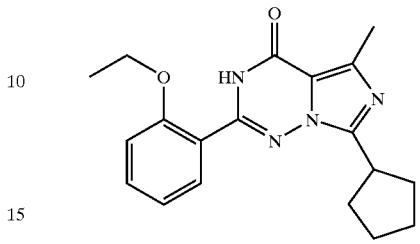

The preparation is carried out analogously to the procedure of example 16A using 19.9 g (100 mmol) of 2-cyclopentanoylaminopropionic acid (example 9A) and 20 g (100 mmol) of ethoxybenzamidine hydrochloride (example 13A). Purification is carried out by silica gel chromatography using methylene chloride/methanol 50:1.

Yield: 7.1 g (20.9%) $^1$H-NMR (200 MHz, CD$_3$OD): ,45 (t, 3H); 1.65–1.80 (m, 2H); 1.80–2.00 (m, 4H); 2.05–2.20 (m, 2H); 2.60 (s, 3H); 3.65 (quin., 1H); 4.20 (quar., 2H); 7.10 (t, 1H); 7.15 (d, 1H); 7.50 (t, 1H); 7.70 (d, 1H).

EXAMPLE 26A 2-(2-Propoxyphenyl)-5-methyl-7-cyclopentyl-3H-imidazo[5,1-f][1,2,4]-triazin-4-one

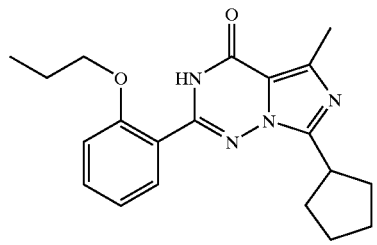

The preparation is carried out analogously to the procedure of example 16A using 8.33 g (45.0 mmol) of 2-cyclopentanoylaminopropionic acid (example 9A) and 9.65 g (45.0 mmol) of 2-propoxybenzamidine hydrochloride (example 15A). Purification is carried out by silica gel chromatography using the mobile phase dichloromethane/methanol 50:1. The product can be crystallized from ethyl acetate/petroleum ether.

Yield: 1.82 g (11.5% of theory) white solid. $^1$H-NMR (200 MHz, CDCl$_3$): 1.15 (t, 3H), 1.70 (m, 2H), 1.95 (m, 4H), 2.15 (m, 2H), 2.65 (s, 3H), 3.65 (quin., 1H), 4.15 (t, 2H), 7.05 (d, 1H), 7.10 (t, 1H), 7.50 (td, 1H), 8.20 (dd, 1H).

EXAMPLE 27A 2-(2-Ethoxyphenyl)-5-ethyl-7-cyclopentyl)-3H-imidazo[5,1-f][1,2,4]triazin-4-one

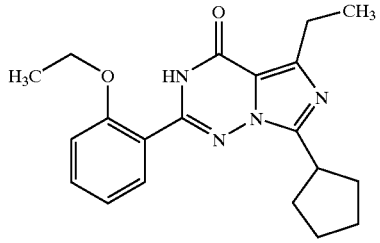

The preparation is carried out analogously to the procedure of example 16A using 8.77 g (44 mmol) of 2-cyclopentanoylaminobutyric acid (example 10A) and 8.83 g (44 mmol) of 2-ethoxybenzamidine hydrochloride (example 13A). The product is purified by silica gel chromatography using the mobile phase cyclohexane/ethyl acetate (6:4).

Yield: 0.355 g (6.7%), white solid $^1$H-NMR (CDCl$_3$): 1.32 (t, 3H); 1.57 (t, 3H); 1.94 (m, 8H); 3.03 (quar, 2H)); 3.64 (quin, 1H); 4.27 (quar, 2H), 7.06 8d, 1H); 7.12 (t, 1H); 7.50 (t, 1H); 8.16 (dd, 1H); 9.91 (s, 1H).

EXAMPLE 28A 2-(2-Ethoxyphenyl)-5-methyl-7-cycloheptyl-3H-imidazo[5,1-f][1,2,4]-triazin-4-one

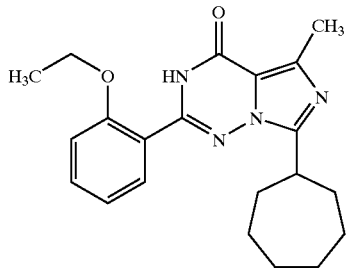

The preparation is carried out analogously to the procedure of example 16A using 14.9 g (70 mmol) of 2-cycloheptanoylaminopropionic acid (example 11A) and 14 g (70 mmol) of 2-ethoxybenzamidine hydrochloride (example 13). Purification of the product is carried out by silica gel chromatography using the mobile phase methylene chloride/methanol 10:1, then 50:1.

Yield: 5.35 g (20.9%) $^1$H-NMR (CD$_3$OD): 1.45 (t, 3H); 1.6–2.0 (m, 10H); 2.1–2.2 (m, 2H); 2.7 (s, 3H); 3.65 (quin., 1H), 4.2 (quar., 2H); 7.1 (t, 1H); 7.2 (d, 1H); 7.6 (td, 1H); 7.75 (dd, 1H).

EXAMPLE 29A 2-(2-Ethoxyphenyl)-5-ethyl-7-cycloheptyl-3H-imidazo[5,1-f][1,2,4]-triazin-4-one

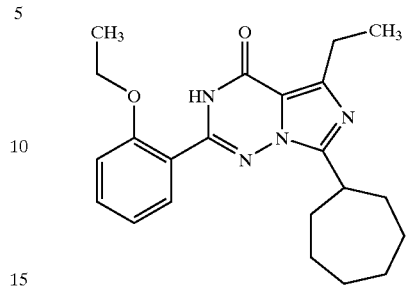

The preparation is carried out analogously to the procedure of example 16A using 1.02 g (4.5 mmol) of 2-cycloheptanoylaminobutyric acid (example 12A) and 0.98 g (4.9 mmol) of 2-ethoxybenzamidine hydrochloride (example 13A). Purification is carried out by silica gel chromatography using ethyl acetate/cyclohexane 1:1.

Yield: 0.391 mg (14%) $^1$H-NMR (200 MHz, D$_6$-DMSO): δ=1.21 (t, 3H, CH$_3$), 1.30 (t, 3H, CH$_3$), 1.40–2.01 (m, 12H, CH$_2$), 2.86 (g, 2H, CH$_2$), 3.32 (m, 1H, CH), 4.10 (g, 2H, CH$_2$), 7.05 (t, 1H), 7.15 (d, 1H), 7.51 (m, 2H), 11.50 (bs, 1H, NH).

EXAMPLE 30A

4-Benzyloxy-2-bromophenol

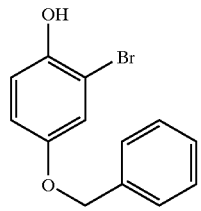

183 g of 4-benzyloxyphenol (914 mmol) are brominated according to the literature (J. C. S Perkin 1, 1981, 223). Following recrystallization from petroleum ether (with 5% ether), the product is obtained as a colorless solid.

Yield: 189 g (74.1% of theory) MS (DCI, NH$_3$): m/z (%)=296/298 (M+18) (100) $^1$H-NMR (200 MHz, CDCl$_3$): δ=4.96 (s, 2 H); 5.19 (s, 1H); 6.70–6.95 (m, 2 H); 7.10 (d, 1 H); 7.39–7.45 (m, 5 H).

EXAMPLE 31A

5-Benzyloxy-2-ethoxybrombenzene

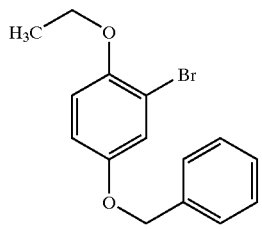

186.18 of 4-benzyloxy-2-bromophenol (667 mmol) (example 30A) and potassium carbonate (276.56 g, 2 mol)

are initially charged in 2 l of acetone. 74.7 ml of bromoethane (1 mol) are added dropwise, and the mixture is stirred at reflux for 24 h. The mixture is filtered off and concentrated. The resulting oily residue is dissolved in 1200 ml of ethanol. With vigorous stirring, the product is crystallized by slowly adding 900 ml of water. The product is filtered off with suction and the light-beige crystals are dried under high vacuum.

Yield 178.9 g (95.1% of theory) MS (DCI, NH$_3$): m/z (%)=326/328 (M+18) (100) $^1$H-NMR (200 MHz, CDCl$_3$): δ=1.45 (t, 3 H); 4.05 (q, 2 H); 4.98 (s, 2 H), 6.79–6.90 (m, 2 H); 7.18–7.46 (m, 6 H).

EXAMPLE 32A

5-Benzyloxy-2-ethoxybenzonitrile

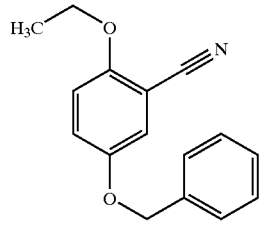

178.17 g of 5-benzyloxy-2-ethoxybromobenzene (580 mmol) (example 31A) are added to 57.14 g of copper cyanide (638 mmol), and the two components are mixed by shaking. Following addition of 65 ml of dry pyridine, the mixture is heated to 160° C. The mixture melts and forms a homogeneous solution. The solution is stirred at 160° C. for 6 h. After cooling to about 100° C., toluene is added and the mixture is stirred until the reaction mixture has cooled. The mixture is filtered through kieselguhr, and the kieselguhr is washed repeatedly with toluene. The filtrate is then washed with dilute ammonia solution until the aqueous phase is no longer blue. The mixture is washed with saturated sodium chloride solution, dried and concentrated. The resulting residue is recrystallized from 500 ml of ethanol, complete crystallization is achieved by addition of 100 ml of water. The crystals are filtered off with suction and washed repeatedly with petroleum ether. The brownish crystals are dried at 45° C. under reduced pressure.

Yield 140.4 g (92.5% of theory) MS (DCI, NH$_3$): m/z (%): 271 (M+18) (100) $^1$H-NMR (200 MHz, CDCl$_3$): δ=1.45 (t, 3 H), 4.08 (q, 2 H); 5.01 (s, 2 H); 6.85–6.90 (1 H); 7.10–7.18 (2 H), 7.31–7.42 (m, 5 H).

EXAMPLE 33A

3-Benzyloxy-6-ethoxybenzamidine Hydrochloride

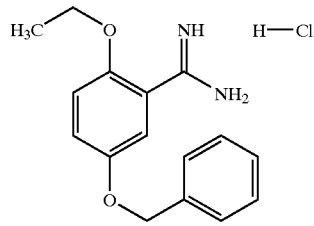

46.46 g of ammonium chloride (868.5 mol) are suspended in 650 ml of toluene, and the mixture is cooled to 0–5° C. Trimethylaluminum is added dropwise as a 2M solution in hexane (445 ml, 888.3 mmol), and the mixture is then stirred at room temperature until the evolution of gas has ceased. 5-Benzyloxy-2-ethoxybenzonitrile (100 g, 394.8 mmol) (example 32A) is added, and the mixture is stirred at 80° C. overnight. The cooled reaction mixture is, with ice-cooling, added to a suspension of 200 g of silica gel and 2 l of dichloromethane, and the mixture is stirred for 30 min. The mixture is filtered off with suction and the filter cake is washed with methanol. The organic phases are combined and concentrated. The resulting residue is triturated using a mixture of dichloromethane/methanol 9:1, filtered and concentrated using a rotary evaporator. The residue is then triturated with ether, and the colorless solid is filtered off with suction.

Yield 59.4 g (49% of theory) $^1$H-NMR (300 MHz, D$_6$-DMSO): δ=1.32 (t, 3H); 4.09 (q, 2H); 5.15 (s, 2H); 7.10–7.49 (m, 8 H); 9.1–9.5 (m, 3).

EXAMPLE 34A

2-[5-(benzyloxy)-2-ethoxyphenyl]-7-cyclopentyl-5-methyl-3H-imidazo[5,1-f][1,2,4]triazin-4-one

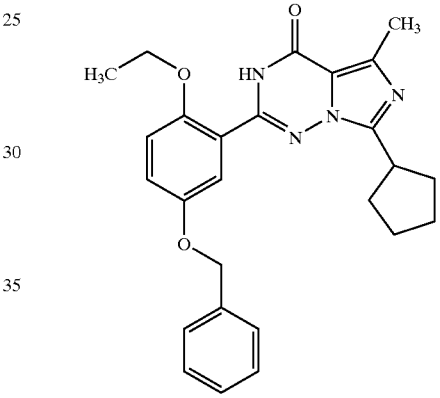

4.07 g of 2-cyclopentanoylaminopropionic acid (22 mmol) (example 9A) are initially charged in 22 ml of dry tetrahydrofuran and 5.3 ml of pyridine (66 mmol), 0.13 g of 4-DMAP are added and the mixture is is heated under reflux. Ethyl oxalyl chloride (6.7 ml, 44 mmol) is slowly added dropwise, and the resulting suspension is heated under reflux for two hours and then, after cooling, diluted with ethyl acetate and filtered, and the aqueous phase is washed with 1N hydrochloric acid (2×), saturated sodium bicarbonate solution (2×) and saturated sodium chloride solution, dried over sodium sulfate and concentrated. After drying under high vacuum, a yellow oil is obtained which is, dissolved in 13 ml of ethanol, added to a solution which is prepared as follows:

3.37 g of 3-benzyloxy-6-ethoxybenzamidine hydrochloride (11 mmol) (example 33A) are initially charged in 13 ml of ethanol, the mixture is cooled to 0° C. and 1.13 g of hydrazine hydrate (16.5 mmol) are added dropwise. The mixture is warmed to ~40° C. and stirred for 10 min.

After the ethanolic solution has been added, the mixture is stirred at 70° C. for 3.5 h. The mixture is concentrated and dried under high vacuum, and the yellow foam is dissolved in 100 ml of 1,2-dichloroethane, 2 ml of phosphorus oxychloride are added and the mixture is heated at reflux for 1.5 h. After cooling, the mixture is diluted with dichloromethane and washed with saturated sodium bicarbonate solution and saturated sodium chloride solution. The organic phase is dried with magnesium sulfate and concentrated. The dark residue is taken up in ethyl acetate, and after addition of petroleum ether precipitation occurs. The mixture is filtered off and the filtrate is then concentrated and the residue is chromatographed (cyclohexane/ethyl acetate 3:2). The product is recrystallized from ethyl acetate/petroleum ether.

Yield 632 mg (12.9% of theory) MS (DCI, $NH_3$): m/z (%)=445 (M+H) (100) $^1$H-NMR (200 MHz, $CDCl_3$): δ=1.55 (t, 3 H); 1.20–2.21 (m, 8H); 2.55 (s, 3H); 3.61 (qui, 1H); 4.21 (q, 2H); 5.12 (s, 2 H); 6.98 (d, 1 H); 7.11 (dd, 1 H); 7.32–7.50 (m, 5 H); 7.78 (d, 1 H); 10.10 (s, 1 H).

EXAMPLE 35A

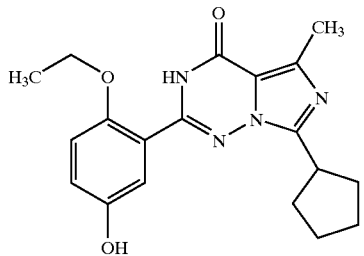

611 mg of the compound from example 34A (1.37 mmol) are suspended in 13 ml of ethanol. 13 ml of ether and a few drops of acetic acid are added (dissolution incomplete). Under an atmosphere of argon, 200 mg of 10% Pd/C are added to the suspension and the suspension is repeatedly flushed with hydrogen, then stirred vigorously under an $H_2$ atmosphere (1 atm) for 2 h and finally filtered off through Celite. The filtrate is concentrated and dried under high vacuum and the residue is treated with ether/petroleum ether, filtered and dried under high vacuum.

Yield 395 mg (81.5% of theory) MS (DCI, $NH_3$): m/z (%)=355 (M+H) (100)

EXAMPLE 36A

Ethoxy-5-hydroxybenzonitrile

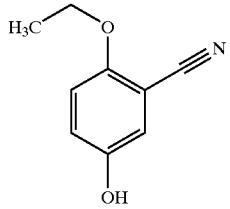

40.02 g of 5-benzyloxy-2-ethoxybenzonitrile (158 mmol) (example 32A) and 5% Pd/C (4.0 g) are initially charged in 1 l of methanol. The mixture is then hydrogenated under an atmosphere of hydrogen (1 atm) for about 4 h. The mixture is filtered through kieselguhr and evaporated and the crystalline residue is dried under reduced pressure.

Yield 25.5 g (99.6% of theory) $^1$H-NMR (200 MHz, $CDCl_3$): δ=1.43 (t, 3 H); 4.05 (q, 2 H), 6.75–6.88 (m, 1 H); 7.0–7.07 (m, 2 H).

EXAMPLE 37A

5-Allyloxy-2-ethoxybenzonitrile

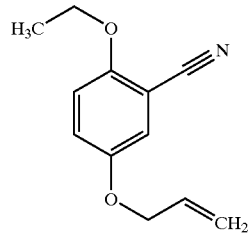

25 g of 2-ethoxy-5-hydroxybenzonitrile (153.2 mmol) (example 36A) and potassium carbonate (63.52 g, 459.6 mmol) are initially charged in 750 ml of acetone. 19.9 ml of allyl bromide (229.8 mmol) are added, and the mixture is stirred under reflux overnight. The mixture is filtered off and concentrated giving a mobile orange oil.

Yield 31 g (99.6% of theory) $^1$H-NMR (200 MHz, $D_6$-DMSO): δ=1.45 (t, 3 H); 4.10 (q, 2 H); 5.28–5.95 (m, 2 H); 5.92–6.11, m 1 H); 6.85–6.92 (m, 1 H); 7.06–7.13 (m, 2 H).

EXAMPLE 38A

3-Allyloxy-6-ethoxybenzamidine Hydrochloride

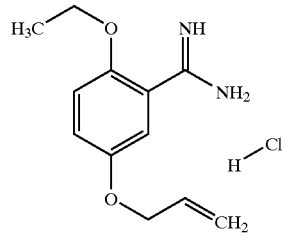

17.95 g of ammonium chloride (335.56 mmol) are suspended in toluene and cooled to 0–5° C. Trimethylaluminum (2M solution in hexane, 172 ml, 343.2 mmol) are added dropwise, and the mixture is then stirred at room temperature until the evolution of gas has ceased. 5-Allyloxy-2-ethoxybenzonitrile (31 g, 152.5 mmol) (example 37A) is then added and the mixture is stirred at 80° C. overnight. The cooled mixture is then added to a mixture of 100 g of silica gel and 1 l of dichloromethane and stirred for 30 min. The mixture is filtered off with suction, the filter cake is washed twice with methanol and the filtrate is concentrated. The residue that is obtained is stirred with dichloromethane/methanol 9:1, filtered off and concentrated using a rotary evaporator. The residue consists of a red-brownish semicrystalline material. Using acetone, 10 g of a colorless solid are obtained after filtration. The mother liquor gives, after concentration using a rotary evaporator, 21 g of a viscous reddish oil which is dissolved in a little dichloromethane. The solution is seeded with a little product and allowed to stand overnight. Filtration with suction and washing with a little acetone gives a further 6 g of solid.

Yield 16 g (38.6% of theory) MS (DCI, $NH_3$): m/z (%)=221 (M−Cl) (100) $^1$H-NMR (200 MHz, $D_6$-DMSO): δ=1.32 (t, 3 H); 4.08 (q, 2 H); 4.60 (d, 2 H); 5.35–5.97 (m, 2 H); 5.94–6.15 (m, 1 H); 7.13–7.22 (m, 3 H); 9.2/9.35 (2× s, in total 4 H).

EXAMPLE 39A

2-[5-(Allyloxy)-2-ethoxyphenyl]-7-cyclopentyl-5-methyl-3H-imidazo[5,1-f][1,2,4]triazin-4-one

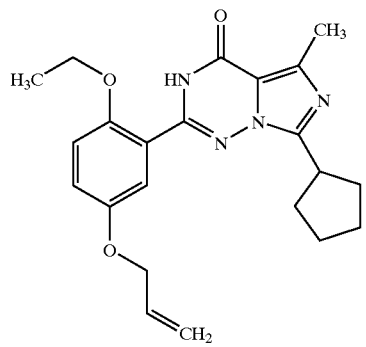

14.82 g of 2-cycloentanoylaminopropionic acid (example 9A) (80 mmol) are initially charged in 80 ml of dry tetrahydrofuran and 19.4 ml of pyridine (240 mmol), 0.49 g of 4-DMAP is added and the mixture is is heated under reflux. Ethyl oxalyl chloride (17.9 ml, 160 mmol) is slowly added dropwise, and the resulting suspension is heated under reflux for two hours. The mixture is poured into ice-water and extracted three times with ethyl acetate. The extracts are dried and concentrated. The resulting oily residue is taken up in methanol, sodium bicarbonate is added and the mixture is boiled for 2.5 hours. After cooling, the mixture is filtered. The filtrate is added to a solution which was prepared as follows: 15 g of 3-allyloxy-6-ethoxybenzamidine hydrochloride (58.4 mmol) (example 38A) are initially charged in ethanol with ice-cooling. Over a period of 10 min, hydrazine hydrage (3.07 g, 61.3 mmol) is added dropwise, and the mixture is then stirred at room temperature for another 30 min. After 4 h at 70° C. the mixture is concentrated and the residue is taken up in 80 ml of 1,2-dichloroethane, mixed with 110 ml of phosphorus oxychloride and stirred under reflux for 1 h. The mixture is diluted with dichloromethane and neutralized using sodium bicarbonate. The mixture is once more washed with water and then dried and concentrated using a rotary evaporator. The crude product is pre-purified by silica gel flash chromatography using cyclohexane/ethyl acetate 1:1. The resulting oily residue is crystallized using ether. Another crystallization from cyclohexane/ethyl acetate 1:1 gives 3.34 g of a solid. The mother liquor is concentrated using a rotary evaporator and chromatographed using dichloromethane/acetone 95:5. This gives a further 2.9 g of product.

Yield 6.24 g (27.1% of theory) MS (DCI, NH$_3$): m/z (%)=395 (M+H) (100) $^1$H-NMR (200 MHz, CDCl$_3$): δ=1.56 (t, 3 H); 1.69–2.21 (m, 8 H); 2.65 (s, 3 H); 3.65 (qui, 1 H); 4.21 (q, 2 H); 4.59 (dd, 2 H) 5.30–5.51 (m, 2 H); 5.99–6.28 (m, 1 H); 6.95–7.09 (m, 2 H); 7.75 (d, 1 H); 10.10 (s, 1 H).

EXAMPLE 40A

7-Cyclopentyl-2-[2-ethoxy-5-(2-oxiranylmethoxy)phenyl]-5-methyl-3H-imidazo[5,1-f][1,2,4]triazin-4-one

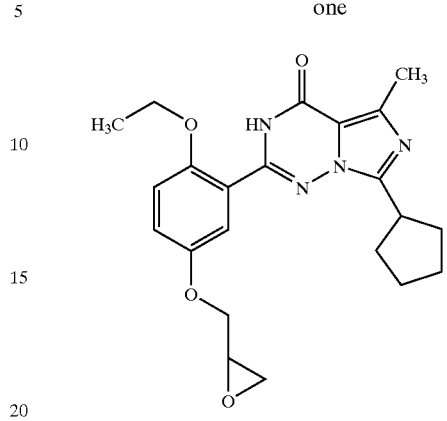

4.26 g (10.8 mmol) of the compound from example 39A are dissolved in dichloromethane. Meta-chloroperbenzoic acid (7.64 g, technical grade, about 50%, 22.1 mmol) is added, and the mixture is stirred at room temperature for 7 h. The mixture is filtered, the filter cake is washed with dichloromethane and the filtrate is then washed with thiosulfite solution and 3 times with sodium bicarbonate solution, dried and concentrated. Flash chromatography using ethyl acetate/cyclohexane 6:4 gives 1.6 g of the starting material LMP 45-1 and 460 mg of product.

Yield 460 mg (9.3% of theory) MS (DCI, NH$_3$): m/z (%)=411 (M+H) (100) $^1$H-NMR (200 MHz, CDCl$_3$): δ=1.55 (t, 3 H); 1.68–2.21 (m, 8 H); 2.67 (s, 3 H); 2.80 (dd, 1 H); 2.95 (t, 1 H); 3.38–3.41 (m, 1 H); 3.67 (qui, 1 H); 3.98 (dd, 1 H); 4.12–4.32 (m, 3 H); 6.92–7.13 (m, 2 H); 7.78 (d, 1 H).

EXAMPLE 41A 2-(2-Ethoxy-5-nitrophenyl)-5-methyl-7-cyclopentyl-3H-imidazo[5,1-f][1,2,4]-triazin-4-one

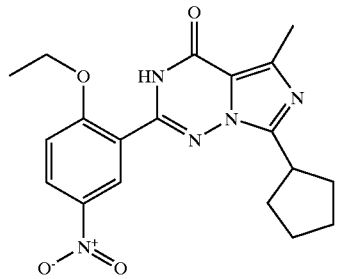

Using an ice-acetone bath, 48.6 ml of trifluoroacetic acid (TFA) and 12.1 ml of 70% strength nitric acid are cooled to −10° C, 3.0 g (8.86 mmol) of the compound from example 25A, dissolved in 7 ml of TFA are added dropwise, and the mixture is stirred at 0° C. for 20 hours. The reaction solution is stirred into 400 ml of ice-water and 200 ml of dichloromethane and neutralized using about 200 ml of saturated sodium bicarbonate solution. The aqueous phase is separated off and extracted 3 times with dichloromethane, and the combined organic phases are dried and concentrated. The residue is chromatographed on silica gel using toluene with added ethyl acetate in a gradient from 11 to 60%.

Yield: 2.56 g (75.5% of theory) $^1$H-NMR (200 MHz, DMSO): 1.37 (t, 3H), 1.58–2.00 (m, 8H), 2.49 (s, 3H), 3.50 (quin., 1H), 4.26 (quar, 2H), 7.39 (d, 1H), 8.39–8.47 (m, 2H), 11.77 (s, 1H).

EXAMPLE 42A 2-(5-Amino-2-ethoxyphenyl)-5-methyl-7-cyclopentyl-3H-imidazo[5,1-f][1,2,4]-triazin-4-one

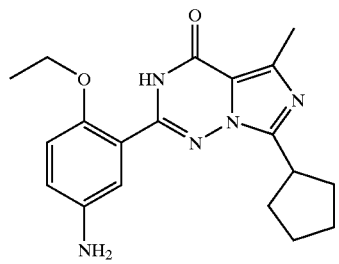

In 86 ml of ethanol and 86 ml of tetrahydrofuran 2.56 g (6.68 mmol) of the compound from example 41A are stirred in the presence of 288 mg of Pd/C (10%) under an H$_2$ atmosphere for 20 hours. The reaction solution is filtered with suction through 30 ml of silica gel, the filter cake is washed with ethanol/tetrahydrofuran and the filtrate is concentrated and dried under high vacuum overnight. The crude product is chromatographed on 500 ml of silica gel using toluene and ethyl acetate in a gradient system.

Yield: 2.1 g (92.8% of theory) $^1$H-NMR (200 MHz, DMSO): 1.25 (t, 3H), 1.58–2.0 (m, 8H), 2.48 (s, 3H), 3.41–3.58 (quin., 1H), 3.97 (quar, 2H), 4.92 (s, 2H), 6.69–6.90 (dd and d, 3H), 11.34 (s, 1H).

EXAMPLE 43A 2-(5-Nitro-2-propoxyphenyl-5-methyl-7-cyclopentyl-3H-imidazo[5,1-f][1,2,4]-triazin-4-one

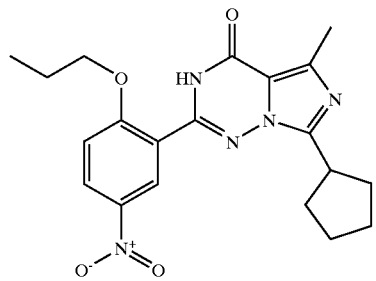

Analogously to the procedure of example 41A, 10.0 g (28.4 mmol) of the compound from example 26A are nitrated in 160 ml of trifluoroacetic acid and 40 ml of 70% strength nitric acid. The product is purified by silica gel chromatography using toluene and ethyl acetate in a gradient system.

Yield: 5.15 g (45.7% of theory). $^1$H-NMR (200 MHz, DMSO): 0.95 (t, 3H), 1.60–1.93 (m, 8H), 1.93–2.10 (m, 2H), 2.50 (s, 3H), 3.50 (quin., 1H), 4.17 (t, 2H), 7.40 (dd, 1H), 8.38–8.46 (m, 2H), 11.62 (s, 1H).

EXAMPLE 44A 2-(5-Amino-2-propoxyphenyl)-5-methyl-7-cyclopentyl-3H-imidazo[5,1-f][1,2,4]-triazin-4-one

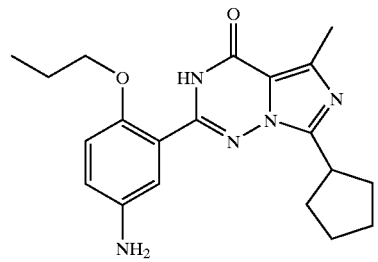

Analogously to the procedure of example 42A 5.13 g (12.96 mmol) of the compound from example 43A are hydrogenated in tetrahydrofuran/ethanol (1:1) using 1.11 g of 10% Pd/C. The product is purified by silica gel chromatography using toluene and ethyl acetate as solvent gradient.

Yield: 4.39 g (92.1% of theory). $^1$H-NMR (200 MHz, DMSO): 0.91 (t, 3H), 1.57–2.00 (mm, 10H), 2.45 (s, 3H), 3.41–3.58 (quin., 1H), 3.88 (t, 2H), 4.93 (s, 2H), 6.72 (dd, 1H), 6.80 (d, 1H), 6.90 (d, 1H), 11.30 (s, 1H).

EXAMPLE 45A 2-(2-Ethoxy-3-nitrophenyl)-5-methyl-7-propyl-3H-imidazo[5,1-f][1,2,4]-triazin-4-one

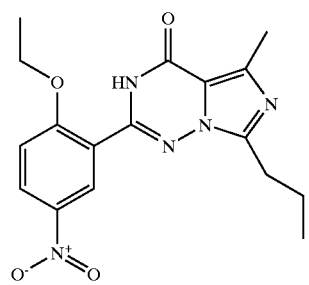

Analogously to the procedure of example 41A, 1.5 g (4.80 mmol) of the compound from example 16A are nitrated in 27 ml of triflouroacetic acid and 6.6 ml of 70% strength nitric acid.

Yield: 1.73 g (83.7% of theory). MS (ESI): 358 (M+H), HPLC (analytic): 83.0% RT: 5.86 min, column: Nucleosil C18 (125×4mm), solvent: 0.01 m H$_3$PO$_4$/acetonitrile (gradient), flow rate: 2 ml/min, 200–400 nm, TLC: R$_f$=0.43 (toluene:ethyl acetate=2:8).

EXAMPLE 46A 2-(5-Amino-2-ethoxyphenyl)-5-methyl-7-propyl-3H-imidazo[5,1-f][1,2,4]-triazin-4-one

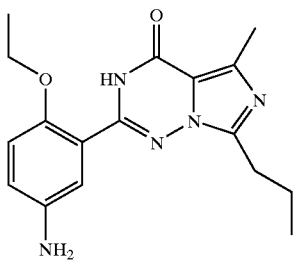

Analogously to the procedure of example 42A, 1.72 g (4.63 mmol) of the compound from example 45A are hydrogenated in 150 ml of ethanol using 200 mg of 10% Pd/C.

Yield: 862 mg (56.9% of theory). $^1$H-NMR (200 MHz, DMSO): 0.92 (t, 3H), 1.25 (t, 3H), 1.64–1.82 (hex, 2H), 2.50 (s, 3H), 2.82 (t, 2H), 3.90–4.01 (quar, 2H), 4.93 (s, 2H), 6.72 (dd, 1H), 6.80 (d, 1H), 6.90 (d, 1H), 11.35 (s, 1H); MS (DCI): 354 (M+H). TLC: $R_f$=0.33 (toluene:ethyl acetate 1:9).

EXAMPLE 47A 2-(2-Ethoxy-5-nitrophenyl)-5-methyl-7-(1-ethylpropyl)-3H-imidazo[5,1-f][1,2,4]-tiazin-4-one

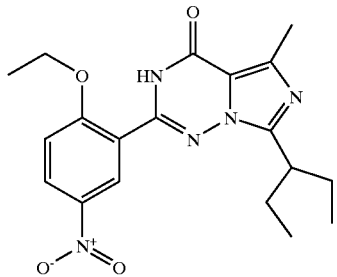

Analogously to the procedure of example 41A, 2.0 g (5.88 mmol) of the compound from example 18A are nitrated in 33 ml of trifluoroacetic acid and 8.3 ml of 70% strength nitric acid. The product is purified by chromatography on 1000 ml of silica gel using toluene and ethyl acetate in a gradient system.

Yield: 1.84 g (81.3% of theory). $^1$H-NMR (200 MHz, DMSO): 0.73 (t, 6H), 1.16 (t, 3H), 1.61–1.82 (m, 4H), 2.50 (s, 3H), 3.01–3.18 (m, 1H), 4.00 (quar, 2H), 7.49 (t, 1H), 7.91 (dd, 1H), 8.12 (dd, 1H), 12.92 (s, 1H).

EXAMPLE 48A 2-(5-Amino-2-ethoxyphenyl)-5-methyl-7-(1-ethylpropyl)-3H-imidazo[5,1-f][1,2,4]-triazin-4-one

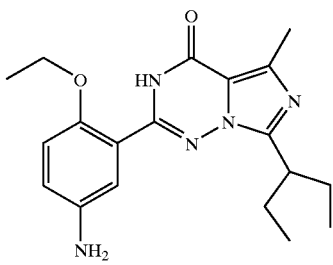

Analogously to the procedure of example 42A, 1.84 g (4.77 mmol) of the compound from example 47A are hydrogenated in 150 g of ethanol using 200 mg of 10% Pd/C.

Yield: 1.57 g (92.4% of theory). $^1$-NMR (200 MHz, DMSO): 0.75 (t, 6H), 1.24 (t, 3H), 1.66–1.84 (m, 4H), 2.50 (s, 3H), 3.11 (quin., 1H), 3.98 (quar, 2H), 4.93 (s, 2H), 6.71 (dd, 1H), 6.78 (d, 1H), 6.90 (d, 1H), 11.33 (s, 1H).

EXAMPLE 49A 2-(2-Ethoxy-5-nitrophenyl)-5-methyl-7-(2-ethylheptyl)-3H-imidazo[5,1-f][1,2,4]-triazin-4-one

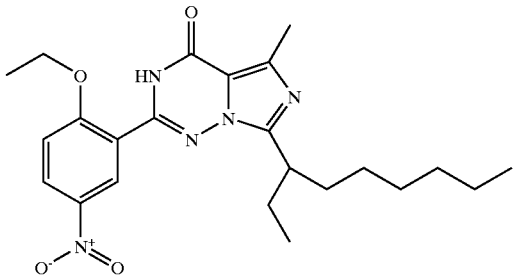

Analogously to the procedure of example 41A, 3.0 g (7.57 mmol) of the compound from example 23A are nitrated in 42.5 ml of trifluoroacetic acid and 10.7 ml of 70% strength nitric acid. The product is purified by chromatography on 500 ml of silica gel using cyclohexane and ethyl acetate in a gradient system of from 95:5 to 40:60.

Yield: 1.95 g (58.4% of theory). TLC: $R_f$=0.65 (cyclohexane:ethyl acetate=2:8).

EXAMPLE 50A 2-(5-Amino-2-ethoxyphenyl)-5-methyl-7-(2-ethylheptyl)-3H-imidazo[5,1-f][1,2,4]-triazin-4-one

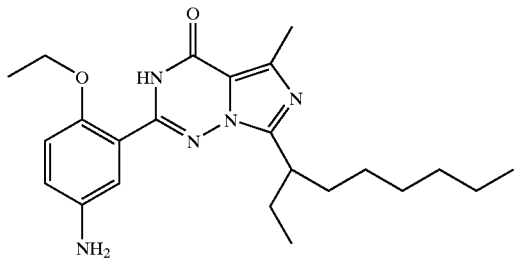

Analogously to the procedure of example 42A, 1.95 g (4.42 mmol) of the compound from example 49A are hydrogenated in 120 g of ethanol using 200 mg of 10% Pd/C. Chromatography on 400 ml of silica gel using cyclohexane and ethyl acetate in a gradient system from 90:10 to 40:60 gives 1.26 g (69.4% of theory).

¹H-NMR (200 MHz, DMSO): 0.70–0.83 (m, 6H), 1.11–1.80 (m, 12H), 1.62–1.81 (m, 3H), 2.50 (s, 3H), 3.11–3.25 (quin., 1H), 3.97 (quar. 2H), 4.95 (s, 2H), 6.70–6.80 (m, 2H), 6.90 (d, 1H), 11.35 (s, 1H).

EXAMPLE 51A 2-(2-Ethoxy-5-chloromethylphenyl)-5-methyl-7-n-propyl-3H-imidazo[5,1-f][1,2,4]-triazin-4-one

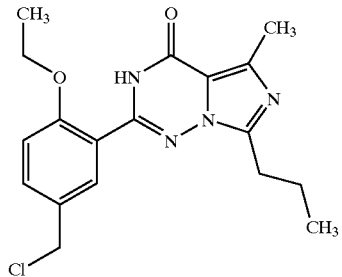

A suspension of 1.50 g (4.8 mmol) of the compound from example 16A and 0.43 g (4.8 mmol) of paraformaldehyde in 25 ml of conc. HCl was heated at 120° C. for 2 h. The reaction mixture was poured into ice-water and extracted twice with ethyl acetate and then twice with $CH_2Cl_2$. The $CH_2Cl_2$ phase was dried over $MgSO_4$ and concentrated under reduced pressure. This gave 1.22 g (70.4%) of the desired product.

MS (DCI, $NH_3$): m/z (%)=361 [M+H] (100) ¹H-NMR (200 MHz, $D_6$-DMSO): δ=0.94 (t, 3H, $CH_3$); 1.32 (t, 3H, $CH_3$); 1.82 (g, 2H, $CH_2$); 2.61 (s, 3H, $CH_3$); 3.02 (t, 2H, $CH_2$); 4.12 (g, 2H, $CH_2$); 4.81 (s, 2H, $CH_2$); 7.21 (d, 1H); 7.57–7.65 (m, 2H), 12.22 (bs, 1H, NH).

EXAMPLE 52A 2-(2-Ethoxy-5-chloromethylphenyl)-5-ethyl-7-n-propyl-3H-imidazo[5,1-f][1,2,4]-triazin-4-one

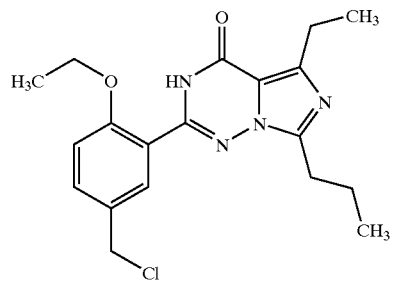

The preparation is carried out analogously to the procedure of example 51A using 1 g (3.06 mmol) of the compound from example 17A and 276 mg (3.06 mmol) of paraformaldehyde.

Yield: 732 mg (59.6%)

EXAMPLE 53A 2-(2-Ethoxy-5-chloromethylphenyl)-5-methyl-7-(1,1-dimethylbutyl)-3H-imidazo[5,1-f][1,2,4]-triazin-4-one

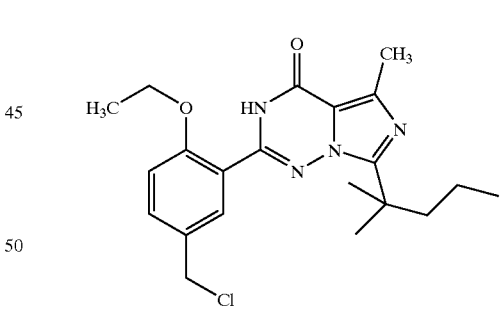

The preparation is carried out analogously to the procedure of example 51A using 1.5 g (4.2 mmol) of the compound from example 19A and 380 mg (4.2 mmol) of paraformaldehyde.

Yield: 850 ng (49.8%) ¹H-NMR (200 MHz, $CDCl_3$): 0.83 (t, 3H), 1.05–1.2 (m, 2H), 1.55 (s, 6H); 1.6 (t, 3H); 1.95–2.1 (m, 2H); 2.65 (s, 3H); 4.3 (quar., 2H); 4.62 (s, 2H); 7.05 (d, 1H); 7.53 (dd, 1H); 8.12 (d, 1H); 9.9 (s, 1H).

EXAMPLE 54A 2-(2-Ethoxy-5-chloromethylphenyl)-5-ethyl-7-cyclopentyl-3H-imidazo[5,1-f][1,2,4]-triazin-4-one

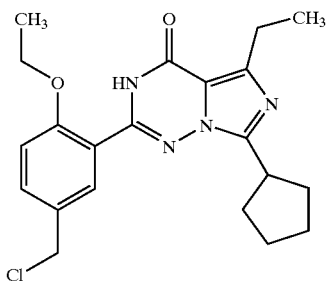

A suspension of 1.0 g (2.8 mmol) of the compound from example 27A and 256 mg (2.8 mmol) of paraformaldehyde in 20 ml of conc. HCl was heated at 120° C. for 2 h, giving a homogeneous solution. This solution was poured into ice-water and extracted twice with $CH_2Cl_2$, and the organic phase was dried over $MgSO_4$ and concentrated under reduced pressure. Recrystallization from $CH_2Cl_2$/ether gave 314 mg (27.6%) of the desired product. Concentration of the mother liquor gave a further 806 mg (70.9%) of product.

MS (EI): m/z (%)=400 [M+] (28) $^1$H-NMR (200 MHz, $CDCl_3$): δ=1.50 (t, 3H, $CH_3$), 1.61 (t, 3H, $CH_3$), 1.62–2.45 (m, 8H, 4×$CH_2$), 3.33 (t, 2H, $CH_2$), 3.91 (m, 1H, CH), 4.28 (q, 2H, $CH_2O$), 4.61 (s, 2H, $CH_2$), 7.10 (d, 1H), 7.63 (dd, 1H), 8.15 (d, 1H), 10.51 (bs, 1H, NH).

EXAMPLE 55A 2-(2-Ethoxy-5-chloromethylphenyl)-5-methyl-7-cycloheptyl-3H-imidazo[5,1-f][1,2,4]-triazin-4-one

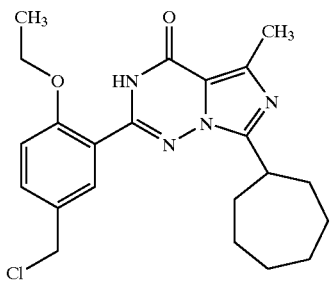

A suspension of 600 mg (1.6 mmol) of the compound from example 28A and 147 mg (1.6 mmol) of paraformaldehyde in 10 ml of conc. HCl was heated at 120° C. for a total of 4 h, with foaming reaction product being rinsed from the condenser. The mixture was poured into ice-water, the aqueous phase was extracted twice with ethyl acetate and the organic phase was dried over $MgSO_4$. The organic phase was concentrated and the residue was then triturated with ether, and precipitated product was filtered off. This gave 558 mg of a 9:1—mixture of product and starting material and another 189 mg (26.5%) of product by concentration of the mother liquor.

MS (DCI, $NH_3$): m/z (%)=415 [M+H] (100) $^1$H-NMR (200 MHz, $D_6$-DMSO): δ=1.30 (t, 3H, $CH_3$), 1.45–2.15 (m, 12H, 6×$CH_2$), 2.60 (s, 3H, $CH_3$), 3.45 (m, 1H, CH), 4.13 (q, 2H, $CH_2$), 4.82 (s, 2H, $CH_2$), 7.19 (dd, 1H), 7.62 (m, 2H), 12.18 (bs, 1H, NH).

EXAMPLE 56A 2-(2-Ethoxy-5-chloromethylphenyl)-5-ethyl-7-cycloheptyl-3H-imidazo[5,1-f][1,2,4]-triazin-4-one

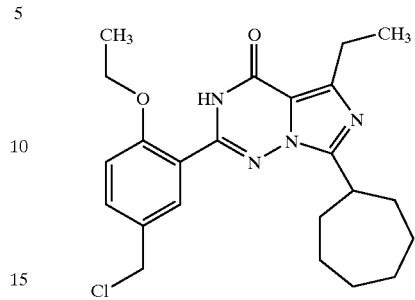

Analogously to example 51A, 100 mg (0.26 mmol) of the compound from Example 29A in 2 ml of conc. HCl were heated with 23.7 mg (0.26 mmol) of paraformaldehyde at 120° C. for 2 h. Chromatographic purification (gradient: $CH_2Cl_2$: MeOH=1→50:1) gave 60.8 mg (53.9%) of the desired product.

MS (DCI, $NH_3$): m/z (%)=429 [M+H] (100) $^1$H-NMR (200 MHz, $CDCl_3$): δ=1.32 (t, 3H, $CH_3$), 1.58 (t, 3H, $CH_3$), 1.60–2.08 (m, 12H, 6×$CH_2$), 3.02 (q, 2H, $CH_2$), 3.44 (m, 1H, CH), 4.26 (q, 2H, $CH_2O$), 4.63 (s, 2H, $CH_2$), 7.06 (d, 1H), 7.54 (dd, 1H), 8.16 (d, 1H), 9.84 (bs, 1H, NH).

EXAMPLE 57A

2-[5-(2-Bromoacetyl)-2-ethoxyphenyl)]-5-methyl-7-propyl-3H-imidazo[5,1-f][1,2,4]-triazin-4-o

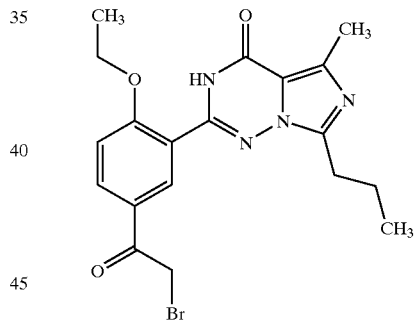

A solution, cooled to 0° C., of 4 g (12.8 mmol) of the compound from example 16A in 80 ml of $CH_2Cl_2$ was initially admixed dropwise with 5.17 g (25.6 mmol) of bromoacetyl bromide and then, a little at a time, with 5.12 g (38.4 mmol) of $AlCl_3$. The mixture was warmed to room temperature and then stirred for 30 min, and heated at reflux for 2 h. The reaction mixture was poured into ice-water and extracted once with $CH_2Cl_2$, and the organic phase was washed with sat. NaCl solution and dried over $MgSO_4$. The residue obtained after concentration under reduced pressure was triturated with ether, and the product was filtered off with suction. This gave 6.2 g (>95%) of the desired product as a mixture of phenacyl bromide and phenacyl chloride.

MS (ESI): m/z=435 [M (Br)+H] (100). 389 [M (Cl)+H] (85) $^1$H-NMR (200 MHz, $D_6$-DMSO): δ=0.94 (t, 3H, $CH_3$), 1.32 (t, 3H, $CH_3$), 1.78 (m, 2H, $CH_2$), 2.61 (s, 3H, $CH_3$), 3.03 (t, 2H, $CH_2$), 4.25 (q, 2H, $CH_2$), 4.89 (s, 2H, $CH_2$—Br), 5.18 (s, 2H, $CH_2$—Cl), 7.34 (d, 1H), 8.07–8.25 (m, 2H), 12.40 (bs, 1H, NH)

EXAMPLE 58A

2-[5-(2-Bromoacetyl)-2-ethoxyphenyl-5-ethyl-7-propyl-3H-imidazo[5,1-f][1,2,4]triazin-4-one

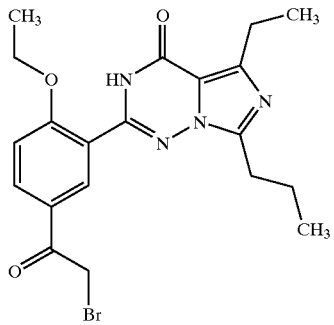

A solution, cooled to 0° C., of 1 g (3.1 mmol) of the compound from example 17A in 80 ml of $CH_2Cl_2$ was admixed dropwise with 1.2 g (6.1 mmol) of bromoacetyl bromide and a little at a time with 1.2 g (9.1 mmol) of $AlCl_3$. The reaction mixture was warmed to room temperature (30 min.) and then heated at reflux for 2 h and carefully poured into ice-water. Following extraction with $CH_2Cl_2$, drying over $MgSO_4$ and concentration under reduced pressure, the residue was triturated with ether. This gave 1.33 g (33% pure according to LC-MS) of the desired product which was reacted further without further purification.

MS (ESI): m/z (%)=447 [M+H] (100)

EXAMPLE 59A

2-[5-(2-Bromoacetyl)-2-ethoxyphenyl]-5-methyl-7-cyclopentyl-3H-imidazo[5,1]-f][1,2,4]triazin-4-one

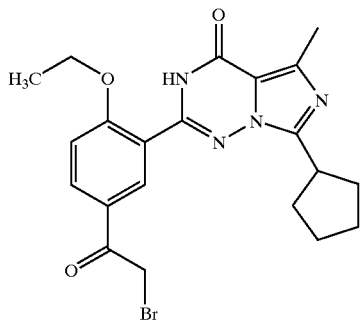

The compound was obtained analogously to the compound from example 57A from 1 g (2.95 mmol) of the compound from example 25A and 1.19 g (5.9 mmol) of bromoacetyl bromide in the presence of 1.18 g (8.86 mmol) of aluminum trichloride.

M.p.: 186° C. (ethyl acetate/ether) Yield: 770 mg (57%)

EXAMPLE 60A

2-[5-(2-Bromoacetyl)-2-ethoxyphenyl]-5-methyl-7-cycloheptyl-3H-imidazo[5,1-f][1,2,4]triazin-4-one

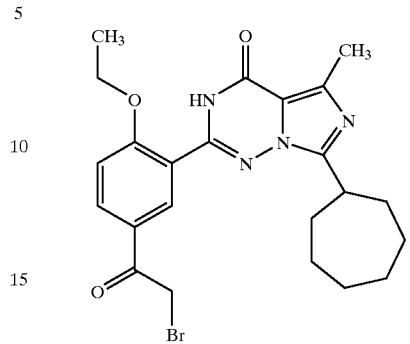

Analogously to example 57A, 1.36 g (3.7 mmol) of the compound from example 28A were reacted with 1.5 g (7.4 mmol) of bromoacetyl bromide and 1.48 g (1.1 mmol) of aluminum trichloride. Trituration with ether gave 1.2 g (66.3%) of the desired product.

MS (DCI/$NH_3$): m/z (%)=487 [M+H] (27%) $^1$H-NMR (200 MHz, $CDCl_3$): δ=1.63 (t, 3H, $CH_3$), 1.75 (bs, 6H,), 1.89–2.42 (m, 6H), 2.94 (s, 3H, $CH_3$), 3.75 (m, 1H, CH), 4.37 (s, 2H, $CH_2$—Br), 4.43 (g, 2H, $CH_2$), 4.63 (s, 2H, $CH_2Cl$), 7.23 (d, 1H), 8.25 (dd, 1H), 8.35 (d, 1H), 10.38 (bs, 1H, NH)

Preparation of the Active Compounds

EXAMPLE 1

2-[2-Ethoxy-5-(4-morpholinyl-sulfonamido)phenyl]-5-methyl-7-cyclopentyl-3H-imidazo-[5,1-f][1,2,4]-triazin-4-one

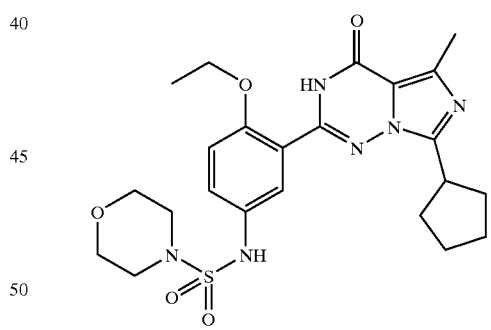

250 mg (0.71 mmol) of the amino compound from example 42A are dissolved in 10 g of dichloromethane and cooled to 0° C., and 525 mg (2.83 mmol) of morpholine N-sulfonyl chloride, dissolved in 5 g of dichloromethane, are added under argon. The mixture is stirred without cooling for 30 minutes, and 336 mg (4.24 mmol) of pyridine p.a. are then added dropwise. After a further 30 minutes, another 3.4 ml of pyridine are added dropwise, and the mixture is stirred at room temperature overnight. The reaction solution is concentrated under reduced pressure at 40° C., whereupon the color of the solution changes to an intensive red. The mixture is stirred with 20 ml of ammonium chloride solution, with addition of a little sodium bicarbonate solution, for about 10 minutes and then extracted 4 times with ethyl acetate, and the extracts are dried and concentrated. The red oil is dissolved in 10 ml of toluene, applied to 100 ml of silica gel and chromatographed using toluene/ethyl acetate in a gradient system of from 80:20 to 20:80. The desired fractions are combined, concentrated and dried under reduced pressure.

Yield: 211 mg (59.0% of theory). $^1$H-NMR (200 MHz, DMSO): 1.31 (t, 3H), 1.55–2.10 (m, 8H), 2.48 (s, 3H), 3.10 (m, 4H), 3.41–3.51 (quin., 1H), 3.55 (m, 4H), 4.09 (quar, 2H), 7.10–7.26 (m, 2H), 7.38 (dd, 1H), 9.90 (s, 1H), 11.51 (s, 1H). HPLC (analytic): 99.9% RT: 3.62 min. column: Nucleosil C18 (125×4 mm), mobile phase: 0.01 M H$_3$PO$_4$/acetonirile (gradient), flow rate: 2 ml/min, 200–400 nm.

The following compounds are prepared analogously to the procedure of example 1 (example 2 to example 12):

EXAMPLE 2

2-[2-Ethoxy-5-(4-methanesulfonylamino)phenyl]-5-methyl-7-cyclopentyl-3H-imidazo-[5,1-f][1,2,4]-triazin-4-one

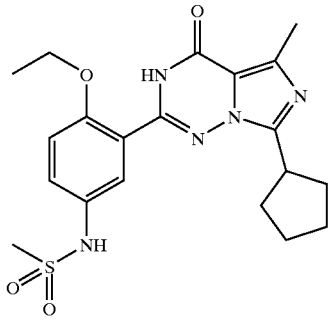

150 mg (0.42 mmol) of the compound from example 42A are reacted with 72.9 mg (0.64 mmol) of methanesulfonyl chloride.

Yield: 172 mg (93.9% of theory). $^1$H-NMR (200 MHz, DMSO): 1.30 (t, 3H), 1.59–2.03 (m, 8H), 2.47 (s, 3H), 2.97 (s, 3H), 3.47 (quin., 1H), 3.99–4.14 (m, 2H), 7.17 (d, 1H), 7.33–7.40 (dd, 2H).

EXAMPLE 3

2-[2-Ethoxy-5-(4-isopropylsulfonylamino)phenyl]-5-methyl-7-cyclopentyl-3H-imidazo-[5,1-f][1,2,4]-triazin-4-one

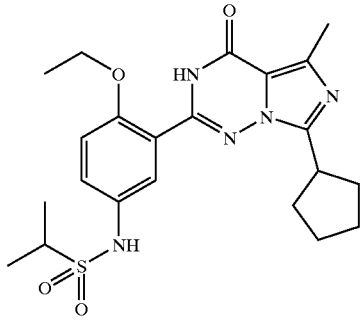

100 mg (0.28 mmol) of the compound from example 42A are reacted with 60.5 mg (0.42 mmol) of isopropylsulfonyl chloride.

Yield: 112 mg (86.1% of theory). MS (DCI): 460 (M+H). HPLC (analytic): 81.6% RT: 5.85 min, column: Nucleosil C18 (125×4 mm), mobile phase: 0.01 M H$_3$PO$_4$/acetonirile (gradient), flow rate: 2 ml/min, 200–400 nm, TLC: R$_f$=0.55 (cyclohexane:ethyl acetate=2:8).

EXAMPLE 4

2-[5-(4-N,N-Dimethylsulfamoylamino)-2-ethoxyphenyl]-5-methyl-7-cyclopentyl-3H-imidazo-[5,1-f][1,2,4]-triazin-4-one

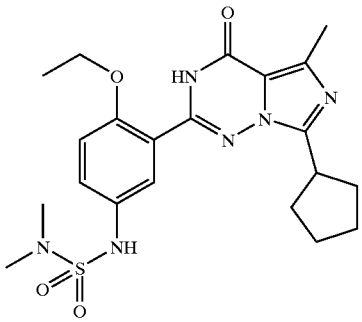

100 mg (0.28 mmol) of the compound from example 42A are stirred with 183 mg (1.27 mmol) of N,N-dimethylsulfamoyl chloride and 0.30 ml (3.71 mmol) of pyridine for 2 days. Yield: 90.8 mg (69.7% of theory).

$^1$H-NMR (300 MHz, DMSO): 1.30 (t, 3H), 1.59–2.07 (m, 8H), 2.47 (s, 3H), 2.70 (s, 6H), 3.45 (quin., 1H), 4.07 (quar, 2H), 7.10 (d, 1H), 7.32 (dd, 1H), 7.39 (d, 1H); MS (DCI): 461 (M+H).

EXAMPLE 5

2-[2-Ethoxy-5-(benzofurazane-4-sulfonylamino)phenyl]-5-methyl-7-cyclopentyl-3H-imidazo-[5,1-f][1,2,4]-triazin-4-one

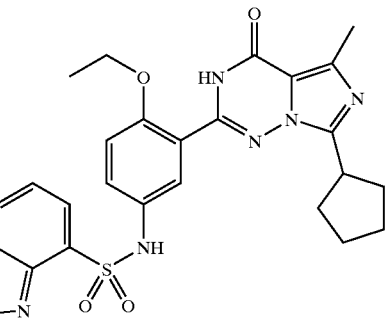

120 ml (0.34 mmol) of the compound from example 42A are reacted with 111 mg (0.509 mmol) of benzofurazane-4-sulfonyl chloride and 0.17 ml (2.10 mmol) of pyridine. Yield: 109 mg (60.1% of theory).

$^1$H-NMR (200 MHz, DMSO): 1.10 (t, 3H), 1.63–2.05 (m, 8H), 2.45 (s, 3H), 3.39 (quin., 1H), 4.00 (quar, 2H), 7.04 (d, 1H), 7.12–7.28 (m, 2H), 7.70 (dd, 1H), 8.09 (d, 1H), 8.38 (d, 1H), 10.84 (s, 1H), 11.39 (s, 1H); MS (DCI): 536 (M+H).

EXAMPLE 6

2-[5-(4-n-Butoxybenzenesulfonylamino)-2-ethoxyphenyl]-5-methyl-7-cyclopentyl-3H-imidazo-[5,1-f][1,2,4]-triazin-4-one

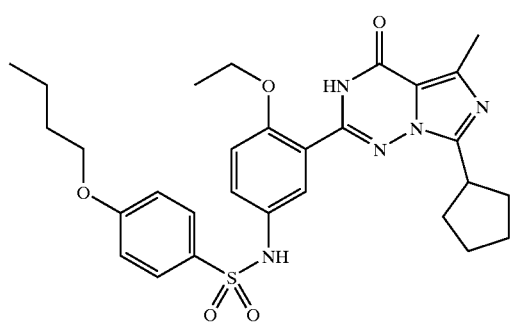

150 mg (0.424 mmol) of the compound from example 42A are reacted with 186 mg (0.747 mmol) of 4-(n-butoxy)-benzenesulfonyl chloride and 0.34 g (4.30 mmol) of pyridine in 6 ml of tetrahydrofuran.

Yield: 99.5 mg (41.4% of theory). $^1$H-NMR (300 MHz, DMSO): 0.92 (t, 3H), 1.25 (t, 3H), 1.40 (hex., 2H), 1.60–2.05 (m, 10H), 2.45 (s, 3H), 3.43 (quin., 1H), 4.00 (m, 4H), 7.03 (dd, 3H), 7.15–7.28 (m, 2H), 7.67 (d, 2H), 10.03 (s, 1H), 11.43 (s, 1H); MS (ESI): 566 (M+H).

EXAMPLE 7

2-[5-Bis(N,N-4-Butoxybenzenesulfonyl)amino-2-ethoxy-phenyl]-5-methyl-7-cyclopentyl-3H-imidazo[5,1-f][1,2,4]-triazin-4-one

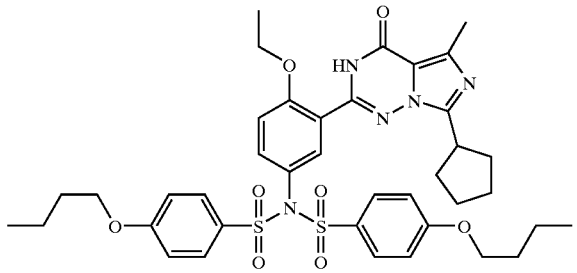

In example 6, 63.3 mg (19.2% of theory) of the bis derivative are isolated as a by-product.

$^1$H-NMR (200 MHz, DMSO): 0.95 (t, 6H), 1.30–1.52 (m, 8H), 1.65–2.03 (m, 1H), 2.47 (s, 3H), 3.47 (quin., 1H), 4.04–4.21 (m, 6H), 7.06–7.25 (m, 7H), 7.72 (d, 4H), 11.54 (s, 1H); MS (ESI): 778 (M+H).

EXAMPLE 8

2-[2-Ethoxy-5-(1-methylimidazole-4-sulfonylamino)phenyl]-5-methyl-7-cyclopentyl-3H-imidazo-[5,1-f][1,2,4]-triazin-4-one

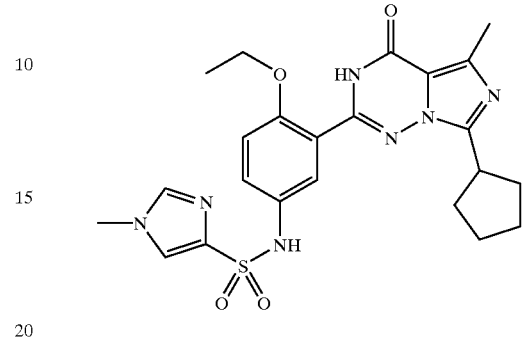

150 mg (0.424 mmol) of the compound from example 42A are reacted with 307 mg (1.70 mmol) of 1-methylimidazole-4-sulfonyl chloride and 0.34 ml (4.24 mmol) of pyridine in 5 ml of tetrahydrofuran.

Yield: 155 mg (73.8% of theory). $^1$H NMR (200 MHz, DMSO): 1.27 (t, 3H), 1.55–2.10 (m, 8H), 2.47 (s, 3H), 3.47 (quint., 1H), 3.65 (s, 3H), 4.02 (quar, 2H), 7.05 (d, 1H), 7.30 (dd, 2H), 7.75 (dd, 2H), 10.13 (s, 1H), 11.47 (s, 1H); MS (ESI): 498 (M+H).

EXAMPLE 9

2-[2-Ethoxy-5-(4-methylpiperazin-1-yl-sulfonylamino)phenyl]-5-methyl-7-cyclopentyl-3H-imidazo-[5,1-f][1,2,4]-triazin-4-one

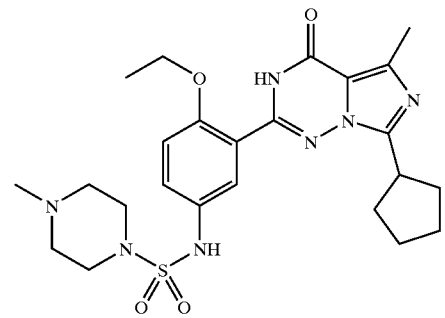

120 mg (0.34 mmol) of the compound from example 42A are reacted with 319 mg (1.36 mmol) of 4-methyl-1-piperazinesulfonyl chloride in 8 ml (98.9 mmol) of pyridine overnight.

Yield: 25.8 mg (14.7% of theory). $^1$H NMR (200 MHz, CDCL$_3$): 1.56 (t, 3H), 1.65–2.20 (m, 9H), 2.27 (s, 3H), 2.42 (t, 4H), 2.62 (s, 3H), 3.30 (t, 4H), 3.62 (quin., 1H), 4.22 (quar, 2H), 7.02 (d, 1H), 7.40 (dd, 1H), 7.97 (d, 1H), 10.00 (s, 1H); MS (ESI): 516 (M+H).

EXAMPLE 10

2-[5-(6-Chloroimidazo(2,1-b)thiazole-5-sulfonylamino)-2-ethoxyphenyl]-5-methyl-7-cyclopentyl-3H-imidazo[5,1-f][1,2,4]-triazin-4-one

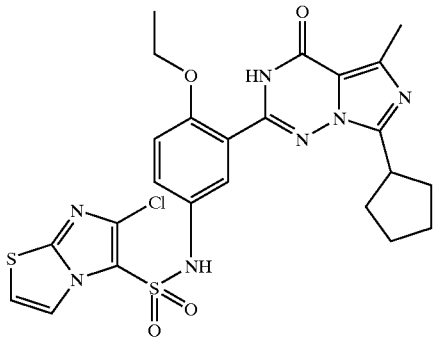

149 mg (0.42 mmol) of the compound from example 42A are reacted with 328 mg (1.28 mmol) of 6-chloroimidazo(2,1-b)thiazole-5-sulfonyl chloride and 0.68 ml (8.41 mmol) of pyridine in tetrahydrofuran, initially at room temperature and then at 50° C.

Yield: 9.6 mg (4.0% of theory). MS (ESI): 574 (M+H). TLC: $R_f$=0.54 (toluene:ethyl acetate=2:8).

EXAMPLE 11

2-[5-(4-Carboxybenzenesulfonylamino)-2-ethoxyphenyl]-5-methyl-7-cyclopentyl-3H-imidazo[5,1-f][1,2,4]-triazin-4-one

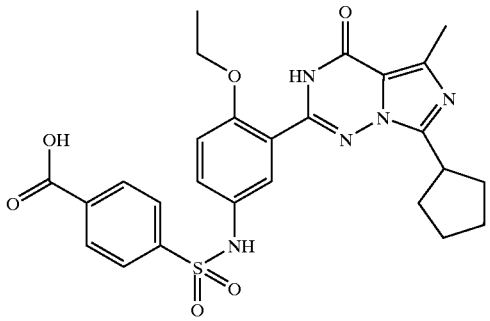

100 mg (0.283 mmol) of the compound from example 42A are reacted with 187 mg (0.849 mmol) of 4-chlorosulfonylbenzoic acid and 224 mg (2.83 mmol) of pyridine in 6 ml of tetrahydrofuran overnight.

Yield: 131 mg (85.9% of theory). MS (DCI/NH$_3$): 538 (M+H). HPLC (analytical): 89.6% RT: 5.66 min, column: Nucleosil C18 (125×4 mm), mobile phase: 0.01 m H$_3$PO$_4$/acetonirile (gradient), flow rate: 2 ml/min, 200–400 nm; TLC: $R_f$=0.30 (ethyl acetate:methanol=2:8).

EXAMPLE 12

2-[5-(3-Carboxybenzenesulfonylamido)-2-ethoxyphenyl]-5-methyl-7-cyclopentyl-3H-imidazo[5,1-f][1,2,4]-triazin-4-one

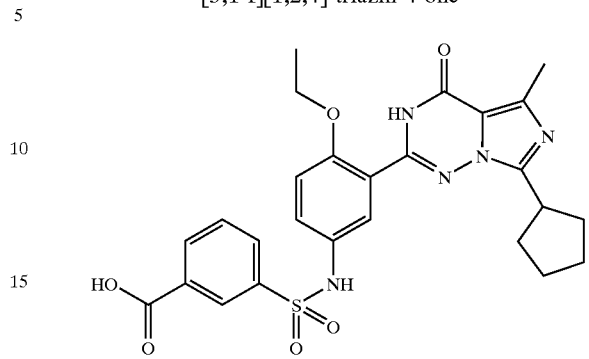

100 mg (0.283 mmol) of the compound from example 42A are reacted with 187 mg (0.849 mmol) of 3-chlorosulfonylbenzoic acid and 224 mg (2.829 mmol) of pyridine in 6 ml of tetrahydrofuran overnight.

Yield: 110 mg (72.0% of theory). $^1$H-NMR (200 MHz, DMSO): 1.25 (t, 3H), 1.57–2.08 (m, 8H), 2.47 (s, 3H), 3.37 (m, 1H), 4.02 (quar, 2H), 7.09 (d, 1H), 7.17 (m, 2H), 7.70 (t, 1H), 7.92 (d, 1H), 8.15 (d, 1H), 8.31 (s, 1H), 10.30 (s, 1H), 11.42 (s, 1H), 13.52 (s, 1H); MS (DCI/NH$_3$): 538 (M+H).

EXAMPLE 13

2-(5-Methylsulfonylamino-2-propoxyphenyl)-5-methyl-7-cyclopentyl-3H-imidazo[5,1-f][1,2,4]-triazin-4-one

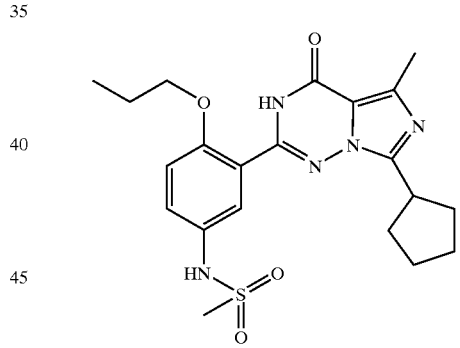

With ice-cooling, 646 mg (8.16 mmol) of pyridine and, after 15 minutes of stirring, 140 mg (1.23 mmol) of methanesulfonyl chloride (dropwise) are added to 300 mg (0.816 mmol) of the amino compound from example 44A in 10 ml of dichloromethane. After 2.5 hours of stirring at room temperature, 60 ml of dichloromethane, 30 ml of water and 20 ml of NH$_4$Cl solution are stirred into the reaction mixture, the organic phase is separated off, the aqueous phase is reextracted with dichloromethane and the organic phases are combined, washed with saturated NaCl solution, dried and concentrated. Chromatography on 100 ml of silica gel using dichloromethane and methanol as a solvent gradient gives 315 mg (86.7% of theory).

$^1$H-NMR (200 MHz, DMSO): 0.91 (t, 3H), 1.58–2.09 (m, 10H), 2.44 (s, 3H), 2.98 (s, 3H), 3.49 (quin., 1H), 4.00 (t, 2H), 7.18 (d, 1H), 7.35 (dd, 2H), 9.62 (s, 1H), 11.50 (s, 1H); MS (ESI): 446 (M+H), TLC: $R_f$=0.30 (toluene:ethyl acetate=6:4).

The following compounds (example 14 to example 24) are prepared analogously to the procedure of example 19:

EXAMPLE 14

2-[2-Propoxy-5-(3-trifluoromethlylbenzenesulfonamido)phenyl]-5-methyl-7-cyclopentyl-3H-imidazo[5,1-f][1,2,4]-triazin-4-one

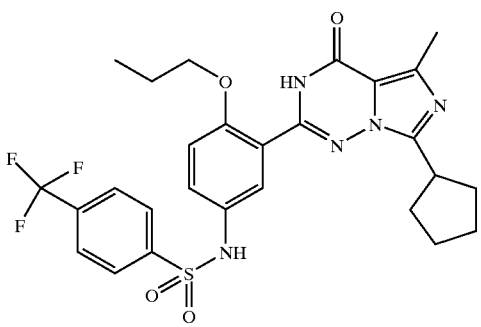

120 mg (0.327 mmol) of the compound from example 44A are reacted with 120 mg (0.49 mmol) of 3-(trifluoromethyl)benzenesulfonyl chloride and 0.28 ml (3.27 mmol) of pyridine in 5 ml of tetrahydrofuran overnight.

Yield: 128 mg (68.3% of theory). $^1$H-NMR (400 MHz, DMSO): 0.90 (t, 3H), 1.65 (m, 4H), 1.80 (m, 4H), 1.95 (m, 2H), 2.45 (s, 3H), 3.43 (quin., 1H), 3.93 (t, 2H), 7.06 (d, 1H), 7.12–7.26 (m, 2H), 7.82 (t, 1H), 7.98 (t, 1H), 8.03 (d, 2H), 10.36 (s, 1H), 11.37 (s, 1H); MS (DCI/NH$_3$): 576 (M+H).

EXAMPLE 15

2-[5-(3-Chloropropanesulfonamido)-2-propoxyphenyl]-5-methyl-7-cyclopentyl-3H-imidazo[5,1-f][1,2,4]-triazin-4-one

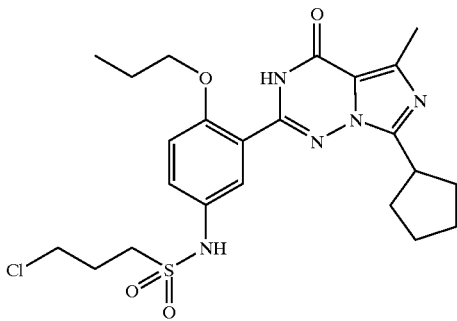

368 mg (1.0 mmol) of the compound from example 44A are reacted with 266 mg (1.5 mmol) of 3-chloropropanesulfonyl chloride and 0.81 ml (10.0 mmol) of pyridine in 12 ml of dichloromethane for 3 hours.

Yield: 508 mg (85.7% of theory). $^1$H-NMR (200 MHz, DMSO): 0.92 (t, 3H), 1.55–2.22 (m, 12H), 2.47 (s, 3H), 3.20 (t, 2H), 3.47 (quin., 1H), 3.75 (t, 2H), 3.97 (t, 2H), 7.18 (d, 1H), 7.39 (dd, 2H), 9.80 (s, 1H), 11.47 (s, 1H); MS (ESI): 508 (M+H).

EXAMPLE 16

2-[5-(p-Nitrobenzenesulfonamido)-2-propoxyphenyl]-5-methyl-7-cyclopentyl-3H-imidazo[5,1-f][1,2,4]-triazin-4-one

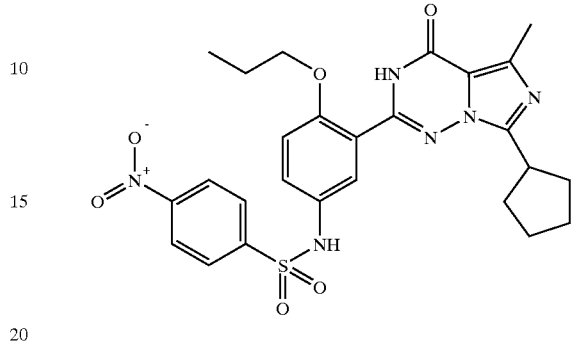

150 mg (0.408 mmol) of the compound from example 44A are reacted with 136 mg (0.612 mmol) of p-nitrobenzenesulfonyl chloride and 0.33 ml (4.08 mmol) of pyridine in 6 ml of tetrahydrofuran overnight.

Yield: 205 mg (91.1% of theory). $^1$H NMR (300 MHz, DMSO): 0.90 (t, 3H), 1.57–2.02 (m, 10H), 2.45 (s, 3H), 3.40 (quin., 1H), 3.92 (t, 2H), 7.08 (d, 1H), 7.23 (t, 2H), 7.97 (d, 2H), 8.38 (d, 2H), 10.52 (s, 1H), 11.43 (s, 1H); MS (DCI/NH$_3$): 553 (M+H).

EXAMPLE 17

2-[5-(Quinoline-8-sulfonamido)-2-propoxyphenyl]-5-methyl-7-cyclopentyl-3H-imidazo[5,1-f][1,2,4]-triazin-4-one

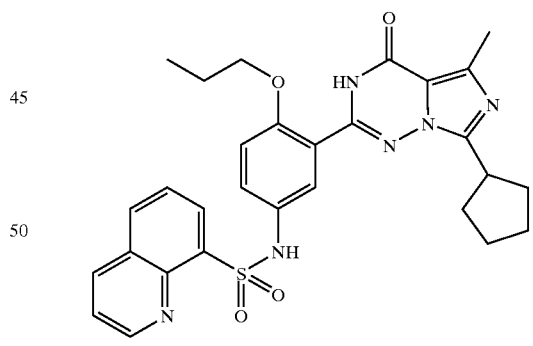

150 mg (0.408 mmol) of the compound from example 44A are reacted with 221 mg (0.96 mmol) of quinoline-8-sulfonyl chloride and 0.33 ml (4.08 mmol) of pyridine in 8 ml of tetrahydrofuran overnight.

Yield: 180 mg (79.0% of theory). $^1$H NMR (200 MHz, DMSO): 0.85 (t, 3H), 1.50–2.03 (m, 10H), 2.43 (s, 3H), 3.30 (m, 1H), 3.82 (t, 2H), 6.93 (d, 1H), 7.17 (m, 2H), 7.63–7.77 (m, 2H), 8.30 (m, 2H), 8.53 (dd, 1H), 9.17 (dd, 1H), 9.90–10.17 (bs, 1H), 11.17–11.43 (bs, 1H); MS: 559 (M+H).

EXAMPLE 18

2-[5-(4-tert-Butylbenzenesulfonamido)-2-propoxyphenyl]-5-methyl-7-cyclopentyl-3H-imidazo[5,1-f][1,2,4]-triazin-4-one

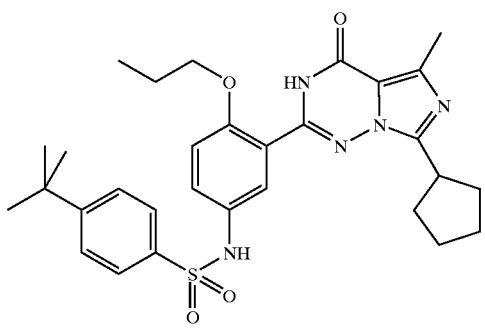

150 mg (0.408 mmol) of the compound from example 44A are reacted with 143 mg (0.612 mmol) of 4-tert-butylbenzenesulfonyl chloride and 0.33 ml (4.08 mmol) of pyridine in 8 ml of tetrahydrofuran for 1 hour.

Yield: 203 mg (88.0% of theory). $^1$H NMR (200 MHz, DMSO): 0.91 (t, 3H), 1.25 (s, 9H), 1.55–2.12 (m, 10H), 2.47 (s, 3H), 3.45 (quint., 1H), 3.93 (t, 2H), 7.07 (d, 1H), 7.20–7.30 (m, 2H), 7.57 (d, 2H), 7.70 (d, 2H), 10.25 (bs, 1H), 1.41 (bs, 1H); MS (DCI/NH$_3$): 564 (M+H).

EXAMPLE 19

2-[5-(4-Methylpiperazin-1-yl-sulfonylamino)-2-propoxy-phenyl]-5-methyl-7-cyclopentyl-3H-imidazo[5,1-f][1,2,4]-triazin-4-one

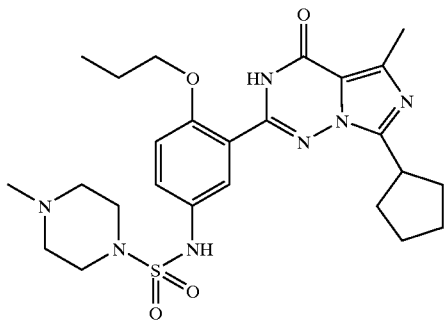

150 mg (0.408 mmol) of the compound from example 44A are treated with 576 mg (2.45 mmol) of 4-methyl-1-piperazinesulfonyl chloride in 6.6 ml (81.6 mmol) of pyridine for 3.5 hours.

Yield: 106 mg (48.8% of theory). $^1$H NMR (300 MHz, DMSO): 0.93 (t, 3H), 1.53–2.10 (m, 10H), 2.17 (s, 3H), 2.27 (s, 4H), 2.47 (s, 3H), 3.08 (s, 4H), 3.48 (quin., 1H), 3.97 (t, 2H), 7.13 (d, 1H), 7.32 (dd, 1H), 7.40 (d, 1H), 9.87 (s, 1H), 11.48 (s, 1H); MS (ESI): 530 (M+H).

EXAMPLE 20

2-[5-(4-Methylpiperazin-1-yl-sulfonylamino)-2-propoxyphenyl]-5-methyl-7-cyclopentyl-3H-imidazo[5,1-f][1,2,4]-triazin-4-one dihydrochloride

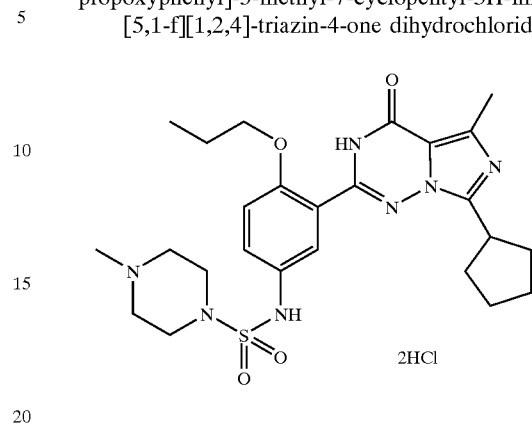

2HCl 62.9 mg (0.119 mmol) of the compound from example 19 are dissolved in 5 ml of dichloromethane and filtered through a small glass frit, and the filter residue is washed with 1 ml of dichloromethane. 1 ml of 1M HCl in ether is added dropwise to the filtrate, giving a somewhat sticky precipitate which crystallizes after further stirring and scratching. After 15 minutes of stirring in 15 ml of ether, the crystalline product is filtered off with suction, washed with ether and dried under high vacuum.

Yield: 36.3 mg (50.2% of theory). MS (ESI): 530 (M+H) for the free base. HPLC (analytic): 97.4% RT: 4.70 min, column: Nucleosil C18 (125×4 mm), mobile phase: 0.01 m H$_3$PO$_4$/acetonitrile (gradient), flow rate: 2 ml/min, 200–400 nm.

EXAMPLE 21

2-[5-(2,5-Dichlorothiophene-3-sulfonamido)-2-propoxyphenyl]-5-methyl-7-cyclopentyl-3H-imidazo[5,1-f][1,2,4]-triazin-4-one

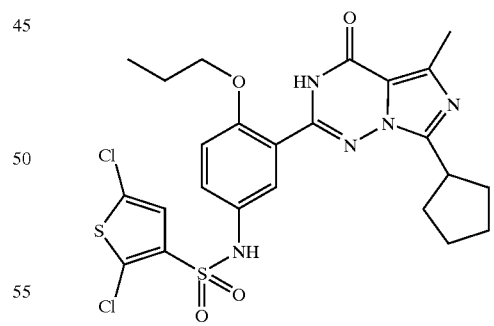

150 mg (0.408 mmol) of the compound from example 44A are reacted with 308 mg (1.224 mmol) of 2,5-dichlorothiophene-3-sulfonyl chloride and 0.33 ml (4.08 mmol) of pyridine in tetrahydrofuran for 4 hours.

Yield: 66.1 mg (27.8% of theory). $^1$H NMR (300 MHz, DMSO): 0.93 (t, 3H), 1.58–2.10 (m, 10H), 2.45 (s, 3H), 3.47 (quin., 1H), 3.97 (t, 2H), 7.12 (d, 1H), 7.22–7.31 (m, 3H), 10.57 (s, 1H), 11.48 (s, 1H); MS (ESI): 582 (M+H).

EXAMPLE 22

2-[2-Propoxy-5-(4,4,4-trifluoro-1-butanesulfonylamino)phenyl]-5-methyl-7-cyclopentyl-3H-imidazo[5,1-f][1,2,4]-triazin-4-one

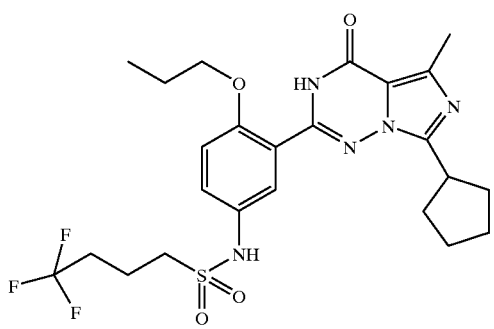

150 mg (0.408 mmol) of the compound from example 44A are reacted with 183 mg (0.87 mmol) of 4,4,4-trifluoro-1-butanesulfonyl chloride and 484 mg (6.12 mmol) of pyridine in 8 ml of tetrahydrofuran for 3 hours.

Yield: 33.5 mg (15.2% of theory). MS (DCI/NH$_3$): 542 (M+H) HPLC (analytic): 97.5% RT: 6.99 min, column: Nucleosil C18 (125×4 mm), mobile phase: 0.01 m H$_3$PO$_4$/acetonitrile (gradient), flow rate: 2 ml/min, 200–400 nm; TLC: R$_f$=0.64 (toluene:ethyl acetate=2:8).

EXAMPLE 23

2-[5-(3-Cyanobenzenesulfonamido)-2-propoxyphenyl]-5-methyl-7-cyclopentyl-3H-imidazo[5,1-f][1,2,4]-triazin-4-one

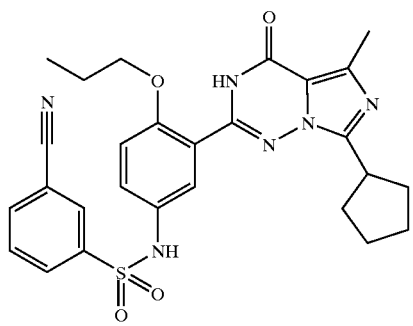

200 mg (0.566 mmol) of the compound from example 44A are reaccted with 342 mg (1.70 mmol) of 3-cyanobenzenesulfonyl chloride and 0.46 ml (5.66 mmol) of pyridine in 15 ml of tetrahydrofuran overnight.

Yield: 58.8 mg (19.5% of theory). $^1$H-NMR (200 MHz, DMSO): 0.90 (t, 3H), 1.55–2.08 (m, 10H), 2.45 (s, 3H), 3.42 (quin., 1H), 3.93 (t, 2H), 7.06–7.28 (m, 3H), 7.82 (quar, 1H), 8.00 (d, 1H), 8.12 (d, 2H), 10.38 (s, 1H), 11.42 (s, 1H); MS (ESI): 533 (M+H).

EXAMPLE 24

2-[5-(γ-Morpholinopropanesulfonylamino)-2-propoxy-phenyl]-5-methyl-7-cyclopentyl-3H-imidazo[5,1-f][1,2,4]-triazin-4-one

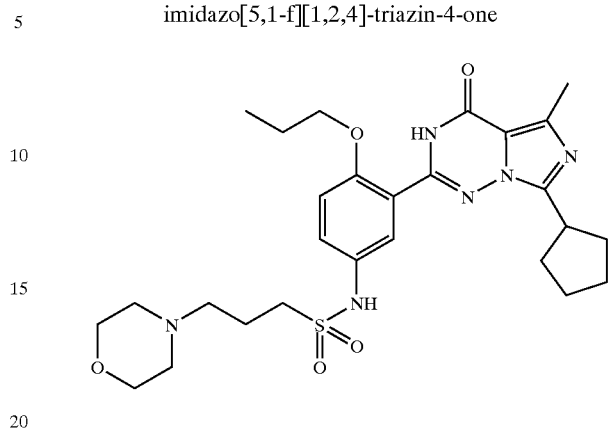

100 mg (0.272 mmol) of the compound from example 44A are reacted with 250 mg (1.09 mmol) of γ-morpholinopropanesulfonyl chloride and 0.22 ml (2.73 mmol) of pyridine in 5 ml of tetrahydrofuran overnight.

Yield: 137 mg (90.0% of theory). MS (DCI/NH$_3$): 559 (M+H), HPLC (analytic): 90.0% RT: 4.68 min, column: Nucleosil C18 (125×4 mm), mobile phase: 0.01 H$_3$PO$_4$/acetonitrile (gradient), flow rate: 2 ml/min, 200–400 nm; TLC: R$_f$=0.28 (ethyl acetate:methanol=9:1).

EXAMPLE 25

2-[5-(N,N-Bismethylsulfonyl)amino-2-propoxy-phenyl]-5-methyl-7-cyclopentyl-3H-imidazo[5,1-f][1,2,4]-triazin-4-one

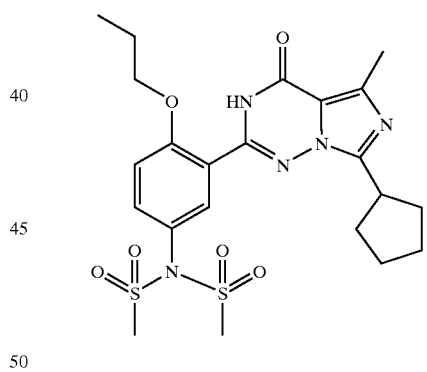

37.9 mg (0.38 mmol) of triethylamine and 42.9 mg (0.38 mmol) of methanesulfonyl chloride are added successively to 55.1 mg (0.15 mmol) of the amino compound from example 44A in 5 ml of tetrahydrofuran, and the mixture is stirred at room temperature for 1 hour. The reaction solution is concentrated, the residue is partitioned between water and ethyl acetate and the organic phase is separated off, dried and concentrated. The residue is chromatographed on 30 ml of silica gel using dichloromethane and methanol in a gradient system.

Yield: 51.7 mg (77.4% of theory). MS (ESI): 524 (M+H), TLC: R$_f$=0.52 (toluene:ethyl acetate=6:4). 5.8 mg (8.7% of theory) of the monomesyl derivative=example 13 are isolated as a by-product.

The following compounds (example 26 to example 35) are prepared analogously to the procedure of example 25:

EXAMPLE 26

2-[5-(N,N-Bisisopropylsulfonyl)amino-2-propoxyphenyl]-5-methyl-7-cyclopentyl-3H-imidazo[5,1-f][1,2,4]-triazin-4-one

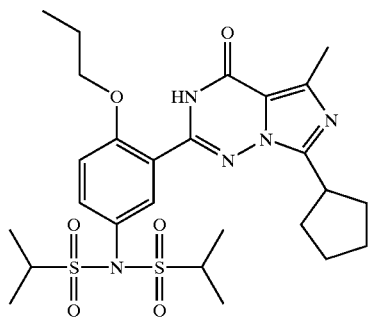

150 mg (0.408 mmol) of the compound from example 44A are reacted with 116 mg (0.816 mmol) of 2-propanesulfonyl chloride and 0.12 ml (0.857 mmol) of triethylamine in 15 ml of tetrahydrofuran for 1 hour.

Yield: 41.0 mg (17.4% of theory). MS (ESI): 580 (M+H), HPLC (analytic): 98.9% RT: 7.91 min, column: Kromasil (125×2 mm), mobile phase: 0.01 m $H_3PO_4$/acetonitrile (gradient), flow rate: 2 ml/min, 200–400 nm; TLC: $R_f$=0.40 (toluene:ethyl acetate=1:1).

EXAMPLE 27

2-(5-Isopropylsulfonylamino-2-propoxyphenyl)-5-methyl-7-cyclopentyl-3H-imidazo[5,1-f][1,2,4]-triazin-4-one

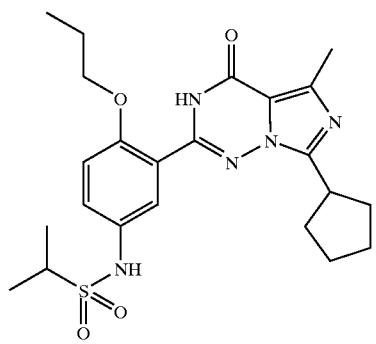

In example 26, 11.4 mg (5.90% of theory) of the monoisopropyl derivative are isolated as a by-product.

MS (ESI): 474 (M+H), TLC: $R_f$=0.35 (toluene:ethyl acetate=1:1).

EXAMPLE 28

2-{2-Propoxy-5-[2-(2,2,2-trifluoro-1-trifluoromethylethoxy)ethanesulfonylamino]-phenyl}-5-methyl-7-cyclopentyl-3H-imidazo[5,1-f][1,2,4]-triazin-4-one

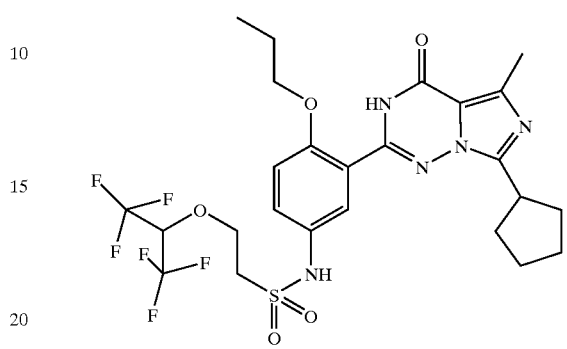

150 mg (0.408 mmol) of the compound from example 44A are reacted with 180 mg (0.612 mmol) of 2-(2,2,2-trifluoro-1-trifluoromethylethoxy)ethanesulfonyl chloride and 0.085 ml (0.612 mmol) of triethylamine for 1 hour.

Yield: 77.0. mg (30.2% of theory). $^1$H-NMR (200 MHz, DMSO): 0.93 (t, 3H), 1.53–2.07 (m, 10H), 2.47 (s, 3H), 3.42 (quin., 1H), 3.97 (t, 2H), 4.20 (t, 2H), 5.60 (quin., 1H), 7.17 (d, 1H), 7.37 (dd, 2H), 9.88 (bs, 1H), 11.50 (bs, 1H); MS (DCI/$NH_3$): 626 (M+H).

EXAMPLE 29

2-(2-Propoxy-5-vinylsulfonylaminophenyl)-5-methyl-7-cyclopentyl-3H-imidazo[5,1-f][1,2,4]-triazin-4-one

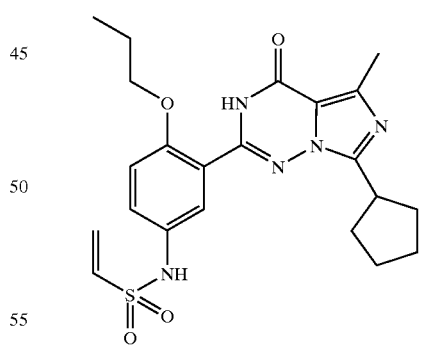

During the preparation of example 28, the vinylsulfonylamido derivative is formed as a by-product.

Yield: 64.5 mg (25.3% of theory). $^1$H-NMR (200 MHz, DMSO): 0.92 (t, 3H), 1.52–2.08 (m, 10H), 2.43 (s, 3H), 3.47 (quint., 1H), 3.97 (t, 2H), 6.03 (dd, 2H), 6.79 (dd, 1H), 7.13 (d, 1H), 7.27 (d, 1H), 7.37 (m, 1H), 9.97 (bs, 1H), 11.45 (bs, 1H); MS (DCI/$NH_3$): 458 (M+H).

EXAMPLE 30

2-[2-Propoxy-5-(4,4,5,5,5-pentafluoropentanesulfonylamino)phenyl]-5-methyl-7-cyclopentyl-3H-imidazo[5,1-f][1,2,4]-triazin-4-one

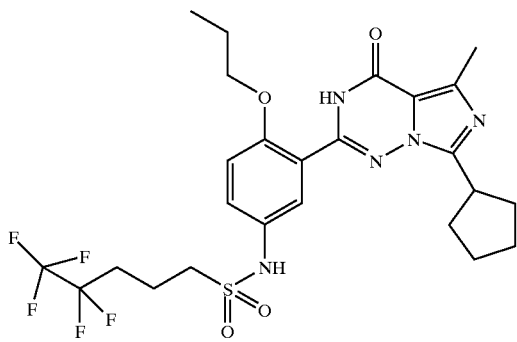

150 mg (0.408 mmol) of the compound from example 44A are treated with 160 mg (0.612 mmol) of 4,4,5,5,5-pentafluoropentanesulfonyl chloride and 62 mg (0.612 mmol) of triethylamine in 8 ml of tetrahydrofuran for 1 hour.

Yield: 171 mg (70.9% of theory). $^1$H-NMR (200 MHz, DMSO): 0.93 (t, 3H), 1.53–2.09 (m, 12H), 2.23–2.42 (m, 2H), 2.47 (s, 3H), 3.22 (t, 2H), 3.47 (quin., 1H), 3.97 (t, 2H), 7.17 (d, 1H), 7.37 (dd, 2H), 9.83 (s, 1H), 11.48 (s, 1H); MS (DCI/NH$_3$): 592 (M+H).

EXAMPLE 31

2-[5-Bis(N,N-4,4,5,5,5-pentafluoropentanesulfonyl)amino-2-propoxyphenyl]-5-methyl-7-cyclopentyl-3H-imidazo[5,1-f][1,2,4]-triazin-4-one

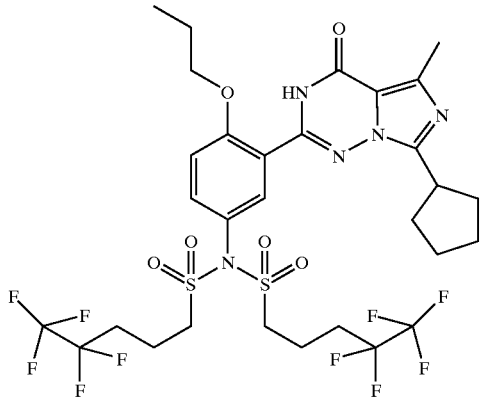

In example 30, 10.2 mg (4.20% of theory) of the bis derivative are isolated as a by-product.

MS (ESI): 816 (M+H), TLC: R$_f$=0.74 (toluene:ethyl acetate:formic acid=2:7.5:0.5).

EXAMPLE 32

2-[5-Bis(N,N-4,4,4-trifluoro-1-butanesulfonyl)amino-2-propoxyphenyl]-5-methyl-7-cyclopentyl-3H-imidazo[5,1-f][1,2,4]-triazin-4-one

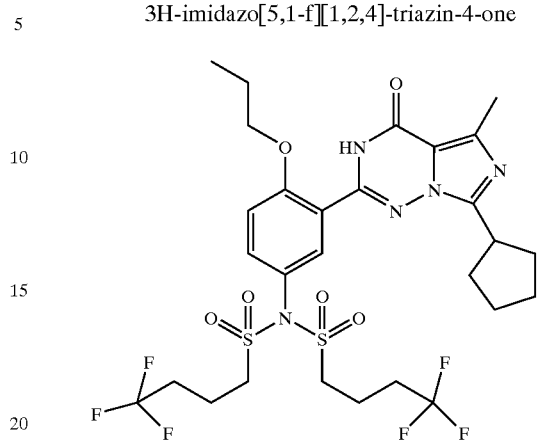

150 mg (0.408 mmol) of the compound from example 44A are reacted with 529 mg (2.512 mmol) of 4,4,4-trifluoro-1-butanesulfonyl chloride and 0.49 ml (3.516 mmol) of triethylamine in 12 ml of tetrahydrofuran for 5 hours.

Yield: 194 mg (66.8% of theory). $^1$H-NMR (200 MHz, DMSO): 0.95 (t, 3H), 1.53–2.15 (m, 18H), 2.47 (s, 3H), 3.50 (quin., 1H), 3.80 (t, 4H), 4.08 (t, 2H), 7.28 (d, 1H), 7.62 (m, 2H), 11.62 (s, 1H); MS (ESI): 716 (M+H).

EXAMPLE 33

2-[5-Bis(N,N-3-trifluoromethylbenzenesulfonyl)amino-2-propoxyphenyl]-5-methyl-7-cyclopentyl-3H-imidazo[5,1-f][1,2,4]-triazin-4-one

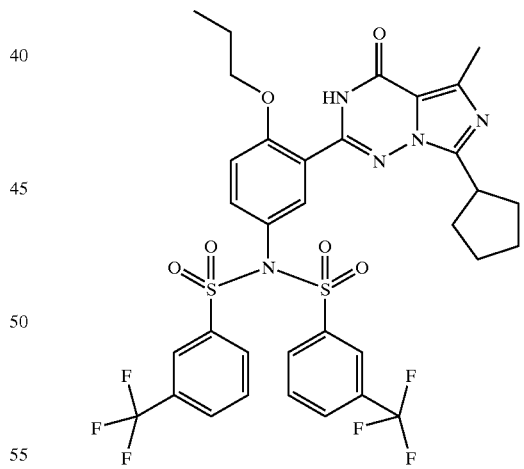

150 mg (0.408 mmol) of the compound from example 44A are reacted with 399 mg (1.632 mmol) of 3-(trifluoromethyl)benzenesulfonyl chloride and 0.239 ml (1.714 mmol) of pyridine in 8 ml of tetrahydrofuran for 3 hours.

Yield: 169 mg (52.8% d.Th.). $^1$H-NMR (200 MHz, DMSO): 0.95 (t, 3H), 1.57–2.00 (m, 10H), 2.47 (s, 3H), 3.42 (m, 1H), 4.07 (t, 2H), 7.22 (s, 1H), 7.27 (s, 2H), 7.97 (t, 2H), 8.07 (s, 2H), 8.17 (d, 2H), 8.27 (d, 2H), 11.57 (s, 1H); MS (ESI): 784 (M+H).

EXAMPLE 34

2-(2-Propoxy-5-propanesulfonylaminophenyl)-5-methyl-7-cyclopentyl-3H-imidazo[5,1-f][1,2,4]-triazin-4-one

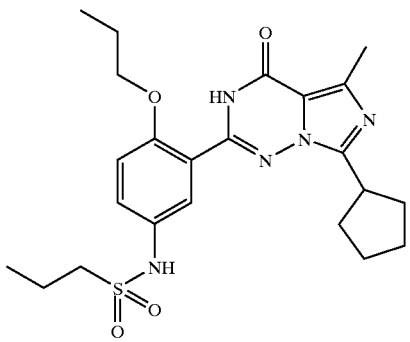

150 mg (0.408 mmol) of the compound from example 44A are treated with 116 mg (0.816 mmol) of 1-propanesulfonyl chloride and 87 mg (0.816 mmol) of triethylamine in 15 ml of tetrahydrofuran for 1 hour.

Yield: 72.6 mg (37.6% of theory). $^1$H-NMR (300 MHz, DMSO): 0.94 (quar, 6H), 1.58–2.05 (m, 12H), 2.48 (s, 3H), 3.02 (m, 2H), 3.45 (quin., 1H), 3.98 (t, 2H), 7.13 (d, 1H), 7.34 (dd, 1H), 7.40 (d, 1H), 9.63 (s, 1H), 11.40 (s, 1H); MS (ESI): 474 (M+H).

EXAMPLE 35

2-[5-Bis(N,N-propanesulfonyl)amino-2-propoxyphenyl]-5-methyl-7-cyclopentyl-3H-imidazo[5,1-f][1,2,4]-triazin-4-one

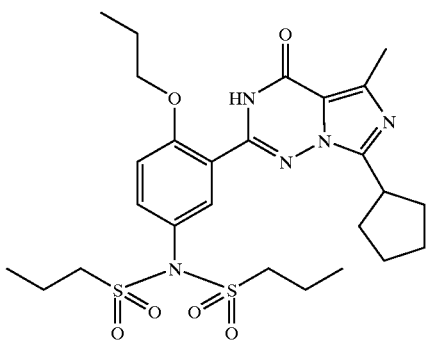

In example 34, 73.3 mg (31.0% of theory) of the bis derivative are isolated as a by-product.

$^1$H-NMR (300 MHz, DMSO): 1.00 (tt, 9H), 1.59–2.04 (m, 14H), 2.48 (s, 3H), 3.48 (quin., 1H), 3.64 (t, 4H), 4.07 (t, 2H), 7.23 (d, 1H), 7.62 (m, 2H), 11.56 (s, 1H); MS (ESI): 580 (M+H).

EXAMPLE 36

2-[2-Ethoxy-5-(4-ethylpiperazin-1-yl-sulfonylamino)phenyl]-5-methyl-7-propyl-3H-imidazo[5,1-f][1,2,4]-triazin-4-one

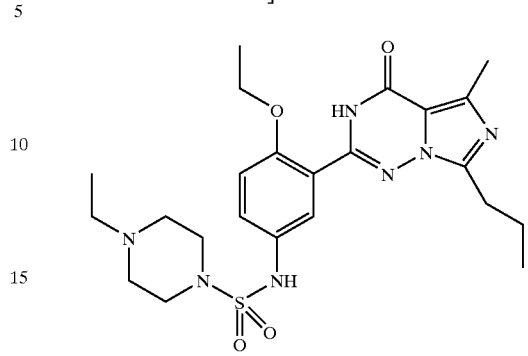

Under argon, 400 mg (1.22 mmol) of the amino compound from example 46A in 19.3 g (244 mmol) of pyridine are reacted with 1.22 g (4.89 mmol) of 4-ethyl-1-piperazinesulfonyl chloride hydrochloride at room temperature for 16 hours. The solution is then concentrated and the residue is taken up in toluene and re-concentrated. The residue is then partitioned between 170 ml of dichloromethane, 10 ml of NaHCO$_3$ solution and 5 ml of water, the organic layer is separated off, the aqueous layer is washed twice with dichloromethane and the organic phase is dried and concentrated. Purification of the crude product is carried out by chromatography on 140 ml of silica gel using ethyl acetate with acetone added in increasing proportions of from 11% to 43%.

Yield: 394 mg (64.0% of theory). TLC: R$_f$=0.48 (acetone).

Formation of the hydrochloride: 383 mg (0.76 mmol) of the free base are dissolved in 2 ml of dichloromethane and stirred with 2 ml of 1 M HCl in ether. 15 ml of ether are then added and the mixture is stirred for 20 minutes, resulting in the precipitation of a solid material which is filtered off with suction, washed with 15 ml of ether and dried under reduced pressure.

Yield: 235 mg (51.1% of theory). $^1$H-NMR (200 MHz, DMSO): 0.95 (t, 3H), 1.24 (m, 6H), 1.80 (hex, 2H), 2.58 (s, 3H), 2.83–3.90 (mm, 12H), 4.08 (quar., 2H), 7.18 (d, 1H), 7.39 (d, 1H) 7.42 (s, 1H), 10.15 (s, 1H), 12.02 (s, 1H); MS (ESI): 504 (M+H).

EXAMPLE 37

2-[2-Ethoxy-5-(morpholinylsulfonamido)phenyl]-5-methyl-7-propyl-3H-imidazo[5,1-f][1,2,4]-triazin-4-one

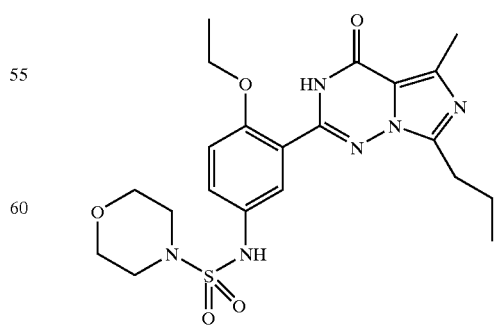

Analogously to the procedure of example 36, 150 mg (0.458 mmol) of the amino compound from example 46A are reacted with 680 mg (3.67 mmol) of morpholine N-sulfonyl chloride in 7.4 ml of pyridine under argon at 40° C. for 8 hours.

Yield: 128 mg (58.5% of theory). MS (DCI/NH$_3$): 477 (M+H), HPLC (analytic): 92.8% RT: 5.13 min, column: Nucleosil C18 (125×4 mm), mobile phase: 0.01 m H$_3$PO$_4$/acetonitrile (gradient), flow rate: 2 ml/min, 200–400 nm.

EXAMPLE 38

2-[2-Ethoxy-5-(4-ethylpiperazin-1-yl-sulfonylamino) phenyl]-7-(1-ethylpropyl)-5-methyl-3H-imidazo[5,1-f][1,2,4]-triazin-4-one

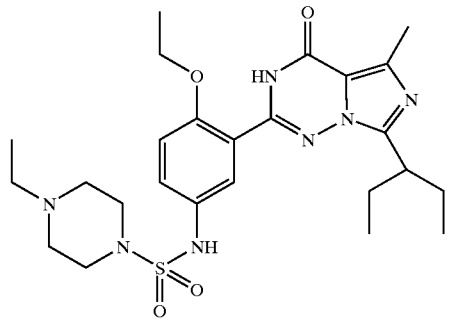

The preparation was carried out analogously to the procedure of example 36 using 150 mg (0.422 mmol) of the amino compound of example 48A and 421 mg (1.69 mmol) of 4-ethylpiperazinesulfonyl chloride hydrochloride in 6.81 ml of pyridine. The crude product is purified by chromatography on 100 ml of silica gel using ethyl acetate and acetone as mobile phase in a gradient system of from 9:1 to 1:1.

Yield: 22.4 mg (10.0% of theory). MS (DCI/NH$_3$): 532 (M+H). HPLC (analytic): 93.5% RT: 4.64 min, column: Nucleosil C18 (125×4 mm), mobile phase: 0.01 m H$_3$PO$_4$/acetonitrile (gradient), flow rate: 2 ml/min, 200–400 nm.

EXAMPLE 39

2-[2-Ethoxy-5-(4-ethylpiperazin-1-yl-sulfonylamino) phenyl]-5-methyl-7-(2-ethyl-heptyl)-3H-imidazo[5,1-f][1,2,4]-triazin-4-one

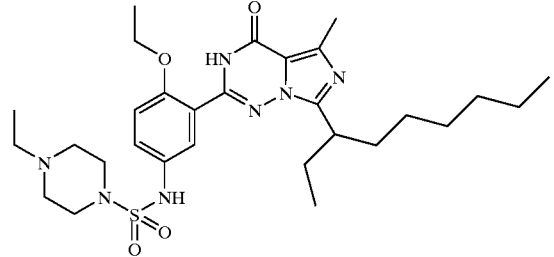

The preparation is carried out analogously to the procedure of example 36 using 120 mg (0.292 mmol) of the amino compound from example 50A and 581 mg (2.33 mmol) of 4-ethyl-piperazinesulfonyl chloride hydrochloride in 4.71 ml of pyridine at room temperature. The crude product is purified by chromatography on 40 ml of silica gel using ethyl acetate and methanol as mobile phase.

Yield: 63.6 mg (37.1% of theory). MS (ESI): 588 (M+H). TLC: R$_f$=0.57 (ethyl acetate:methanol=8:2).

EXAMPLE 40

2-[5-(4-Carboxybenzenesulfonlamino)-2-ethoxyphenyl]-5-methyl-7-(2-ethylheptyl)-3H-imidazo[5,1-f][1,2,4]-triazin-4-one

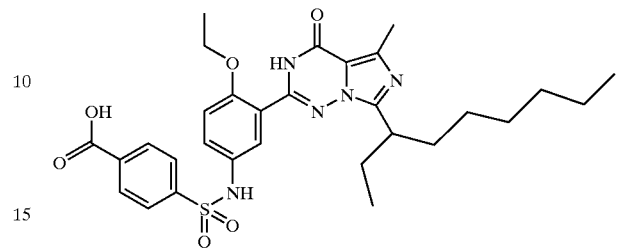

Analogously to the procedure of example 36, 50 mg (0.121 mmol) of the amino compound from example 50A are reacted with 80.4 mg, (0.364 mmol) of 4-chlorosulfonylbenzoic acid and 0.10 ml (1.22 mmol) of pyridine in 6 ml of tetrahydrofuran overnight. The product is purified by chromatography on 40 ml of silica gel using ethyl acetate and methanol as mobile phase in a gradient system of from 95:5 to 8:2.

Yield: 65.4 mg (90.4% of theory). MS (DCI/NH$_3$): 596 (M+H), HPLC (analytic): 90.4% RT: 7.08 min, column: Nucleosil C18 (125×4 mm), mobile phase: 0.01 m H$_3$PO$_4$/acetonitrile (gradient), flow rate: 2 ml/min, 200–400 nm.

EXAMPLE 41

2-[2-Ethoxy-5-(γ-Morpholinopropanesulfonylamino) phenyl]-5-methyl-7-(2-ethyl-heptyl)-3H-imidazo[5,1-f][1,2,4]-triazin-4-one

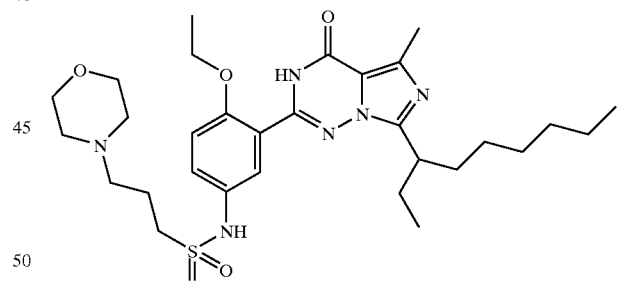

Analogously to the procedure of example 36, 50 mg (0.121 mmol) of the amino compound from example 50A are reacted with 111 mg (0.486 mmol) of γ-morpholinopropanesulfonyl chloride and 0.10 ml (1.22 mmol) of pyridine in 6 ml of tetrahydrofuran overnight. Purification of the product on silica gel using ethyl acetate and methanol as mobile phase gives 66.3 mg (90.5% of theory).

MS (ESI): 603 (M+H), HPLC (analytic): 95.9% RT: 7.05 mm, column: Gromisil ODSB (125×4 mm), mobile phase: 0.01 m H$_3$PO$_4$/acetonitrile (gradient), flow rate: 2 ml/min, 200–400 nm.

EXAMPLE 42

2-[2-Ethoxy-5-(1-methylimidazole-4-sulfonylamino)phenyl]-5-methyl-7-(2-ethylheptyl)-3H-imidazo[5,1-f][1,2,4]-triazin-4-one

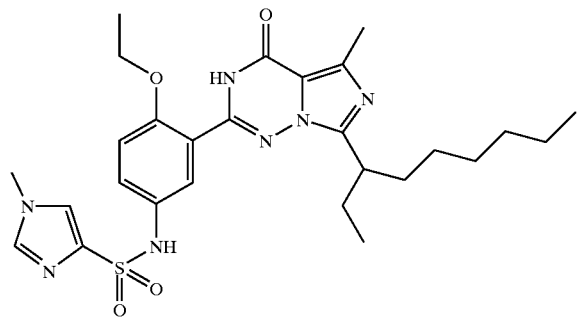

Analogously to the procedure of example 36, 50 mg (0.121 mmol) of the amino compound from example 50A are reacted with 87.8 mg (0.486 mmol) of 1-methylimidazole-4-sulfonyl chloride and 0.10 ml (1.22 mmol) of pyridine in 6 ml of tetrahydrofuran overnight. Purification of the product over silica gel using ethyl acetate and methanol as mobile phase gives 65.2 mg (96.6% of theory).

MS (ESI): 556 (M+H), HPLC (analytic): 92.9% RT: 6.74 min, column: Nucleosil C18 (125×4 mm), mobile phase: 0.01 m $H_3PO_4$/acetonitrile (gradient), flow rate: 2 ml/min, 200–400 nm.

EXAMPLE 43

2-[2-Ethoxy-5-methylsulfonylaminophenyl]-5-methyl-7-(2-ethylheptyl)-3H-imidazo-[5,1-f][1,2,4]-triazin-4-one

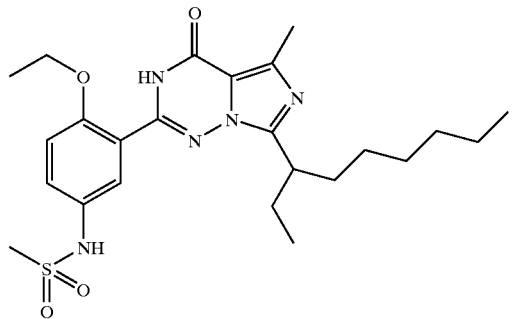

Analogously to the procedure of example 36, 50 mg (0.121 mmol) of the amino compound from example 50A are reacted with 55.7 mg (0.486 mmol) of methanesulfonyl chloride and 0.10 ml (1.22 mmol) of pyridine in 6 ml of tetrahydrofuran overnight. Purification of the product on silica gel using toluene and ethyl acetate from 8:2 to 5:5 gives 23.4 mg (39.3% of theory).

MS (ESI): 490 (M+H), TLC: $R_f$=0.47 (toluene:ethyl acetate=2:8).

EXAMPLE 44

2-[2-Ethoxy-5-isopropylsulfonylaminophenyl]-5-methyl-7-(2-ethylheptyl)-3H-imidazo[5,1-f][1,2,4]-triazin-4-one

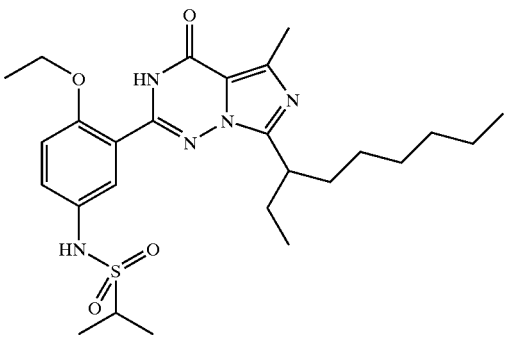

Analogously to the procedure of example 36, 50 mg (0.121 mmol) of the amino compound from example 50A are reacted with 333 mg (2.34 mmol) of isopropylsulfonyl chloride and 0.12 ml (1.46 mmol) of pyridine in 6 ml tetrahydrofuran overnight. Purification of the product on 40 ml of silica gel using ethyl acetate and methanol as mobile phase gives 37.0 mg (49.0% of theory).

MS (DCI/NH$_3$): 518 (M+H), TLC: $R_f$=0.65 (toluene:ethyl acetate=2:8).

EXAMPLE 45

2-[2-Ethoxy-5-(4-morpholinylsulfonamido)phenyl]-5-methyl-7-(2-ethylhleptyl)-3H-imidazo[5,1-f][1,2,4]-triazin-4-one

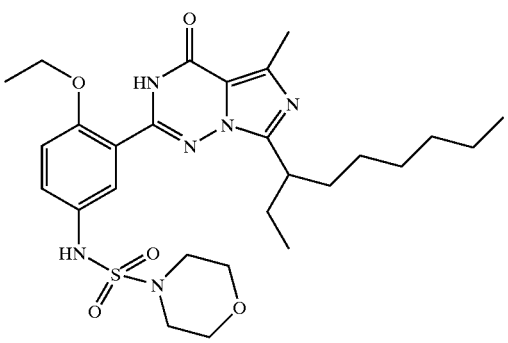

Analogously to the procedure of example 36, 50 mg (0.121 mmol) of the amino compound from example 50A are reacted with 360 mg (1.94 mmol) of morpholine N-sulfonyl chloride and 0.10 ml (1.22 mmol) of pyridine in tetrahydrofuran overnight. Purification of the crude product on 40 ml of silica gel using toluene and ethyl acetate, 6:4 to 5:5, as mobile phase gives 9.3 mg (13.7% of theory).

MS (ESI): 561 (M+H), HPLC (analytic): 94.8% RT: 7.74 min, column: Nucleosil C18 (125×4 mm), mobile phase: 0.01 m $H_3PO_4$/acetonitrile (gradient), flow rate: 2 ml/min, 200–400 nm.

EXAMPLE 46

2-[2-Ethoxy-5-(4-morpholinocarbonylamino)phenyl]-5-methyl-7-cyclopentyl-3H-imidazo[5,1-f][1,2,4]-triazin-4-one

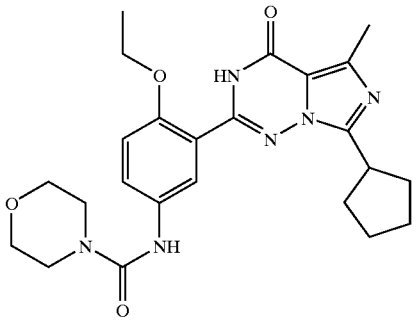

213 mg (0.601 mmol) of the amino compound from example 42A and 0.2 ml (1.43 mmol) of triethylamine are dissolved in 6 ml of tetrahydrofuran; the solution is cooled to 5° C., and 0.489 ml (4.22 mmol) of 4-morpholinocarbonyl chloride, dissolved in 4 ml of tetrahydrofuran, is injected. The reaction solution is stirred at room temperature overnight, ethyl acetate, $NH_4Cl$ solution and $NaHCO_3$ solution are added, the organic phase is separated off, the aqueous phase is re-extracted 3 times with ethyl acetate and the organic phases are combined, dried and concentrated. The product is chromatographed on 60 ml of silica gel using ethyl acetate/methanol as mobile phase.

Yield: 275 mg (98% of theory). $^1$H-NMR (200 MHz, DMSO): 1.30 (t, 3H), 1.58–2.07 (m, 8H), 2.48 (s, 3H), 3.12 (t, 4H), 3.41 (quin., 1H), 3.55 (t, 4H), 4.08 (quar., 2H), 7.08 (d, 1H), 7.55–7.62 (m, 2H), 8.56 (s, 1H).

EXAMPLE 47

2-[5-(3,4-Dimethoxyphenylacetylamino)-2-ethoxyphenyl]-5-methyl-7-cyclopentyl-3H-imidazo[5,1-f][1,2,4]-triazin-4-one

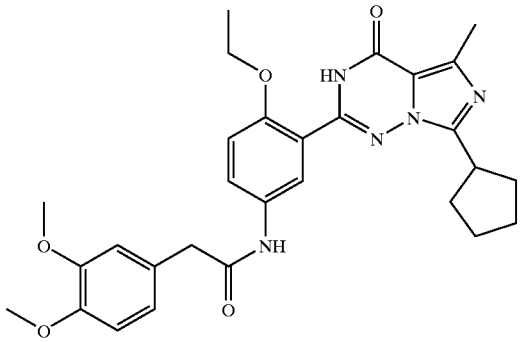

Analogously to the preparation of example 46, 100 mg (0.283 mmol) of the compound from example 42A are reacted with 182 mg (0.849 mmol) of 3,4-dimethoxyphenylacetyl chloride and 0.23 ml (2.84 mmol) of pyridine in 6 ml of tetrahydrofuran.

Yield: 141 mg (93.9% of theory). $^1$H-NMR (400 MHz, DMSO): 1.30 (t, 3H), 1.57–2.05 (m, 8H), 2.47 (s, 3H), 3.45 (quin., 1H), 3.53 (s, 2H), 3.73 (d, 6H), 4.07 (quar., 2H), 6.82–6.95 (m, 2H), 7.10 (d, 2H), 7.73 (m, 2H), 10.12 (s, 1H), 11.50 (s, 1H); MS (ESI): 532 (M+H).

EXAMPLE 48

2-[5-(1,4-Di-tert-butyloxycarbonyl-(±)-piperazine-2-carbonylamino)-2-ethoxyphenyl]-5-methyl-7-cyclopentyl-3H-imidazo[5,1-f][1,2,4]-triazin-4-one

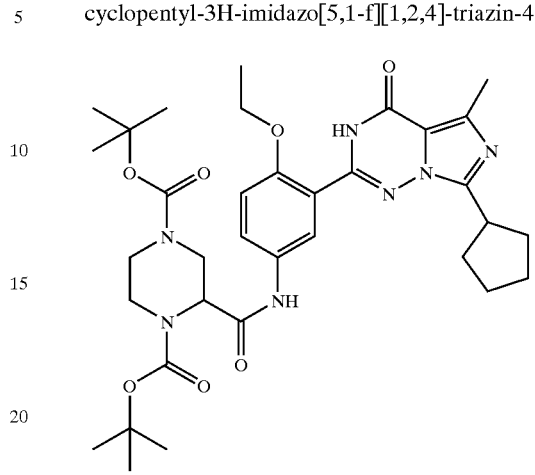

110 mg (0.311 mmol) of the amino compound from example 42A and 247 mg (0.747 mmol) of N,N'-di-tert-butyloxycarbonyl(±)-piperazine-2-carboxylic acid are stirred at room temperature in 30 ml of dichloromethane with 154 mg (0.747 mmol) of dicyclohexylcarbodiimide for 2 days. The reaction solution is poured onto 120 ml of silica gel and washed with dichloromethane, and the product is then eluted using cyclohexane and ethyl acetate in a gradient system of from 8:2 to 1:1.

Yield: 203 mg (98.0% of theory). $^1$H-NMR (200 MHz, DMSO): 1.12–1.44 (m, 21H), 1.57–2.07 (m, 8H), 2.45 (s, 3H), 2.76–3.04 (m, 1H), 3.38–3.94 (m, 5H), 4.08 (quar, 2H), 4.28–4.58 (m, 2H), 7.13 (d, 1H), 7.70 (m, 2H), 10.16 (s, 1H), 11.52 (s, 1H); MS (DCI/$NH_3$): 666 (M+H).

EXAMPLE 49

2-[2-Ethoxy-5-((±)-piperazine-2-carbonylamino)phenyl]-5-methyl-7-cyclopentyl-3H-imidazo[5,1-f][1,2,4]-triazin-4-one

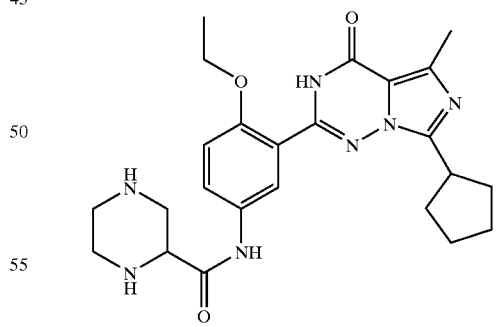

132 mg (0.198 mmol) of the compound from example 48 are treated with 5 ml of trifluoroacetic acid for 90 minutes the solution is then concentrated dichloromethane and 10% strength $NaHCO_3$ solution are added to the residue and the organic phase is dried and concentrated under reduced pressure.

Yield: 59.4 mg (64.4% of theory). $^1$H-NMR (200 MHz, $CDCl_3$): 1.51 (t, 3H), 1.61–2.21 (m, 10H), 2.64 (s, 3H), 2.80–3.07 (m, 5H), 3.22 (dd, 1H), 3.48 (dd, 1H), 3.66 (quin., 1H), 4.20 (quar, 2H) 7.00 (d, 1H), 7.94 (dd, 1H), 8.07 (d, 1H) 9.12 (s, 1H).

EXAMPLE 50

2-[2-Ethoxy-5-(4-methylpiperazineacetylamino) phenyl]-5-methyl-7-cyclopentyl-3H-imidazo[5,1-f] [1,2,4]-triazin-4-one

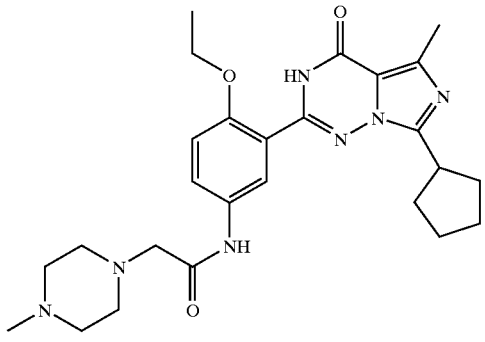

Analogously to the preparation of example 48, 60 mg (0.17 mmol) of the amino compound from example 42A are reacted with 64.5 mg (0.407 mmol) of 4-methyl-1-piperazineacetic acid in the presence of 84.1 mg (0.407 mmol) of dicyclohexylcarbodiimide in 20 ml of dichloromethane for 4 days.

Yield: 75.6 mg (90.2% of theory). MS (ESI): 494 (M+H), HPLC (analytic): 66.0% RT: 2.13 min, column: Nucleosil C18 (125×4 mm), mobile phase: 75% $H_2O$ with 1% trifluoroacetic acid 25% acetonitrile, flow rate: 2 ml/min, 200–400 nm.

EXAMPLE 51

2-[5-(4-Morpholinocarbonylamino)-2-propoxyphenyl]-5-methyl-7-cyclopentyl-3H-imidazo [5,1-f][1,2,4]-triazin-4-one

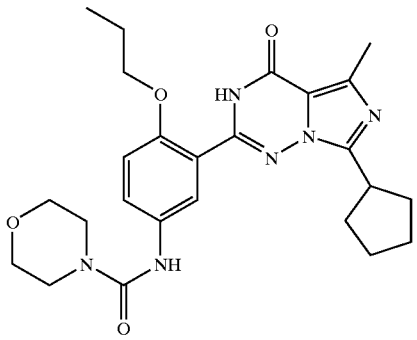

Unter argon, 0.32 g (4.082 mmol) of pyridine and, a little at a time, 0.449 g (3.0 mmol) of 4-morpholino-N-carbonyl chloride are added to 150 mg (0.408 mmol) of the amino compound from example 44A in 6 ml of tetrahydrofuran, and the mixture is stirred at room temperature overnight. The reaction solution is diluted with ethyl acetate and water, the aqueous phase is re-extracted with ethyl acetate and the combined organic phases are dried and concentrated under reduced pressure. The residue is chromatographed on 50 ml of silica gel using toluene and ethyl acetate in a gradient system.

Yield: 139 mg (70.7% of theory). $^1$H-NMR (300 MHz, DMSO): 0.93 (t, 3H), 1.57–2.08 (m, 10H), 2.48 (s, 3H), 3.42 (t, 4H), 3.50 (quin., 1H), 3.61 (t, 4H), 3.97 (t, 2H), 7.08 (d, 1H), 7.60 (m, 2H), 8.58 (s, 1H), 11.47 (s, 1H); MS (ESI): 481 (M+H).

EXAMPLE 52

2-[2-Ethoxy-5-(1,4-di-tert-butyloxycarbonyl-(±)-piperazine-2-carbonylamino)-phenyl]-5-methyl-7-(2-ethylheptyl)-3H-imidazo[5,1-f][1,2,4]-triazin-4-one

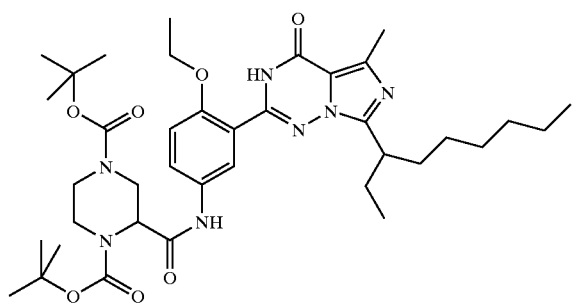

Analogously to the procedure of example 48, 186 mg (0.452 mmol) of the amino compound from example 50A are reacted with 358 mg (1.085 mmol) of N,N-di-tert-butyloxycarbonyl-(±)-piperazine-2-carboxylic acid in the presence of 224 mg (1.085 mmol) of dicyclohexylcarbodiimide in 20 ml of dichloromethane for 2 days. The crude product is purified by chromatography on 150 ml of silica gel eluted with cyclohexane and ethyl acetate in gradient system of from 8:2 to 1:1.

Yield: 295 mg (90.2% of theory). MS (DCI/NH$_3$): 724 (M+H), HPLC (analytic): 98.0% RT: 6.68 min, column: Nucleosil C18 (125×4 mm), mobile phase: 0.01 m H$_3$PO$_4$/acetonitrile (gradient), flow rate: 2 ml/min, 200–400 nm.

EXAMPLE 53

2-[2-Ethoxy-5-(1,4-di-tert-butyloxycarbonyl-(±)-piperazine-2-carbonylamino)-phenyl]-5-methyl-7-(2-ethylheptyl)-3H-imidazo[5,1-f][1,2,4]-triazin-4-one

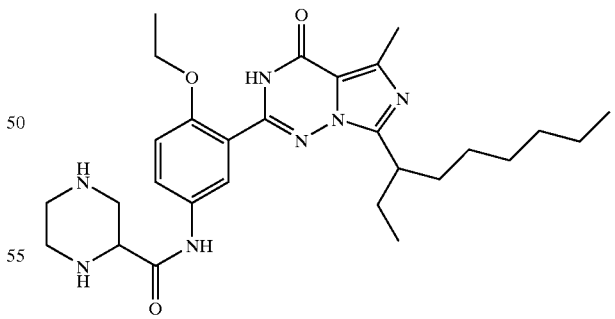

Analogously to the procedure of example 49, 358 mg (0.495 mmol) of the compound from example 52 are treated with 15 ml of trifluoroacetic acid.

Yield: 260 mg (100% of theory). $^1$H-NMR (200 MHz, CDCl$_3$): 0.82 (quar, 6H), 1.06–1.35 (m, 9H), 1.53 (t, 3H), 1.62–1.98 (m, 7H), 2.64 (s, 3H), 2.80–3.41 (mm, 6H), 3.48 (quin., 1H), 4.21 (quar., 2H), 7.00 (d, 1H), 7.95 (dd, 1H), 8.01 (dd, 1H), 9.00 (s, 1H); MS (DCI/NH$_3$): 524 (M+H), HPLC (analytic): 97.6% RT: 4.57 min, column: Gromsil ODSB (250×4.6 mm), mobile phase: water/acetonitrile (gradient), flow rate: 2 ml/min, 200–400 nm.

EXAMPLE 54

1-{3-(7-Cyclopentyl-5-methyl-4-oxo-3,4-dihydroimidazo[5,1-f][1,2,4]-triazin-2-yl)-4-propoxyphenyl}-3-(4-trifluoromethylthiophenyl)-urea

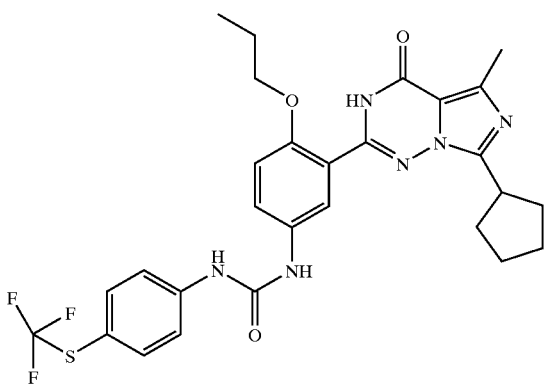

Unter argon, 179 mg (0.816 mmol) of 4-(trifluoromethylthio)phenyl isocyanate, dissolved in 4 ml of tetrahydrofuran, are added to a solution of 150 mg (0.408 mmol) of the amino compound from example 44A in 8 ml of tetrahydrofuran, and the mixture is stirred at room temperature for 1 hour. Ethyl acetate, water and 6 ml of NH$_4$Cl solution are added to the reaction solution, the organic phase is separated off, the aqueous layer is re-extracted with ethyl acetate and the combined organic phases are dried and concentrated under reduced pressure. The residue is chromatographed on 40 ml of silica gel using toluene and ethyl acetate in a gradient system of from 9:1 to 6:4.

Yield: 77.7 mg (32.4% of theory). $^1$H-NMR (200 MHz, DMSO): 0.95 (t, 3H), 1.52–2.10 (m, 10H), 2.47 (s, 3H), 3.50 (quin., 1H), 3.98 (t, 2H), 7.12 (d, 1H), 7.60 (s, 6H), 8.82 (s, 1H), 9.08 (s, 1H), 11.47 (s, 1H); MS (DCI/NH$_3$): 587 (M+H).

Additionally, a 2nd fraction contaminated with a little starting material is obtained (185 mg=77.3% of theory).

EXAMPLE 55

1-{3-(7-(1-Ethylpropyl)-5-methyl-4-oxo-3,4-dihydroimidazo[5,1-f][1,2,4]-triazin-2-yl)-4-ethoxyphenyl}-3-(4-trifluoromethylthiophenyl)-urea

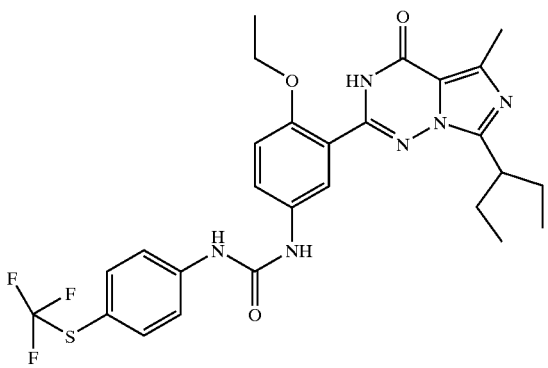

Analogously to the procedure of example 54, 230 mg (0.647 mmol) of the amino compound from example 48A are reacted with 284 mg (1.29 mmol) of 4-(trifluoromethylthio)phenyl isocyanate in 20 ml of tetrahydrofuran for 4 hours. The crude product is purified by silica gel chromatography using toluene and ethyl acetate as mobile phase.

Yield: 138 mg (37.2% of theory). $^1$H-NMR (200 MHz, DMSO): 0.77 (t, 6H), 1.30 (t, 3H), 1.63–1.81 (m, 4H), 2.50 (s, 3H), 3.11 (quin., 1H), 4.09 (quar, 2H), 7.12 (d, 1H), 7.56 (d, 1H), 7.62 (s, 4H), 7.68 (d, 1H), 8.34 (s, 1H), 13.52 (s, 1H); MS (ESI): 575 (M+H).

EXAMPLE 56

1-{3-(7-(1-Ethylpropyl)-5-methyl-4-oxo-3,4-dihydroimidazo[5,1]-f][1,2,4]-triazin-2-yl)-4-ethoxyphenyl}-3-(4-fluorophenylsulfonyl)-urea

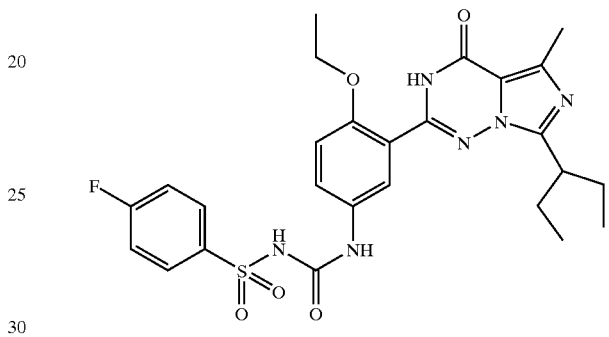

The preparation was carried out analogously to the procedure of example 54 using 230 mg (0.647 mmol) of the amino compound from example 48A and 260 mg (1.294 mmol) of 4-fluorobenzenesulfonyl isocyanate in 15 ml of tetrahydrofuran. The mixture is stirred at room temperature for 4 hours, and the crude product is then isolated on silica gel using toluene and ethyl acetate.

Yield: 54.6 mg (15.2% of theory). MS (ESI): 557 (M+H), HPLC (analytic): 70.0% RT: 6.68 min, column: Nucleosil C18 (125×4 mm), mobile phase: 0.01 m H$_3$PO$_4$/acetonitrile (gradient), flow rate: 2 ml/min, 200–400 nm.

EXAMPLE 57

1-{3-(7-Cyclopentyl-5-methyl-4-oxo-3,4-dihydroimidazo[5,1-f][1,2,4]-triazin-2-yl)-4-propoxyphenyl}-3-(4-fluorophenylsulfonyl)-urea

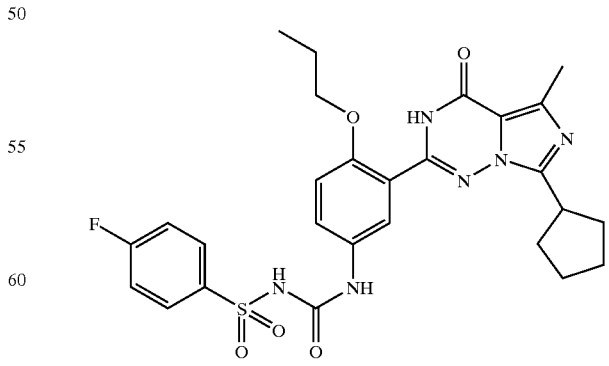

The preparation is carried out analogously to the procedure of example 54 using 150 mg (0.408 mmol) of the amino compound from example 44A and 411 mg (2.04 mmol) of 4-fluorobenzenesulfonyl isocyanate in 12 ml of tetrahydrofuran, which are reacted overnight.

Yield: 163 mg (70.1% of theory). $^1$H-NMR (400 MHz, DMSO): 0.90 (t, 3H), 1.54–2.08 (m, 10H), 2.45 (s, 3H), 3.45 (quin., 1H), 3.88 (t, 2H), 6.92 (d, 1H), 7.17 (t, 2H), 7.53 (d, 1H), 7.63 (s, 1H), 7.82 (m, 2H), 8.47 (s, 1H), 11.37 (s, 1H); MS (ESI): 569 (M+H).

EXAMPLE 58

1-{3-[7-(2-Ethylheptyl)-5-methyl-4-oxo-3,4-dihydroimidazo[5,1-f][1,2,4]-triazin-2-yl]-4-ethoxyphenyl}-3-(4-fluorophenylsulfonyl)-urea

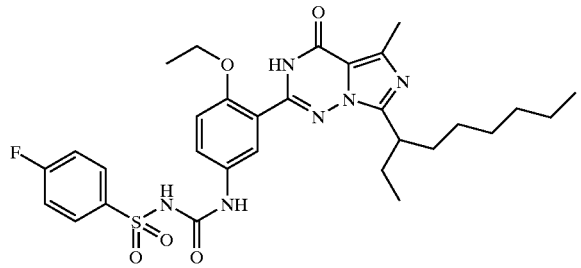

Analogously to the procedure of example 54, 50 mg (0.121 mmol) of the amino compound from example 50A are reacted with 548 mg (2.72 mmol) of 4-fluorobenzenesulfonyl isocyanate in tetrahydrofuran for 2 days. Purification of the crude product on silica gel using toluene and ethyl acetate, 4:6 to 3:7, as mobile phase, gives 36.2 mg (48.6% of theory).

MS (ESI): 613 (M+H), HPLC (analytic): 81.0% RT: 4.92 min, column: Nucleosil C18 (125×4 mm), mobile phase: 0.01 m $H_3PO_4$/acetonitrile (gradient), flow rate: 2 ml/min, 200–400 nm.

EXAMPLE 59

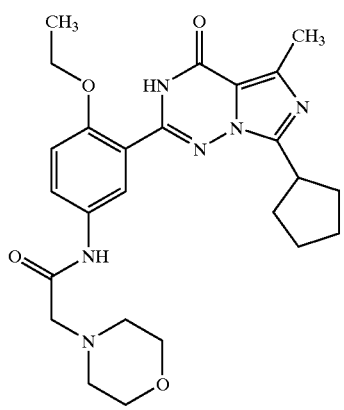

12.4 µl (0.16 mmol) of chloroacetyl chloride were slowly added dropwise to a solution of 50 mg (0.14 mmol) of the amine example 42A in 1,2-dichloroethane and 21.6 µl (0.16 mmol) of $Et_3N$. After 2 h, 1 ml of sat. $NaHCO_3$ solution was added and the mixture was filtered through 1 g of Extrelut ($CH_2Cl_2$). The crude product was re-dissolved in 1,2-dichloroethane, 87.1 µl (0.34 mmol) of morpholine were added and the mixture was heated at 100° C. for 10 h. The mixture was stirred at room temperature overnight, 0.5 ml of sat. $NaHCO_3$ solution was added and the mixture was filtered through 500 mg of Extrelut/500 mg of $SiO_2$ (ethyl acetate). The concentrated crude product was purified by preparative thin-layer chromatography ($CH_2Cl_2$:MeOH= 15:1). This gave 18.9 mg (34.5%) of the desired product (81% pure according to HPLC).

MS (ESI): m/z (%) 481 [M+H] (100) $^1$H-NMR (200 MHz, $D_6$-DMSO): δ=1.29 (t, 3H, $CH_3$), 1.55–2.05 (m, 8H, $CH_2$), 3.12 (s, 2H, $CH_2$), 3.45 (m, 1H, CH), 3.63 (t, 4H, $CH_2$), 4.07 (g, 2H, $CH_2$), 7.11 (d, 1H), 7.76 (m, 2H), 9.78 (bs, 1H, NH), 11.53 (bs, 1H, NH).

EXAMPLE 60

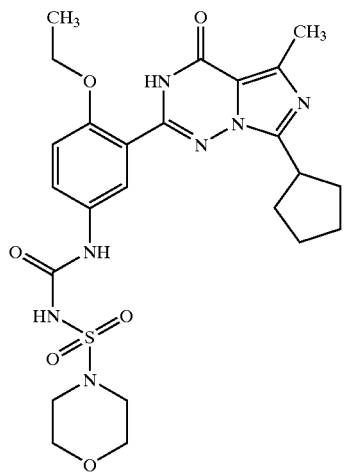

12.3 µl (0.014 mmol) of chlorosulfonyl isocyanate were slowly added dropwise to a solution, cooled to 0° C. of 50 mg (0.014 mmol) of the amine example 42A in 1,2-dichloroethane. The mixture was allowed to warm to room temperature and then stirred for another hour, and 12.3 mg (0.014 mmol) of morpholine and 1 equivalent of morpholinomethyl-polystyrene (3.47 mmol/g) were added. The mixture was stirred overnight and then filtered through 1 g of silica gel (ethyl acetate), and the crude product was purified by preparative thin-layer chromatography ($CH_2Cl_2$:MeOH=20:1). This gave 2.3 mg (3.0%) of the sulfonylurea derivative (91% pure according to HPLC)

$^1$H-NMR (200 MHz, $CDCl_3$): δ=1.55 (t, 3H, $CH_3$), 1.64–2.15 (m, 8H), 2.63 (s, 3H, $CH_3$), 3.51 (t, 4H, $CH_2$), 3.64 (m, 1H), 3.78 (t, 4H, $CH_2$), 4.23 (g, 2H, $CH_2$), 6.38 (bs, 1H, NH), 7.02 (d, 1H), 7.73 (dd, 1H), 7.86 (d, 1H), 9.95 (bs, 1H, NH).

EXAMPLE 61

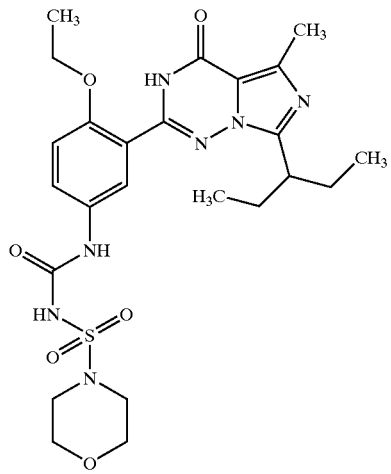

Initially, 7.4 µl (0.08 mmol) of chlorosulfonyl isocyanate were added dropwise to a solution, cooled to 0° C, of 30 mg (0.08 mmol) of the amine example 48A in 1,2-dichloroethane. The mixture was allowed to wain to room temperature and then stirred for another hour, and 7.3 mg (0.08 mmol) of morpholine and a suspension of 30 mg of morpholinomethyl-polystyrene (3.47 mmol/g) in 1,2-dichloroethane were added. After 3 h, the reaction mixture was filtered and the crude product was purified chromatographically (gradient: $CH_2Cl_2+CH_2Cl_2$:MeOH=100+40:1). This gave 4.8 mg (10.9%) of the sulfonylurea (91% pure according to HPLC).

$^1$H-NMR (200 MHz, $D_6$-DMSO): δ=0.75 (t, 6H, $CH_3$), 1.29 (t, 3H, $CH_3$), 1.72 (m, 4H, $CH_2$), 2.53 (s, $CH_3$ shoulder o/$D_6$-DMSO), 3.12 (m, 1H, CH), 3.42 (bt, 4H, $CH_2$), 3.59 (bt, 4H, $CH_2$), 4.06 (g, 2H, $CH_2$), 7.07 (d, 1H), 7.57 (m, 2H), 8.55 (bs, 1H, NH), 11.45 (bs, 1H, NH).

EXAMPLE 62

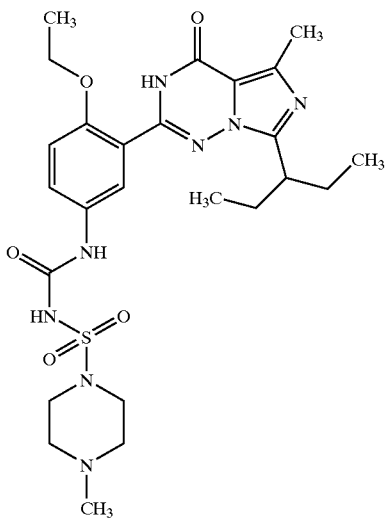

Analogously to example 61, 30 mg (0.08 mmol) of the amine example 48A were converted into 9.5 mg (20.1%) of the sulfonylurea (86% pure according to HPLC).

MS (ESI): m/z (%)=561 [M+H] (30) $^1$H-NMR (300 MHz, $D_3$COD): δ=0.80 (t, 6H, $CH_3$), 1.42 (t, 3H, $CH_3$), 1.83 (m, 4H, $CH_2$, CH), 2.34 (s, 3H $CH_3$), 2.52 (t, 4H, $CH_2$), 2.54 (s, 3H, $CH_3$), 3.57 (t, 4H, $CH_2$), 4.17 (g, 2H, $CH_2$), 7.09 (d, 1H), 7.49 (dd, 1H), 7.69 (d, 1H).

EXAMPLE 63

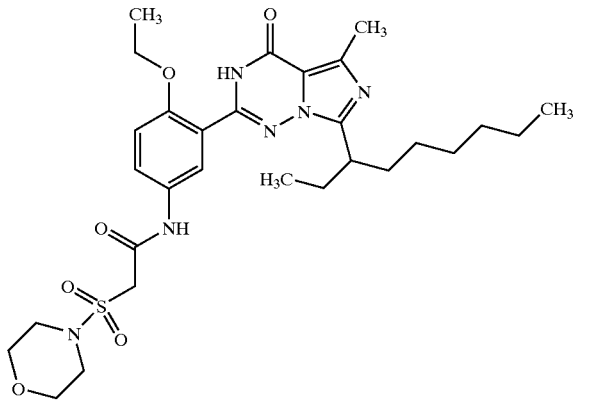

A second solution of 15 mg (0.04 mmol) of the amine example 50A in 1 ml of dioxane was slowly added dropwise to a solution cooled to −78° C., of 3.2 mg (0.02 mmol) of chlorosulfonyl isocyanate in 1 ml of ether. A suspension was formed, which was briefly warmed to 0° C, and then stirred at −78° C. for 1 h, and 12.6 mg (0.14 mmol) of morpholine were then added at 0° C. After 2 h, 2 ml of 1 M $H_2SO_4$ were added, and the mixture was filtered through 3 g of Extrelut (mobile phase: $CH_2Cl_2$). The concentrated crude product was purified by preparative thin-layer chromatography ($CH_2Cl_2$:MeOH=20:1) giving 6.6 mg (30.2%) of the desired product.

MS (ESI): m/z (%)=603 [M+H] (100) $^1$H-NMR (300 MHz, $D_3$COD): δ=0.86 (m, 6H, 2×$CH_3$), 1.24 (m, 8H, 4×$CH_2$), 1.47 (t, 3H, $CH_3$), 1.71–2.02 (m, 4H, 2×$CH_2$), 2.63 (s, 3H, $CH_3$), 3.63–3.85 (m, 7H, 3×$CH_2$, CH), 4.23 (g, 2H, $CH_2O$), 7.18 (d, 1H), 7.76 (dd, 1H), 8.06 (d, 1H).

EXAMPLE 64

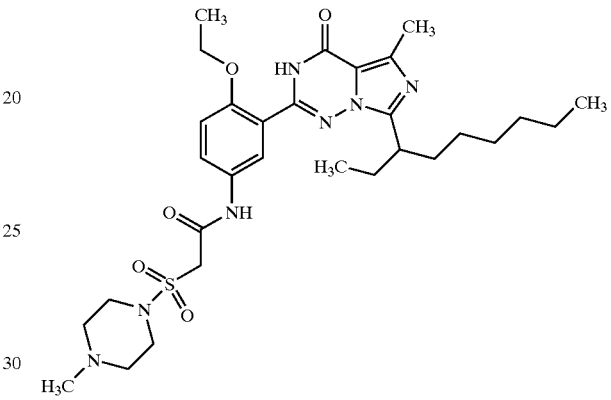

Analogously to example 63, 14.9 mg (0.04 mmol) of the amine example 50A were reacted with 3.2 mg (0.02 mmol) of chlorosulfonyl isocyanate and 14.5 mg (0.14 mmol) of N-methylpiperazine. Preparative thin-layer chromatography gave 2.4 mg (10.8%) of the desired product.

MS (ESI): m/z (%)=616 [M+H] (100) $^1$H-NMR (200 MHz, $CDCl_3$): δ=0.83 (m, 6H, 2×$CH_3$), 1.09–1.34 (m, 11H, 4×$CH_2$ $CH_3$), 1.85 (m, 4H, 2×$CH_2$), 2.31 (s, 3H, $CH_3$), 2.49 (bt, 4H, 2×$CH_2$), 2.65 (s, 3H, $CH_3$), 3.40 (bt, 4H, 2×$CH_2$), 4.01 (s, 2H, $CH_2$), 4.26 (g, 2H, $CH_2$), 7.05 (d, 1H), 7.83 (dd, 1H), 8.13 (d, 1H), 8.29 (bs, 1H).

EXAMPLE 65

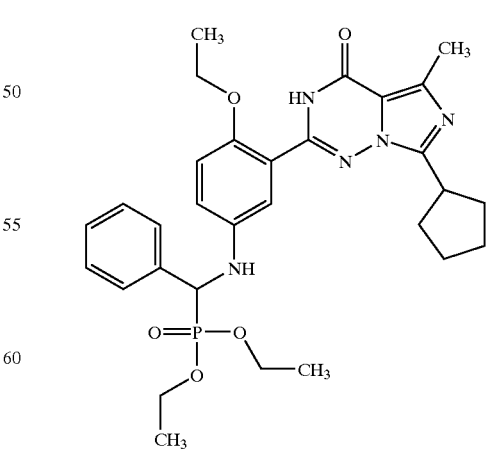

A solution of 50 mg (0.14 mmol) of the amine example 42A, 18.0 mg (0.17 mmol) of freshly distilled benzaldehyde and 23.5 mg (0.17 mmol) of diethyl phosphite was heated at 80° C. for 20 h. The volatile components were removed under high vacuum and the residue was purified chromatographically (gradient: $CH_2Cl_2 + CH_2Cl_2$:MeOH=10:1). The two product-containing fractions were combined and re-purified by preparative thin-layer chromatography ($CH_2Cl_2$:MeOH=20:1). This gave 20.1 mg (24.5%) of the desired product.

MS (ESI): m/z (%)=580 [M+H] (100) $^1$H-NMR (200 MHz, $D_6$-DMSO): δ=1.05 (t, 3H, $CH_3$), 1.22 (m, 9H, 3×$CH_2$), 1.55–2.05 (m, 8H, 4×$CH_2$), 3.65–4.15 (m, 7H, 3×$CH_2$, CH), 5.02 (dd, 1H, CHN), 6.32 (dd, 1H, NH), 6.90 (m, 2H), 7.05 (d, 1H), 7.29 (m, 3H), 7.52 (m, 2H), 11.32 (bs, 1H, NH).

EXAMPLE 66

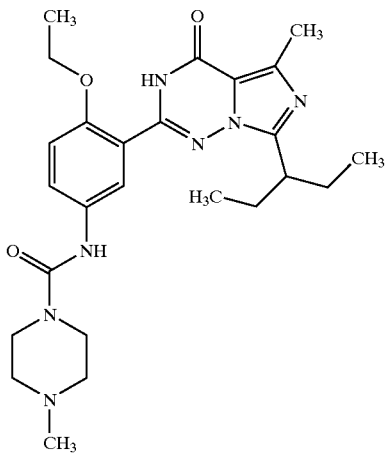

19 μl (0.16 mmol) of diphosgene were added dropwise to a solution of 80 mg (0.23 mmol) of the amine example 48A in 1,4-dioxane, and the mixture was stirred for 20 h. Following concentration under reduced pressure, the residue was twice taken up in benzene and re-concentrated. 30 mg (0.07 mmol) of the resulting carbamoyl chloride were, as a crude product, dissolved in 1 ml of 1,2-dichloroethane, 8.6 mg (0.09 mmol) of N-methylpiperazine were added and the mixture was stirred at room temperature for 20 h. Quenching with 0.5 ml of $H_2O$ and filtration through Extrelut/silica gel ($CH_2Cl_2$:MeOH=95:5) gave 30 mg (87%) of the urea derivative (90% pure according to HPLC).

MS (DCI, $NH_3$): m/z (%) 482 [M+H] (10) $^1$H-NMR (200 MHz, $D_6$-DMSO): δ=0.75 (t, 6H, $CH_3$), 1.28 (t, 3H, $CH_3$), 1.72 (m, 4H, $CH_2$), 2.22 (bt, 4H, $CH_2$), 3.12 (m, 1H, CH), 3.43 (bt, 4H, $CH_2$), 3.91 (s, 3H, $CH_3$), 4.05 (g, 2H, $CH_2$), 7.05 (d, 1H), 7.58 (m, 2H), 8.53 (bs, 1H, NH), 11.48 (bs, 1H, NH).

EXAMPLE 67

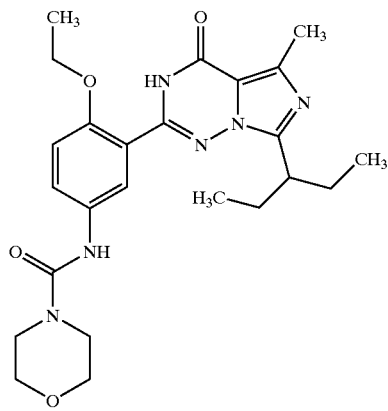

Analogously to example 66, 30 mg (0.08 mmol) of the carbamoyl chloride were reacted with 7.51 (0.09 mmol) of morpholine. For work-up, 0.5 ml of 2 N HCl were added, and the mixture was filtered through 500 mg of Extrelut and 500 mg of $SiO_2$ ($CH_2Cl_2$). This gave 26.2 mg (77.9%) of the urea (95.2% pure according to HPLC).

MS (DCI, $NH_3$): m/z (%) 469 [M+H] (10%); 382 [M−87] (100) $^1$H-NMR (200 MHz, $D_6$-DMSO): δ=0.75 (t, 6H, $CH_3$), 1.28 (t, 3H, $CH_3$), 1.72 (m, 4H, $CH_2$), 3.10 (m, 1H, CH), 3.42 (t, 4H, $CH_2$), 3.59 (t, 4H, $CH_2$), 4.06 (g, 2H, $CH_2$), 7.05 (d, 1H) 7.58 (m, 2H), 8.57 (bs, 1H, NH) 11.49 (bs, 1H, NH)

EXAMPLE 68

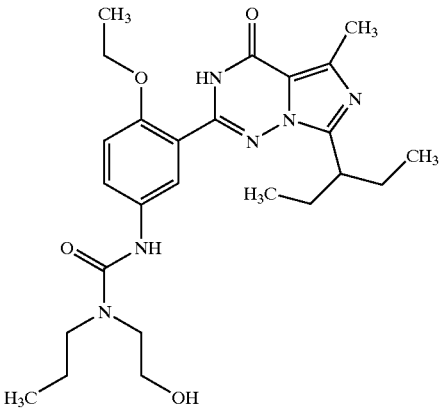

Analogously to example 66, 30 mg (0.08 mmol) of the carbamoyl chloride were reacted to give 33 mg (95%) of the urea (87% pure according to HPLC).

MS (DCI, $NH_3$): m/z (%) 485 [M+H] (10); 382 [M−87] (100) $^1$H-NMR (200 MHz, $D_6$-DMSO): δ=0.74 (t, 6H, $CH_3$), 0.83 (t, 3H, $CH_3$), 1.28 (t, 3H, $CH_3$), 1.50 (m, 2H, $CH_2$), 1.72 (m, 4H, $CH_2$), 3.05–3.61 (m, 6H, $CH_2$), 4.07 (g, 2H, $CH_2$), 7.07 (d, 1H), 7.51 (m, 2H), 8.42 (bs, 1H, NH), 11.49 (bs, 1H, NH).

In parallel synthesis analogously to example 66, the compounds of Table 1 below were prepared from the amine example 48A, diphosgene and the appropriate amine. Neutral end products were quenched with 0.5 ml of 1 molar sulfuric acid solution, basic end products were quenched with 0.5 ml of saturated sodium bicarbonate solution.

| Ex. No. | Structure | MW [g/mol] | HPLC area % at 210 nm | Mz + H |
|---|---|---|---|---|
| 69 | 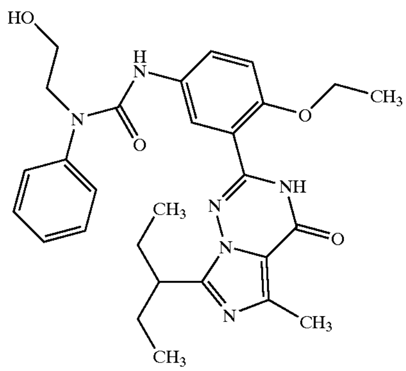 | 518.621 | 80 | 519 |
| 70 | 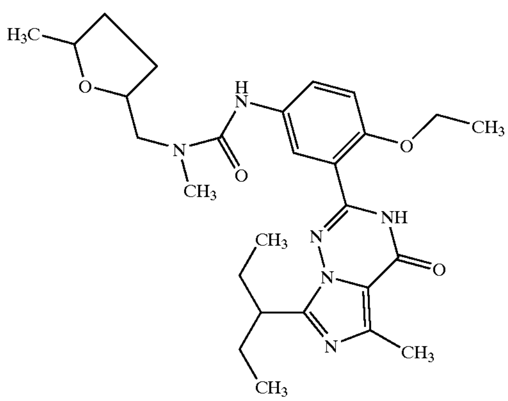 | 510.642 | 87 | 511 |
| 71 | 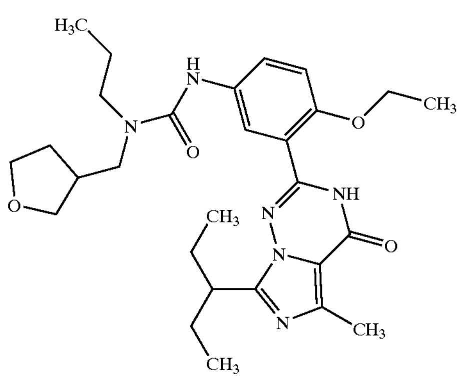 | 524.669 | 76 | 525 |
| 72 | 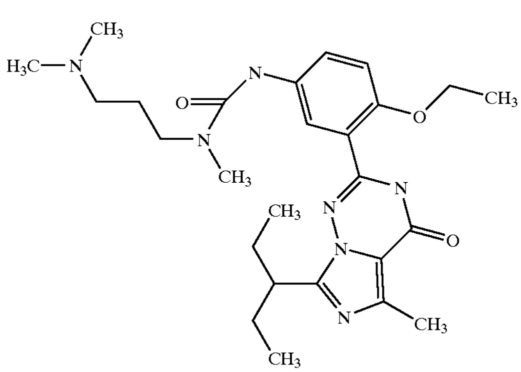 | 497.646 | 69 | 498 |

-continued
| Ex. No. | Structure | MW [g/mol] | HPLC area % at 210 nm | Mz + H |
|---|---|---|---|---|
| 73 | 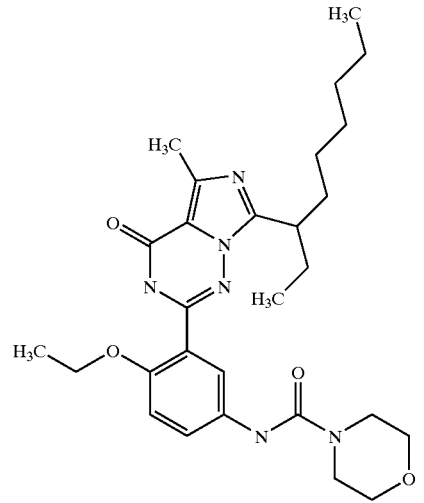 | 524.669 | 82 | 525 |
| 74 | 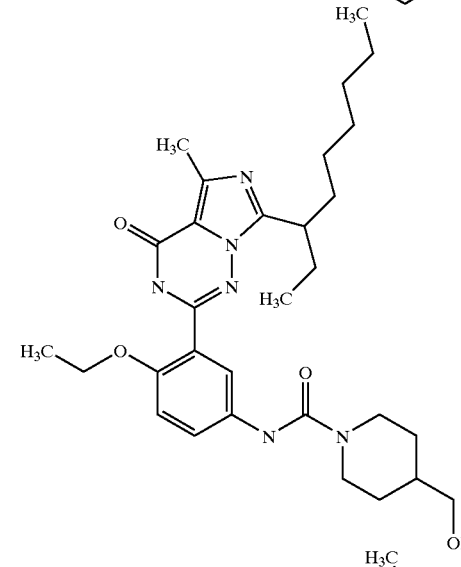 | 552.723 | 82 | 553 |
| 75 | 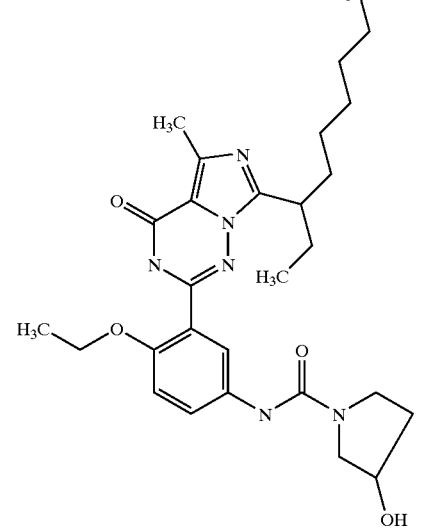 | 524.669 | 72 | 525 |

EXAMPLE 76

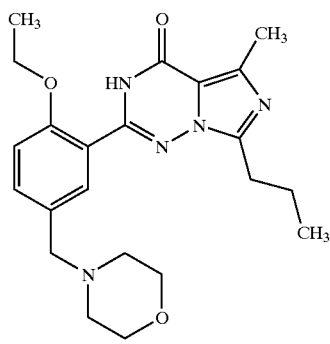

A solution of 300 mg (0.83 mmol) of the chloromethyl compound example 51 A and 217 mg (2.5 mmol) of morpholine in 10 ml of 1,2-dichloroethane was heated at 80° C. for 15 h. The resulting precipitate was filtered off with suction. The concentrated crude product was triturated with ether and filtered, giving a mixture of product and starting material which was purified chromatographically (gradient $CH_2Cl_2$/MeOH=50:1→20:1). This gave 163 mg (47.8%) of the desired product.

MS (ESI): m/z=412 [M+H] (100) $^1$H-NMR (200 MHz, $CDCl_3$): δ=1.05 (t, 3H, $CH_3$); 1.57 (t, 3H, $CH_3$); 1.89 (m, 2H, $CH_2$); 2.48 (bt, 4H, 2×$CH_2$); 2.65 (s, 3H, $CH_3$); 3.02 (t, 2H, $CH_2$); 3.52 (s, 2H, $CH_2$); 3.72 (t, 4H, 2×$CH_2$); 4.25 (g, 2H, $CH_2$); 7.02 (d, 1H); 7.49 (dd, 1H); 8.08 (d, 1H); 9.90 (bs, 1H, NH).

EXAMPLE 77

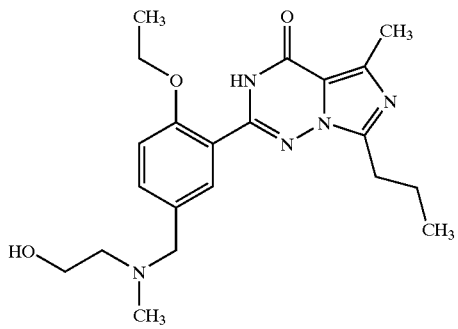

A solution of 300 mg (0.8 mmol) of the chloromethyl compound example 51A and 222 mg (2.5 mmol) of N-ethyl-2-aminoethanol in 10 ml of 1,2-dichloromethane was heated at reflux for 6 hours, cooled and, after filtration, concentrated under reduced pressure. Chromatographic purification (gradient: $CH_2Cl_2$→$CH_2Cl_2$/MeOH=10:1) gave 190 mg (55%) of slightly contaminated product and 68 mg (20%) of purer product.

MS (ESI): m/z=414 [M+H] (100) $^1$H-NMR (200 MHz, $CDCl_3$): δ=1.05 (t, 3H, $CH_3$); 1.09 (t, 3H, $CH_3$); 1.57 (t, 3H, $CH_3$); 1.88 (m, 2H, $CH_2$); 2.63 (m, 4H, 2×$CH_2$); 2.65 (s, 3H, $CH_3$); 3.01 (t, 2H, $CH_2$); 3.59 (t, 2H, $CH_2$); 3.65 (s, 2H, $CH_2$); 4.25 (m, 2H, $CH_2$); 7.02 (d, 1H); 7.43 (dd, 1H); 8.08 (d, 1H); 9.95 (bs, 1H, NH).

EXAMPLE 78

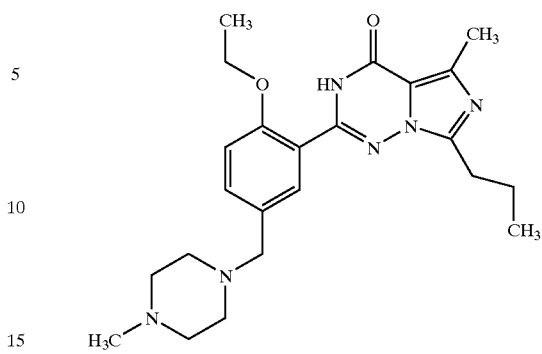

6.7 mg (0.07 mmol) of N-methylpiperazine and 8.4 mg (0.08 mmol) of $Et_3N$ were added to a solution of 20 mg (0.06 mmol) of the chloromethyl compound example 51A in 0.5 ml of 1,2-dichloroethane, and the mixture was stirred at room temperature for 15 h. 0.5 ml of sat. $NaHCO_3$ solution was added, and the mixture was filtered through 500 mg of Extrelut/500 mg of $SiO_2$ (mobile phase: ethyl acetate). The mixture was concentrated and purified by thin-layer chromatography ($CH_2Cl_2$:MeOH=10:1). This gave 7.7 mg (32.7%) of the desired product.

MS (ESI): m/z (%)=425 [M+H] (50) $^1$H-NMR (200 MHz, $CD_3OD$): δ=1.02 (t, 3H, $CH_3$), 1.45 (t, 3H, $CH_3$), 1.84 (m, 2H, $CH_2$), 2.33 (s, 3H, $CH_3$), 2.43–2.65 (m, 8H, 4×$CH_2$), 2.58 (s, 3H, $CH_3$), 2.97 (t, 2H, $CH_2$), 3.56 (s, 2H, $CH_2$), 4.20 (g, 2H, $CH_2$), 7.16 (d, 1H), 7.51 (dd, 1H), 7.72 (d, 1H).

EXAMPLE 79

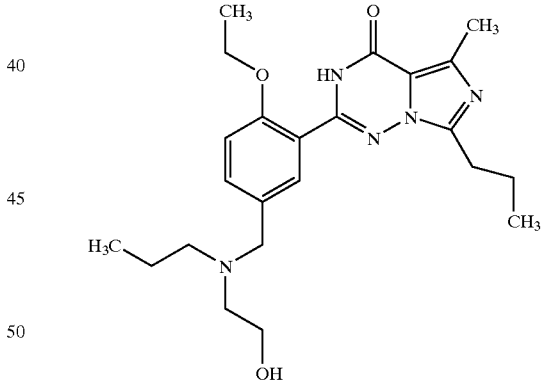

Analogously to example 78, 20 mg (0.06 mmol) of the chloromethyl compound example 51A were reacted with 6.9 mg (0.07 mmol) of N-propyl-2-aminoethanol and 8.4 mg (0.08 mmol) of $Et_3N$. Preparative thin-layer chromatography ($CH_2Cl_2$:MeOH=10:1) gave 3.6 mg (15.2%) of the desired product.

$^1$H-NMR (200 MHz, $CD_3OD$): δ=0.89 (t, 3H, $CH_3$), 0.99 (t, 3H, $CH_3$), 1.44 (t, 3H, $CH_3$), 1.55 (m, 2H, $CH_2$), 1.82 (g, 2H, $CH_2$), 2.48 (t, 2H, $CH_2$), 2.58 (s, 3H, $CH_3$), 2.64 (t, 2H, $CH_2$), 2.96 (t, 2H, $CH_2$), 3.62 (t, 2H, $CH_2$), 3.67 (s, 2H, $CH_2$), 4.18 (g, 2H, $CH_2$), 4.60 (bs, 1H, OH), 7.12 (d, 1H), 7.50 (dd, 1H), 7.73 (d, 1H).

EXAMPLE 80

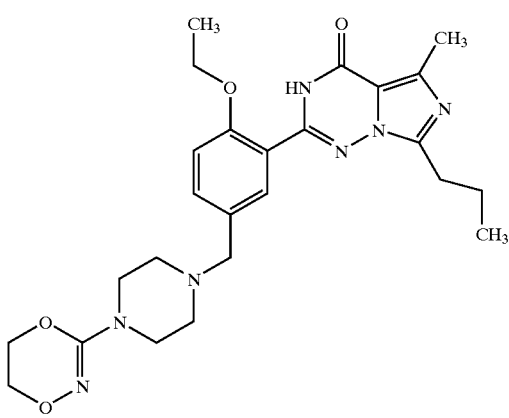

Analogously to example 76, 300 mg (0.83 mmol) of the chloromethyl compound example 51A were reacted with 424 mg (2.5 mmol) of 4-(1-dioxazinyl)piperidine at 80° C. After 15 h, $H_2O$ was added. Repeated chromatographic work-up gave 14.5 mg (3.5%) of the desired product.

MS (ESI): m/z (%)=495 [M+H] (100) $^1$H-NMR (200 MHz, $CDCl_3$): δ=1.05 (t, 3H, $CH_3$), 1.56 (t, 3H, $CH_3$), 1.70–2.10 (m, 8H, 4×$CH_2$), 1.90 (m, 2H, $CH_2$), 2.64 (s, 3H, $CH_3$), 3.02 (t, 2H, $CH_2$), 3.51 (s, 2H, $CH_2$), 4.03 (t, 2H, $CH_2$), 4.25 (g, 2H, $CH_2$), 4.30 (m, 2H, $CH_2$), 7.01 (d, 1H), 7.47 (dd, 1H), 8.05 (d, 1H), 10.91 (bs, 1H, NH).

In a parallel synthesis analogously to example 78, the compounds of the table below were prepared from the chloromethyl compound example 51 A and the appropriate amine. If after 24 h at RT, there was still starting material detected in the TLC, stirring was continued at 60° C. for another 24 h.

| Ex. No. | Structure | MW [g/mol] | HPLC area % at 210 nm | Mz + H |
|---|---|---|---|---|
| 81 | 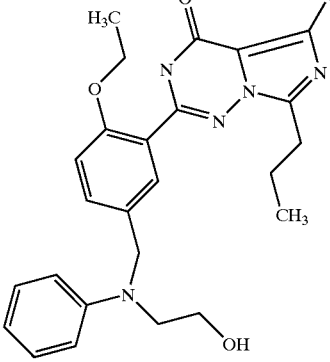 | 461.569 | 51 | 462 |
| 82 | 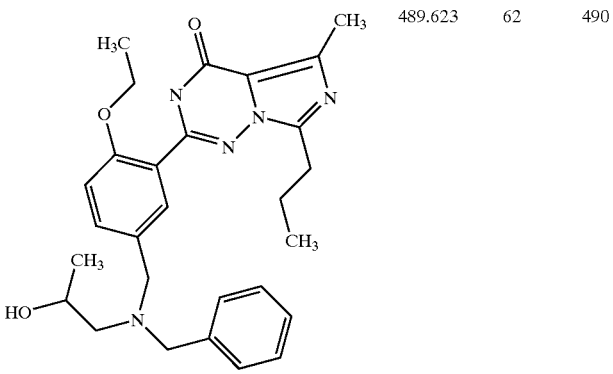 | 489.623 | 62 | 490 |

-continued

| Ex. No. | Structure | MW [g/mol] | HPLC area % at 210 nm | Mz + H |
|---|---|---|---|---|
| 83 | 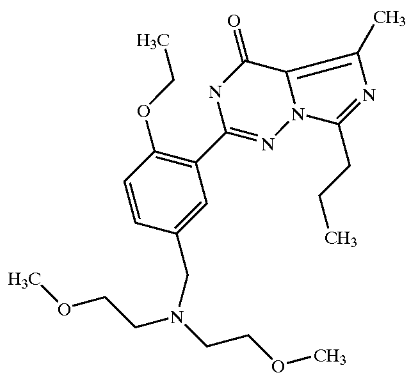 | 457.578 | 45 | 458 |
| 84 | 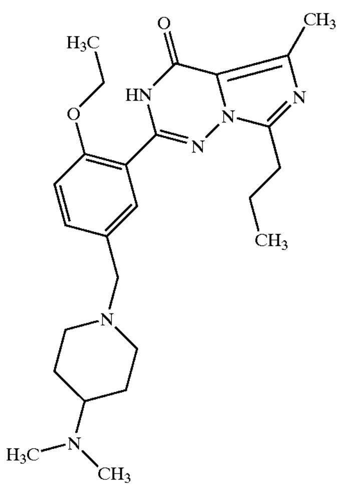 | 453.613 | 66 | 454 |
| 85 | 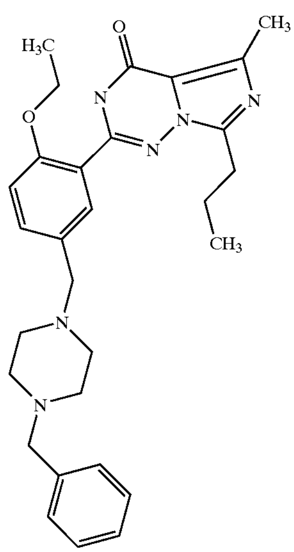 | 500.649 | 56 | 501 |

-continued

| Ex. No. | Structure | MW [g/mol] | HPLC area % at 210 nm | Mz + H |
|---|---|---|---|---|
| 86 | 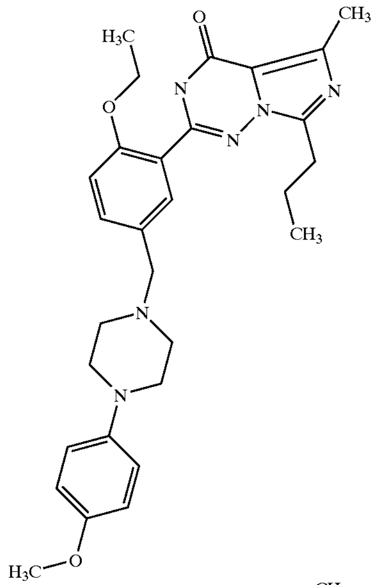 | 516.649 | 53 | 517 |
| 87 | 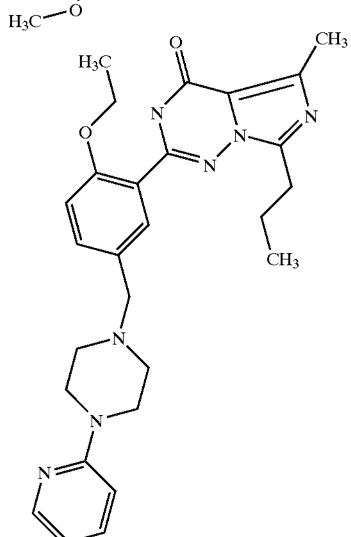 | 487.61 | 64 | 488 |
| 88 | 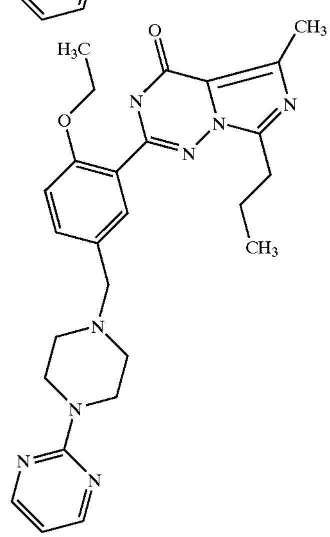 | 488.597 | 71 | 489 |

-continued

| Ex. No. | Structure | MW [g/mol] | HPLC area % at 210 nm | Mz + H |
|---|---|---|---|---|
| 89 | 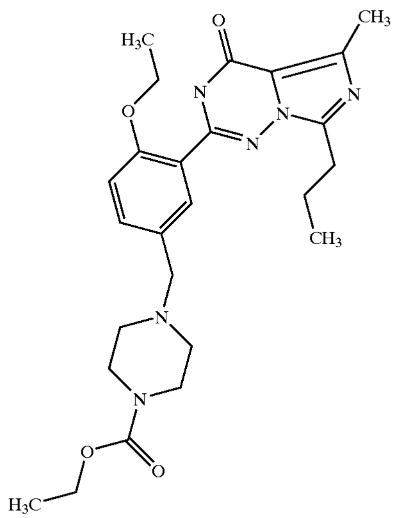 | 482.588 | 72 | 483 |

In a parallel synthesis analogously to example 78, the compounds of the table below were prepared from the chloromethyl compound example 53 A and the appropriate amine. If, after 24 h at RT, there was still starting material detectable in the TLC, stirring was continued at 60° C. for another 24 h.

| Ex. No. | Structure | MW [g/mol] | HPLC area % at 210 nm | Mz + H |
|---|---|---|---|---|
| 90 | 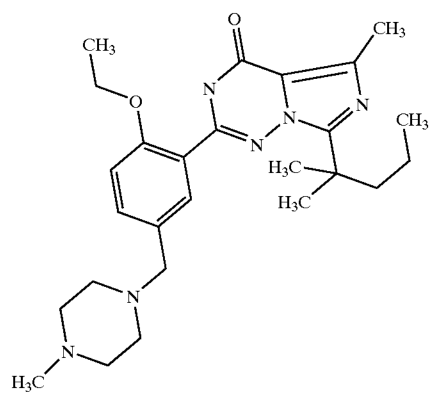 | 466.63176 | 100 | 467.3 |
| 91 | 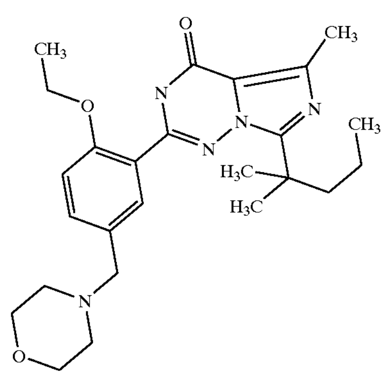 | 453.5894 | 92.65 | 454.3 |

-continued

| Ex. No. | Structure | MW [g/mol] | HPLC area % at 210 nm | Mz + H |
|---|---|---|---|---|
| 92 | 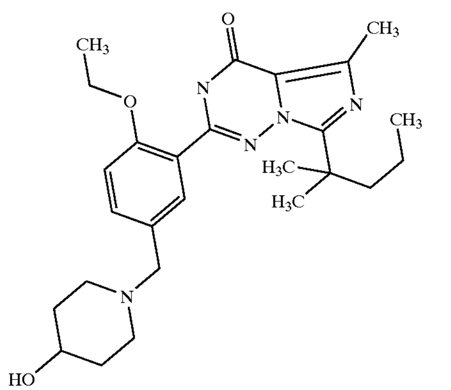 | 467.61649 | 86.42 | 468.3 |
| 93 | 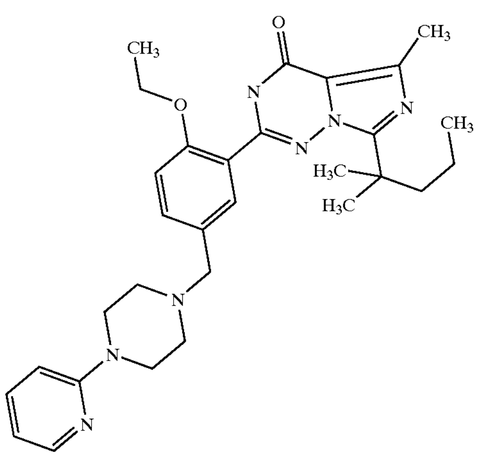 | 529.69103 | 100 | 530.3 |
| 94 | 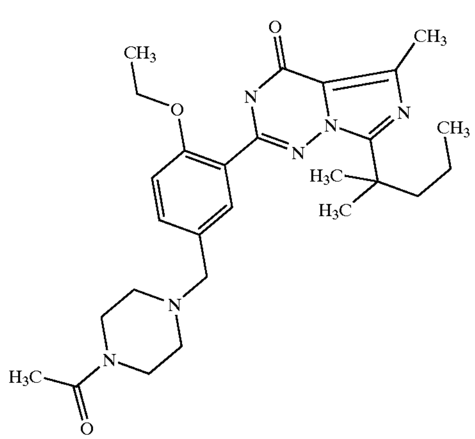 | 494.64231 | 73.53 | 495.3 |

EXAMPLE 95

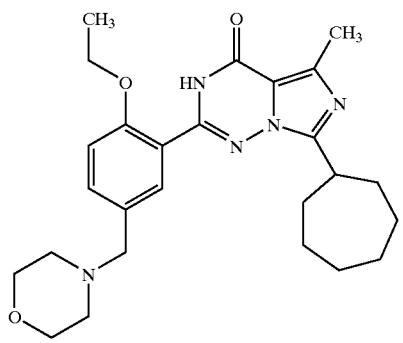

Analogously to example 76, 50 mg (0.12 mmol) of the chloromethyl compound example 55A were reacted with 311.5 mg (0.36 mmol) of morpholine at 80° C. for 5 h. Purification by thin-layer chromatography (CH$_2$Cl$_2$/MeOH= 10:1) gave 25.5 mg (46%) of the desired product.

MS (ESI): m/z (%)=466 [M+H] (100) $^1$H-NMR (200 MHz, CDCl$_3$): δ=1.56 (t, 3H, CH$_3$); 1.57–2.12 (m, 12H, 6×CH$_2$); 2.48 (bt, 4H, 2×CH$_2$); 2.62 (s, 3H, CH$_3$); 3.43 (m, 1H, CH); 3.52 (s, 2H, CH$_2$); 3.72 (bt, 4H, 2×CH$_2$); 4.25 (g, 2H, CH$_2$); 7.01 (d, 1H); 7.47 (dd, 1H); 8.11 (d, 1H); 9.89 (bs, 1H, NH).

EXAMPLE 96

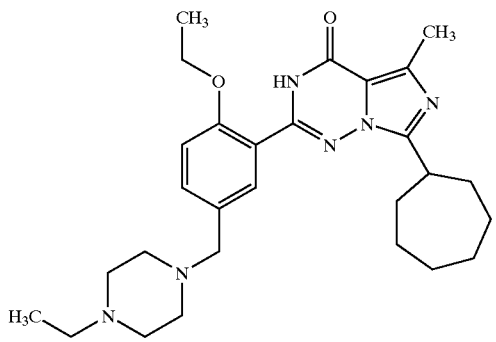

Analogously to example 76, 50 mg (0.12 mmol) of the chloromethyl compound example 55A were reacted with 41.3 mg (0.36 mmol) of N-ethylpiperazine at 80° C. for 15 h. Purification by, thin-layer chromatography (CH$_2$Cl$_2$:MeOH=5:1) gave 18.9 mg (32%) of the desired product (92% pure according to HPLC).

MS (ESI): m/z (%)=493 [M+H] (56) $^1$H-NMR (200 MHz, CDCl$_3$): δ=1.09 (t, 3H, CH$_3$); 1.56 (t, 3H, CH$_3$); 1.57–2.12 (m, 12H, 6×CH$_2$); 2.44 (g, 2H, CH$_2$); 2.52 (bm, 8H, 4×CH$_2$); 2.66 (s, 3H, CH$_3$); 3.42 (m, 1H, CH); 3.54 (s, 2H, CH$_2$); 4.25 (g, 2H, CH$_2$); 6.99 (d, 1H); 7.43 (dd, 1H); 8.10 (d, 1H); 9.89 (bs, 1H, NH).

EXAMPLE 97

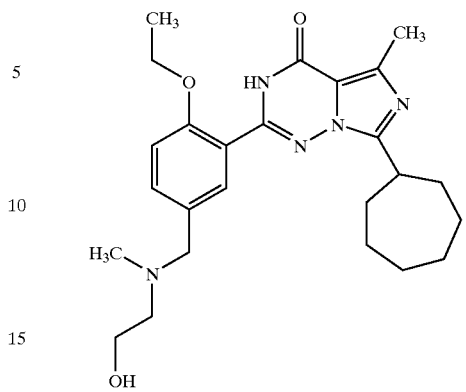

Analogously to example 76, 50 mg (0.12 mmol) of the chloromethyl compound example 55A were reacted with 32 mg (0.36 mmol) of N-ethyl-2-aminoethanol at 80° C. for 15 h. Purification by preparative thin-layer chromatography (CH$_2$Cl$_2$:MeOH=20:1) gave 17.3 mg (31%) of the desired product (87% pure according to HPLC).

MS (ESI): m/z (%)=468 [M+H] (80) $^1$H-NMR (200 MHz, D$_6$-DMSO): δ=0.99 (t, 3H, CH$_3$); 1.28 (t, 3H, CH$_3$); 1.42–2.05 (m, 12H); 3.46 (g, 2H, CH$_2$); 3.55 (s, 2H, CH$_2$); 4.07 (g, 2H, CH$_2$); 4.35 (m, 1H, CH); 7.09 (d, 1H); 7.43 (dd, 1H); 7.49 (d, 1H).

EXAMPLE 98

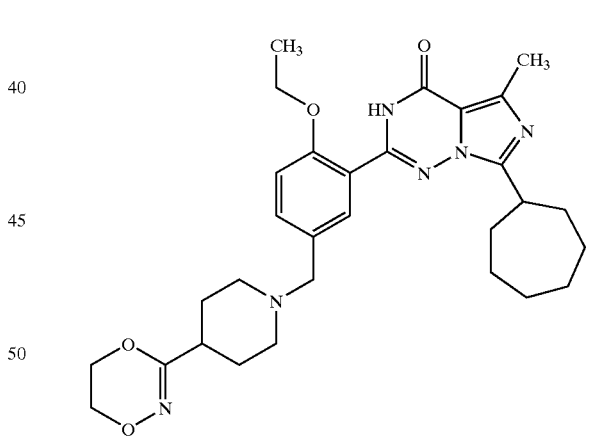

Analogously to example 76, 50 mg (0.12 mmol) of the chloromethyl compound example 55A were reacted with 61 mg (0.36 mmol) of 4-(1-dioxazinyl)piperidine. This gave 17 mg (26%) of the desired product.

MS (ESI): m/z (%)=549 [M+H] (50) $^1$H-NMR (200 MHz, CDCl$_3$): δ=1.5–2.1 (m, 25H); 2.63 (s, 3H, CH$_3$); 2.93 (bd, 1H); 3.45 (m, 1H, CH); 3.52 (s, 2H, CH$_2$); 4.02 (m, 2H, CH$_2$); 4.2–4.4 (m, 4H, 2×CH$_2$); 6.95 (d, 1H); 7.45 (dd, 1H); 8.08 (d, 1H); 9.85 (bs, 1H, NH).

EXAMPLE 99

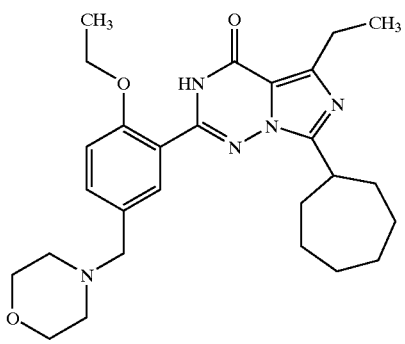

Analogously to example 76, 60 mg (0.14 mmol) of the chloromethyl compound example 56A were heated with 36.6 mg (0.42 mmol) of morpholine at 80° C. for 15 h. Preparative thin-layer chromatography (CH$_2$Cl$_2$:MeOH=10:1) gave 38.7 mg (57.7%) of the desired product.

MS (ESI): m/z (%)=480 [M+H] (100) $^1$H-NMR (200 MHz, CDCl$_3$): δ=133 (t, 3H, CH$_3$), 1.58 (t, 3H, CH$_3$), 1.60–2.10 (m, 12H, 6×CH$_2$), 2.49 (m, 4H, 2×CH$_2$), 3.02 (g, 2H, CH$_2$), 3.45 (m, 1H, CH), 3.54 (s, 2H, CH$_2$), 3.73 (bt, 4H, 2×CH$_2$), 4.25 (g, 2H, CH$_2$), 7.02 (d, 1H), 7.46 (dd, 1H), 8.11 (d, 1H), 9.90 (bs, 1H, NH).

EXAMPLE 100

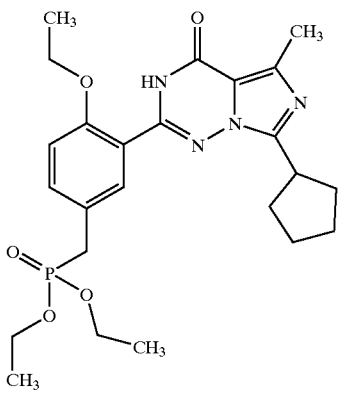

20.8 μl (0.15 mmol) of Et$_3$N were added to a suspension of 50 mg (0.13 mmol) of the chloromethyl compound example 54A in 1 ml of triethyl phosphite, and the mixture was initially heated at 100° C. for 30 min and then stirred at room temperature for another 48 h. 0.5 ml of sat. NaHCO$_3$ solution was added, and the mixture was filtered through a two-phase cartridge (500 mg of Extrelut/500 mg of SiO$_2$, mobile phase: ethyl acetate). The mixture was concentrated under reduced pressure and purified by thin-layer chromatography (CH$_2$Cl$_2$:MeOH=20:1). This eave 14.4 mg (23%) of the desired product.

MS (ESI): m/z (%)=503 [M+H] (100) $^1$H-NMR (200 MHz, CDCl$_3$): δ=1.30 (t, 6H, 2×CH$_3$), 1.58 (t, 3H, CH$_3$), 1.61–2.17 (m, 8H, 4×CH$_2$), 3.02 (g, 2H, CH$_2$), 3.19 (d, 2H, CH$_2$P), 3.62 (m, 1H, CH), 4.07 (g, 4H, 2×CH$_2$), 4.24 (g, 2H, CH$_2$), 7.02 (g, 1H), 7.45 (dt, 1H), 8.02 (t, 1H), 9.89 (bs, 1H, NH).

EXAMPLE 101

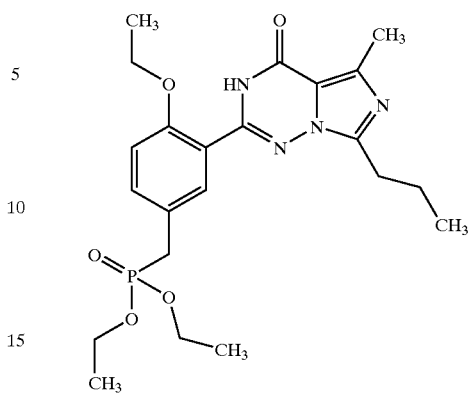

Analogously to example 100, 50 mg (0.14 mmol) of the chloromethyl compound example 51A were reacted with 1 ml of triethyl phosphite and 23.1 μl (0.17 mmol) of Et$_3$N. Preparative thin-layer chromatography (CH$_2$Cl$_2$:MeOH=20.1) gave 20 mg of the desired product, which was contaminated with the unsubstituted triazinone NUN 4792 (2:1 according to HPLC).

MS (ESI): m/z (%)=463 [M+H] (100) $^1$H-NMR (200 MHz, CDCl$_3$): δ=1.03 (t, 3H, CH$_3$), 1.29 (t, 6H, 2×CH$_2$), 1.58 (t, 3H, CH$_3$), 1.89 (m, 2H, CH$_2$), 2.65 (s, 3H, CH$_3$), 3.02 (g, 2H, CH$_2$), 3.19 (d, 2H, CH$_2$P), 4.08 (m, 4H, 2×CH$_2$), 4.25 (g, 2H, CH$_2$), 7.03 (d, 1H), 7.48 (dt, 1H), 8.05 (t, 1H), 9.95 (bs, 1H, NH).

EXAMPLE 102

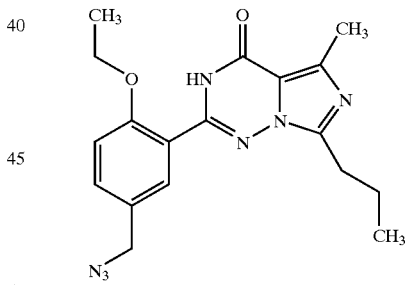

0.2 g (3.0 mmol) of NaN$_3$ was added to a suspension of 1 g (2.7 mmol) of the chloroethyl compound example 51A in 30 ml of DMF, and the mixture was stirred for 17 h. 1 M NaOH was added, and the mixture was extracted twice with ethyl acetate. The organic phase was dried over MgSO$_4$ and concentrated under high vacuum (the sample was warmed only in a lukewarm water bath), giving 0.82 g (80.5%) of the desired product.

MS (DCI, NH$_3$): m/z (%)=368 [M+H] (100) $^1$H-NMR (200 MHz, D$_6$-DMSO): δ=0.93 (t, 3H, CH$_3$), 1.32 (t, 3H, CH$_3$), 1.73 (m, 2H, CH$_2$), 2.83 (t, 2H, CH$_2$), 4.12 (g, 2H, CH$_2$), 4.45 (s, 2H, CH$_2$), 7.20 (d, 1H), 7.54 (m, 1H), 11.57 (bs, 1H, NH).

EXAMPLE 103

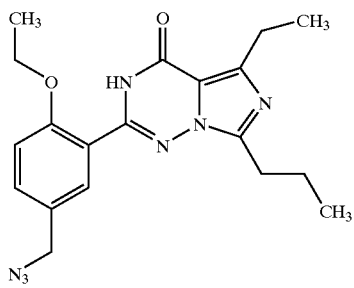

48 mg (0.73 mmol) of NaN$_3$ were added to a suspension of 250 mg (0.66 mmol) of the chloromethyl compound example 52A in 6 ml of DMF, and the mixture was stirred at room temperature for 17 h. 1 N NaOH was added, and the mixture was then extracted twice with ethyl acetate and the extracts were concentrated under reduced pressure and purified chromatographically (gradient:cyclohexane:ethyl acetate=5:1+1:2). This gave 68 mg (28%) of the azide (88% according to HPLC).

MS (ESI): m/z (%)=382 [M+H] (100) $^1$H-NMR (400 MHz, CDCl$_3$): δ=1.03 (t, 3H, CH$_3$); 1.33 (t, 3H, CH$_3$); 1.58 (t, 3H, CH$_3$), 1.89 (m, 2H, CH$_2$); 3.01–3.07 (m, 4H, 2×CH$_2$) 4.26 (g, 2H, CH$_2$); 4.49 (s, 2H, CH$_2$); 7.07 (d, 1H); 7.46 (dd, 1H); 8.09 (d, 1H); 9.86 (bs, 1H, NH).

EXAMPLE 104

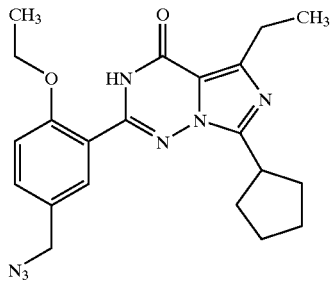

36 mg (0.55 mmol) of NaN$_3$ were added to a suspension of 200 mg (0.5 mmol) of the chloromethyl compound example 54A in 6 ml of DMF, and after 17 h at room temperature, 1 M NaOH was added. The aqueous phase was extracted twice with ethyl acetate and the organic phase was dried over MgSO$_4$ and concentrated under reduced pressure. Chromatographic purification (cyclohexane:ethyl acetate= 1:1) gave 105 mg (52%) of the azide (75% according to HPLC).

MS (ESI): m/z (%)=408 [M+H] (100) $^1$H-NMR (200 MHz, CDCl$_3$): δ=1.32 (t, 3H, CH$_3$); 1.57 (t, 3H, CH$_3$); 1.68–2.25 (m, 8H, CH$_2$); 3.02 (g, 2H, CH$_2$); 3.63 (m, 1H, CH); 4.27 (g, 2H, CH$_2$); 4.39 (s, 2H, CH$_2$); 7.06 (d, 1H); 7.45 (dd, 1H): 8.11 (d, 1H); 9.84 (bs, 1H, NH).

EXAMPLE 105

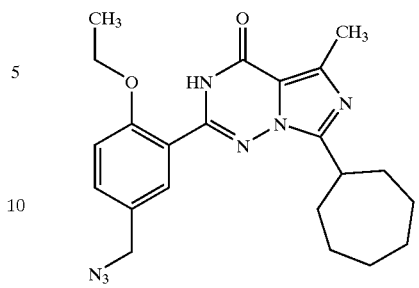

Analogously to example 102, 150 mg of the chloromethyl compound example 55a were reacted. Chromatographic purification (gradient: CH$_2$Cl$_2$+CH$_2$Cl$_2$:MeOH=1+10:1) gave 35.4 mg (23%) of the azide (67% pure according to HPLC).

MS (ESI): m/z (%)=422 [M+H] (100) $^1$H-NMR (400 MHz, CDCl$_3$): δ=1.56 (t, 3H, CH$_3$); 1.59–2.09 (m, 12H, 6×CH$_2$); 2.64 (s, 3H, CH$_3$), 3.45 (m, 1H, CH); 4.24 (g, 2H, CH$_2$); 4.38 (s, 2H, CH$_2$); 7.08 (d, 1H); 7.45 (dd, 1H); 8.09 (d, 1H); 9.82 (bs, 1H, NH).

EXAMPLE 106

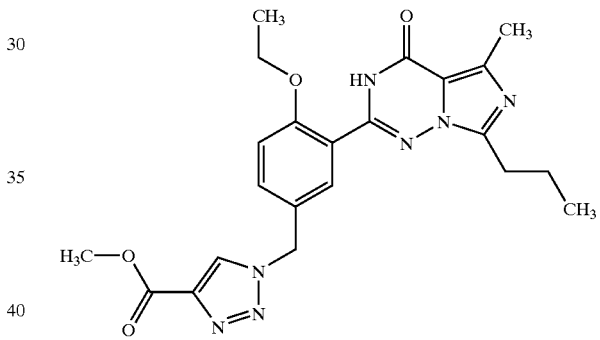

DMF was added dropwise to a suspension of 40 mg (0.11 mmol) of the azide example 102 in 1 ml DME until a homogeneous solution was formed, and 13.3 mg (0.16 mmol) of methyl propiolate were then added dropwise. The mixture was heated under reflux for 20 h, the solvent was condensed off under high vacuum and 1 ml of H$_2$O was added to the residue. Following filtration through 1 g of Extrelut (mobile phase: ethyl acetate), the concentrated crude product was purified by preparative thin-layer chromatography (CH$_2$Cl$_2$:MeOH=20:1). This gave 24.3 mg (49.4%) of the desired product as a mixture of regioisomers (12.5:1 according to NMR)

MS (ESI): m/z (%)=452 [M+H] (100)

Main regioisomer:

$^1$H-NMR (200 MHz, CDCl$_3$): δ=1.03 (t, 3H, CH$_3$), 1.57 (t, 3H, CH$_3$), 1.98 (m, 2H, CH$_2$), 2.64 (s, 3H, CH$_3$), 2.99 (t, 2H, CH$_2$), 3.95 (s, 3H, OCH$_3$), 4.27 (g, 2H, CH$_2$), 5.62 (s, 2H, CH$_2$), 7.08 (d, 1H), 7.43 (dd, 1H), 8.05 (s, 1H), 8.11 (d, 1H), 9.79 (bs, 1H, NH).

The compounds of the table below were prepared in a parallel synthesis analogously to example 106 from the azide example 102. In each case, a 3-fold excess of alkyne was used.

| Ex. No. | Structure | MW [g/mol] | HPLC area % at 210 nm | Mz + H |
|---|---|---|---|---|
| 107 | 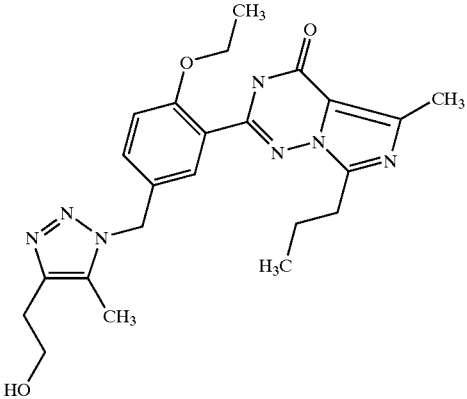 | 451.53 | 88.4 | 452.5327 |
| 108 | 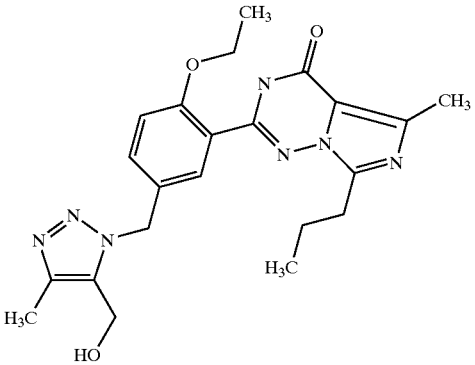 | 437.51 | 100 | 438.5056 |
| 109 | 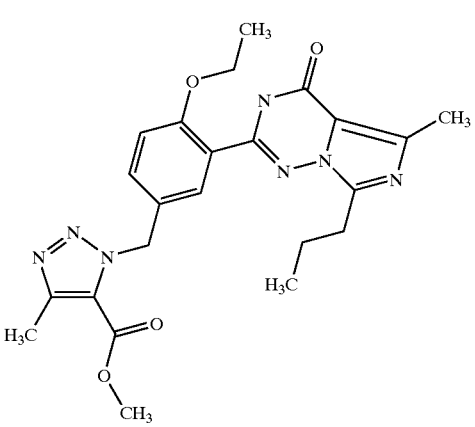 | 465.52 | 100 | 466.5161 |

-continued

| Ex. No. | Structure | MW [g/mol] | HPLC area % at 210 nm | Mz + H |
|---|---|---|---|---|
| 110 | 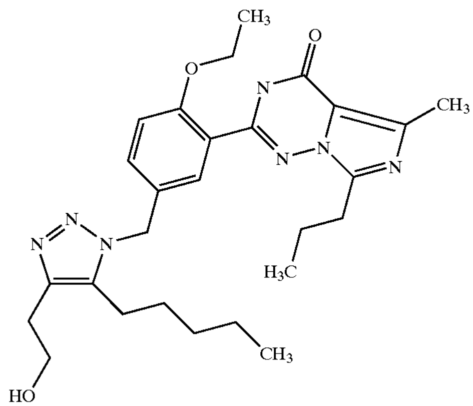 | 507.64 | 82.7 | 508.641 |
| 111 | 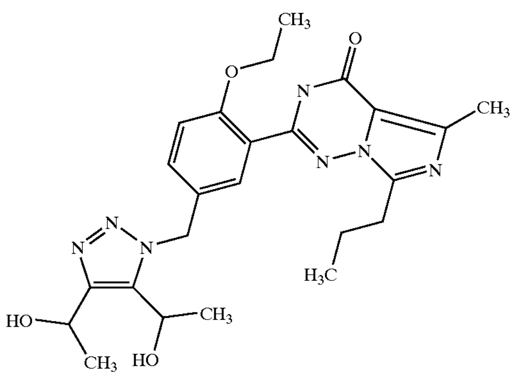 | 481.56 | 100 | 482.5592 |
| 112 | 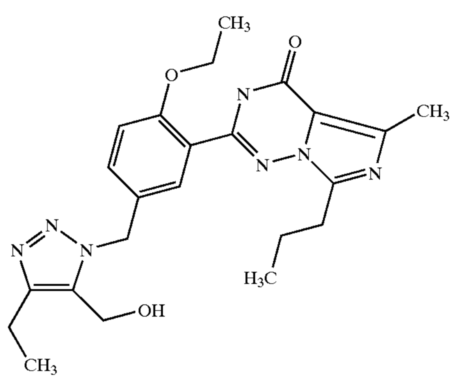 | 451.53 | 100 | 452.5327 |
| 113 | 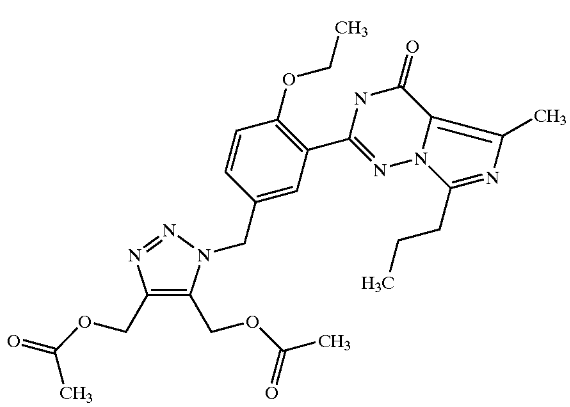 | 537.58 | 100 | 538.5803 |

-continued

| Ex. No. | Structure | MW [g/mol] | HPLC area % at 210 nm | Mz + H |
|---|---|---|---|---|
| 114 | 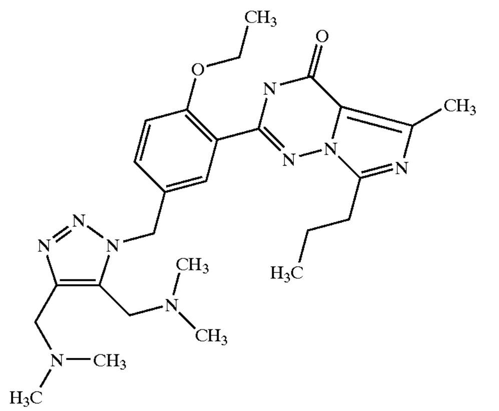 | 507.64 | 93.5 | 508.6439 |
| 115 | 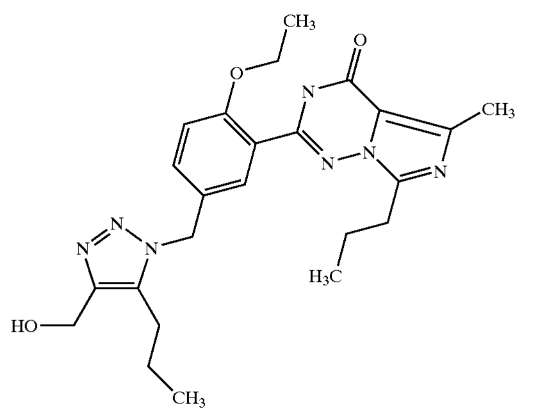 | 465.56 | 100 | 466.5598 |
| 116 | 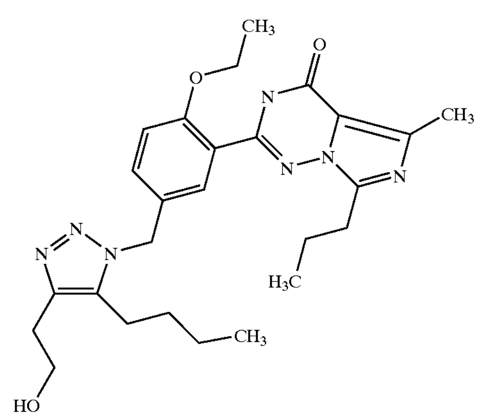 | 493.61 | 96.5 | 494.614 |

-continued
| Ex. No. | Structure | MW [g/mol] | HPLC area % at 210 nm | Mz + H |
|---|---|---|---|---|
| 117 | 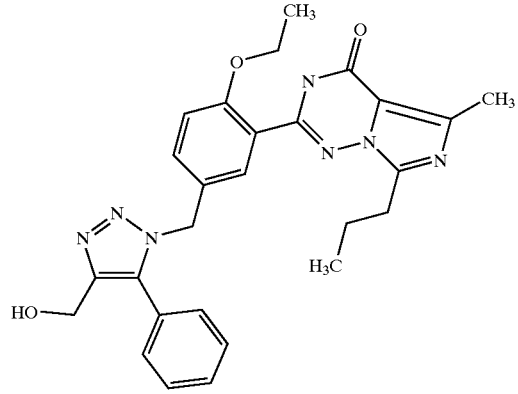 | 499.58 | 100 | 500.5773 |
| 118 | 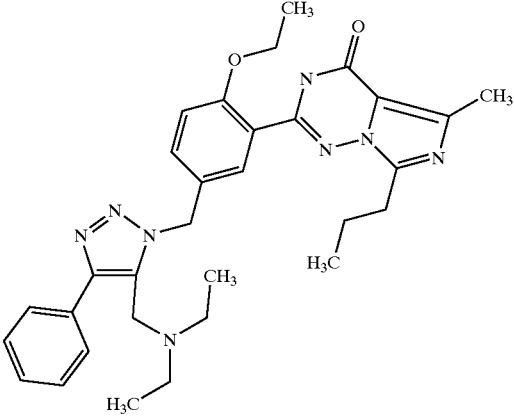 | 554.70 | 97.4 | 555.7009 |
| 119 | 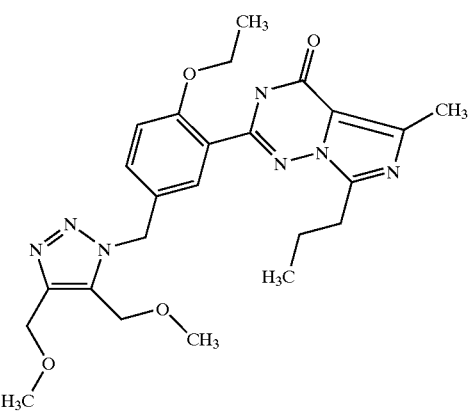 | 481.56 | 100 | 482.5592 |

-continued

| Ex. No. | Structure | MW [g/mol] | HPLC area % at 210 nm | Mz + H |
|---|---|---|---|---|
| 120 | 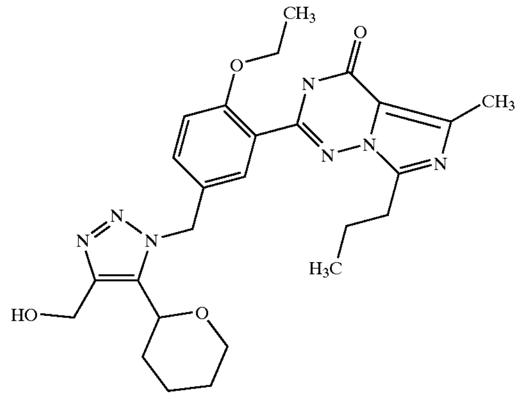 | 507.60 | 100 | 508.5974 |
| 121 | 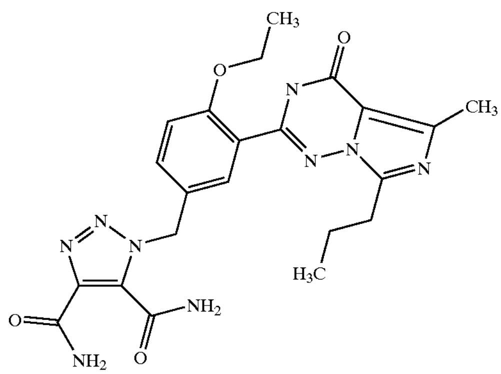 | 479.50 | 96.9 | 480.5025 |

EXAMPLE 122

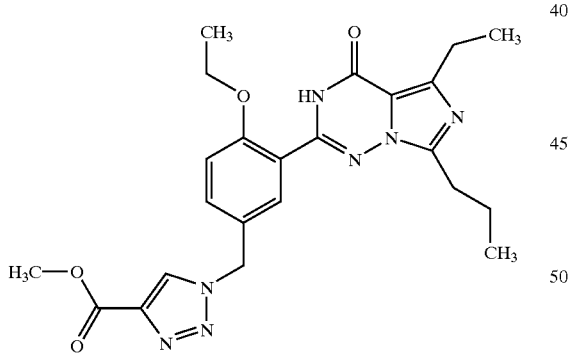

Analogously to example 106, 67 mg (0.18 mmol) of the azide example 103 were heated under reflux with 21.4 mg (0.25 mmol) of methyl propionate for 20 h. The crude product was triturated with ether. This gave 29.6 mg (36.2%) of the product which was enriched with the main regioisomer (9.3:1 according to NMR). According to LC-MS, the mother liquor contained inter alia more of the regioisomeric product mixture (1:1.82).

MS (ESI): m/z (%)=466 [M+H] (100)

Main regioisomer:

$^1$H-NMR (200 MHz, CDCl$_3$): δ=1.04 (t, 3H, CH$_3$), 1.35 (t, 3H, CH$_3$), 1.59 (t, 3H, CH$_3$), 1.88 (m, 2H, CH$_2$), 3.03 (m, 4H, 2×CH$_2$), 3.96 (s, 3H, OCH$_3$), 4.27 (q, 2H, CH$_2$), 5.62 (s, 2H, CH$_2$), 7.08 (d, 1H), 7.43 (dd, 1H), 8.12 (d, 1H), 9.82 (bs, 1H, NH).

EXAMPLE 123

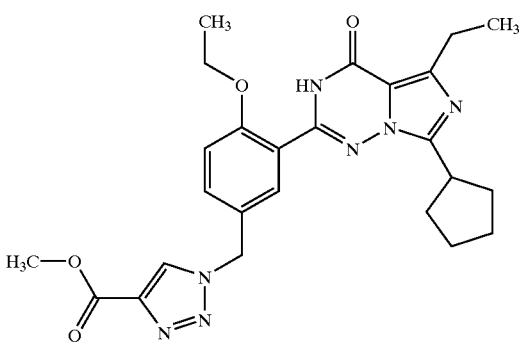

Analogously to example 106, 100 mg (0.25 mmol) of the azide example 104 were heated under reflux with 29.9 mg (0.36 mmol) of methyl propionate for 20 h. The precipitated solid was filtered off and washed with ether, giving 47.8 mg (39.6%) of the product in the form of the main regioisomer. According to LC-MS, the mother liquor contained inter alia more regioisomeric product mixture (1:2.3).

MS (ESI): m/z (%)=492 [M+H] (100)

Main regioisomer:

$^1$H-NMR (200 MHz, CDCl$_3$): δ=1.32 (t, 3H, CH$_3$), 1.58 (t, 3H, CH$_3$), 1.66–2.18 (m, 8H, 4×CH$_2$), 3.03 (q, 2H, CH$_2$), 3.62 (m, 1H, CH), 3.95 (s, 3H, OCH$_3$), 4.27 (q, 2H, CH$_2$) 5.63 (s, 2H, CH$_2$), 7.08 (d, 1H) 7.43 (dd, 1H), 8.05 (s, 1H), 8.10 (d, 1H), 9.88 (bs, 1H, NH).

EXAMPLE 124

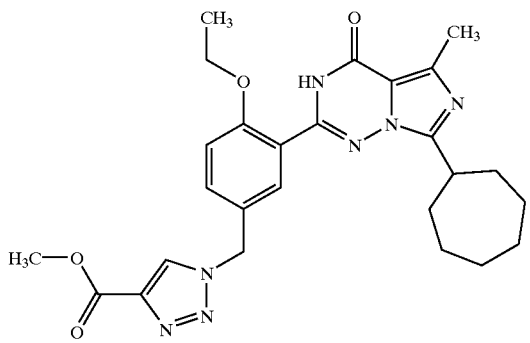

Analogously to example 106, 70 mg (0.17 mmol) of the azide example 106 were reacted with 20.3 mg (0.24 mmol) of methyl propionate. The crude product was recrystallized from ether. This gave 24.5 mg (29.2%) of the main regioisomer. According to LC-MS, the mother liquor contained a mixture of the two regioisomers (15:22).

MS (ESI): m/z (%)=506 [M+H] (100) $^1$H-NMR (200 MHz, CDCl$_3$): δ=1.22 (t, 3H, CH$_3$), 1.45–2.05 (m, 12H, 6×CH$_2$), 2.65 (s, 3H, CH$_3$), 3.48 (m, 1H, CH), 3.95 (s, 3H, OCH$_3$), 4.27 (q, 2H, CH$_2$), 5.63 (s, 2H, CH$_2$), 7.08 (d, 1H), 7.43 (dd, 1H), 8.05 (s, 1H), 8.10 (d, 1H), 9.87 (bs, 1H, NH).

EXAMPLE 125

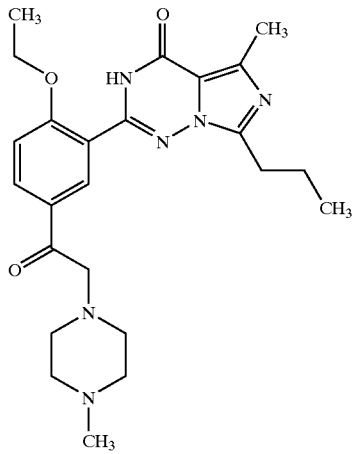

18.5 mg (0.18 mmol) of N-methylpiperazine were added to a suspension of 20 mg (0.046 mmol) of the phenacyl bromide example 57A in 0.5 ml of 1,2-dichloroethane, and the mixture was heated at 80° C. for 4 h. 0.5 ml of sat. NaHCO$_3$ solution was added after cooling, and the mixture was worked up by, filtration through 500 mg of Extrelut/500 mg of silica gel (mobile phase:ethyl acetate). The concentrated crude product was purified chromatographically (gradient: CH$_2$Cl$_2$+CH$_2$Cl$_2$:MeOH 10:1+5.1). This gave 18.4 mg (88%) of product.

MS (ESI): m/z (%)=453 [M+H] (60) $^1$H-NMR (200 MHz, CDCL$_3$): δ=1.05 (t, 3H, CH$_3$), 1.58 (3H, CH$_3$), 1.88 (m, 2H, CH$_2$), 2.65 (s, 3H, CH$_3$), 2.75 (s, 3H, CH$_3$), 3.17 (q, 2H, CH$_2$), 3.17–3.25 (m, 8H, 4×CH$_2$), 3.98 (s, 2H, CH$_2$), 4.35 (q, 2H, CH$_2$), 7.13 (d, 1H), 8.08 (dd, 1H), 8.70 (d, 1H), 9.57 (bs, 1H, NH)

EXAMPLE 126

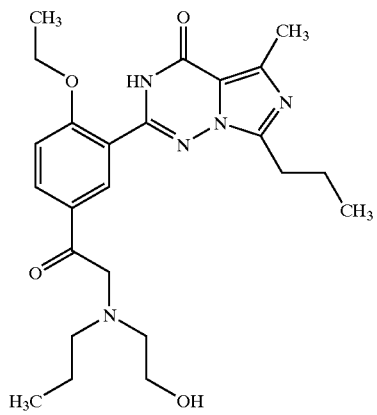

A suspension of 25 mg (0.057 mmol) of the phenacyl bromide example 57A and 23.8 mg (0.23 mmol) of N-propyl-2-aminoethanol in 0.5 ml of 1,2-dichloromethane was heated at 80° C. for 10 h. 0.5 ml of sat. NaHCO$_3$ solution was added to the reaction mixture, which was then filtered through a biphasic cartridge (upper phase: 500 mg of Extrelut, 500 mg of silica gel) (mobile phase: ethyl acetate). Concentration gave 23.6 mg of crude product which was purified by preparative thin-layer chromatography (CH$_2$Cl$_2$:MeOH=20:1). This gave 9.4 mg (35.8%) of product.

MS (ESI): m/z (%)=456 (100) [M+H] $^1$H-NMR (200 MHz, CDCL$_3$): δ=0.95 (t, 3H, CH$_3$), 1.03 (t, 3H, CH$_3$), 1.43–1.68 (m, 5H), 1.88 (m, 2H), 2.20–2.45 (m, 4H), 2.84 (bd, 2H), 3.02 (t, 2H), 4.25 (q, 2H), 7.03 (d, 1H), 7.75 (dd, 1H), 8.38 (d, 1H), 9.82 (bs, 1H, NH).

EXAMPLE 127

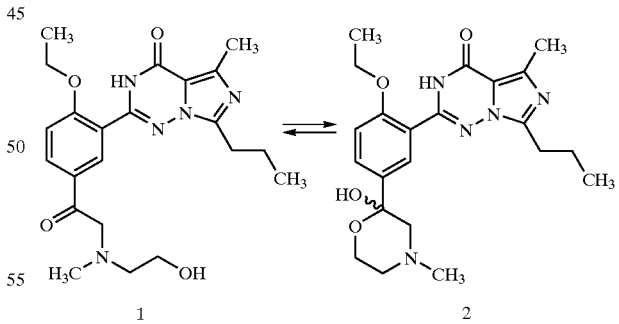

1           2

27.7 mg (0.37 mmol) of N-methyl-2-aminoethanol were added to a suspension of 40 mg (0.09 mmol) of the phenacyl bromide example 57A in 0.5 ml of 1,2-dichloroethane, and the mixture was healed at 60° C. for 4 h. 1 ml of H$_2$O was added, and the mixture was filtered through 1 g of Extrelut (mobile phase: CH$_2$Cl$_2$). The crude product was initial purified chromatographically (gradient: CH$_2$Cl$_2$/MeOH 40:1+10:1), and the product fraction was purified by preparative thin-layer chromatography (CH$_2$Cl$_2$/MeOH 20:1).

This gave 9.5 mg (24.1%) of the desired product as a mixture of the open-chain form 1 and the cyclized form 2.

MS (ESI): m/z (%)=428 [M+H] (100) 2: $^1$H-NMR (200 MHz, CDCl$_3$): δ=1.03 (t, 3H, CH$_3$), 1.53 (t, 3H, CH$_3$), 1.89 (m, 2H, CH$_2$), 2.22 (t, 2H, CH$_2$), 2.33 (s, 3H, CH$_3$), 2.64 (s, 3H, CH$_3$), 2.78 (bt, 2H, CH$_2$), 3.02 (t, 2H, CH$_2$), 3.87 (dd, 1H), 4.19 (dd, 1H), 4.26 (g, 2H, CH$_2$), 7.03 (d, 1H), 7.75 (dd, 1H), 8.38 (d, 1H), 9.79 (bs, 1H, NH).

EXAMPLE 128

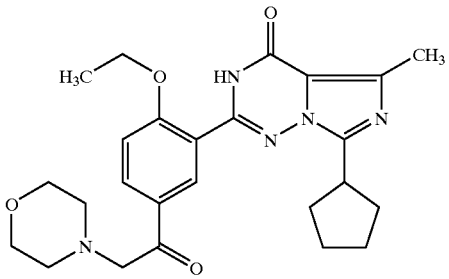

0.42 g (4.8 mmol) of morpholine are added to a solution of 1.0 g (2.2 mmol) of the phenacyl bromide example 59A in 10 ml of methylene chloride. After addition of a little methanol, the reaction mixture once more becomes clear. After 2 h of stirring at RT, the mixture is extracted with water and the organic phase is dried over sodium sulfate and concentrated. The residue is purified by silica gel chromatography using methylene chloride/methanol 20:1.

Yield: 0.56 g (55.3%) $^1$H NMR (300 MHz, CD$_3$OD): 1.47 (t, 3H), 1.56–2.20 (m, 8H), 2.60 (s, 3H), 2.64 (t, 4H), 3.67 (quin., 1H), 3.74 (t, 4H), 3.90 (s, 2H), 4.30 (quart., 2H), 7.28 (d, 1H), 8.25 (dd, 1H), 8.38 (d, 1H).

EXAMPLE 129

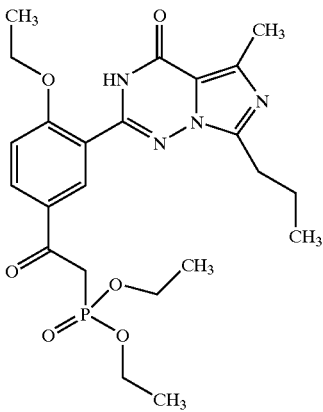

5.6 mg (0.06 mmol) of Et$_3$N were added to a suspension of 20 mg (0.05 mmol) of the phenacyl bromide example 57A in 1 ml of triethyl phosphite, and the mixture was stirred at room temperature for 2 h. 0.5 ml of sat. NaHCO$_3$ solution was added, and the mixture was filtered through 500 mg of Extrelut/500 mg of SiO$_2$ (mobile phase: ethyl acetate). The mixture was concentrated and purified by preparative thin-layer chromatography (CH$_2$Cl$_2$:MeOH=20:1). This gave 7.9 mg (34.9%) of the desired product.

MS (DCI, NH$_3$): m/z (%)=491 [M+H] (100) $^1$H-NMR (200 MHz, D$_6$-DMSO): δ=0.93 (t, 3H, CH$_3$), 1.27 (m, 9H, 3×CH$_3$), 1.72 (g, 2H, CH$_2$), 2.82 (t, 2H, CH$_2$), 4.13 (m, 6H, 3×CH$_2$), 5.07 (t, 1H, CH$_2$P), 5.48 (t, 1H, CH$_2$P), 7.21 (d, 1H), 7.75 (m, 2H).

EXAMPLE 130

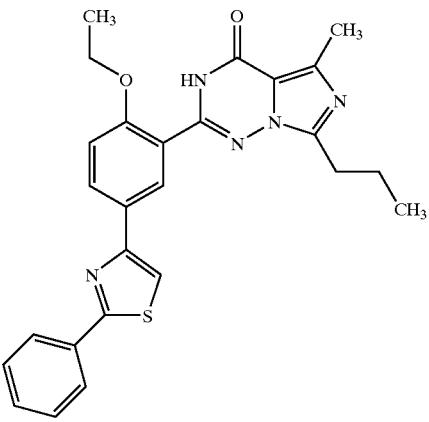

A solution of 100 mg (0.23 mmol) of the phenacyl bromide example 57A and 31.7 g (0.23 mmol) of thiobenzamide in 3.8 ml of EtOH was heated at 60° C. for 30 min. The product was filtered off with suction and washed with diethyl ether. Concentration under reduced pressure gave 31.1 mg (28.6%) of the desired product.

MS (ESI): m/z=472 [M+H] (100) $^1$H-NMR (200 MHz, D$_6$-DMSO): δ=0.95 (t, 3H, CH$_3$) 1.34 (t, 3H, CH$_3$); 1.77 (m, 2H, CH$_2$); 2.58 (s, 3H, CH$_3$); 2.99 (t, 3H, CH$_2$); 4.20 (g, 2H, CH$_2$); 7.30 (d, 1H); 7.52 (m, 3H); 8.02 (m, 2H); 8.17 (m, 3H); 12.16 (bs, 1H, NH).

EXAMPLE 131

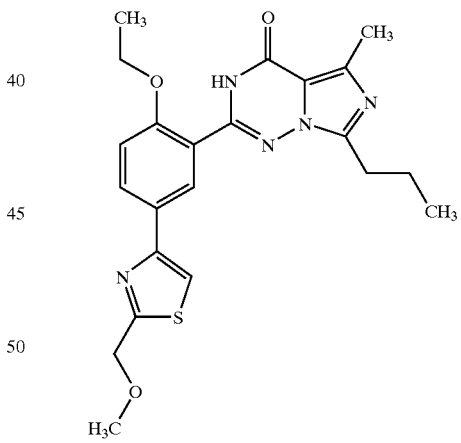

A solution of 30 mg (0.07 mmol) of the phenacyl bromide example 57A and 8.7 mg (0.08 mmol) of 2-methoxyrthioacetamide in 2 ml of isopropanol was heated at 80° C. for 6 h and then concentrated using a rotary evaporator. The crude product was stirred with ether and filtered off with suction. This gave 22.3 mg (73.30%) of the desired product.

MS (DCI, NH$_3$): m/z (%)=440 [M+H] (100) $^1$H-NMR (200 MHz, D$_6$-DMSO): δ=0.95 (t, 3H, CH$_3$) 1.32 (t, 3H, CH$_3$); 1.78 (m, 2H, CH$_2$); 2.59 (s, 3H, CH$_3$); 3.01 (t, 2H, CH$_2$); 3.43 (s, 3H, OCH$_3$); 4.18 (g, 2H, CH$_2$); 4.77 (s, 2H, CH$_2$); 7.28 (d, 1H); 8.11 (m, 3H); 12.10 (bs, 1H, NH).

In a parallel synthesis, the compounds of the following table were prepared by the following procedure: 0.1 mmol of the thioamide and 32.5 mg (0.075 mmol) of the phenacyl bromide example 57 A in 1 ml of DMF were heated at 70° C. for 2 h and then stirred at RT overnight. 0.5 ml of saturated sodium bicarbonate solution was added to the mixture, which was then filtered through a two-phase cartridge (500 mg of Extrehit/500 mg of silica gel) (mobile phase: ethyl acetate). The filtrate was then concentrated in a Speed-Vac, and the purity was determined by LC-MS.

| Ex. No. | Structure | MW [g/mol] | HPLC area % at 210 nm | Mz + H |
|---|---|---|---|---|
| 132 | 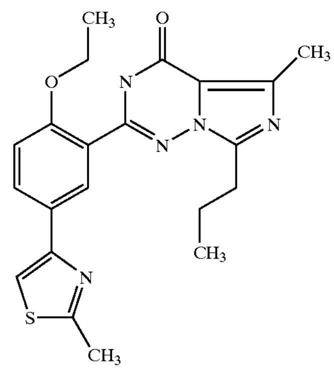 | 409.51376 | 92 | 410 |
| 133 | 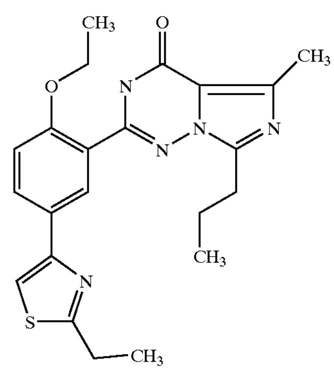 | 423.54085 | 80 | 424 |
| 134 | 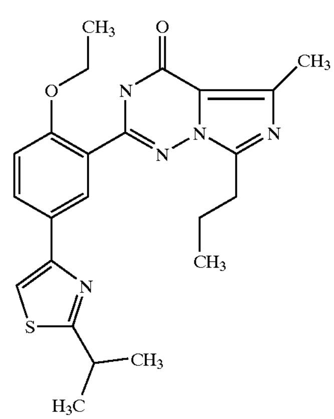 | 437.56794 | 85 | 438 |

-continued

| Ex. No. | Structure | MW [g/mol] | HPLC area % at 210 nm | Mz + H |
|---------|-----------|------------|------------------------|--------|
| 135 | 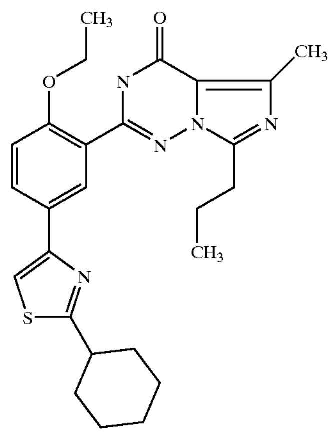 | 477.63327 | 81 | 478 |
| 136 | 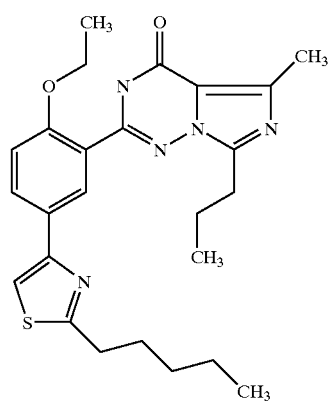 | 465.62212 | 84 | 466 |
| 137 | 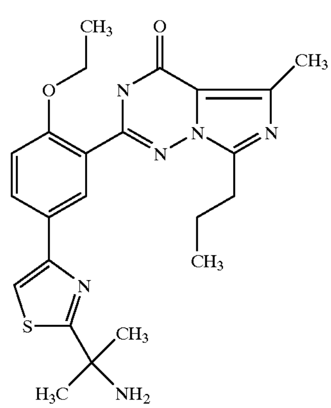 | 452.58261 | 71 | 453 |

-continued

| Ex. No. | Structure | MW [g/mol] | HPLC area % at 210 nm | Mz + H |
|---|---|---|---|---|
| 138 | 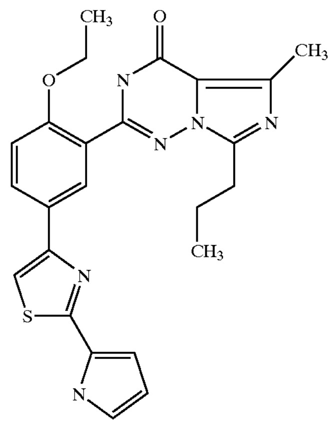 | 460.56188 | 72 | 461 |
| 139 | 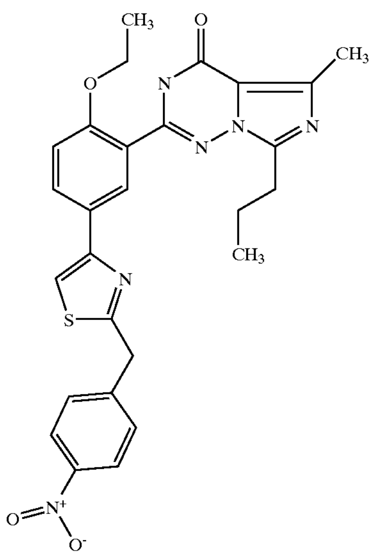 | 530.61007 | 79 | 531 |
| 140 | 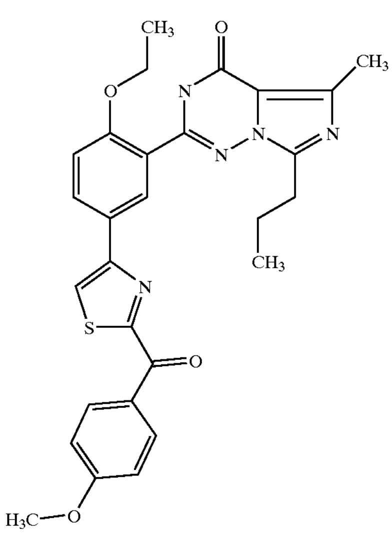 | 529.62249 | 69 | 530 |

EXAMPLE 141

2-{[2-Ethoxy-5-[4-(2-aminiothiazole)]phenyl}-5-methyl-7-propyl-3H-imidazo[5,1-f]-1,2,4]triazin-4-one

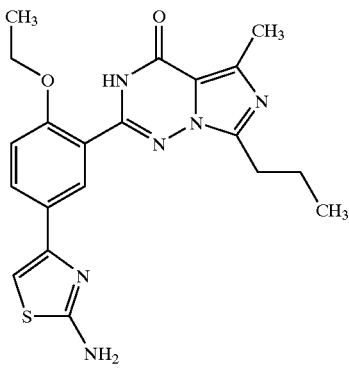

A solution of 40 mg (0.1 mmol) of the phenacyl bromide example 57A in 2 ml of isopropanol was added to 9.13 mg (0.12 mmol) of thiourea, and the mixture was heated at 80° C. for 10 h. 1 ml of H$_2$O was added, and the reaction mixture was then filtered through a cartridge filled with 1 g of Extrelut (upper phase) and 500 mg of SiO$_2$ (mobile phase: ethyl acetate). The filtrate was concentrated under reduced pressure, giving 7.1 mg (18.7% of theory,) of 2-{[2-ethoxy-5-[4-(2-aminothiazole)]phenyl}-5-methyl-7-propyl-3H-imidazo[5,1-f]-[1,2,4]triazin-4-one (77% according to HPLC).

$^1$H-NMR (300 MHz, CD$_3$OD, D$_6$-DMSO): δ=0.97 (t, 3H); 1.42 (t, 3H); 1.82 (m, 2H); 2.57 (s, 3H); 2.95 (t, 2H); 4.17 (dd, 2H); 6.84 (s, 1H); 7.17 (d, 1H); 7.93 (dd, 1H), 8.06 (d, 1H).

EXAMPLE 142

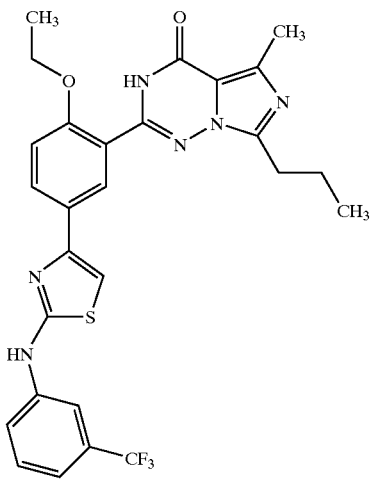

66 mg (0.3 mmol) of 3-trifluoromethylphenylthiourea were added to a solution of 100 mg (0.23 mmol) of the phenacyl bromide example 57A in 3 ml of DMF, and the mixture was heated at 40° C. for 16 h. The DMF was condensed off under high vacuum and 1 ml of H$_2$O and CH$_2$Cl$_2$ was added to the residue. The product precipitate that formed was filtered off with suction. This gave 59.6 mg (46.6%) of the desired product.

MS (ESI): m/z (%)=555 [M+H] (100) $^1$H-NMR (200 MHz, D$_6$-DMSO): δ=0.93 (t, 3H, CH$_3$); 1.34 (t, 3H, CH$_3$); 1.78 (m, 2H, CH$_2$); 2.58 (s, 3H, CH$_3$); 2.97 (t, 2H, CH$_2$); 4.18 (g, 2H, CH$_2$); 7.28 (d, 2H); 7.48 (s, 1H); 7.54 (t, 1H); 7.86 (d, 1H); 8.09 (m, 1H); 8.34 (bs, 1H); 10.67 (bs, 1NH); 12.11 (bs, 1H, NH).

EXAMPLE 143

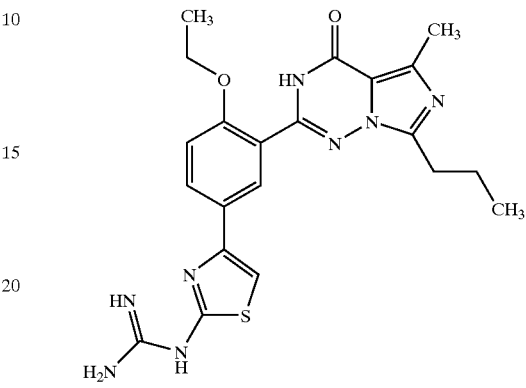

Initially, 6.4 mg (0.05 mmol) of N-amidinothiourea were dissolved in 2 ml of hot EtOH and added to a hot solution of 21.4 mg (0.05 mmol) of the phenacyl bromide example 57A in 2 ml of CH$_3$CN, and the mixture was heated under reflux for 3 h. After cooling, 0.7 ml of H$_2$O was added, the mixture was filtered through 500 mg of Extrelut/500 mg of SiO$_2$ (mobile phase: 1. ethyl acetate, 2. MeOH), and only the methanol phase was concentrated. The residue was purified by preparative thin-layer chromatography (CH$_2$Cl$_2$:MeOH= 5:1). This gave 13.6 mg (60.9%) of the desired product.

MS (ESI): m/z (%)=453 [M+H] (100) $^1$H-NMR (300 MHz, D$_3$COD with suppression of water): δ=0.90 (t, 3H, CH$_3$), 1.35 (t, 3H, CH$_3$), 1.75 (m, 2H, CH$_2$), 2.49 (s, 3H, CH$_3$), 2.90 (t, 2H, CH$_2$), 4.13 (g, 2H, CH$_2$O), 6.90 (s, 1H), 7.10 (d, 1H), 7.89 (dd, 1H), 8.07 (d, 1H).

EXAMPLE 144

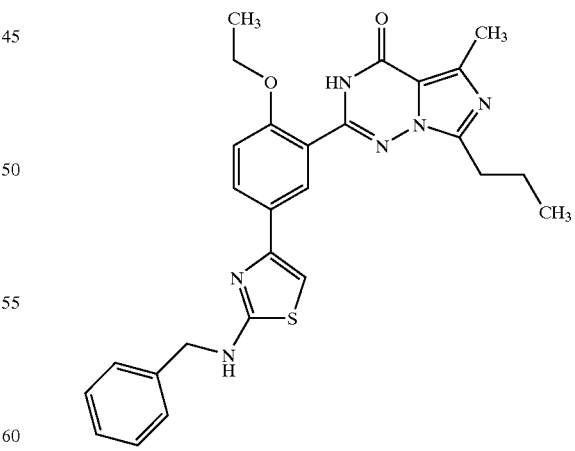

A solution of 30 mg (0.07 mmol) of the phenacyl bromide example 57A and 12.7 mg (0.08 mmol) of N-benzylthiourea in DMF was initially heated at 60° C. for 3 h, 7 mg (0.07 mmol) of Et$_3$N were then added and the reaction mixture was, after a further 10 min, cooled to room temperature. The DMF was condensed off under high vacuum, 1 ml of sat. NaHCO₃ solution was added to the residue and the mixture was filtered through 1 g of Extrelut (mobile phase: CH₂Cl₂). The crude product was purified chromatographically (ethyl acetate:cyclohexane=85:15). This gave 12.9 mg (37.2%) of the desired product.

MS (DCI/NH₃): m/z (%)=501 [M+H] (100) ¹H-NMR (400 MHz, CDCl₃): δ=1.03 (t, 3H, CH₃), 1.58 (t, 3H, CH₃), 1.85 (m, 2H, CH₂), 2.65 (s, 3H, CH₃), 2.93 (t, 2H, CH₂), 4.27 (g, 2H, CH₂O), 4.96 (s, 2H, CH₂), 5.83 (s, 1H), 6.98 (d, 1H), 7.15–7.29 (m, 6H), 7.99 (d, 1H).

EXAMPLE 145

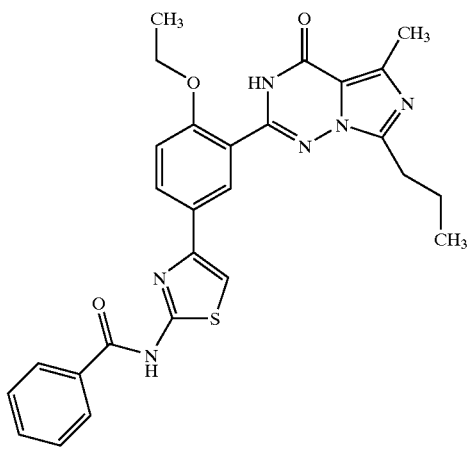

22.9 mg (0.13 mmol) of N-benzoylthiourea were added to a suspension of 50 mg (0.12 mmol) of the phenacyl bromide example 57A in acetone. The mixture was heated at 60° C. and DMF was added until a homogeneous solution was formed. After 20 h, the DMF was condensed off under high vacuum, the residue was triturated with CH₂Cl₂/ether and the precipitated product was filtered off with suction. This gave 56.7 mg (95%) of the desired product.

MS (ESI): m/z (%)=515 [M+H] (100) ¹H-NMR (400 MHz, D₆-DMSO, with suppression of water): δ=1.08 (t, 3H, CH₃), 1.44 (t, 3H, CH₃), 1.94 (m, 2H, CH₂), 2.75 (s, 3H, CH₃), 3.23 (t, 2H, CH₂), 4.25 (g, 2H, CH₂O), 7.28 (d, 1H), 7.45 (s, 1H), 7.58 (m, 2H), 7.65 (m, 1H), 8.05 (d, 2H), 8.19 (dd, 1H), 8.24 (d, 1H).

EXAMPLE 146

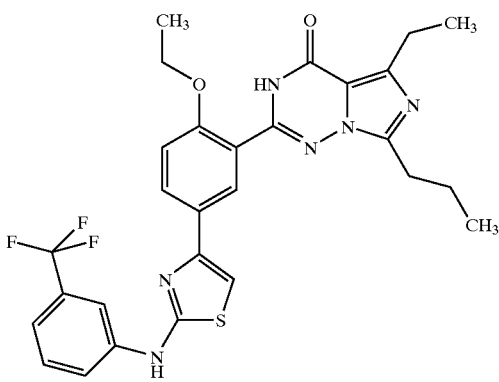

88.6 mg (0.4 mmol) of N-(3-trifluoromethylphenyl) thiourea were added to a solution of 150 mg (0.3 mmol) of the phenacyl bromide example 58A in 3 ml of DMF, and the mixture was heated at 40° C. for 16 h. The DMF was condensed off under high vacuum, 3 ml of H₂O were added to the residue and the mixture was filtered through 3 g of Extrelut (mobile phase: CH₂Cl₂). Chromatographic purification (CH₂Cl₂+CH₂Cl₂:MeOH=50:1) save 182 mg (95%) of the desired product.

MS (ESI): m/z (%) 569 [M+H] (100) ¹H-NMR (200 MHz, D₆-DMSO): δ=0.93 (t, 3H, CH₃), 1.25 (t, 3H, CH₃), 1.33 (t, 3H, CH₃), 1.75 (m, 2H, CH₂), 2.89 (2×t, 4H, 2×CH₂), 4.18 (g, 2H, CH₂), 7.28 (m, 2H), 7.55 (t, 1H), 7.82 (bd, 1H), 8.05 (m, 2H), 8.38 (bs, 1H), 10.69 (bs, 1H, NH), 11.65 (bs, 1H, NH).

EXAMPLE 147

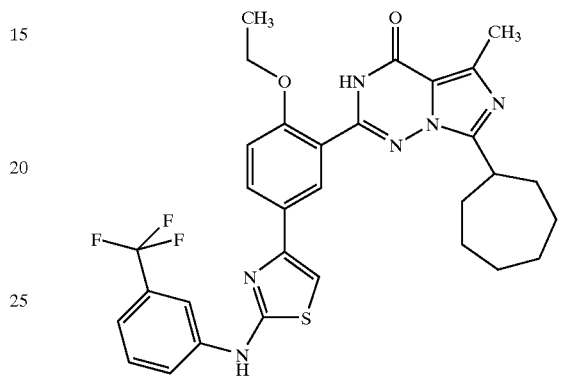

A solution of 150 mg (0.31 mmol) of the phenacyl bromide example 60A and 81.3 mg (0.37 mmol) of N-(3-trifluoromethylphenyl)thiourea in 3 ml of DMF was heated at 40° C. for 16 h. The volatile components were condensed off under high vacuum and the residue was taken up in 3 ml of H₂O and CH₂Cl₂. The resulting precipitate was filtered off, giving 94.2 mg (49.3%) of the desired product. Another 42 mg (22.4%) of product were isolated from the mother liquor, which was filtered through 3 g of Extrelut (mobile phase: CH₂Cl₂), concentrated and recrystallized from ether.

MS (ESI): m/z (%)=609 [M+H] (100) ¹H-NMR (200 MHz, D₆-DMSO): δ=1.33 (t, 3H, CH₃), 1.45–2.02 (m, 12H, 6×CH₂), 3.35 (m, 1H, CH), 4.16 (g, 2H, CH₂), 7.27 (m, 2H), 7.40 (s, 1H), 7.54 (t, 1H), 7.82 (d, 1H), 8.05 (m, 2H), 8.39 (bs, 1H), 10.68 (s, 1H, NH), 11.63 (s, 1H, NH).

EXAMPLE 148

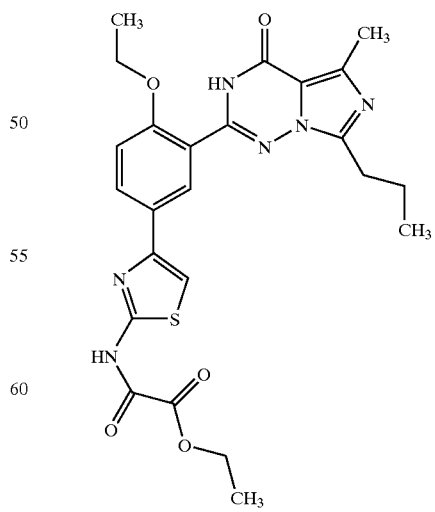

5.4 μl (0.05 mmol) of ethyl oxalyl chloride were added dropwise to a suspension of 20 mg (0.05 mmol) of the aminothiazole example 141 in 1 ml of pyridine, and the mixture was stirred at room temperature for 20 h. The pyridine was condensed off under high vacuum, 0.5 ml of sat. NaHCO$_3$ solution was added to the residue and the mixture was filtered through a two-phase cartridge (500 mg of Extrelut/500 mg of SiO$_2$, mobile phase: ethyl acetate). Recrystallization from ether gave 8.3 mg (33.4) of the desired product.

MS (DCI, NH$_3$): m/z (%)=511 [M+H] (100) $^1$H-NMR (200 MHz, D$_6$-DMSO): δ=0.93 (t, 3H, CH$_3$), 1.32 (t, 6H, 2×CH$_3$), 1.75 (m, 2H, CH$_2$), 2.84 (t, 2H, CH$_2$), 4.16 (g, 2H, CH$_2$), 4.31 (g, 2H, CH$_2$), 7.26 (d, 1H), 7.75 (s, 1H), 8.08 (m, 2H), 11.65 (bs, 1H, NH), 13.09 (bs, 1H, NH).

EXAMPLE 149

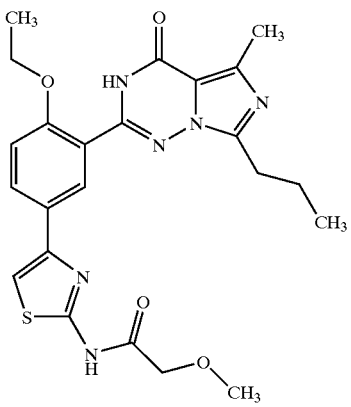

5.3 mg (0.05 mmol) of 2-methoxyacetyl chloride were added to a suspension of 20 mg (0.05 mmol) of the aminothiazole example 141 in 1 ml of pyridine. After 20 h, the pyridine was separated off under high vacuum and the crude product was taken up in 0.5 ml of saturated NaHCO$_3$ and filtered through a 2-phase cartridge (500 mg of Extrelut/500 mg of SiO$_2$; mobile phase: ethyl acetate). Crystallization from diethyl ether gave 7 mg (29.8%) of the desired product.

MS (ESI): m/z (%)=483 [M+H] (100). $^1$H-NMR (200 MHz, D$_6$-DMSO): δ=0.93 (t, 3H, CH$_3$); 1.32 (t, 3H, CH$_3$); 1.75 (m, 2H, CH$_2$); 2.52 (s, CH$_3$ under the DMSO signal); 2.85 (t, 2H, CH$_2$); 3.33 (s, 3H, OCH$_3$); 4.16 (m, 4H, 2×CH$_2$); 7.23 (d, 1H); 7.61 (s, 1H); 8.03 (m, 2H); 11.63 (bs, 1H, NH); 12.20 (bs, 1H, NH).

EXAMPLE 150

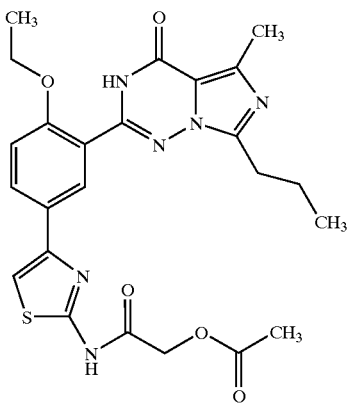

A solution of 30 mg (0.073 mmol) of the aminothiazole example 141 in 0.5 ml of pyridine and 10 mg (0.073 mmol) of 2-acetoxyacetyl chloride was stirred at RT for 4 h. The pyridine was distilled off under reduced pressure, 0.5 ml of sat. NaHCO$_3$ was added and the reaction mixture was filtered through a two-phase cartridge (upper phase: 500 mg of Extrelut, lower phase: 500 mg of silica gel, mobile phase: ethyl acetate). This gave 30.3 mg (81%) of the desired product in a purity of 84% according to LC-MS.

MS (ESI): m/z (%)=511 [M+H] (100) $^1$H-NMR (200 MHz, CDCl$_3$): δ=1.02 (t, 3H, CH$_3$); 1.13 (t, 3H, CH$_3$); 1.87 (m, 2H, CH$_2$); 2.29 (s, 3H, CH$_3$); 2.71 (s, 3H, CH$_3$); 3.53 (bt, 2H, CH$_2$); 4.97 (s, 2H, CH$_2$); 6.53 (d, 1H); 7.03 (s, 1H); 7.46 (dd, 1H); 7.72 (d, 1H); 11.67 (bs, 1H, NH); 12.45 (bs, 1H, NH).

EXAMPLE 151

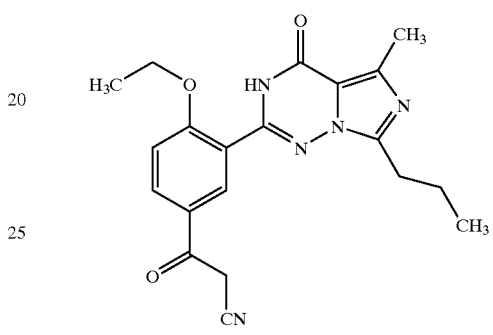

5 g (11.54 mmol) of the phenacyl bromide example 57A are suspended in 100 ml of ethanol and cooled to 0° C. Since the suspension is slightly acidic, it is neutralized by addition of a little potassium carbonate. At 0° C., 2.25 g (34.6 mmol) of potassium cyanide in 10 ml of water are added dropwise. After 2 h, the mixture is allowed to warm to RT and stirred at this temperature for 15 h. 300 ml of water are added, the mixture is then extracted 2× with in each case 100 ml of dichloromethane and the combined organic phases are dried (MgSO$_4$) and concentrated using a rotary evaporator. The product is purified by flash chromatography on silica gel (mobile phase: CH$_2$Cl$_2$+CH$_2$Cl$_2$/MeOH 100:1+CH$_2$Cl$_2$/MeOH 40:1). The product-containing fractions are concentrated and the product is then dissolved in dichloromethane and crystallized by addition of ether.

Yield: 1.78 g (40.6%)

EXAMPLE 152

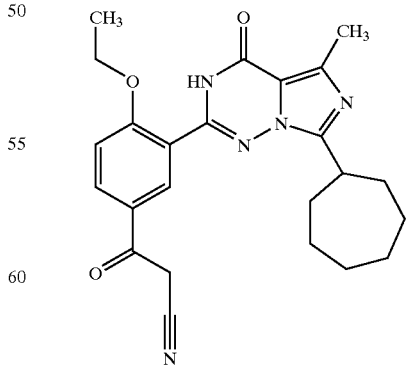

At 0° C., 80.2 mg (1.2 mmol) of NaCN and a crystal of K$_2$CO$_3$ as a solution in 0.4 ml of H$_2$O were added to a suspension of 200 mg (0.41 mmol) of the phenacyl bromide example 60A in 4 ml of ethanol. After 30 min, the mixture was warmed to room temperature and stirred for another 15 h. The mixture was quenched with three times the amount of H₂O and then extracted twice with CH₂Cl₂, and the extract was dried over MgSO₄ and concentrated under reduced pressure. This gave 152 mg (86%) of the nitrile.

¹H-NMR (200 MHz, CDCl₃): δ=1.62 (t, 3H, CH₃), 1.62–2.03 (m, 12H, 6×CH₂); 2.63 (s, 3H, CH₃); 3.42 (m, 1H, CH); 4.08 (s, 2H, CH₂); 4.38 (g, 2H, CH₂); 7.16 (d, 1H); 8.11 (dd, 1H); 8.69 (d, 1H); 9.61 (bs, 1H, NH).

EXAMPLE 153

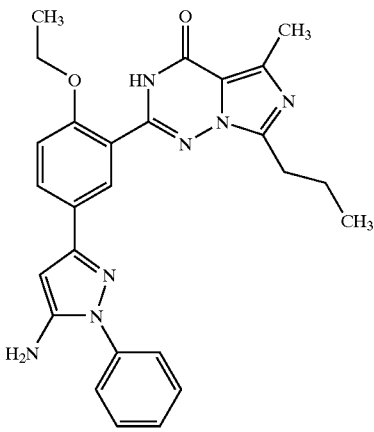

A solution of 20 mg (0.052 mmol) of the nitrile example 151 in 0.5 ml of glacial acetic acid was heated at 50° C., and 6.8 mg (0.063 mmol) of phenylhydrazine were added dropwise. After 5 h, 1 ml of sat. NaHCO₃ solution was added to the reaction mixture, and the mixture was filtered through 1 g of Extrelut (mobile phase: CH₂Cl₂). Concentration under high vacuum was initially followed by chromatographic purification (CH₂Cl₂:MeOH=80:1+20:1) and then by preparative thin-layer chromatography (CH₂Cl₂:MeOH=20:1). This gave 14.6 mg (59%) of the aminopyrrazole.

MS (DCI, NH₃): m/z (%)=470 (100) [M+H] ¹H-NMR (200 MHz, CDCl₃): δ=1.07 (t, 3H, CH₃); 1.55 (t, 3H, CH₃); 1.92 (m, 2H); 2.69 (s, 3H, CH₃); 3.19 (t, 2H); 3.92 (bs, 2H, NH₂); 4.30 (g, 2H); 5.99 (s, 1H); 7.08 (d, 1H), 7.30–7.70 (m, 5H); 8.03 (dd, 1H); 8.51 (d, 1H); 9.98 (bs, 1H, NH).

EXAMPLE 154

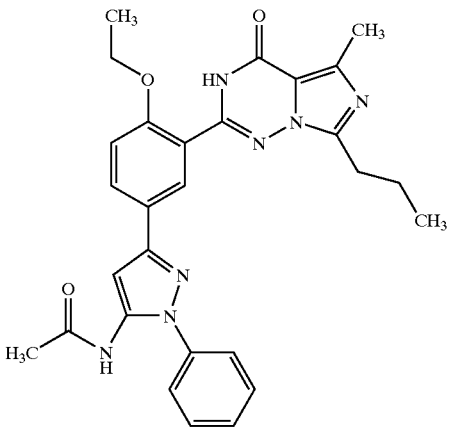

In the reaction of example 153, 9.3 mg (34%) of the N-acetylpyrrazole are obtained as a by-product.

LC-MS (ESI): m/z (%)=512 (100%) [M+H]¹H-NMR (200 MHz, CDCl₃): δ=0.92 (t, 3H, CH₃); 1.32 (t, 3H, CH₃); 1.74 (dd, 2H); 2.0 (s, 3H, CH₃); 2.85 (t, 2H); 4.15 (g, 2H); 6.89 (s, 1H); 7.22 (d, 1H); 7.45–7.62 (m, 6H); 7.9–8.05 (m, 2H); 10.05 (bs, 1H, NH); 11.63 (bs, 1H, NH).

EXAMPLE 155

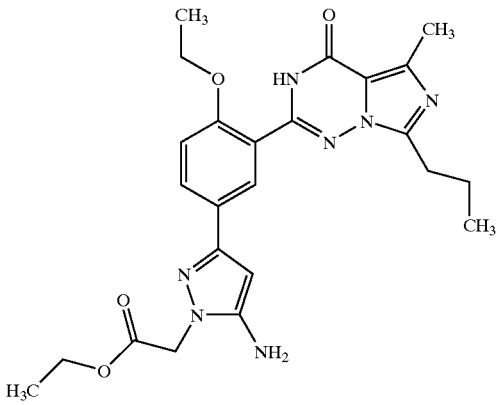

Analogously to example 153, 30 mg (0.08 mmol) of the nitrile example 151 were reacted with 13.5 mg (0.09 mmol) of ethyl 2-hydrazinoacetate at 50° C. After cooling to room temperature, 20 mg of aldehyde-functionalized Wang resin were added, and the mixture was stirred at 70° C. for 2 h. 0.5 ml of sat. NaHCO₃ solution was added, the mixture was filtered through 500 mg of Extrelut/500 mg of SiO₂ (mobile phase) and the concentrated crude product was initially purified chromatographically (ethyl acetate:cyclohexane= 5:1) and the product fraction was then purified again by preparative thin-layer chromatography (CH₂Cl₂:MeOH= 10:1). This gave 4.1 mg (10.8%) of the desired product, in addition to 3.2 mg (8.4%) of starting material.

MS (ESI): m/z (%)=480 [M+H] (100) ¹H-NMR (200 MHz, CDCl₃): δ=1.04 (t, 3H, CH₃), 1.33 (t, 3H, CH₃), 1.58 (t, 3H, CH₃), 1.89 (m, 2H, CH₂), 2.65 (s, 3H, CH₃), 3.05 (t, 2H, CH₂), 3.75 (bs, 2H, CH₂), 4.26 (g, 4H, 2×CH₂O), 4.86 (s, 2H, NH₂), 5.98 (s, 1H), 7.05 (d, 1H), 7.89 (dd, 1H), 8.43 (d, 1H), 9.86 (bs, 1H, NH).

EXAMPLE 156

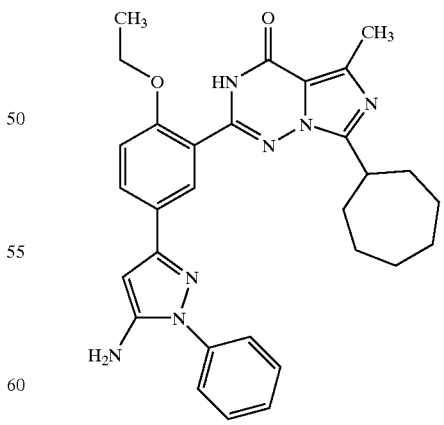

41 μl (0.42 mmol) of phenylhydrazine were added dropwise to a solution of 150 mg (0.35 mmol) of the nitrile example 60A in 3 ml of 2M trifluoroacetic acid in CH₂Cl₂, and the mixture was heated under reflux for 15 h. Addition of 3 ml of sat. NaHCO₃ solution and filtration through 3 g of Extrelut (mobile phase: CH₂Cl₂) gave, after concentration under reduced pressure, the crude product, which was purified chromatographically (gradient: CH₂Cl₂+CH₂Cl₂/MeOH=50:1). This gave 149 mg (82%) of the desired product (91.3% pure according to HPLC).

MS (DCI, NH₃): m/z (%)=524 [M+H] (100) ¹H-NMR (200 MHz, CDCL₃): δ=1.60 (t, 3H, CH₃), 1.67 (bs, 6H,3× CH₂), 1.82–2.17 (m, 6H, 3×CH₂), 2.76 (s, 3H, CH₃), 3.63 (m, 1H, CH), 4.35 (g, 2H, CH₂) 5.95 (s, 1H), 6.62 (bs, 2H, NH₂), 7.12 (d, 1H), 7.36–7.68 (m, 5H, phenyl), 8.02 (dd, 1H), 8.63 (d, 1H), 10.54 (bs, 1H, NH).

EXAMPLE 157

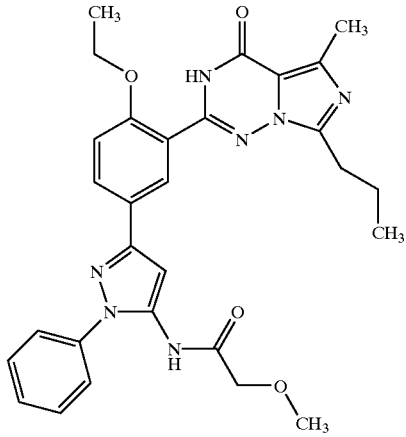

At room temperature, 23.1 mg (0.21 mmol) of methoxyacetyl chloride were added to a solution of 100 mg (0.21 mmol) of the aminopyrrazole example 153 in 2 ml of pyridine, and the mixture was stirred for 1 h. The pyridine was condensed off under high vacuum. 0.5 ml of sat. NaHCO₃ solution was added to the residue and the resulting precipitate was dissolved using ethyl acetate. The mixture was filtered through 500 mg of Extrelut/500 mg of SiO₂ (mobile phase: ethyl acetate), and the crude product was recrystallized from ethyl acetate/ether. This gave 14.8 mg (12.8%) of the desired product. A further 55 mg (47.7%) were obtained by recrystallization of the product which precipitated on the cartridge during filtration.

MS (ESI): m/z (%)=542 [M+H] (100) ¹H-NMR (200 MHz, D₆-DMSO): δ=0.94 (t, 3H, CH₃), 1.33 (t, 3H, CH₃), 1.74 (m, 2H, CH₂), 2.86 (t, 2H, CH₂), 3.32 (s, 3H, OCH₃), 3.98 (s, 2H, CH₂), 4.18 (g, 2H, CH₂O), 6.91 (s, 1H), 7.25 (d, 1H), 7.35–7.63 (m, 5H), 8.00 (m, 2H), 9.93 (bs, 1H, NH), 11.62 (bs, 1H, NH).

EXAMPLE 158

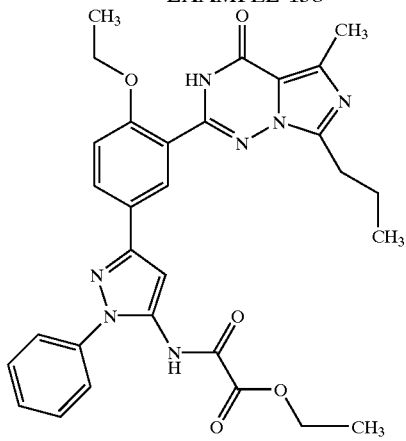

Analogously to example 157, 25 mg (0.053 mmol) of the aminopyrrazole example 153 were reacted in 0.5 ml of pyridine with 7.3 mg (0.053 mmol) of ethyl oxalyl chloride at room temperature for 4 h. Chromatographic purification (gradient: CH₂Cl₂+CH₂Cl₂:MeOH=50:1) gave 21.8 mg (71.9%) of the desired product.

MS (ESI): m/z (%)=570 [M+H] (100) ¹H-NMR (200 MHz, CDCl₃): δ=1.05 (t, 3H, CH₃), 1.43 (t, 3H, CH₃), 1.58 (t, 3H, CH₃), 1.90 (m, 2H, CH₂), 2.65 (s, 3H, CH₃), 3.04 (t, 2H, CH₂), 4.30 (g, 2H, CH₂O), 4.42 (g, 2H, CH₂O), 7.11 (d, 1H), 7.21 (s, 1H), 7.45–7.65 (m, 5H), 8.05 (dd, 1H), 8.60 (d, 1H), 9.24 (bs, 1H, NH), 9.79 (bs, 1H, NH).

EXAMPLE 159

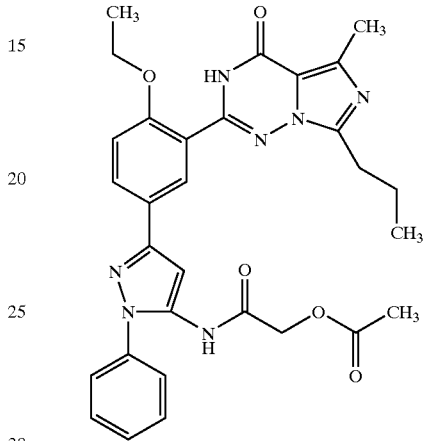

Analogously to example 157, 200 mg (0.43 mmol) of the aminopyrrazole example 153 in 4 ml of pyridine were reacted with 58.1 mg (0.43 mmol) of 2-acetoxyacetyl chloride. The crude product was triturated with ether, giving 158 mg (65.1%) of the desired product.

MS (ESI): m/z (%)=570 [M+H] (100) ¹H-NMR (200 MHz, D₆-DMSO): δ=0.93 (t, 3H, CH₃), 1.33 (t, 3H, CH₃), 1.74 (m, 2H, CH₂), 2.11 (s, 3H, CH₃), 2.53 (s, 3H, CH₃), 2.85 (t, 2H, CH₂), 4.17 (g, 2H, CH₂), 4.65 (s, 2H, CH₂), 6.92 (s, 1H), 7.25 (d, 1H), 7.35–7.60 (m, 5H), 7.99 (m, 2H), 10.25 (bs, 1H, NH), 11.63 (bs, 1H, NH).

EXAMPLE 160

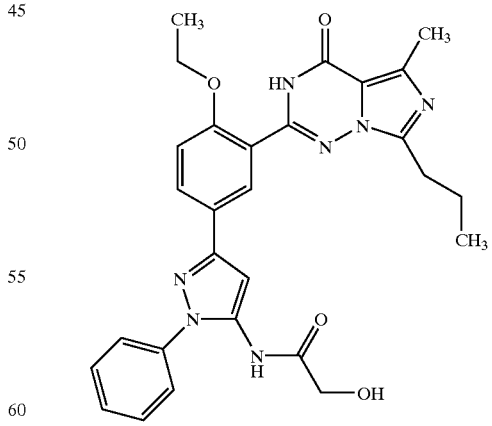

7.9 mg (0.19 mmol) of LiOH were added to a solution of 90 mg (0.16 mmol) of the amidopyrrazole example 159 in 2 ml of THF/H₂O (1:1), and the mixture was stirred at room temperature for 30 min. The mixture was diluted with 1 ml of H₂O and filtered through 3 g of Extrelut (mobile phase:

CH$_2$Cl$_2$). The crude product was recrystallized from CH$_2$Cl$_2$, giving 49 mg (58.8%) of the desired product.

MS (ESI): m/z (%)=528 [M+H] (100) $^1$H-NMR (200 MHz, D$_6$-DMSO): δ=0.93 (t, 3H, CH$_3$), 1.32 (m, 3H, CH$_3$), 1.75 (m, 2H, CH$_2$), 2.84 (t, 2H, CH$_2$), 3.95 (s, 2H, CH$_2$), 4.15 (g, 2H, CH$_2$), 6.91 (s, 1H), 7.22 (d, 1H), 7.33–7.68 (m, 5H), 7.98 (m, 2H).

EXAMPLE 161

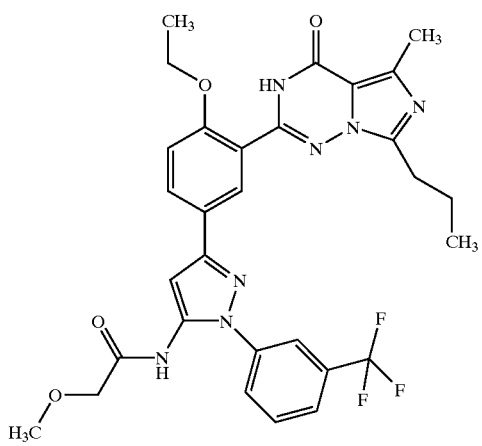

Analogously to example 156, 25 mg (0.068 mmol) of the nitrile example 151 were stirred with 14.3 mg (0.081 mmol) of 3-trifluorophenylhydrazine and 0.27 ml (0.135 mmol) of a 0.5 M solution of trifluoroacetic acid in 1,2-dichloroethane at room temperature for 20 h. 0.5 ml of sat. NaHCO$_3$ solution was added and the mixture was filtered through 0.5 g of Extrelut/0.5 g of SiO$_2$ (mobile phase: ethyl acetate), and the crude product was then dissolved in 0.5 ml of pyridine, and 157 μl (0.018 mmol) of 2-methoxyacetyl chloride were added. After 3 h at room temperature, another 1 ml of sat. NaHCO$_3$ was added, the mixture was filtered through 1 g of Extrelut (mobile phase: CH$_2$Cl$_2$) and the filtrate was concentrated under reduced pressure. Purification by thin-layer chromatography (CH$_2$Cl$_2$:MeOH=20.1) gave 4.5 mg (40.1%) of the desired product (90% pure according to HPLC).

MS (ESI): m/z (%)=610 [M+H] (100) $^1$H-NMR (200 MHz, CDCl$_3$): δ=1.05 (t, 3H, CH$_3$); 1.57 (t, 3H, CH$_3$); 1.90 (m, 2H, CH$_2$); 2.67 (s, 3H; CH$_3$); 3.07 (t, 2H, CH$_2$); 3.47 (s, 3H, OCH$_3$); 4.06 (s, 2H; CH$_2$); 4.32 (g, 2H, CH$_2$); 7.05–7.13 (m, 2H); 7.61–7.87 (m, 4H); 8.03 (dd, 1H); 8.59 (d, 1H); 8.68 (bs, 1H, NH); 9.88 (bs, 1H, NH).

The compounds of the table below were prepared in a parallel synthesis analogously to example 161 from the nitrile example 151, the appropriate hydrazine and 2-methoxyacetyl chloride.

| Ex. No. | Structure | MW [g/mol] | HPLC area % at 210 nm | Mz + H |
|---|---|---|---|---|
| 162 | 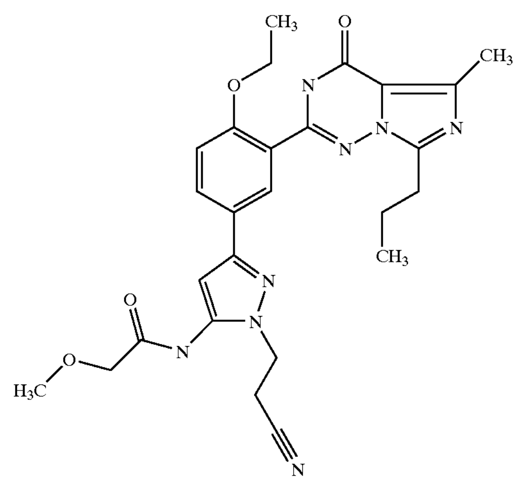 | 518.58 | 81 | 519.5802 |
| 163 | 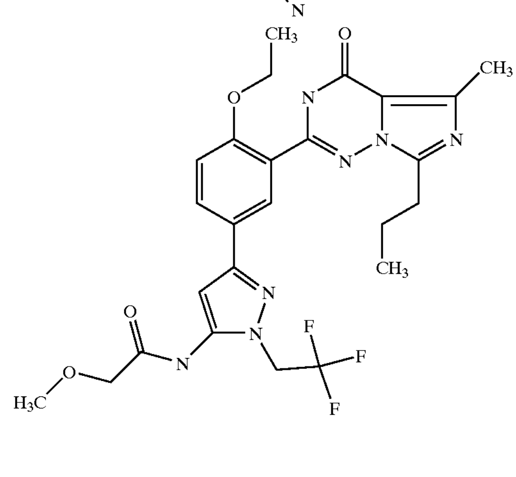 | 547.54 | 72 | 548.5416 |

-continued

| Ex. No. | Structure | MW [g/mol] | HPLC area % at 210 nm | Mz + H |
|---|---|---|---|---|
| 164 | 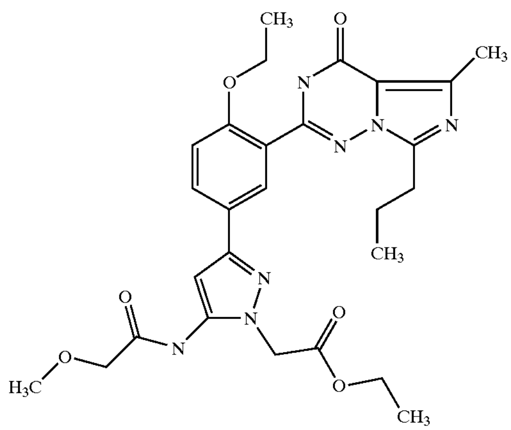 | 551.61 | 87 | 552.6074 |
| 165 | 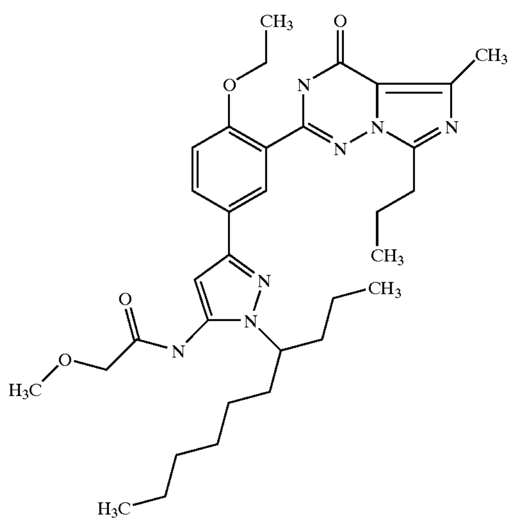 | 605.79 | 67 | 606.787 |
| 166 | 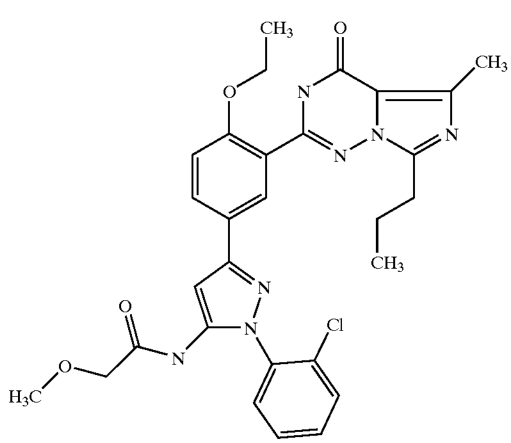 | 576.06 | 62 | 577.06 |

-continued

| Ex. No. | Structure | MW [g/mol] | HPLC area % at 210 nm | Mz + H |
|---|---|---|---|---|
| 167 | 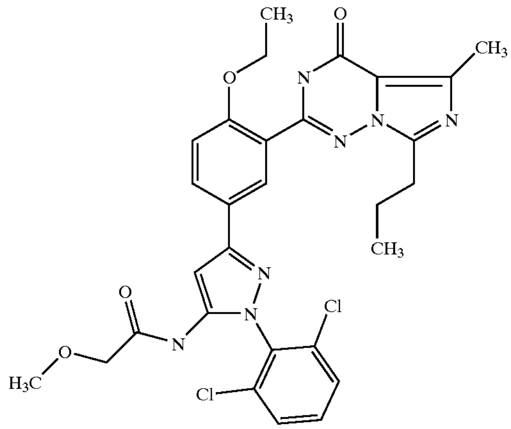 | 610.50 | 76 | 611.505 |

EXAMPLE 168

2-(2-Ethoxy-5-(2-oxiranyl)phenyl)-5-methyl-7-n-propyl-3H-imidazo[5,1-f][1,2,4]-triazin-4-one

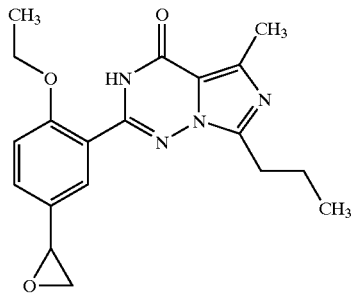

57 mg (1.5 mmol) of NaBH$_4$ (evolution of gas) and 1 ml of 2 N NaOH were added to a suspension, cooled to −20° C., of 500 mg (1.12 mmol) of the phenacyl bromide example 57A in 2 ml of THF. The frozen solution was warmed to 0° C. and stirred for 30 min. Addition of 10% strength acetic acid (strong evolution of gas) and two extractions with ethyl acetate gave, after drying of the extracts over MgSO$_4$ and concentration under reduced pressure, the crude product, which was purified chromatographically (gradient: CH$_2$Cl$_2$:MeOH from 100% to 100:1+50:1+30:1). The product fraction was concentrated and then triturated with ether, giving 221.7 mg (54.2%) of the epoxide.

MS (DCI, NH$_3$): m/z (%)=355 [M+H] (57) $^1$H-NMR (300 MHz, D$_3$COD): δ=0.98 (t, 3H, CH$_3$), 1.44 (t, 3H, CH$_3$), 1.83 (m, 2H, CH$_2$), 2.57 (s, 3H, CH$_3$), 3.98 (t, 2H, CH$_2$), 3.55–3.75 (m, 2H), 4.19 (g, 2H, CH$_2$), 4.87 (m, 1H), 7.17 (d, 1H), 7.58 (dd, 1H), 7.78 (d, 1H).

EXAMPLE 169

2-(2-Ethoxy-5-(2-oxiranyl)phenyl)-5-methyl-7-cycloheptyl-3H-imidazo[5,1-f][1,2,4]-triazin-4-one

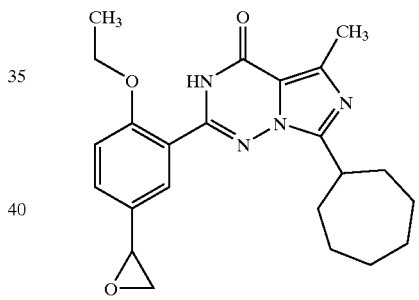

20.2 mg (0.53 mmol) of NaBH$_4$ (evolution of gas) and 2 ml of N NaOH solution were added to a suspension, cooled to −20° C., of 200 mg (0.41 mmol) of the phenacyl bromide example 60A in 0.8 ml of EtOH/0.8 ml of THF. The mixture was allowed to warm to 0° C. and, after 30 min a 10% strength solution of glacial acetic acid was added (strong evolution of gas), the mixture was extracted with ethyl acetate and the extract was dried over MgSO$_4$. The mixture was concentrated and the residue was purified chromatographically (gradient: CH$_2$Cl$_2$:MeOH=50:1). This gave 29 mg (17.3%) of the desired product and 104 mg (54%) of the ring-opening product example 170.

MS (DCI, NH$_3$): m/z (%)=409 [M+H] (53) $^1$H-NMR (400 MHz, D$_3$COD): δ=1.43 (t, 3H, CH$_3$), 1.55–2.05 (m, 12H, 6×CH$_2$), 2.57 (s, 3H, CH$_3$), 3.45 (m, 1H, CH), 3.71 (2×dd, 2H), 7.17 (d, 1H), 7.57 (dd, 1H), 7.78 (d, 1H).

EXAMPLE 170

Ring-Opening Product:

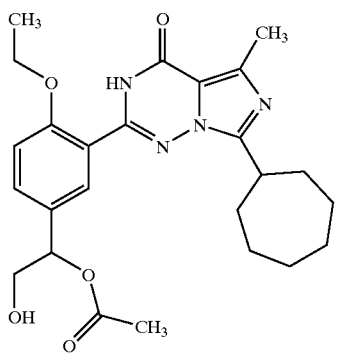

MS (DCI, NH₃): m/z (%)=469 [M+H] (100) ¹H-NMR (400 MHz, D₃COD): δ=1.43 (t, 3H, CH₃), 1.55–2.05 (m, 12H, 6×CH₂), 2.57 (s, 3H, CH₃), 3.45 (m, 1H, CH), 3.74 (dd, 1H), 3.83 (dd, 1H), 4.19 (g, 2H, CH₂O), 5.78 (dd, 1H, CH), 7.16 (d, 1H), 7.52 (dd, 1H), 7.71 (d, 1H).

EXAMPLE 171

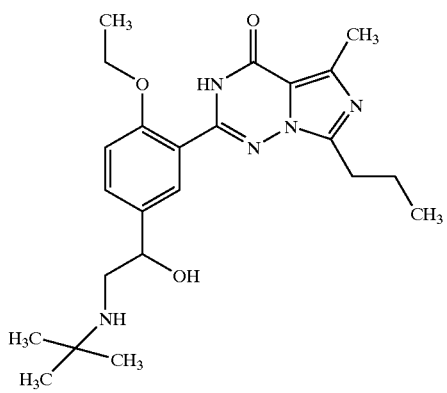

0.6 ml (5.6 mmol) of tert-butylamine was added to a suspension of 100 mg (0.282 mmol) of the epoxide example 168 in 2.5 ml of isopropanol, and the mixture was heated under reflux for 30 h. The reaction mixture was concentrated and purified by flash charomatography (gradient: CH₂Cl₂+ CH₂Cl₂/MeOH=10:1). This gave 105 mg of a mixture of two regioisomers which were separated by preparative HPLC.

42 mg (35%) as second fraction

¹H-NMR (200 MHz, CDCL₃): δ=1.02 (t, 3H, CH₃), 1.12 (s, 9H, C(CH₃)₃), 1.54 (t, 3H, CH₃), 1.88 (m, 2H, CH₂), 2.59 (dd, 1H), 2.64 (s, 3H, CH₃), 2.93 (dd, 1H), 3.01 (t, 2H, CH₂), 4.25 (g, 2H, CH₂), 4.61 (dd, 1H), 7.02 (d, 1H), 8.11 (d, 1H).

EXAMPLE 172

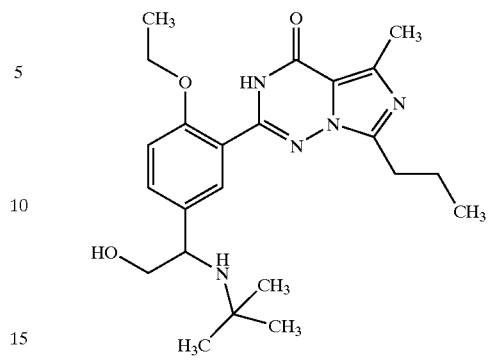

In the reaction example 171, as first fraction, 9 mg (7.5%) of the regioisomer are obtained as by-product.

¹H-NMR (200 MHz, CDCL₃): δ=1.03 (t, 3H, CH₃), 1.07 (s, 9H, C(CH₃)₃), 1.57 (t, 3H, CH₃), 1.89 (m, 2H, CH₂), 2.63 (s, 3H, CH₃), 3.03 (t, 2H, CH₂), 3.32 (dd, 1H), 3.61 (dd, 1H), 4.36 (dd, 1H), 4.25 (g, 2H, CH₂), 7.01 (d, 1H), 7.44 (dd, 1H), 8.08 (d, 1H).

EXAMPLE 173

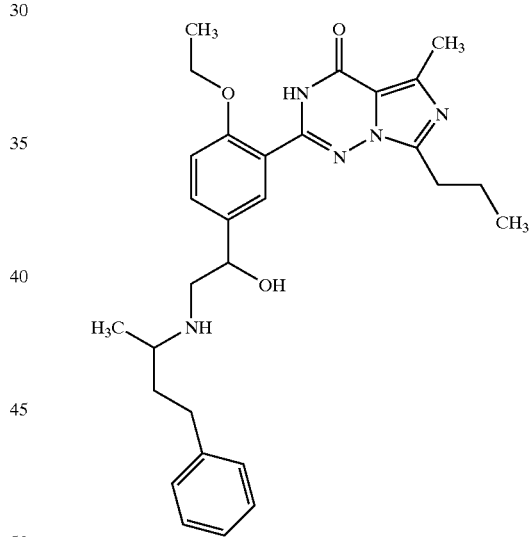

Analogously to example 171, 100 mg (0.28 mmol) of the epoxide example 168 were heated under reflux with 0.91 ml (5.6 mmol) of 1-phenyl-3-butylamine in 2.5 ml of isopropanol for 24 h. After concentration under reduced pressure, the two regioisomers were separated by preparative chromatography.

This gives 51.8 mg (36.5%) as second fraction

MS (ESI): m/z (%)=504 [M+H] (100) ¹H-NMR (200 MHz, CDCL₃): δ=1.02 (t, 3H, CH₃), 1.15 (d, 3H, CH₃), 1.56 (t, 3H, CH₃), 1.62–1.95 (m, 4H, 2×CH₂), 2.64 (s, 3H, CH₃), 2.68 (m, 2H), 3.01 (m, 3H), 4.25 (g, 2H, CH₂), 4.64 (dd, 1H, CHO), 7.03 (d, 1H), 7.12–7.33 (m, 5H, phenyl), 7.53 (dd, 1H), 8.09 (d, 1H)

EXAMPLE 174

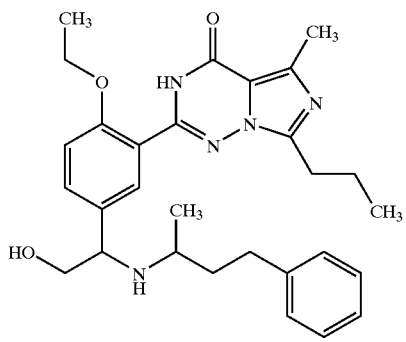

In the reaction example 173, as first fraction, 21.4 mg (15.1%) of the regioisomer are obtained as a by-product.

MS (ESI): m/z (%)=504 [M+H] (100) ¹H-NMR (200 MHz, CDCL₃): δ=0.93–1.13 (m, 9H, 3×CH₃), 1.57 (t, 3H, CH₃), 1.63–1.97 (m, 4H, 2×CH₂), 2.65 (m, 3H, CH₃), 2.65 (m, 1H, CH), 2.99 (q, 2H, CH₃), 3.42–3.75 (m, 2H), 3.92 (m, 1H), 4.25 (g, 2H, CH₂), 7.01 (d, 1H), 7.05–7.44 (m, 6H), 8.04 (dd, 1H), 9.90 (bs, 1H, NH)

EXAMPLE 175

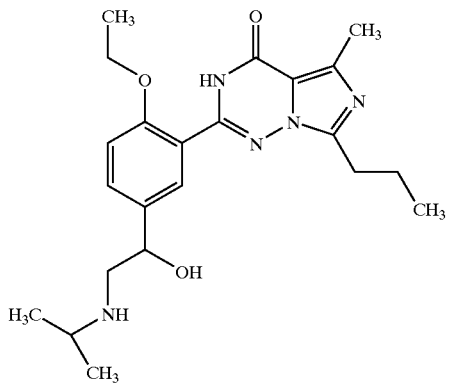

Analogously to example 171, 100 mg (0.28 mmol) of the epoxide example 168 were reacted with 0.48 ml (5.6 mmol) of isopropylamine. After chromatographic pre-purification (gradient: CH₂Cl₂+CH₂Cl₂/MeOH=10:1), 77.9 mg (67%) of the regioisomer mixture were separated by preparative HPLC.

10 mg (8.6%) are obtained as second fraction.

MS (ESI): m/z (%)=4.14 [M+H] (65) ¹H-NMR (200 MHz, CDCL₃): δ=1.03 (t, 3H, CH₃), 1.09 (d, 6H. 2×CH₃), 1.55 (t, 3H, CH₃), 1.88 (m, 2H, CH₂), 2.64 (s, 3H, CH₃), 2.66 (dd, 1H,), 2.88 (m, 1H, CH), 2.95 (m, 3H, CH, CH₂), 4.25 (g, 2H, CH₂), 4.69 (dd, 1H), 7.03 (d, 1H), 7.52 (dd, 1H), 8.09 (d, 1H).

EXAMPLE 176

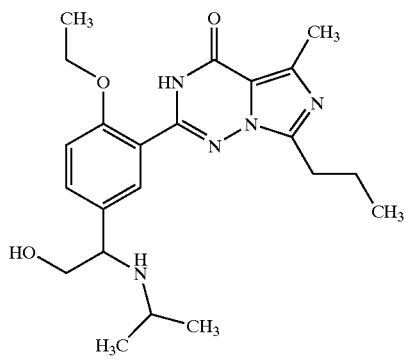

In the reaction example 175, as first fraction, 20 mg (8.6%) of the regioisomer are obtained as a by-product.

MS (ESI): m/z (%)=414 [M+H] (65) ¹H-NMR (200 MHz, CDCL₃): δ=1.04 (t, 3H, CH₃), 1.07 (2×d, 6H, 2×CH₃), 1.55 (t, 3H, CH₃), 1.88 (m, 2H, CH₂), 2.62 (s, 3H, CH₃), 2.75 (m, 1H, CH), 3.02 (t, 2H, CH₂), 3.49 (dd, 1H), 3.72 (dd, 1H), 3.94 (dd, 1H), 4.25 (g, 2H, CH₂), 7.03 (d, 1H), 7.43 (dd, 1H), 8.04 (d, 1H)

EXAMPLE 177 AND EXAMPLE 178

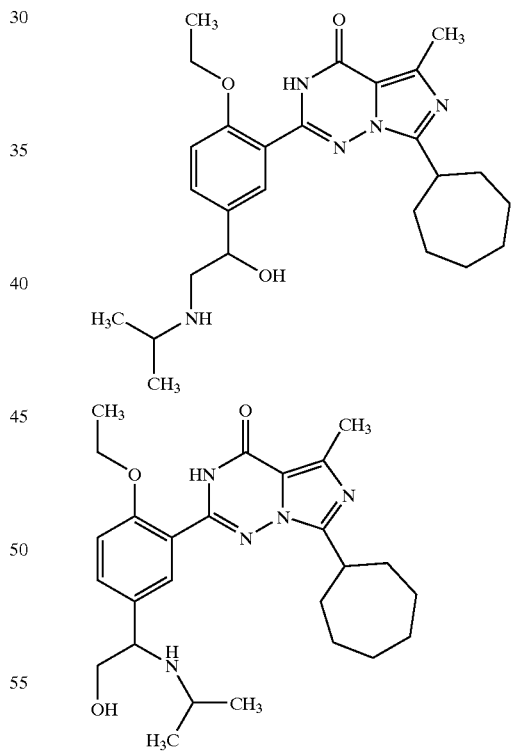

A solution of 20 mg (0.05 mmol) of the epoxide example 169 and 589 mg (0.98 mmol) of isopropylamine in 0.5 ml of isopropanol was heated at 80° C. for 20 h. The mixture was concentrated and the residue was then purified by preparative thin-layer chromatography. This gave 15 mg (65.5%) of the desired product as a mixture of two regioisomers.

MS (DCI, NH₃): m/z (%)=468 [M+H] (100)

Main regioisomer:

¹H-NMR (400 MHz, CDCl₃): δ=1.25 (2×d, 6H, 2×CH₃), 1.55 (t, 3H, CH₃), 1.57–2.10 (m, 12H, 6×CH₂), 2.64 (s, 3H, CH₃), 2.83 (dd, 1H), 3.08 (m, 2H), 3.43 (m, 1H, CH), 4.23 (q, 2H, CH₂O), 4.95 (dd, 1H, CH), 7.01 (d, 1H), 7.55 (dd, 1H), 8.10 (d, 1H).

2nd Regioisomer:

¹H-NMR (400 MHz, CDCl₃): δ=1.12 (2d, 6H, 2×CH₃), 1.53 (t, 3H, CH₃), 1.57–2.10 (m, 12H, 6×CH₂), 3.43 (m, 1H, CH), 3.62 (dd, 1H), 3.75 (dd, 1H), 4.00 (dd, 1H), 4.23 (q, 2H, CH₂O), 7.03 (d, 1H), 7.50 (dd, 1H), 8.06 (d, 1H).

EXAMPLE 179

2-(2-Ethoxy-5-carboxyphenyl)-5-methyl-7-n-propyl-3H-imidazo[5,1-f][1,2,4]-triazine-4-one

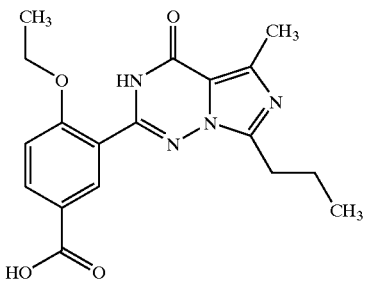

1.1 g (6.9 mmol) of bromine, dropwise, and then 1 g (2.3 mmol) of the phenacyl bromide example 57A, a little at a time, were added at 10° C. to a solution of 1.8 g (46 mmol) of NaPH in 10 ml of H₂O. The mixture was allowed to slowly warm to room temperature and, after 2 h, diluted with water and extracted once with CH₂Cl₂. The aqueous phase was then acidified (pH 1) and extracted twice with CH₂Cl₂ and five times with ethyl acetate. The organic phase was dried over MgSO₄ and concentrated under reduced pressure, and the residue was purified chromatographically (gradient: CH₂Cl₂+CH₂Cl₂:MeOH=20:1). The product fraction was once more triturated with CH₂Cl₂. This gave 146 mg (17.8%) of the desired product.

MS (DCI, NH₃): m/z (%)=357 [M+H] (100) ¹H-NMR (200 MHz, D₆-DMSO): δ=0.94 (t, 3H, CH₃), 1.35 (t, 3H, CH₃), 1.75 (m, 2H, CH₂), 2.84 (t, 2H, CH₂), 4.18 (q, 2H, CH₂), 7.25 (d, 1H), 7.99 (dd, 1H), 8.10 (d, 1H), 11.62 (bs, 1H, NH), 12.92 (bs, 1H, COOH).

EXAMPLE 180

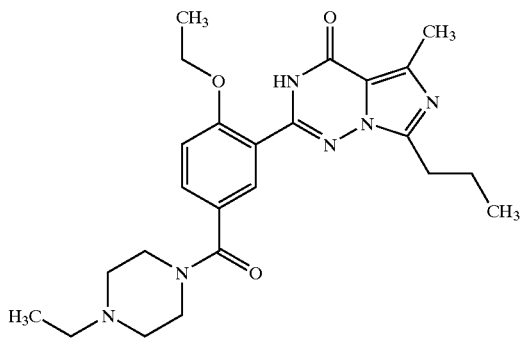

5.1 mg (0.04 mmol) of N-ethylpiperazine. 18 mg (0.06 mmol) of o-(benzotriazol-1-yl)-N,N,N',N'-tetramethyluronium tetrafluoroborate (TBTU) and 10.8 mg of N-ethyldiisopropylamine were added to a solution of 20 mg (0.06 mmol) of the carboxylic acid example 179 in 2 ml of DMF, and the mixture was stirred at room temperature for 1 h. The DMF was condensed off under high vacuum, 0.5 ml of water were added to the residue and the mixture was filtered through a two-phase cartridge (500 mg of Extrelut/500 mg of SiO₂, mobile phase: 1. ethyl acetate, 2 CH₂Cl₂:MeOH=10:1) The CH₂Cl₂/MeOH phase was concentrated, and the residue was separated by preparative thin-layer chromatography. This gave 245 mg (96.5%) of the desired product.

MS (DCI, NH₃): m/z (%)=453 [M+H] (100) ¹H-NMR (400 MHz, D₃COD): δ=0.98 (t, 3H, CH₃), 1.13 (t, 3H, CH₃), 1.45 (t, 3H, CH₃), 1.82 (m, 2H), 2.48 (q, 2H, CH₂), 2.53 (bs, 4H, 2×CH₂), 2.57 (s, 3H, CH₃), 2.95 (t, 2H, CH₂), 3.45 (m, 4H, 2×CH₂), 4.25 (q, 2H, CH₂), 7.23 (d, 1H), 7.63 (dd, 1H), 7.78 (d, 1H).

EXAMPLE 181

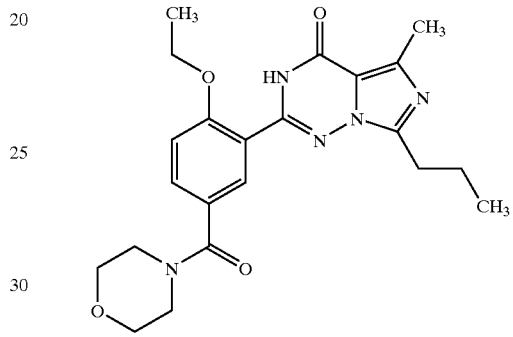

20 mg (0.06 mmol) of the carboxylic acid example 179 and 5.4 mg (0.06 mmol) of morpholine were added to a suspension, cooled to 0° C., of 77.8 mg (0.06 mmol) of polymer-bound N-(3-dimethylaminopropyl)-N-ethylcarbodiimide (EDC) in 3 ml of CHCl₃. The mixture was allowed to warm to room temperature overnight and then heated under reflux for 20 h. 1 ml of sat. NaHCO₃ solution was added and the mixture was filtered through 1 g of Extrelut (mobile phase: CH₂Cl₂). The concentrated residue was purified by preparative thin-layer chromatography (CH₂Cl₂:MeOH=20:1). This gave 3.5 mg (14.7%) of the desired product.

MS (ESI): m/z (%)=426 [M+H] (100) ¹H-NMR (200 MHz, CDCl₃): δ=1.03 (t, 3H, CH₃), 1.59 (t, 3H, CH₃), 1.87 (m, 2H, CH₂), 2.64 (s, 3H, CH₃), 2.99 (t, 2H, CH₂), 3.55–3.81 (m, 8H, 4×CH₂), 4.31 (q, 2H, CH₂O), 7.10 (d, 1H), 7.62 (dd, 1H), 8.25 (d, 1H), 9.89 (bs, 1H, NH).

EXAMPLE 182

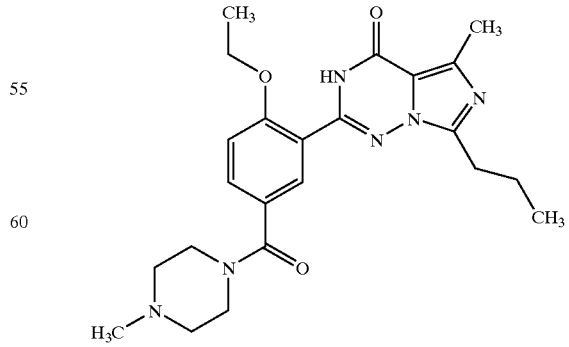

Analogously to example 181, 10 mg (0.03 mmol) of the carboxylic acid example 179 were reacted with 3.1 mg (0.031 mmol) of N-methylpiperazine and 38.4 mg (0.038 mmol) of polymer-bound EDC. Preparative thin-layer chromatography (CH$_2$Cl$_2$:MeOH=10:1) gave 4.2 mg (34.1%) of the desired product.

MS (ESI): m/z (%)=439 [M+H] (38) $^1$H-NMR (200 MHz, CDCl$_3$): δ=1.02 (t, 3H, CH$_3$), 1.59 (t, 3H, CH$_3$), 1.85 (m, 2H, CH$_2$), 2.34 (s, 3H, CH$_3$), 2.48 (bs, 4H, 2×CH$_2$), 2.63 (s, 3H, CH$_3$), 3.00 (t, 2H, CH$_2$), 3.65 (bm, 4H, 2×CH$_2$), 4.31 (g, 2H, CH$_2$), 7.09 (d, 1H), 7.60 (dd, 1H), 8.24 (d, 1H), 9.83 (bs, 1H, NH).

EXAMPLE 183

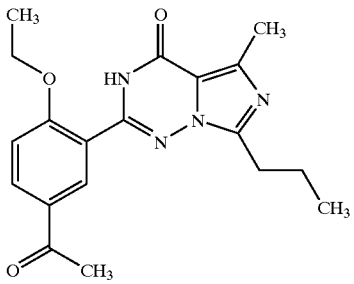

1.7 ml of a 0.1 M solution of SmJ$_2$ (0.17 mmol) in THF were added to a solution of 50 mg (0.12 mmol) of the phenacyl bromide example 57A, and the mixture was heated under reflux for 20 h. Two more times, in each case after 24 h, 1.7 ml of SmJ$_2$ solution were added. Cooling and filtration through 500 mg of silica gel gave 60 mg of crude product which was purified chromatographically (gradient: CH$_2$Cl$_2$+ CH$_2$Cl$_2$/MeOH 100:1+50:1). This gave 27.6 mg (67.5%) of the desired product (81% according to LC-MS)

MS (ESI): m/z (%)=355 [M+H] (100) $^1$H-NMR (200 MHz, CDCl$_3$): δ=1.05 (t, 3H, CH$_3$), 1.59 (t, 3H, CH$_3$), 1.91 (m, 2H, CH$_2$), 2.63 (s, 3H, CH$_3$), 2.64 (s, 3H, CH$_3$), 3.02 (t, 2H, CH$_2$), 4.33 (g, 2H, CH$_2$), 7.11 (d, 1H) 8.12 (dd, 1H), 8.72 (d, 1H), 9.64 (bs, 1H, NH)

EXAMPLE 184

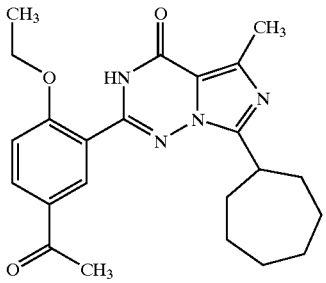

Analogously to example 183, 50 mg (0.10 mmol) of the phenacyl bromide example 60A were heated under reflux with 5.1 ml (0.51 mmol) of a 0.1 M solution of SmI$_2$ in THF for 10 h. Purification by thin-layer chromatography (CH$_2$Cl$_2$:MeOH=20:1) gave 14.4 mg (34.4%) of the desired product (94.1% according to HPLC).

MS (ESI) m/z (%)=409 [M+H] (100) $^1$H-NMR (200 MHz, CDCL$_3$). δ=1.59 (t, 3H, CH$_3$), 1.60–2.10 (m, 12H, 6×CH$_2$), 2.63 (s, 6H, 2×CH$_3$), 3.43 (m, 1H, CH), 4.33 (g, 2H, CH$_2$), 7.11 (d, 1H), 8.12 (dd, 1H), 8.72 (d, 1H), 9.82 (bs, 1H, NH)

EXAMPLE 185

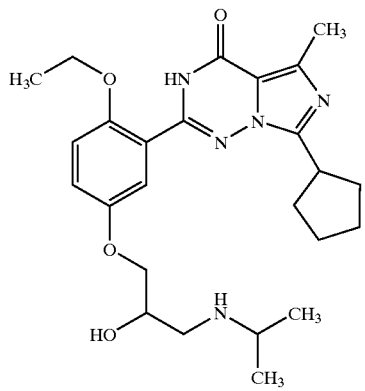

A suspension of 180 mg of the epoxide example 40A (0.44 mmol) in 3.5 ml of isopropanol is slowly added to a solution of 1.9 ml of isopropylamine (21.9 mmol) in 1.5 ml of isopropanol. Immediately, a clear yellow solution is formed. After stirring overnight, the precipitated solid is filtered off with suction, washed with a little isopropanol and with petroleum ether and dried under high vacuum.

Yield: 83.6 mg (39.9% of theory) MS (DCI, NH$_3$): m/z (%)=470 (M+H) (100) $^1$H-NMR (400 MHz, D$_4$-MeOD): δ=1.11 (t, 6H); 1.42 (t, 3H); 1.70–1.78 (m, 2 H); 1.86–1.95 (m, 4 H); 2.10–2.18 (m, 2 H); 2.58 (s, 3 H); 2.69 (dd, 1 H); 2.85–2.90 (m, 2H); 3.66 (qui, 1 H); 3.96–4.07 (m, 3 H); 4.14 (2 H); 7.09–7.17 (m, 2 H); 7.38 (d, 1 H).

EXAMPLE 186

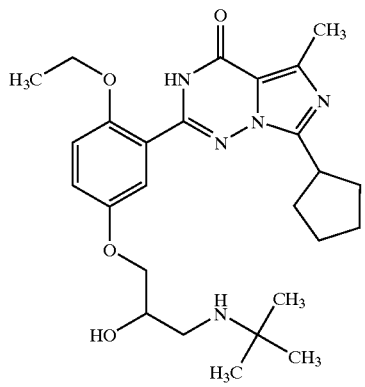

tert-Butylamine (2.6 ml, 25 mmol) is initially charged in 1.5 ml of isopropanol, and the mixture is cooled to 0° C. A suspension of 205 mg of the epoxide example 40A (0.5 mmol) and 3.5 ml of isopropanol is then added. With stirring, the mixture is allowed to warm to room temperature and then stirred overnight. The mixture is concentrated using a rotary evaporator and the residue is purified by column chromatography using dichloromethane/methanol/ammonia solution 95:5:1.

Yield: 177 mg (73% of theory) MS (ESI-pos): m/z (%)=484 (M+H) (100), 428 (68), 325 (21) $^1$H-NMR (400 MHz, D$_4$-MeOD): δ=1.15 (s, 9 H); 1.42 (t, 3 H); 1.68–1.78 (m, 2 H); 1.85–1.98 (m, 4 H); 2.07–2.16 (m, 2 H); 2.55 (s, 3 H); 2.68–2.81 (m, 2 H); 3.55 (qui, 1H); 3.95–4.05 (m, 3 H); 4.14 (q, 2 H); 7.09–7.17 (2 H); 7.48 (d, 1 H).

EXAMPLE 187

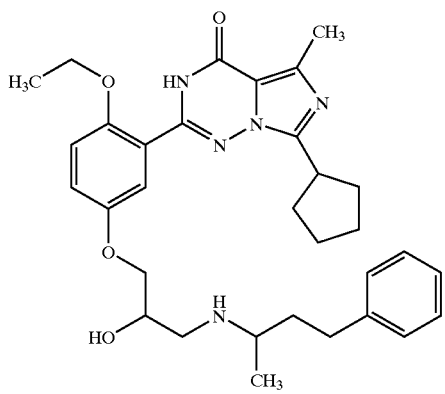

A suspension of 205 mg of the epoxide example 40A (0.5 mmol) in 3.5 ml of isopropanol is added to an ice-cooled solution of 1-methyl-3-phenylpropylamine (1.2 ml, 7.5 mmol) in 1.5 ml of isopropanol. With stirring, the mixture is allowed to warm to room temperature and then stirred overnight. Following concentration, the crude product is purified by column chromatography using dichloromethane/methanol/ammonia solution 97:3:1. The product fractions are concentrated using a rotary evaporator and the resulting residue is crystallized with ether. The product is filtered off with suction and dried under high vacuum.

Yield: 192 mg (67.7% of theory) MS (DCI, $NH_3$): m/z (%)=560 (M+H) (100) $^1$H-NMR (200 MHz, $D_4$-MeOD): δ=1.15 (d, 3 H); 1.42 (t, 3 H); 1.55–2.20 (m, 10H); 2.55–3.92 (m, 9 H); 3.65 (qui, 1 H); 3.98–4.20 (m, 5 H); 7.06–7.27 (m, 6 H); 7.38 (d, 1 H).

What is claimed is:
1. An imidazotriazinone of formula (I)

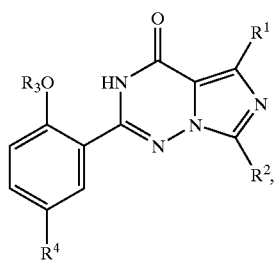
(I)

in which
  $R^1$ represents $C_1$–$C_6$-alkyl,
  $R^2$ represents ($C_3$–$C_8$)-cycloalkyl or ($C_1$–$C_{12}$)-alkyl,
  $R^3$ represents ($C_1$–$C_6$)-alkyl,
  $R^4$ represents a radical of the formulae in which

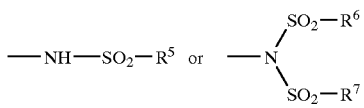

in which
  $R^5$, $R^6$ and $R^7$ are identical or different and represent vinyl or ($C_1$–$C_6$)-alkyl which is optionally substituted up to 3 times by identical or different substituents from the group consisting of trifluoromethyl, halogen, ($C_1$–$C_6$)-alkoxy or by radicals of the formulae

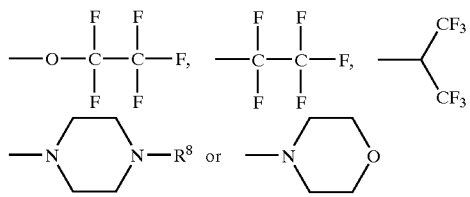

in which
  $R^8$ represents hydrogen or ($C_1$–$C_4$)-alkyl, or
  $R^5$, $R^6$ and/or $R^7$ represent ($C_6$–$C_{12}$)-aryl which is optionally substituted up to 3 times by identical or different substituents from the group consisting of halogen, trifluoromethyl, nitro, cyano, carboxyl, ($C_1$–$C_6$)-alkyl and ($C_1$–$C_6$)-alkoxy or
  $R^5$ represents quinolyl or a 5- to 6-membered aromatic or saturated heterocycle having up to 3 heteroatoms from the group consisting of S, N and O, which heterocycle may optionally be substituted up to 3 times, in the case of an N function also via this N function, by identical or different substituents from the group consisting of halogen and ($C_1$–$C_6$)-alkyl or
  $R^5$ represents a radical of the formula

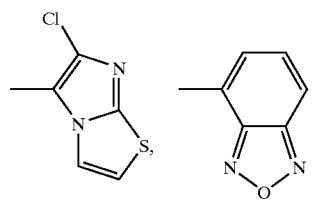

or $-NR^9R^{10}$,
in which
  $R^9$ and $R^{10}$ are identical or different and represent hydrogen, ($C_1$–$C_6$)-alkyl or phenyl, or
  $R^4$ represents carboxyl or represents a radical of the formulae

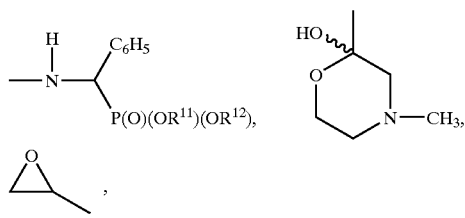

$-CO-R^{13}$ or $-O-R^{14}$, in which
  $R^{11}$ and $R^{12}$ are identical or different and represent hydrogen or ($C_1$–$C_4$)-alkyl,
  $R^{13}$ represents ($C_1$–$C_6$)-alkyl,
  $R^{14}$ represents ($C_1$–$C_6$)-alkyl which is optionally substituted up to 3 times by identical or different substituents from the group consisting of hydroxyl, phenyl or by a radical of the formula $-NR^{15}R^{16}$,
in which
  $R^{15}$ and $R^{16}$ are identical or different and represent hydrogen, phenyl or ($C_1$–$C_4$)-alkyl which for its part may be substituted by phenyl, or R⁴ represents a radical of the formula —NH—CO—NR¹⁷R¹⁸,
in which
R¹⁷ and R¹⁸ are identical or different and represent hydrogen or (C₁–C₆)-alkyl which is optionally substituted by hydroxyl or by a radical of the formulae

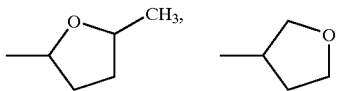

or —NR¹⁹R²⁰,
in which
R¹⁹ and R²⁰ are identical or different and represent hydrogen, phenyl or (C₁–C₆)-alkyl or
R¹⁷ and R¹⁸ together with the nitrogen atom to which they are attached form a heterocyclic ring of the formulae

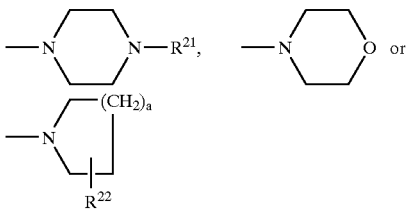

in which
R²¹ represents hydrogen or (C₁–C₆)-alkyl,
a represents either 1 or 2,
R²² represents hydroxyl or (C₁–C₆)-alkyl which is optionally substituted by hydroxyl, or
R¹⁷ and/or R¹⁸ represent (C₆–C₁₂)-alkyl which is optionally substituted by halogen, trifluoroethyl or by —SCF₃
or
R¹⁷ represents hydrogen and
R¹⁸ represents a radical of the formula —SO₂—R²³,
in which
R²³ represents (C₁–C₆)-alkyl or (C₆–C₁₂)-aryl which is optionally substituted by halogen, or represents a radical of the formulae

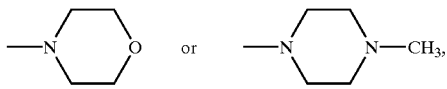

or
R⁴ represents a radical of the formula

—NH—CO—R²⁴, in which
R²⁴ represents a radical of the formula

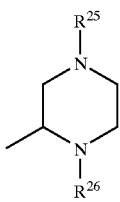

in which
R²⁵ and R²⁶ are identical or different and represent hydrogen, (C₁–C₆)-alkyl or (C₁–C₆)-alkoxycarbonyl, or R²⁴ represents (C₁–C₆)-alkyl which is optionally substituted by (C₆–C₁₂)-aryl which for its part may be substituted by hydroxyl or (C₁–C₆)-alkoxy or
(C₁–C₆)-alkyl optionally substituted by a radical of the formula —(SO₂)ᵦ—R²⁷,
in which
b represents either 0 or 1 and
R²⁷ represents a radical of the formulae

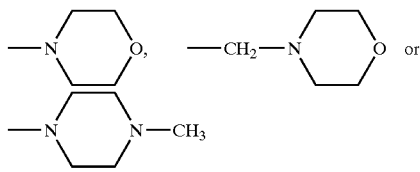

or
R⁴ represents (C₁–C₁₂)-alkyl which is optionally substituted up to 3 times by identical or different radicals from the group consisting of hydroxy, azide, phenyl or by radicals of the formulae —NR²⁸R²⁹, —O—CO—R³⁰ or —P(O){O—[(C₁–C₆)-alkyl]}₂, in which
R²⁸ and R²⁹ are identical or different and represent hydrogen, phenyl or (C₁–C₆)-alkyl which is optionally substituted by hydroxyl, (C₁–C₆)-alkoxy or phenyl,
or
R²⁸ and R²⁹ together with the nitrogen atom to which they are attached form a heterocyclic ring of the formulae

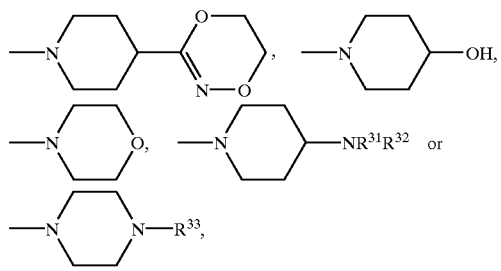

in which
R³¹ and R³² are identical or different and represent hydrogen or (C₁–C₆)-alkyl
R³³ represents (C₁–C₆)-alkyl, benzyl, (C₁–C₆)-alkoxycarbonyl, (C₁–C₆)-alkylcarbonyl, carboxyl, pyridyl, pyrimidyl or phenyl which is optionally substituted by (C₁–C₆)-alkoxy, and
R³⁰ represents (C₁–C₆)-alkyl, or
(C₁–C₁₂)-alkyl optionally substituted by triazolyl which for its part may be substituted up to 2 times by identical or different substituents from the group consisting of halogen, phenyl, tetrahydrofuranyl, tetrahydropyranyl, (C₁–C₆)-alkoxycarbonyl, aminocarbonyl or by (C₁–C₆)-alkyl, where the latter may optionally be substituted by hydroxyl, (C₁–C₆)-alkoxy or by a radical of the formulae NR³⁴R³⁵ or —O—CO—R³⁶,
in which
R³⁴ and R³⁵ are identical or different and represent hydrogen or (C₁–C₆)-alkyl,
R³⁶ represents (C₁–C₆)-alkyl, or $R^4$ represents a radical of the formula —CO—$R^{37}$,
in which
$R^{37}$ represents a radical of the formulae

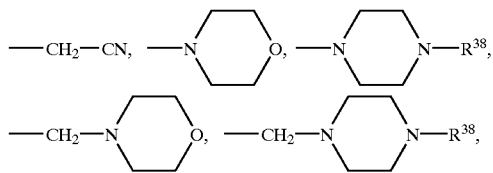

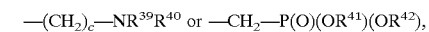

in which
$R^{38}$ represents hydrogen or $(C_1-C_6)$-alkyl,
c represents either 0 or 1,
$R^{39}$ and $R^{40}$ are identical or different and represent hydrogen or $(C_1-C_6)$-alkyl which is optionally substituted by hydroxyl,
$R^{41}$ and $R^{42}$ are identical or different and represent $(C_1-C_6)$-alkyl, or $R^4$ represents a 5-membered heterocycle having up to 3 heteroatoms from the group consisting of S, N and O, which heterocycle is optionally substituted altogether up to 3 times, in the case of an N function also via this N function, by identical or different substituents from the group consisting of halogen, trifluoromethyl or by phenyl which for its part may be mono- or polysubstituted by halogen or trifluoromethyl,
and/or is optionally substituted by $(C_3-C_6)$-cycloalkyl, pyrryl or by $(C_1-C_{12})$-alkyl which for its part may be substituted by cyano, trifluoromethyl, $(C_1-C_6)$-alkoxycarbonyl, $(C_1-C_6)$-alkoxy, amino or by phenyl or nitro-substituted phenyl,
and/or may optionally be substituted by —$NR^{43}R^{44}$, —NH—CO—CO—$R^{45}$,

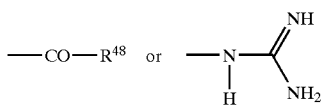

in which
$R^{43}$ and $R^{44}$ are identical or different and represent hydrogen, benzyl, $(C_1-C_6)$-alkyl or phenyl which is optionally substituted by halogen or trifluoromethyl,
$R^{45}$ represents $(C_1-C_6)$-alkoxy,
$R^{46}$ represents $(C_1-C_6)$-alkyl or phenyl,
$R^{47}$ represents hydroxyl, $(C_1-C_6)$-alkoxy or a radical of the formula —O—CO—$R^{49}$,
in which
$R^{49}$ represents $(C_1-C_4)$-alkyl
$R^{48}$ represents a radical of the formula —CH2—CN or phenyl which is optionally substituted by halogen, trifluoromethyl or $(C_1-C_6)$-alkoxy,
or a tautomer, a pharmaceutically acceptable salt thereof.

2. An imidazotriazinone of formula (I) as claimed in claim 1,
where
$R^1$ represents $(C_1-C_4)$-alkyl,
$R^2$ represents cyclopentyl, cycloheptyl or $(C_1-C_{10})$-alkyl,
$R^3$ represents $(C_1-C_4)$-alkyl, $R^4$ represents a radical of the formulae

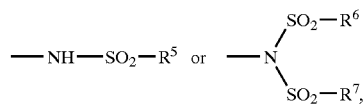

in which
$R^5$, $R^6$ and $R^7$ are identical or different and represent vinyl or $(C_1-C_4)$-alkyl which is optionally substituted up 3 times by identical or different substituents from the group consisting of trifluoromethyl, chlorine, $(C_1-C_4)$-alkoxy or by radicals of the formulae

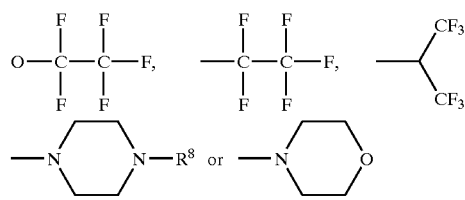

in which
$R^8$ represents hydrogen, methyl or ethyl, or $R^5$, $R^6$ and/or $R^7$ represent phenyl which is optionally substituted up to 3 times by identical or different substituents from the group consisting of halogen, trifluoromethyl, nitro, cyano, carboxyl, $(C_1-C_4)$-alkyl and $(C_1-C_4)$-alkoxy or $R^5$ represents quinolyl or a radical of the formulae

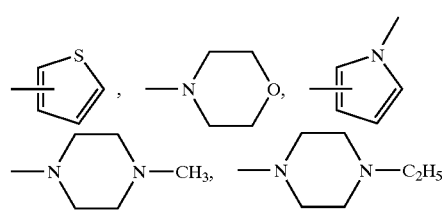

which may optionally be substituted up to 2 times by identical or different substituents from the group consisting of chlorine and $(C_1-C_4)$-alkyl or $R^5$ represents a radical of the formulae

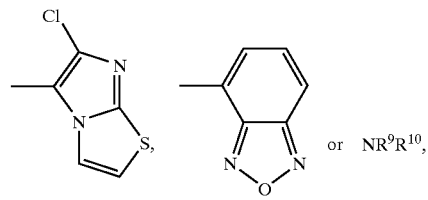

in which
$R^9$ and $R^{10}$ are identical or different and represent hydrogen, $(C_1-C_6)$-alkyl or phenyl, or $R^4$ represents carboxyl or represents a radical of the formulae

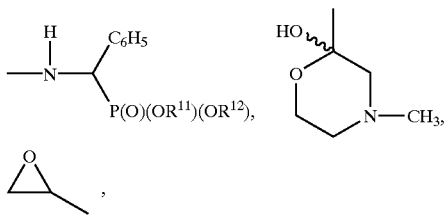

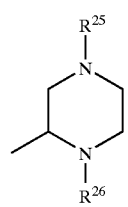

—CO—R$^{13}$ or O—R$^{14}$, in which
R$^{11}$ and R$^{12}$ are identical or different and represent hydrogen or (C$_1$–C$_4$)-alkyl,
R$^{13}$ represents C$_1$–C$_4$-alkyl,
R$^{14}$ represents (C$_1$–C$_4$)-alkyl which is optionally substituted up 3 times by identical or different substituents from the group consisting of hydroxyl, phenyl or by a radical of the formula —NR$^{15}$R$^{16}$,
in which
R$^{15}$ and R$^{16}$ are identical or different and represent hydrogen, phenyl or (C$_1$–C$_4$)-alkyl which for its part may be substituted by phenyl, or
R$^4$ represents a radical of the formula —NH—CO—NR$^{17}$R$^{18}$,
in which
R$^{17}$ and R$^{18}$ are identical or different and represent hydrogen or (C$_1$–C$_4$)-alkyl which is optionally substituted by hydroxyl or by a radical of the formulae

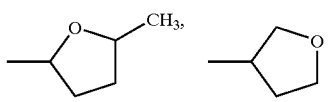

or —NR$^{19}$R$^{20}$,
in which
R$^{19}$ and R$^{20}$ are identical or different and represent hydrogen, phenyl or (C$_1$–C$_4$)-alkyl or
R$^{17}$ and R$^{18}$ together with the nitrogen atom to which they are attached form a heterocyclic ring of the formulae

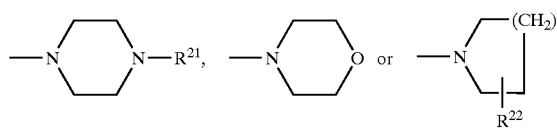

in which
R$^{21}$ represents hydrogen or (C$_1$–C$_4$)-alkyl,
a represents either 1 or 2,
R$^{22}$ represents hydroxyl or (C$_1$–C$_4$)-alkyl which is optionally substituted by hydroxyl, or
R$^{17}$ and/or R$^{18}$ represent phenyl which is optionally substituted by chlorine, trifluoroethyl or by —SCF$_3$ or
R$^{17}$ represents hydrogen and
R$^{18}$ represents a radical of the formula —SO$_2$—R$^{23}$,
in which
R$^{23}$ represents (C$_1$–C$_4$)-alkyl or phenyl which is optionally substituted by halogen, or represents a radical of the formulae

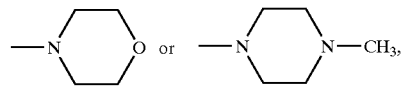

or

R$^4$ represents a radical of the formula
—NH—CO—R$^{24}$, in which
R$^{24}$ represents a radical of the formula

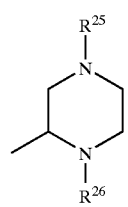

in which
R$^{25}$ and R$^{26}$ are identical or different and represent hydrogen, (C$_1$–C$_4$)-alkyl or (C$_1$–C$_4$)-alkoxycarbonyl, or
R$^{24}$ represents (C$_1$–C$_4$)-alkyl which is optionally substituted by phenyl which for its part may be substituted by hydroxyl or (C$_1$–C$_4$)-alkoxy or
(C$_1$–C$_4$)-alkyl optionally substituted by a radical of the formula —(SO$_2$)$_b$—R$^{27}$,
in which
b represents either 0 or 1 and
R$^{27}$ represents a radical of the formulae

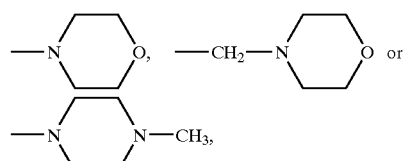

R$^4$ represents (C$_1$–C$_{11}$)-alkyl which is optionally substituted up to 3 times by identical or different substituents from the group consisting of hydroxyl, azide, phenyl or by radicals of the formulae —NR$^{28}$R$^{29}$, —O—CO—R$^{30}$ or —P(O){O—[(C$_1$–C$_6$)-alkyl]}$_2$,
in which
R$^{28}$ and R$^{29}$ are identical or different and represent hydrogen, phenyl or (C$_1$–C$_4$)-alkyl which is optionally substituted by hydroxyl, (C$_1$–C$_4$)-alkoxy or phenyl, or
R$^{28}$ and R$^{29}$ together with the nitrogen atom to which they are attached form a heterocyclic ring of the formulae

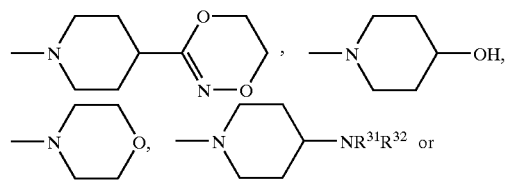

in which
R$^{31}$ and R$^{32}$ are identical or different and represent hydrogen or (C$_1$–C$_4$)-alkyl
R$^{33}$ represents (C$_1$–C$_4$)-alkyl, benzyl, (C$_1$–C$_4$)-alkoxycarbonyl, (C$_1$–C$_4$)-alkylcarbonyl carboxyl, pyridyl, pyrimidyl or phenyl which is optionally substituted by (C$_1$–C$_4$)-alkoxy, and
R$^{30}$ represents (C$_1$–C$_6$)-alkyl, or
(C$_1$–C$_{11}$)-alkyl is optionally substituted by triazolyl which for its part may be substituted up to 2 times by identical or different substituents from the group consisting of halogen, phenyl, tetrahydrofuranyl, tetrahydropyranyl, (C$_1$–C$_4$)-alkoxycarbonyl, aminocarbonyl or by (C$_1$–C$_4$)-alkyl, where the latter may optionally be substituted by hydroxyl, (C$_1$–C$_4$)-alkoxy or by a radical of the formulae NR$^{34}$R$^{35}$ or —O—CO—R$^{36}$,
in which
R$^{34}$ and R$^{35}$ are identical or different and represent hydrogen or (C$_1$–C$_4$)-alkyl,
R$^{36}$ represents (C$_1$–C$_4$)-alkyl, or
R$^4$ represents a radical of the formula —CO—R$^{37}$,
in which
R$^{37}$ represents a radical of the formula

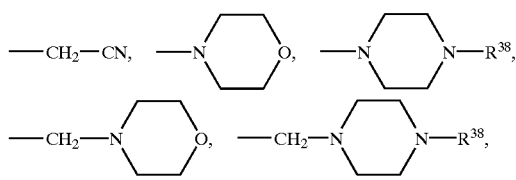

—(CH$_2$)$_c$—NR$^{39}$R$^{40}$ or —CH$_2$—P(O)(OR$^{41}$)(OR$^{42}$), in which
R$^{38}$ represents hydrogen or (C$_1$–C$_4$)-alkyl,
c represents either 0 or 1,
R$^{39}$ and R$^{40}$ are identical or different and represent hydrogen or (C$_1$–C$_4$)-alkyl which is optionally substituted by hydroxyl,
R$^{41}$ and R$^{42}$ are identical or different and represent (C$_1$–C$_4$)-alkyl, or
R$^4$ represents a radical of the formula

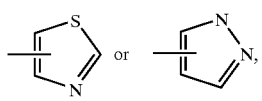

which is optionally substituted altogether up to 3 times, in the case of the pyrazole also via the N function, by identical or different substitutents from the group consisting of chlorine, trifluoromethyl or by phenyl which for its part may be mono- or polysubstituted by chlorine or trifluoromethyl,
and/or is optionally substituted by cyclopentyl, cyclohexyl, pyrryl or by (C$_1$–C$_{12}$)-alkyl which for its part may be substituted by cyano, trifluoromethyl, (C$_1$–C$_4$)-alkoxycarbonyl, (C$_1$–C$_4$)-alkoxy, amino or by phenyl or nitro-substituted phenyl,
and/or may optionally be substituted by —NR$^{43}$R$^{44}$, —NH—CO—CO—R$^{45}$,

—NH—CO—R$^{46}$,   —NH—CO—CH$_2$—R$^{47}$,

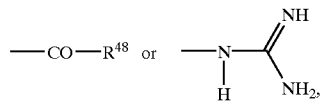

in which
R$^{43}$ and R$^{44}$ are identical or different and represent hydrogen, benzyl, (C$_1$–C$_4$)-alkyl or phenyl which is optionally substituted by halogen or trifluoromethyl,
R$^{45}$ represents (C$_1$–C$_5$)-alkoxy,
R$^{46}$ represents (C$_1$–C$_5$)-alkyl or phenyl,
R$^{47}$ represents hydroxyl, (C$_1$–C$_4$)-alkoxy or a radical of the formula —O—CO—R$^{49}$,
in which
R$^{49}$ represents (C$_1$–C$_3$)-alkyl
R$^{48}$ represents a radical of the formula —CH$_2$—CN or phenyl which is optionally substituted by chlorine, trifluoromethyl or (C$_1$–C$_4$)-alkoxy,
or a tautomer, a pharmaceutically acceptable salt thereof.

3. An imidazotriazinone of formula (I) as claimed in claim 1,
where
R$^1$ represents (C$_1$–C$_4$)-alkyl,
R$^2$ represents cyclopentyl, cyclohexyl, cycloheptyl or (C$_1$–C$_{10}$)-alkyl,
R$^3$ represents (C$_1$–C$_4$)-alkyl,
R$^4$ represents a radical of the formulae

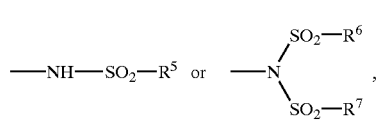

in which
R$^5$, R$^6$ and R$^7$ are identical or different and represent vinyl or (C$_1$–C$_4$)-alkyl which is optionally substituted up to 3 times by identical or different, substituents from the group consisting of trifluoromethyl, chlorine, (C$_1$–C$_4$)-alkoxy or by radicals of the formulae

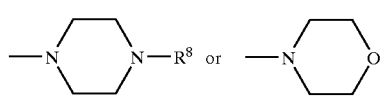

in which
R$^8$ represents hydrogen, methyl or ethyl,
or
R$^5$, R$^6$ and/or R$^7$ represent phenyl which is optionally substituted up to 3 times by identical or different substituents from the group consisting of halogen, cyano, (C$_1$–C$_4$)-alkyl and (C$_1$–C$_4$)-alkoxy or
R$^5$ represents a radical of the formulae

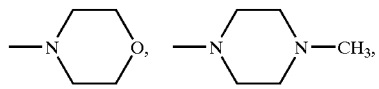

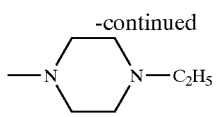

which may optionally be substituted up to 2 times by identical or different substituents from the group consisting of chlorine and $(C_1-C_4)$-alkyl or $R^5$ represents a radical of the formulae —$NR^9R^{10}$,
in which
$R^9$ and $R^{10}$ are identical or different and represent hydrogen, $(C_1-C_4)$-alkyl or phenyl, $R^4$ represents carboxyl or represents a radical of the formulae

or

—CO—$R^{13}$ or O—$R^{14}$, in which
$R^{13}$ represents $(C_1-C_4)$-alkyl,
$R^{14}$ represents $(C_1-C_4)$-alkyl which is optionally substituted up to 3 times by identical or different substituents from the group consisting of hydroxyl or by a radical of the formula —$NR^{15}R^{16}$,
in which
$R^{15}$ and $R^{16}$ are identical or different and represent hydrogen or $(C_1-C_4)$-alkyl which for its part may be substituted by phenyl, or $R^4$ represents a radical of the formula —NH—CO—$NR^{17}R^{18}$,
in which
$R^{17}$ and $R^{18}$ are identical or different and represent hydrogen or $(C_1-C_4)$-alkyl which is optionally substituted by hydroxyl, or
$R^{17}$ and $R^{18}$ together with the nitrogen atom to which they are attached form a heterocyclic ring of the formulae

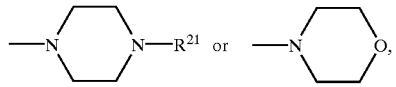

in which
$R^{21}$ represents hydrogen or $(C_1-C_4)$-alkyl, or
$R^{17}$ and/or $R^{18}$ represent phenyl which is optionally substituted by chlorine, trifluoroethyl or by —$SCF_3$ or
$R^{17}$ represents hydrogen and
$R^{18}$ represents a radical of the formula —$SO_2$—$R^{23}$,
in which
$R^{23}$ represents $(C_1-C_4)$-alkyl or phenyl which is optionally substituted by halogen, or represents a radical of the formulae

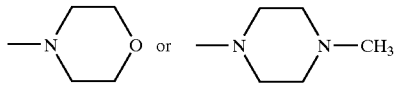

or $R^4$ represents a radical of the formula

—NH—CO—$R^{24}$, in which
$R^{24}$ represents $(C_1-C_4)$-alkyl which is optionally substituted by phenyl which for its part may be substituted by hydroxyl or $(C_1-C_4)$-alkoxy or
$(C_1-C_4)$-alkyl is optionally, substituted by a radical of the formula —$(SO_2)_b$—$R^{27}$,
in which
b represents either 0 or 1 and
$R^{27}$ represents a radical of the formulae

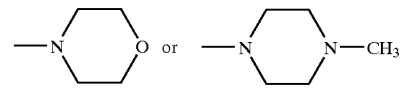

or $R^4$ represents $(C_1-C_6)$-alkyl which is optionally substituted up to 3 times by identical or different substituents from the group consisting of hydroxyl, phenyl or by radicals of the formulae —$NR^{28}R^{29}$ or —O—CO—$R^{30}$,
in which
$R^{28}$ and $R^{29}$ are identical or different and represent hydrogen, phenyl or $(C_1-C_4)$-alkyl which is optionally substituted by hydroxyl, $(C_1-C_4)$-alkoxy or phenyl, or
$R^{28}$ and $R^{29}$ together with the nitrogen atom to which they are attached form a heterocyclic ring of the formulae

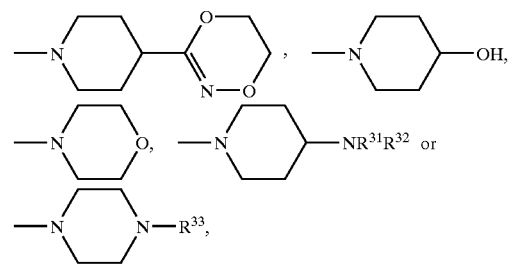

in which
$R^{31}$ and $R^{32}$ are identical or different and represent hydrogen or $(C_1-C_4)$-alkyl
$R^{33}$ represents $(C_1-C_4)$-alkyl, benzyl, $(C_1-C_4)$-alkoxycarbonyl, $(C_1-C_4)$-alkylcarbonyl, carboxyl, pyridyl, pyrimidyl or phenyl which is optionally substituted by $(C_1-C_4)$-alkoxy, and
$R^{30}$ represents $(C_1-C_6)$-alkyl, or
$(C_1-C_6)$-alkyl is optionally substituted by triazolyl which for its part may optionally be substituted up to 2 times by identical or different substituents from the group consisting of $(C_1-C_4)$-alkyl, where the latter may optionally be substituted by hydroxyl or $(C_1-C_4)$-alkoxy, or
$R^4$ represents a radical of the formula —CO—$R^{37}$,
in which $R^{37}$ represents a radical of the formula

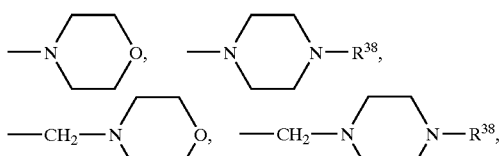

or $—(CH_2)_c—NR^{39}R^{40}$, in which
$R^{38}$ represents hydrogen or $(C_1-C_4)$-alkyl,
c represents either 0 or 1,
$R^{39}$ and $R^{40}$ are identical or different and represent hydrogen or $(C_1-C_4)$-alkyl which is optionally substituted by hydroxyl, or
$R^4$ represents a radical of the formula

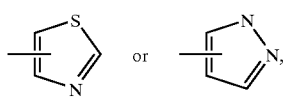

which is optionally substituted altogether up to 3 times, in the case of the pyrazole also via the N function, by identical or different substituents from the group consisting of trifluoromethyl or by phenyl which for its part may be mono- or polysubstituted by chlorine or trifluoromethyl,
and/or is optionally substituted by cyclopentyl, cyclohexyl or by $(C_1-C_6)$-alkyl which for its part may be substituted by $(C_1-C_4)$-alkoxy, amino or by phenyl,
and/or ma)y optionally be substituted by $—NR^{43}R^{44}$, $—NH—CO—R^{46}$, $—NH—CO—CH_2—R^{47}$, $—CO—R^{48}$,
in which
$R^{43}$ and $R^{44}$ are identical or different and represent hydrogen, benzyl, $(C_1-C_4)$-alkyl or phenyl which is optionally substituted by halogen or trifluoromethyl,
$R^{46}$ represents $(C_1-C_4)$-alkyl or phenyl,
$R^{47}$ represents hydroxyl or $(C_1-C_4)$-alkoxy,
$R^{48}$ represents phenyl which is optionally substituted by chlorine, trifluoromethyl or $(C_1-C_4)$-alkoxy,
or a tautomer, a pharmaceutically acceptable salt, or hydrate thereof.

4. An imidazotriazinone as claimed in claim 1 having the following structures:

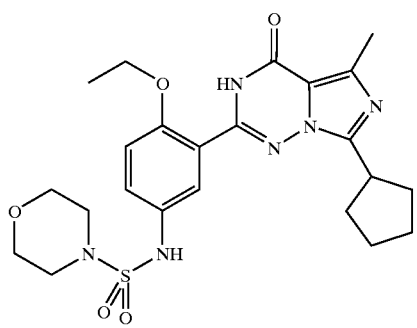

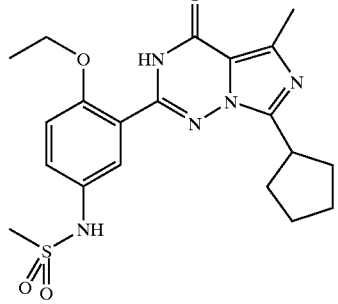

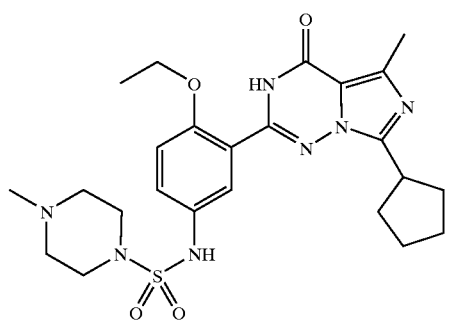

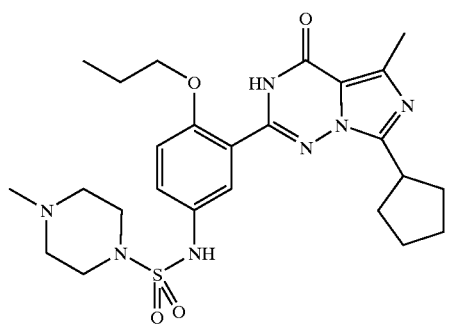

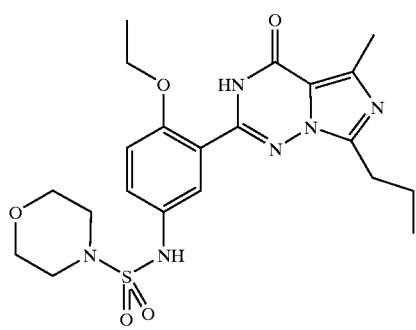

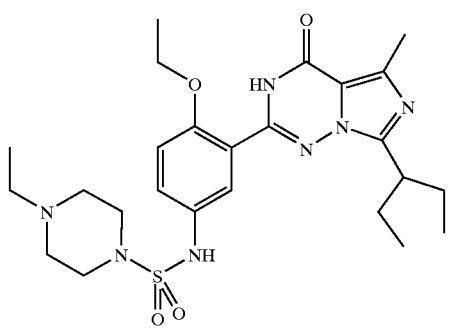

177
-continued
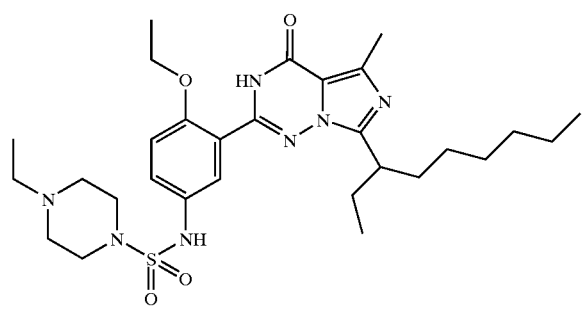
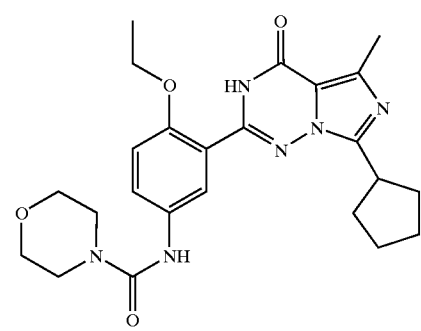
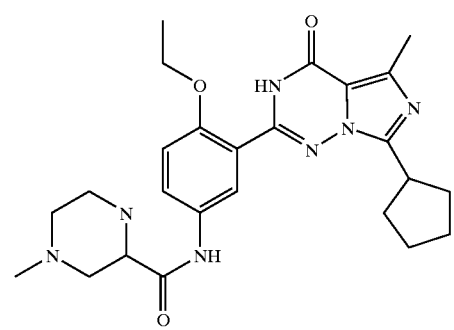
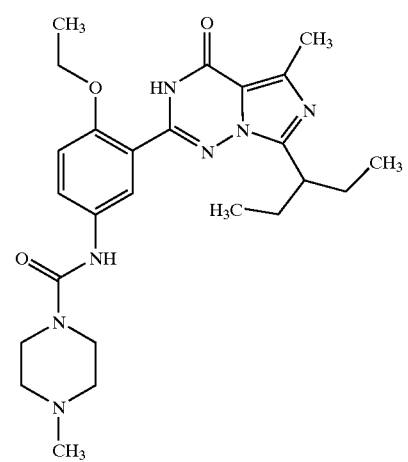
178
-continued
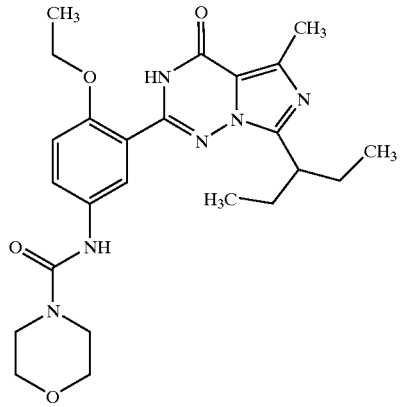
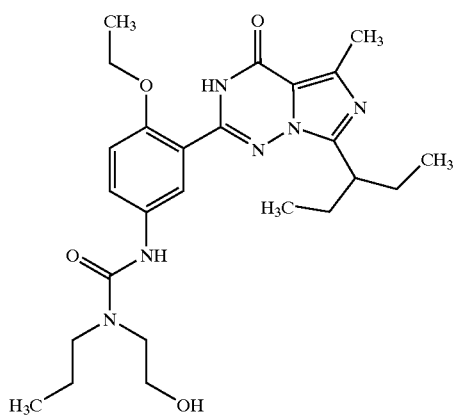
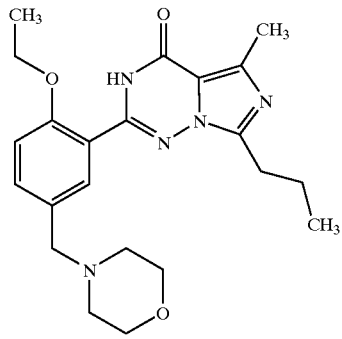
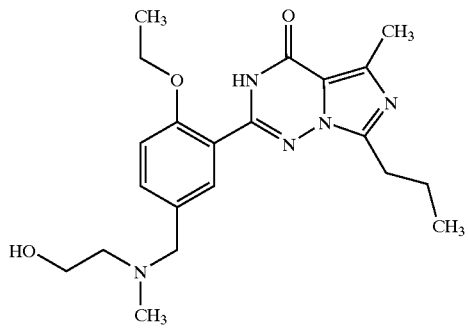

179
-continued
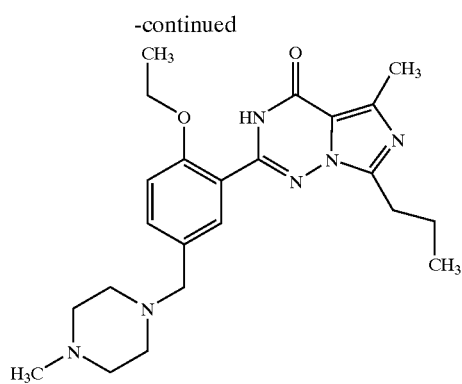
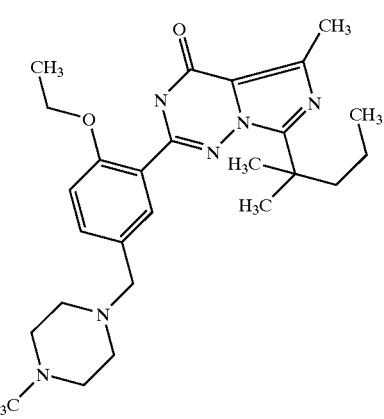
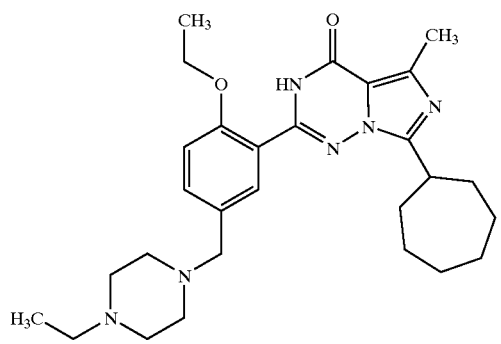
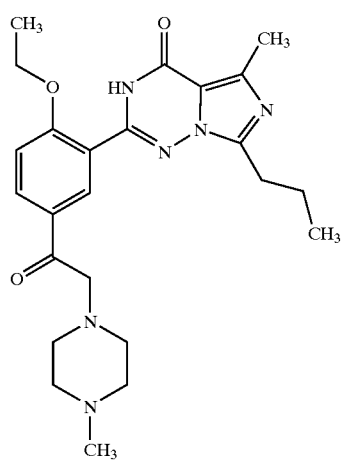
180
-continued
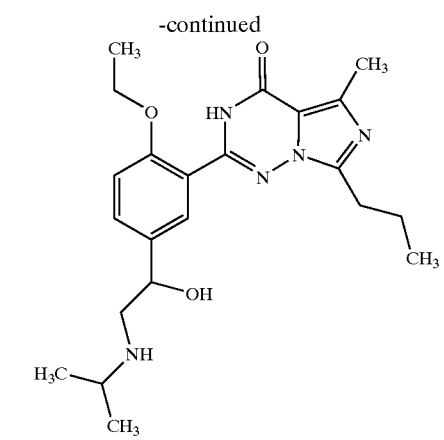
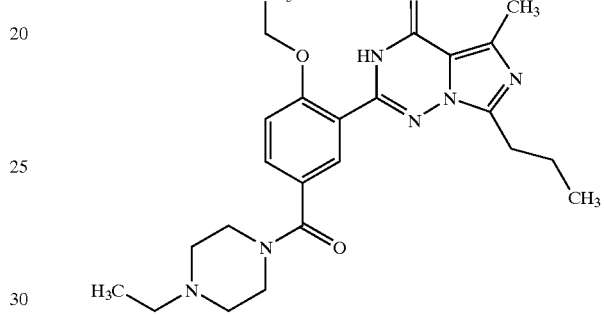
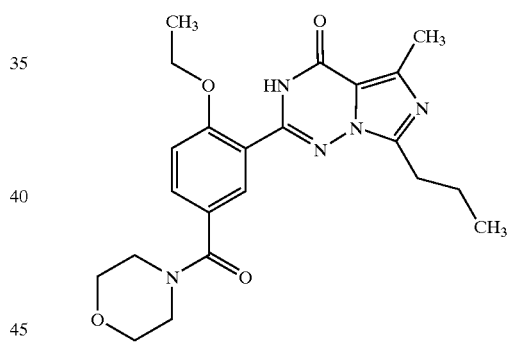
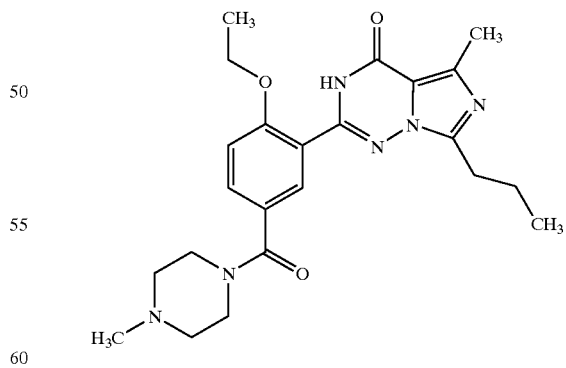
or a tautomer, a pharmaceutically acceptable salt thereof.
5. A process for preparing imidazotriazinones as claimed in any of claims 1 to 4, characterized in that
[A] in the case that R4 is a radical as defined above which is attached via a nitrogen atom, compounds of formula (II)

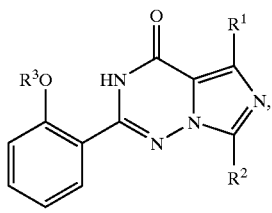

(II)

in which

R$^1$, R$^2$ and R$^3$ are as defined above
are initially converted, by reaction with HNO$_3$/CF$_3$CO$_2$H, into the compounds of formula (III)

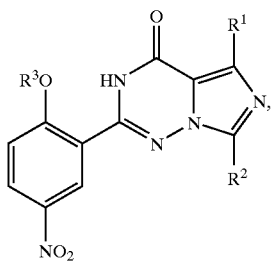

(III)

in which

R$^1$, R$^2$ and R$^3$ are as defined above,
in a next step reduced with H$_2$/Pd—C to give amines of formula (IV)

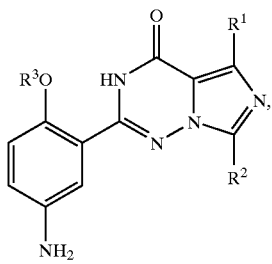

(IV)

in which

R$^1$, R$^2$ and R$^3$ are as defined above, and
finally reacted with compounds of formula (V)

 (V), in which
if
A represents the radicals R$^5$, R$^6$ or R$^7$ listed above under R$^4$,
D represents the radical —SO$_2$Cl,
and if
A represents the radical R$^{24}$ listed above under R$^4$,
D represents the radical —CO—Cl,
and if A represents the radicals R$^{17}$ or R$^{18}$ listed above under R$^4$,
D represents the radicals —NH—CO—Cl, —N═C═O or —SO$_2$—N═C═O,
in inert solvents, if appropriate in the presence of a base and/or an auxiliary, or

[B] if R$^4$ represents a radical as defined above which is attached via —NH—CO, alternatively compounds of formula (IV) are initially reacted with a bifunctional spacer B and then with compounds of formula (VI)

HNR$^{49}$R$^{50}$ (VI), in which
if
B denotes a radical of the formula Cl—CH$_2$—CO—Cl,
R$^{49}$ and R$^{50}$ together with the nitrogen atom to which they are attached are within the scope of the meaning of R$^{27}$ given above,
and if
B denotes a radical of the formula Cl—CO—OCCl$_3$,
R$^{49}$ and R$^{50}$ are within the scope of the meaning of R$^{17}$ and R$^{18}$ given above,
and if
B denotes a radical of the formula ClSO$_2$—N═C═O,
R$^{49}$ and R$^{50}$ together with the nitrogen atom to which they are attached are within the scope of the meaning of R$^{23}$ given above,
if appropriate in an inert solvents, or

[C] if R$^4$ represents a radical as defined above which is attached via a carbon atom, compounds of formula (II) are initially converted by reaction with formaldehyde/HCl into the compounds of formula (VII)

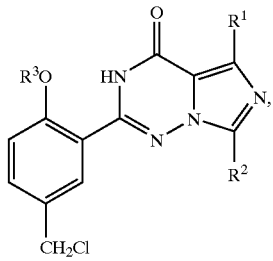

(VII)

in which

R$^1$, R$^2$ and R$^3$ are as defined above,
and then, by methods familiar to the person skilled in the art, reacted
with amines to give the corresponding benzylamines,
with phosphites to give the corresponding phosphonates,
with azide and subsequently alkynes to give the corresponding triazoles, or

[D] if R$^4$ represents a radical as defined above which is attached via —CO— or represents one of the heterocycles listed above,
initially compounds of formula (II) are, by reaction with Br—CH$_2$—CO—Br in the presence of AlCl$_3$, converted into compounds of formula (VIII)

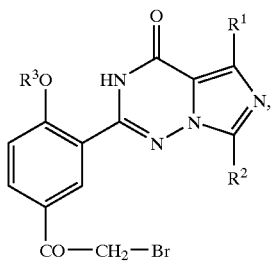

(VIII)

in which
R¹, R² and R³ are as defined above,
and then by methods familiar to the person skilled in the art reacted
with SmJ₂ to give the corresponding acetophenones,
with Br₂/NaOH to give carboxylic acids and then with amines to give the corresponding amides,
with NaBH₄/NaOH to give epoxides and then with amines to give the corresponding α-hydroxyamines,
with KCN and then hydrazines to give the corresponding aminopyrazoles,
with thioureas to give the corresponding 2-aminothiazoles,
with thioamides to give the corresponding thiazoles,
with phosphates to give the corresponding β-ketophosphonates,
with amines to give the corresponding α-aminoketones or

[E] in the case that R⁴ is a radical as defined above which is attached via an oxygen atom, compounds of formula (IX)

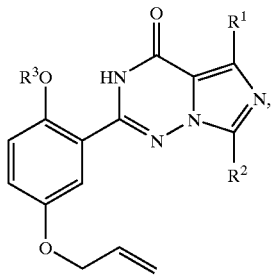

in which
R¹, R² and R³ are as defined above
are initially converted, by reaction with meta-chloroperbenzoic acid (m-CPBA), into compounds of formula (X)

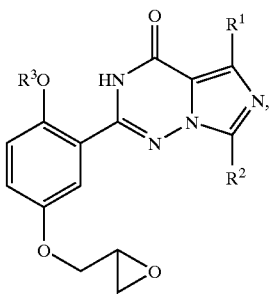

(X)

in which
R¹, R² and R³ are as defined above,
and then reacted with the corresponding amines of formula (XI)

$$HNR^{15}R^{16} \qquad (XI),$$

in which
R¹⁵ and R¹⁶ are as defined above.

6. A medicament or pharmaceutical composition which comprises at least one compound of formula (I) as claimed in any of claims 1 to 4 and one or more pharmacologically acceptable auxiliaries and carriers.

7. A medicament or pharmaceutical composition as claimed in claim 6 for the treatment of disorders of the urogenital system are selected from hypertrophy of the prostate, incontinence, erectile dysfunction and female sexual dysfunction.

8. A medicament or pharmaceutical composition as claimed in claim 6, characterized in that the medicament or the pharmaceutical composition is administered intravenously or orally.

9. A method for the treatment of disorders of the urogenital system selected from hypertrophy of the prostate, incontinence, erectile dysfunction, and female sexual dysfunction comprising administering to a subject in need thereof an effective amount of a compound of claim 1.

10. The method of claim 9, wherein the compound is administered intravenously or orally.

11. A method for the treatment of disorders of the urogenital system selected from hypertrophy of the prostate, incontinence, erectile dysfunction, and female sexual dysfunction comprising administering to a subject in need thereof the medicament or pharmaceutical composition of claim 6.

12. The method of claim 11, wherein the medicament or pharmaceutical composition is administered intravenously or orally.

* * * * *